US012760121B2

(12) United States Patent
Schneider et al.

(10) Patent No.: US 12,760,121 B2
(45) Date of Patent: Oct. 13, 2026

(54) HUMANIZED ANTIBODIES AGAINST iRhom2

(71) Applicants: SCIRHOM GMBH, Planegg (DE); NEW YORK SOCIETY FOR THE RELIEF OF THE RUPTURED AND CRIPPLED, MAINTAINING THE HOSPITAL FOR SPECIAL SURGERY, New York, NY (US)

(72) Inventors: Matthias Schneider, Neufarn (DE); Jens Ruhe, Planegg (DE); Gisela Weskamp, Eastchester, NY (US); Carl Blobel, Eastchester, NY (US)

(73) Assignees: SciRhom GmbH, Planegg (DE); New York Society for the Relief of the Ruptured and Crippled, Maintaining the Hospital for Special Surgery, New York, NY (US)

( * ) Notice: Subject to any disclaimer, the term of this patent is extended or adjusted under 35 U.S.C. 154(b) by 487 days.

(21) Appl. No.: 18/279,715

(22) PCT Filed: Feb. 25, 2022

(86) PCT No.: PCT/EP2022/054853
§ 371 (c)(1),
(2) Date: Aug. 31, 2023

(87) PCT Pub. No.: WO2022/184594
PCT Pub. Date: Sep. 9, 2022

(65) Prior Publication Data
US 2024/0166767 A1 May 23, 2024

(30) Foreign Application Priority Data
Mar. 1, 2021 (EP) .................................... 21160030
Mar. 29, 2021 (EP) .................................... 21165682

(51) Int. Cl.
*C07K 16/40* (2006.01)
*A61P 37/06* (2006.01)
*A61K 39/00* (2006.01)

(52) U.S. Cl.
CPC .............. *C07K 16/40* (2013.01); *A61P 37/06* (2018.01); *A61K 2039/505* (2013.01); *C07K 2317/24* (2013.01)

(58) Field of Classification Search
None
See application file for complete search history.

(56) References Cited

U.S. PATENT DOCUMENTS 5,223,409 A 6/1993 Ladner et al.
5,859,205 A 1/1999 Adair et al.
(Continued)

FOREIGN PATENT DOCUMENTS

CN 106471130 A 3/2017
CN 109045056 A 12/2018
(Continued)

OTHER PUBLICATIONS

Kussie et al., A single engineered amino acid substitution changes antibody fine specificity.J Immunol. Jan. 1, 1994;152(1):146-52. (Year: 1994).*
(Continued)

*Primary Examiner* — Aurora M Fontainhas
(74) *Attorney, Agent, or Firm* — COOLEY LLP; Andrew Wilkins; Megan Coyle

(57) ABSTRACT

The present invention relates to humanized antibodies or target-binding fragments or derivatives thereof retaining target binding capacities, which bind to human iRhom2.

13 Claims, 48 Drawing Sheets

Specification includes a Sequence Listing.

| Clone # | Kd [nM] |
|---|---|
| 16-B-03 | 0,67 |
| 16-B-05 | 1,07 |
| 16-B-07 | 0,99 |
| 23-B-04 | 0,58 |
| 42-B-02 | 0,50 |
| 42-B-04 | 0,48 |

(56) References Cited

U.S. PATENT DOCUMENTS

| | | | |
|---|---|---|---|
| 6,248,516 B1 | 6/2001 | Winter et al. |
| 6,300,064 B1 | 10/2001 | Knappik et al. |
| 6,331,415 B1 | 12/2001 | Cabilly et al. |
| 6,548,640 B1 | 4/2003 | Winter |
| 8,278,036 B2 | 10/2012 | Kariko et al. |
| 9,428,535 B2 | 8/2016 | de Fougerolles et al. |
| 10,024,844 B2 | 7/2018 | Blobel et al. |
| 12,404,345 B2 | 9/2025 | Schneider et al. |
| 2005/0032730 A1 | 2/2005 | Von Der Mulbe et al. |
| 2005/0169925 A1 | 8/2005 | Bardroff et al. |
| 2014/0227251 A1 | 8/2014 | Harding et al. |
| 2015/0241429 A1 | 8/2015 | Issuree et al. |
| 2017/0355756 A1 | 12/2017 | Julien et al. |
| 2022/0204610 A1 | 6/2022 | Schneider et al. |
| 2024/0174744 A1 | 5/2024 | Schneider et al. |
| 2024/0287172 A1 | 8/2024 | Schneider et al. |
| 2025/0145734 A1 | 5/2025 | Schneider et al. |

FOREIGN PATENT DOCUMENTS

| | | |
|---|---|---|
| EP | 1392341 B1 | 3/2005 |
| EP | 1480515 | 10/2005 |
| EP | 3397337 B1 | 7/2020 |
| JP | 2017522540 A | 8/2017 |
| JP | 2022525239 A | 5/2022 |
| WO | WO-2008068048 A2 | 6/2008 |
| WO | WO-2009044158 A2 | 4/2009 |
| WO | WO-2012/140414 A1 | 10/2012 |
| WO | WO-2014/100602 A1 | 6/2014 |
| WO | WO-2015172143 A1 | 11/2015 |
| WO | WO-2020208150 A1 | 10/2020 |
| WO | WO-2021064009 A1 | 4/2021 |
| WO | WO-2022184594 A1 | 9/2022 |
| WO | WO-2022207652 A1 | 10/2022 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

DeLisser, "Epitope Mapping," Methods in Molecular Biology, vol. 96: Adhesion Protein Protocols. Elisabetta Dejana and Monica Corada, 11-20 (1999).

International Search Report and Written Opinion for International Application No. PCT/EP2020/077346, mailed Nov. 18, 2020 (17 pages).

Maney et al., "Deletions in the cytoplasmic domain of iRhom1 and iRhom2 promote shedding of the TNF receptor by the protease ADAM17," Sci Signal. 8(401):ra109 (2015) (11 pages).

Ohba et al., "An immunodominant neutralization epitope on the 'thumb' subdomain of human immunodeficiency virus type 1 reverse transcriptase revealed by phage display antibodies," J Gen Virol. 82(Pt 4):813-820 (2001).

International Preliminary Report on Patentability for International Application No. PCT/EP2020/077346, issued Apr. 5, 2022 (8 pages).

Dulloo et al., "The molecular, cellular and pathophysiological roles of iRhom pseudoproteases," Open Biol. 9(3):190003 (2019) (14 pages).

Coussens et al., "Inflammation and cancer," Nature. 420(6917):860-7 (2002).

Weskamp et al., "ADAM17 stabilizes its interacting partner inactive Rhomboid 2 (iRhom2) but not inactive Rhomboid 1 (iRhom1)," available in JBC Papers in Press Feb. 14, 2020, published in final edited form as: J Biol Chem. 295(13):4350-4358 (2020) (27 pages).

Banik, Soma Sr; Doranz, Benjamin J. Mapping complex antibody epitopes. Genetic Engineering & Biotechnology News, 2010, 30(2) (5 pages).

Baran, Paul, et al. Minimal interleukin 6 (IL-6) receptor stalk composition for IL-6 receptor shedding and IL-6 classic signaling. Journal of Biological Chemistry, 2013, 288. Jg., Nr. 21, S. 14756-14768.

Chothia, Cyrus; Lesk, Arthur M. Canonical structures for the hypervariable regions of immunoglobulins. Journal of molecular biology, 1987, 196. Jg., Nr. 4, S. 901-917.

Deng, Xiaoxiang; Storz, Ulrich; Doranz, Benjamin J. Enhancing antibody patent protection using epitope mapping information. In: MAbs. Taylor & Francis, 2018. S. 10(2):204-209.

Eylenstein, Roy, et al. Molecular basis of in vitro affinity maturation and functional evolution of a neutralizing anti-human GM-CSF antibody. In: MAbs. Taylor & Francis, 2016. S. 8(1):176-186.

Finco, Deborah, et al. Comparison of competitive ligand-binding assay and bioassay formats for the measurement of neutralizing antibodies to protein therapeutics. Journal of pharmaceutical and biomedical analysis, 2011, 54. Jg., Nr. 2, S. 351-358.

Harding, Fiona A., et al. The immunogenicity of humanized and fully human antibodies: residual immunogenicity resides in the CDR regions. In: MAbs. Taylor & Francis, 2010. S. 2(3):256-265.

Huston, James S., et al. Antigen recognition and targeted delivery by the single-chain Fv. Cell biophysics, 1993, 22. Jg., S. 189-224.

Kabat, Elvin A.; Wu, T. Te; Bilofsky, H. Unusual distributions of amino acids in complementarity determining (hypervariable) segments of heavy and light chains of immunoglobulins and their possible roles in specificity of antibody-combining sites. Journal of Biological Chemistry, 1977, 252. Jg., Nr. 19, S. 6609-6616.

Kabat, Elvin Abraham. Sequences of proteins of immunological interest. US Department of Health and Human Services, Public Health Service, National Institutes of Health, 1991 (1,241 pages).

Köhler, Georges; Milstein, Cesar. Continuous cultures of fused cells secreting antibody of predefined specificity. nature, 1975, 256. Jg., Nr. 5517, S. 495-497.

Li, Xue, et al. iRhoms 1 and 2 are essential upstream regulators of ADAM17-dependent EGFR signaling. Proceedings of the National Academy of Sciences, 2015, 112. Jg., Nr. 19, S. 6080-6085.

Maccallum, Robert M.; Martin, Andrew CR; Thornton, Janet M. Antibody-antigen interactions: contact analysis and binding site topography. Journal of molecular biology, 1996, 262. Jg., Nr. 5, S. 732-745.

Plückthun, Andreas; Skerra, Arne. [34] Expression of functional antibody Fv and Fab fragments in *Escherichia coli.* In: Methods in enzymology. Academic Press, 1989. S. 178:497-515.

Wu, Herren, et al. Stepwise in vitro affinity maturation of Vitaxin, an alphavbeta3-specific humanized mAb. Proceedings of the National Academy of Sciences, 1998, 95. Jg., Nr. 11, S. 6037-6042.

Adrain et al., "Tumor necrosis factor signaling requires iRhom2 to promote trafficking and activation of TACE," Science, (Jan. 13, 2012), 335(6065):225-228. doi: 10.1126/science. 1214400.

Almagro et al., "Progress and Challenges in the Design and Clinical Development of Antibodies for Cancer Therapy," Frontiers in Immunology, (Jan. 4, 2018), 8:1751, 19 pages. doi: 10.3389/fimmu. 2017.01751.

Blythe et al., "Benchmarking B cell epitope prediction: underperformance of existing methods," Protein Science, (Jan. 2005), 14(1):246-248. doi: 10.1110/ps.041059505. Epub Dec. 2, 2004.

Gershoni et al., "Epitope mapping: the first step in developing epitope-based vaccines," BioDrugs, (2007), 21(3):145-156. doi: 10.2165/00063030-200721030-00002.

Grieve et al., "Phosphorylation of iRhom2 at the plasma membrane controls mammalian TACE-dependent inflammatory and growth factor signalling," eLife, (Apr. 22, 2017), 6:e23968, 22 pages. doi: 10.7554/eLife.23968.

Issuree et al., "iRHOM2 is a critical pathogenic mediator of inflammatory arthritis," Journal of Clinical Investigation, (Feb. 2013), 123(2):928-932. doi: 10.1172/JCI66168. Epub Jan. 25, 2013.

Koenig et al., "Mutational landscape of antibody variable domains reveals a switch modulating the interdomain conformational dynamics and antigen binding," Proceedings of the National Academy of

(56) References Cited

OTHER PUBLICATIONS

Sciences of the U.S.A., (Jan. 24, 2017), 114(4):E486-E495. doi: 10.1073/pnas.1613231114. Epub Jan. 5, 2017.
Lichtenthaler, "iRHOM2 takes control of rheumatoid arthritis," Journal of Clinical Investigation, (Feb. 2013), 123(2):560-562. doi: 10.1172/JCI67548. Epub Jan. 25, 2013.
Mcilwain et al., "iRhom2 regulation of TACE controls TNF-mediated protection against Listeria and responses to LPS," Science, (Jan. 13, 2012), 335(6065):229-232. doi: 10.1126/science.1214448.
NCBI, Accession No. NP_078875.4, "inactive rhomboid protein 2 isoform 1 [*Homo sapiens*]," [protein database record], NCBI Protein, (label action Apr. 23, 2017; updated Apr. 27, 2025). [Retrieved from Internet on Aug. 17, 2023 at URL: https://www.ncbi.nlm.nih.gov/protein/301069362?sat=46&satkey=71512628], 10 pages.
Ni et al., "Mechanistic insights into how the single point mutation change the autoantibody repertoire," Protein Journal, (Aug. 2024), 43(4):683-696. doi: 10.1007/s10930-024-10225-w. Epub Jul. 28, 2024.
Oikonomidi et al., "iTAP, a novel iRhom interactor, controls TNF secretion by policing the stability of iRhom/TACE," eLife, (Jun. 13, 2018), 7:e35032, 35 pages. doi: 10.7554/eLife.35032.
PCT Application No. PCT/EP2022/054853, International Preliminary Report on Patentability mailed Jun. 5, 2023, Applicant: Scirhom Gmbh et al., 9 pages.
PCT Application No. PCT/EP2022/054853, International Search Report and Written Opinion mailed Jun. 1, 2022, Applicant: Scirhom Gmbh et al., 13 pages.
Rothe et al., "Anticalin® proteins as therapeutic agents in human diseases," BioDrugs, (Jun. 2018), 32(3):233-243. doi: 10.1007/s40259-018-0278-1.
Schmitz et al., "Basic methods in histopathology of joint tissues," Osteoarthritis and Cartilage, (Oct. 2010), 18(Suppl. 3):S113-S116. doi: 10.1016/j.joca.2010.05.026.
Sela-Culang et al., "The structural basis of antibody-antigen recognition," Frontiers in Immunology, (Oct. 8, 2013), 4:302, 13 pages. doi: 10.3389/fimmu.2013.00302.
Siggs et al., "iRhom2 is required for the secretion of mouse TNFa," Blood, (Jun. 14, 2012), 119(24):5769-5771. doi: 10.1182/blood-2012-03-417949. Epub May 1, 2012.
Stumpp et al., "DARPins: a new generation of protein therapeutics," Drug Discovery Today, (Aug. 2008), 13(15-16):695-701. doi: 10.1016/j.drudis.2008.04.013. Epub Jul. 11, 2008.
Tang et al., "Substrate-selective protein ectodomain shedding by ADAM17 and iRhom2 depends on their juxtamembrane and transmembrane domains," FASEB Journal, (Apr. 2020), 34(4):4956-4969. doi: 10.1096/fj.201902649R. Epub Feb. 26, 2020.
Tiede et al., "Affimer proteins are versatile and renewable affinity reagents," eLife, (Jun. 27, 2017), 6:e24903, 35 pages. doi: 10.7554/eLife.24903.
Zhong, "Role of ADAM family metalloproteinases in the regulation of pulmonary inflammation," Acta Medicinae Sinica, (no date provided), 30(4):133-137, with English Abstract.

* cited by examiner

| Clone # | Kd [nM] |
| --- | --- |
| 16-B-03 | 0,67 |
| 16-B-05 | 1,07 |
| 16-B-07 | 0,99 |
| 23-B-04 | 0,58 |
| 42-B-02 | 0,50 |
| 42-B-04 | 0,48 |

FIG. 1

FIG. 17b

| 1 => 30% loss of binding vs wild type | human iRhom2 with deletions/substitutions | | | | | |
|---|---|---|---|---|---|---|
| 2 => 60% loss of binding vs wild type | humanised antibody clones | | | | | |
| 3 => 95% loss of binding vs wild type | #16-B-03 | #16-B-05 | #16-B-07 | #23-B-04 | #42-B-02 | #42-B-04 |
| Q502R | - | - | - | - | - | - |
| N503A | 1 | 1 | 1 | 1 | 1 | 1 |
| D504A | - | - | - | - | - | - |
| H505R | - | - | - | - | - | - |
| H505A | - | - | - | - | - | - |
| S506A | - | - | - | - | - | - |
| G507A | - | - | - | - | - | - |
| C508A | 1 | 1 | 1 | 2 | 2 | 1 |
| I509V | - | - | - | - | - | - |
| I509A | - | - | - | - | - | - |
| Q510A | - | - | - | - | - | - |
| T511A | - | - | - | - | - | - |
| Q512L | - | - | - | - | - | - |
| Q512S | - | - | - | - | - | - |
| Q512A | - | - | - | - | - | - |
| R513K | - | - | - | - | - | - |
| R513E | - | - | - | - | - | - |
| R513A | - | - | - | - | - | - |
| K514E | - | - | - | - | - | - |
| K514A | - | - | - | - | - | - |
| D515E | - | - | - | - | - | - |
| D515A | - | - | - | - | - | - |
| S517A | - | - | - | - | - | - |
| E518S | - | - | - | - | - | - |
| E518A | - | - | - | - | - | - |
| T519A | - | - | - | - | - | - |

FIG. 17c

| 1 => 30% loss of binding vs wild type | human iRhom2 with deletions/substitutions | | | | | |
|---|---|---|---|---|---|---|
| 2 => 60% loss of binding vs wild type | humanised antibody clones | | | | | |
| 3 => 95% loss of binding vs wild type | #16-B-03 | #16-B-05 | #16-B-07 | #23-B-04 | #42-B-02 | #42-B-04 |
| L520A | - | - | - | - | - | - |
| A521S | - | - | - | - | - | - |
| T522V | - | - | - | - | - | - |
| T522A | - | - | - | - | - | - |
| F523W | - | - | - | - | - | - |
| V524A | - | - | - | - | - | - |
| K525A | - | - | - | - | - | - |
| W526A | 1 | 1 | 1 | 1 | 1 | 1 |
| Q527P | 1 | 1 | 1 | 1 | 1 | 1 |
| Q527A | - | - | - | - | - | - |
| D528N | - | - | - | - | - | - |
| D528I | - | - | - | 1 | - | 1 |
| D528A | - | - | - | 1 | - | 1 |
| D529H | - | - | - | 1 | 1 | 1 |
| D529A | - | - | 1 | - | - | 1 |
| T530P | 1 | 1 | 1 | 1 | 1 | 1 |
| T530A | - | - | - | 1 | - | 1 |
| G531S | 1 | 1 | 1 | 1 | 1 | 1 |
| G531A | - | 1 | 1 | - | - | - |
| P532A | 1 | 1 | 1 | 2 | 1 | 1 |
| P533- | 3 | 3 | 3 | 3 | 3 | 3 |
| P533A | - | 1 | 1 | 1 | 1 | 1 |
| M534S | - | 1 | - | 1 | 1 | 1 |
| M534- | 3 | 3 | 3 | 3 | 3 | 3 |
| M534A | - | 1 | 1 | 1 | 1 | 1 |

FIG. 17d

| 1 => 30% loss of binding vs wild type | human iRhom2 with deletions/substitutions | | | | | |
|---|---|---|---|---|---|---|
| 2 => 60% loss of binding vs wild type | humanised antibody clones | | | | | |
| 3 => 95% loss of binding vs wild type | #16-B-03 | #16-B-05 | #16-B-07 | #23-B-04 | #42-B-02 | #42-B-04 |
| D535- | 3 | 3 | 3 | 3 | 3 | 3 |
| D535A | 1 | 1 | 1 | 2 | 2 | 1 |
| K536- | 3 | 3 | 3 | 3 | 3 | 3 |
| K536A | 3 | 3 | 3 | 3 | 3 | 3 |
| S537E | - | - | - | 2 | 2 | 2 |
| S537A | - | - | - | - | - | - |
| D538L | - | - | - | - | - | - |
| D538A | - | - | - | - | - | - |
| L539A | 2 | 1 | 2 | 3 | 3 | 3 |
| G540S | - | - | - | - | - | - |
| G540A | - | - | - | - | - | - |
| Q541H | - | - | - | - | - | - |
| Q541A | - | - | - | - | - | - |
| K542A | 1 | 1 | 1 | - | - | - |
| R543Q | 1 | 1 | 1 | 2 | 2 | 2 |
| R543A | 1 | 1 | 1 | 3 | 2 | 2 |
| T544P | 1 | 1 | 1 | 1 | 1 | 1 |
| T544Q | - | - | - | - | - | - |
| T544A | - | - | - | - | - | - |
| S545F | - | - | - | - | - | - |
| S545A | - | - | - | - | - | - |
| G546A | 1 | 1 | 1 | 1 | 1 | 1 |
| A547V | - | - | - | - | - | - |
| A547S | - | - | - | - | - | - |
| V548A | - | - | - | - | - | - |
| H550A | - | - | - | - | - | - |

FIG. 17e

| 1 => 30% loss of binding vs wild type | human iRhom2 with deletions/substitutions | | | | | |
|---|---|---|---|---|---|---|
| 2 => 60% loss of binding vs wild type | humanised antibody clones | | | | | |
| 3 => 95% loss of binding vs wild type | #16-B-03 | #16-B-05 | #16-B-07 | #23-B-04 | #42-B-02 | #42-B-04 |
| Q551A | - | - | - | - | - | - |
| P553A | - | - | - | - | - | - |
| R554A | - | - | - | - | - | - |
| T555V | - | - | - | - | - | - |
| T555A | - | - | - | - | - | - |
| E557D | - | - | - | - | - | - |
| E557A | - | - | - | - | - | - |
| E558A | - | - | - | - | - | - |
| A560S | - | - | - | - | - | - |
| S561A | - | - | - | 1 | - | - |
| S562E | - | - | - | - | - | - |
| S562A | - | - | - | - | - | - |
| G563D | - | - | - | - | - | - |
| G563A | - | - | - | - | - | - |
| A564P | - | - | - | - | - | - |
| A564S | - | - | - | - | - | - |
| H565A | - | - | - | - | - | - |
| I566E | - | - | - | 2 | 1 | 1 |
| I566A | - | - | - | - | - | - |
| P568A | - | - | - | - | - | - |
| D569E | - | - | - | - | - | - |
| D569A | - | - | - | - | - | - |
| D570A | - | - | - | - | - | - |
| I571A | - | - | - | - | - | - |
| T572A | - | - | - | - | - | - |
| K573A | - | - | - | - | - | - |

FIG. 17f

| 1 => 30% loss of binding vs wild type | human iRhom2 with deletions/substitutions | | | | | |
|---|---|---|---|---|---|---|
| 2 => 60% loss of binding vs wild type | humanised antibody clones | | | | | |
| 3 => 95% loss of binding vs wild type | #16-B-03 | #16-B-05 | #16-B-07 | #23-B-04 | #42-B-02 | #42-B-04 |
| P575A | - | - | - | - | - | - |
| I576A | - | - | - | - | - | - |
| T578A | - | - | - | - | - | - |
| E579K | - | - | - | - | - | - |
| E579A | - | - | - | - | - | - |
| Q580N | - | - | - | - | - | - |
| Q580A | - | - | - | - | - | - |
| A581S | - | - | - | - | - | - |
| R582A | - | - | - | - | - | - |
| S583G | - | - | - | - | - | - |
| S583A | - | - | - | - | - | - |
| N584A | - | - | - | - | - | - |
| H585A | - | - | - | - | - | - |
| T586A | - | - | - | - | - | - |
| G587N | - | - | - | - | - | - |
| G587A | - | - | - | - | - | - |
| F588H | - | - | - | - | - | - |
| F588A | - | - | - | - | - | - |
| L589P | - | - | - | - | - | - |
| L589A | - | - | - | - | - | - |
| H590A | - | - | - | - | - | - |
| M591A | - | - | - | - | - | - |
| D592A | - | - | - | - | - | - |
| C593A | - | - | - | - | - | - |
| E594V | - | - | - | - | - | - |

SEQUENCE LISTING

```
<160> NUMBER OF SEQ ID NOS: 150

<210> SEQ ID NO 1
<211> LENGTH: 120
<212> TYPE: PRT
<213> ORGANISM: artificial sequence
<220> FEATURE:
<223> OTHER INFORMATION: antibody sequences

<400> SEQUENCE: 1

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Ala Leu Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Arg Ile Thr Thr Tyr Tyr Tyr Gly Met Asp Tyr Trp Gly Gln
            100                 105                 110

Gly Thr Leu Val Thr Val Ser Ser
        115                 120


<210> SEQ ID NO 2
<211> LENGTH: 7
<212> TYPE: PRT
<213> ORGANISM: artificial sequence
<220> FEATURE:
<223> OTHER INFORMATION: antibody sequences

<400> SEQUENCE: 2

Thr Phe Ala Leu Gly Val Gly
1               5


<210> SEQ ID NO 3
<211> LENGTH: 16
<212> TYPE: PRT
<213> ORGANISM: artificial sequence
<220> FEATURE:
<223> OTHER INFORMATION: antibody sequences

<400> SEQUENCE: 3

His Ile Trp Trp Asp Asp Asp Lys Tyr Tyr Asn Pro Ala Leu Lys Ser
1               5                   10                  15
```

<210> SEQ ID NO 4
<211> LENGTH: 10
<212> TYPE: PRT
<213> ORGANISM: artificial sequence
<220> FEATURE:
<223> OTHER INFORMATION: antibody sequences

<400> SEQUENCE: 4

```
Ile Thr Thr Tyr Tyr Tyr Gly Met Asp Tyr
1               5                   10
```

<210> SEQ ID NO 5
<211> LENGTH: 107
<212> TYPE: PRT
<213> ORGANISM: artificial sequence
<220> FEATURE:
<223> OTHER INFORMATION: antibody sequences

<400> SEQUENCE: 5

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln Ser Ile Gly Asn His
            20                  25                  30

Leu His Trp Tyr Gln Gln Lys Pro Asp Ala Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Phe Cys Gln Gln Ser Tyr Gln Trp Pro Leu
                85                  90                  95

Thr Phe Gly Gln Gly Thr Lys Leu Glu Ile Lys
            100                 105
```

<210> SEQ ID NO 6
<211> LENGTH: 11
<212> TYPE: PRT
<213> ORGANISM: artificial sequence
<220> FEATURE:
<223> OTHER INFORMATION: antibody sequences

<400> SEQUENCE: 6

```
Arg Ala Ser Gln Ser Ile Gly Asn His Leu His
1               5                   10
```

<210> SEQ ID NO 7
<211> LENGTH: 7
<212> TYPE: PRT
<213> ORGANISM: artificial sequence
<220> FEATURE:
<223> OTHER INFORMATION: antibody sequences

<400> SEQUENCE: 7

```
Tyr Ala Ser Gln Ser Ile Ser
1               5
```

<210> SEQ ID NO 8
<211> LENGTH: 9
<212> TYPE: PRT
<213> ORGANISM: artificial sequence
<220> FEATURE:
<223> OTHER INFORMATION: antibody sequences

<400> SEQUENCE: 8

Gln Gln Ser Tyr Gln Trp Pro Leu Thr
1 5

<210> SEQ ID NO 9
<211> LENGTH: 120
<212> TYPE: PRT
<213> ORGANISM: artificial sequence
<220> FEATURE:
<223> OTHER INFORMATION: antibody sequences

<400> SEQUENCE: 9

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Phe
20 25 30

Ala Leu Gly Val Gly Trp Ile Arg Gln Pro Pro Gly Lys Ala Leu Glu
35 40 45

Trp Leu Ala His Ile Trp Trp Asp Glu Asp Lys Tyr Tyr Asn Pro Ala
50 55 60

Leu Lys Ser Arg Leu Thr Ile Ser Lys Asp Thr Ser Lys Asn Gln Val
65 70 75 80

Val Leu Thr Ile Thr Asn Met Asp Pro Val Asp Thr Ala Thr Tyr Tyr
85 90 95

Cys Ala Arg Ile Thr Thr Tyr Tyr Tyr Gly Met Asp Tyr Trp Gly Gln
100 105 110

Gly Thr Leu Val Thr Val Ser Ser
115 120

<210> SEQ ID NO 10
<211> LENGTH: 7
<212> TYPE: PRT
<213> ORGANISM: artificial sequence
<220> FEATURE:
<223> OTHER INFORMATION: antibody sequences

<400> SEQUENCE: 10

Thr Phe Ala Leu Gly Val Gly
1 5

<210> SEQ ID NO 11
<211> LENGTH: 16
<212> TYPE: PRT
<213> ORGANISM: artificial sequence
<220> FEATURE:
<223> OTHER INFORMATION: antibody sequences

<400> SEQUENCE: 11

His Ile Trp Trp Asp Glu Asp Lys Tyr Tyr Asn Pro Ala Leu Lys Ser
1 5 10 15

<210> SEQ ID NO 12
<211> LENGTH: 10
<212> TYPE: PRT
<213> ORGANISM: artificial sequence
<220> FEATURE:
<223> OTHER INFORMATION: antibody sequences

<400> SEQUENCE: 12

Ile Thr Thr Tyr Tyr Tyr Gly Met Asp Tyr
1 5 10

<210> SEQ ID NO 13
<211> LENGTH: 107
<212> TYPE: PRT
<213> ORGANISM: artificial sequence
<220> FEATURE:
<223> OTHER INFORMATION: antibody sequences

<400> SEQUENCE: 13

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln Ser Ile Gly Asn His
            20                  25                  30

Leu His Trp Tyr Gln Gln Lys Pro Asp Ala Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Phe Cys Gln Gln Ser Tyr Asn Trp Pro Leu
                85                  90                  95

Thr Phe Gly Gln Gly Thr Lys Leu Glu Ile Lys
            100                 105
```

<210> SEQ ID NO 14
<211> LENGTH: 11
<212> TYPE: PRT
<213> ORGANISM: artificial sequence
<220> FEATURE:
<223> OTHER INFORMATION: antibody sequences

<400> SEQUENCE: 14

```
Arg Ala Ser Gln Ser Ile Gly Asn His Leu His
1               5                   10
```

<210> SEQ ID NO 15
<211> LENGTH: 7
<212> TYPE: PRT
<213> ORGANISM: artificial sequence
<220> FEATURE:
<223> OTHER INFORMATION: antibody sequences

<400> SEQUENCE: 15

```
Tyr Ala Ser Gln Ser Ile Ser
1               5
```

<210> SEQ ID NO 16
<211> LENGTH: 9
<212> TYPE: PRT
<213> ORGANISM: artificial sequence
<220> FEATURE:
<223> OTHER INFORMATION: antibody sequences

<400> SEQUENCE: 16

```
Gln Gln Ser Tyr Asn Trp Pro Leu Thr
1               5
```

<210> SEQ ID NO 17
<211> LENGTH: 120
<212> TYPE: PRT
<213> ORGANISM: artificial sequence
<220> FEATURE:
<223> OTHER INFORMATION: antibody sequences

<400> SEQUENCE: 17

-continued

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Phe
20 25 30

Ala Leu Gly Val Gly Trp Ile Arg Gln Pro Pro Gly Lys Ala Leu Glu
35 40 45

Trp Leu Ala His Ile Trp Trp Asp Glu Asp Lys Tyr Tyr Asn Pro Ala
50 55 60

Leu Lys Ser Arg Leu Thr Ile Ser Lys Asp Thr Ser Lys Asn Gln Val
65 70 75 80

Val Leu Thr Ile Thr Asn Met Asp Pro Val Asp Thr Ala Thr Tyr Tyr
85 90 95

Cys Ala Arg Ile Thr Thr Tyr Tyr Tyr Gly Met Asp Tyr Trp Gly Gln
100 105 110

Gly Thr Leu Val Thr Val Ser Ser
115 120

<210> SEQ ID NO 18
<211> LENGTH: 7
<212> TYPE: PRT
<213> ORGANISM: artificial sequence
<220> FEATURE:
<223> OTHER INFORMATION: antibody sequences

<400> SEQUENCE: 18

Thr Phe Ala Leu Gly Val Gly
1 5

<210> SEQ ID NO 19
<211> LENGTH: 16
<212> TYPE: PRT
<213> ORGANISM: artificial sequence
<220> FEATURE:
<223> OTHER INFORMATION: antibody sequences

<400> SEQUENCE: 19

His Ile Trp Trp Asp Glu Asp Lys Tyr Tyr Asn Pro Ala Leu Lys Ser
1 5 10 15

<210> SEQ ID NO 20
<211> LENGTH: 10
<212> TYPE: PRT
<213> ORGANISM: artificial sequence
<220> FEATURE:
<223> OTHER INFORMATION: antibody sequences

<400> SEQUENCE: 20

Ile Thr Thr Tyr Tyr Tyr Gly Met Asp Tyr
1 5 10

<210> SEQ ID NO 21
<211> LENGTH: 107
<212> TYPE: PRT
<213> ORGANISM: artificial sequence
<220> FEATURE:
<223> OTHER INFORMATION: antibody sequences

<400> SEQUENCE: 21

Glu Ile Val Met Thr Gln Ser Pro Asp Phe Gln Ser Val Thr Pro Lys
1 5 10 15

Glu Lys Val Thr Ile Thr Cys Arg Ala Ser Gln Ser Ile Gly Asn His
20 25 30

```
Leu His Trp Tyr Gln Gln Lys Pro Asp Ala Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Phe Cys Gln Gln Ser Tyr Gln Trp Pro Leu
                85                  90                  95

Thr Phe Gly Gln Gly Thr Lys Leu Glu Ile Lys
            100                 105


<210> SEQ ID NO 22
<211> LENGTH: 11
<212> TYPE: PRT
<213> ORGANISM: artificial sequence
<220> FEATURE:
<223> OTHER INFORMATION: antibody sequences

<400> SEQUENCE: 22

Arg Ala Ser Gln Ser Ile Gly Asn His Leu His
1               5                   10


<210> SEQ ID NO 23
<211> LENGTH: 7
<212> TYPE: PRT
<213> ORGANISM: artificial sequence
<220> FEATURE:
<223> OTHER INFORMATION: antibody sequences

<400> SEQUENCE: 23

Tyr Ala Ser Gln Ser Ile Ser
1               5


<210> SEQ ID NO 24
<211> LENGTH: 9
<212> TYPE: PRT
<213> ORGANISM: artificial sequence
<220> FEATURE:
<223> OTHER INFORMATION: antibody sequences

<400> SEQUENCE: 24

Gln Gln Ser Tyr Gln Trp Pro Leu Thr
1               5


<210> SEQ ID NO 25
<211> LENGTH: 123
<212> TYPE: PRT
<213> ORGANISM: artificial sequence
<220> FEATURE:
<223> OTHER INFORMATION: antibody sequences

<400> SEQUENCE: 25

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Glu Lys Tyr Tyr Asn Ser Ala
    50                  55                  60

Leu Lys Ser Arg Leu Thr Ile Ser Lys Asp Thr Ser Lys Asn Gln Val
65                  70                  75                  80
```

```
Val Leu Thr Ile Thr Asn Met Asp Pro Val Asp Thr Ala Thr Tyr Tyr
                85                  90                  95

Cys Ala Arg Ile Ser Asn Tyr Gly Ser Asn Tyr Trp Tyr Phe Asn Val
            100                 105                 110

Trp Gly Gln Gly Thr Leu Val Thr Val Ser Ser
        115                 120


<210> SEQ ID NO 26
<211> LENGTH: 7
<212> TYPE: PRT
<213> ORGANISM: artificial sequence
<220> FEATURE:
<223> OTHER INFORMATION: antibody sequences

<400> SEQUENCE: 26

Thr Phe Gly Met Gly Val Gly
1               5


<210> SEQ ID NO 27
<211> LENGTH: 16
<212> TYPE: PRT
<213> ORGANISM: artificial sequence
<220> FEATURE:
<223> OTHER INFORMATION: antibody sequences

<400> SEQUENCE: 27

His Ile Trp Trp Asp Asp Glu Lys Tyr Tyr Asn Ser Ala Leu Lys Ser
1               5                   10                  15


<210> SEQ ID NO 28
<211> LENGTH: 13
<212> TYPE: PRT
<213> ORGANISM: artificial sequence
<220> FEATURE:
<223> OTHER INFORMATION: antibody sequences

<400> SEQUENCE: 28

Ile Ser Asn Tyr Gly Ser Asn Tyr Trp Tyr Phe Asn Val
1               5                   10


<210> SEQ ID NO 29
<211> LENGTH: 106
<212> TYPE: PRT
<213> ORGANISM: artificial sequence
<220> FEATURE:
<223> OTHER INFORMATION: antibody sequences

<400> SEQUENCE: 29

Ala Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Tyr Trp Tyr Gln Gln Lys Pro Gly Lys Ala Pro Lys Val Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Asn Ala Tyr Pro Leu Thr
                85                  90                  95

Phe Gly Gln Gly Thr Lys Leu Glu Ile Lys
            100                 105
```

<210> SEQ ID NO 30
<211> LENGTH: 10
<212> TYPE: PRT
<213> ORGANISM: artificial sequence
<220> FEATURE:
<223> OTHER INFORMATION: antibody sequences

<400> SEQUENCE: 30

Arg Ala Ser Ser Ser Val Ser Tyr Met Tyr
1 5 10

<210> SEQ ID NO 31
<211> LENGTH: 7
<212> TYPE: PRT
<213> ORGANISM: artificial sequence
<220> FEATURE:
<223> OTHER INFORMATION: antibody sequences

<400> SEQUENCE: 31

Asp Thr Ser Asn Leu Ala Ser
1 5

<210> SEQ ID NO 32
<211> LENGTH: 9
<212> TYPE: PRT
<213> ORGANISM: artificial sequence
<220> FEATURE:
<223> OTHER INFORMATION: antibody sequences

<400> SEQUENCE: 32

Gln Gln Trp Asn Ala Tyr Pro Leu Thr
1 5

<210> SEQ ID NO 33
<211> LENGTH: 123
<212> TYPE: PRT
<213> ORGANISM: artificial sequence
<220> FEATURE:
<223> OTHER INFORMATION: antibody sequences

<400> SEQUENCE: 33

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Phe
20 25 30

Gly Arg Gly Val Gly Trp Ile Arg Gln Pro Pro Gly Lys Ala Leu Glu
35 40 45

Trp Leu Ala His Ile Trp Trp Asp Asp Glu Lys Tyr Tyr Asn Ser Ala
50 55 60

Leu Lys Ser Arg Leu Thr Ile Ser Lys Asp Thr Ser Lys Asn Gln Val
65 70 75 80

Val Leu Thr Ile Thr Asn Met Asp Pro Val Asp Thr Ala Thr Tyr Tyr
85 90 95

Cys Ala Arg Ile Gln Asn Tyr Gly Ser Asn Tyr Trp Tyr Phe Asp Val
100 105 110

Trp Gly Gln Gly Thr Leu Val Thr Val Ser Ser
115 120

<210> SEQ ID NO 34
<211> LENGTH: 7
<212> TYPE: PRT
<213> ORGANISM: artificial sequence
<220> FEATURE:

<223> OTHER INFORMATION: antibody sequences

<400> SEQUENCE: 34

Thr Phe Gly Arg Gly Val Gly
1 5

<210> SEQ ID NO 35
<211> LENGTH: 16
<212> TYPE: PRT
<213> ORGANISM: artificial sequence
<220> FEATURE:
<223> OTHER INFORMATION: antibody sequences

<400> SEQUENCE: 35

His Ile Trp Trp Asp Asp Glu Lys Tyr Tyr Asn Ser Ala Leu Lys Ser
1 5 10 15

<210> SEQ ID NO 36
<211> LENGTH: 13
<212> TYPE: PRT
<213> ORGANISM: artificial sequence
<220> FEATURE:
<223> OTHER INFORMATION: antibody sequences

<400> SEQUENCE: 36

Ile Gln Asn Tyr Gly Ser Asn Tyr Trp Tyr Phe Asp Val
1 5 10

<210> SEQ ID NO 37
<211> LENGTH: 106
<212> TYPE: PRT
<213> ORGANISM: artificial sequence
<220> FEATURE:
<223> OTHER INFORMATION: antibody sequences

<400> SEQUENCE: 37

Ala Ile Gln Leu Thr Gln Ser Pro Ser Ser Leu Ser Ala Ser Val Gly
1 5 10 15

Asp Arg Val Thr Ile Thr Cys Arg Ala Ser Ser Arg Ile Ser Tyr Met
20 25 30

Phe Trp Tyr Gln Gln Lys Pro Gly Lys Ala Pro Lys Val Leu Ile Tyr
35 40 45

Asp Thr Ser Asn Leu Ala Ser Gly Val Pro Ser Arg Phe Ser Gly Ser
50 55 60

Gly Ser Gly Thr Asp Tyr Thr Leu Thr Ile Ser Ser Leu Gln Pro Glu
65 70 75 80

Asp Phe Ala Thr Tyr Tyr Cys Gln Gln Trp Asn Ser Tyr Pro Leu Thr
85 90 95

Phe Gly Gln Gly Thr Lys Leu Glu Ile Lys
100 105

<210> SEQ ID NO 38
<211> LENGTH: 10
<212> TYPE: PRT
<213> ORGANISM: artificial sequence
<220> FEATURE:
<223> OTHER INFORMATION: antibody sequences

<400> SEQUENCE: 38

Arg Ala Ser Ser Arg Ile Ser Tyr Met Phe
1 5 10

<210> SEQ ID NO 39

<211> LENGTH: 7
<212> TYPE: PRT
<213> ORGANISM: artificial sequence
<220> FEATURE:
<223> OTHER INFORMATION: antibody sequences

<400> SEQUENCE: 39

Asp Thr Ser Asn Leu Ala Ser
1 5

<210> SEQ ID NO 40
<211> LENGTH: 9
<212> TYPE: PRT
<213> ORGANISM: artificial sequence
<220> FEATURE:
<223> OTHER INFORMATION: antibody sequences

<400> SEQUENCE: 40

Gln Gln Trp Asn Ser Tyr Pro Leu Thr
1 5

<210> SEQ ID NO 41
<211> LENGTH: 123
<212> TYPE: PRT
<213> ORGANISM: artificial sequence
<220> FEATURE:
<223> OTHER INFORMATION: antibody sequences

<400> SEQUENCE: 41

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Phe
20 25 30

Gly Arg Gly Val Gly Trp Ile Arg Gln Pro Pro Gly Lys Ala Leu Glu
35 40 45

Trp Leu Ala His Ile Trp Trp Asp Asp Glu Lys Tyr Tyr Asn Ser Ala
50 55 60

Leu Lys Ser Arg Leu Thr Ile Ser Lys Asp Thr Ser Lys Asn Gln Val
65 70 75 80

Val Leu Thr Ile Thr Asn Met Asp Pro Val Asp Thr Ala Thr Tyr Tyr
85 90 95

Cys Ala Arg Ile Gln Asn Tyr Gly Ser Asn Tyr Trp Tyr Phe Asp Val
100 105 110

Trp Gly Gln Gly Thr Leu Val Thr Val Ser Ser
115 120

<210> SEQ ID NO 42
<211> LENGTH: 7
<212> TYPE: PRT
<213> ORGANISM: artificial sequence
<220> FEATURE:
<223> OTHER INFORMATION: antibody sequences

<400> SEQUENCE: 42

Thr Phe Gly Arg Gly Val Gly
1 5

<210> SEQ ID NO 43
<211> LENGTH: 16
<212> TYPE: PRT
<213> ORGANISM: artificial sequence
<220> FEATURE:
<223> OTHER INFORMATION: antibody sequences

<400> SEQUENCE: 43

```
His Ile Trp Trp Asp Asp Glu Lys Tyr Tyr Asn Ser Ala Leu Lys Ser
1               5                   10                  15
```

<210> SEQ ID NO 44
<211> LENGTH: 13
<212> TYPE: PRT
<213> ORGANISM: artificial sequence
<220> FEATURE:
<223> OTHER INFORMATION: antibody sequences

<400> SEQUENCE: 44

```
Ile Gln Asn Tyr Gly Ser Asn Tyr Trp Tyr Phe Asp Val
1               5                   10
```

<210> SEQ ID NO 45
<211> LENGTH: 106
<212> TYPE: PRT
<213> ORGANISM: artificial sequence
<220> FEATURE:
<223> OTHER INFORMATION: antibody sequences

<400> SEQUENCE: 45

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Ser Arg Ile Ser Tyr Met
            20                  25                  30

Phe Trp Tyr Gln Gln Lys Pro Gly Lys Ala Pro Lys Val Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Asn Ala Tyr Pro Leu Thr
                85                  90                  95

Phe Gly Gln Gly Thr Lys Leu Glu Ile Lys
            100                 105
```

<210> SEQ ID NO 46
<211> LENGTH: 10
<212> TYPE: PRT
<213> ORGANISM: artificial sequence
<220> FEATURE:
<223> OTHER INFORMATION: antibody sequences

<400> SEQUENCE: 46

```
Arg Ala Ser Ser Arg Ile Ser Tyr Met Phe
1               5                   10
```

<210> SEQ ID NO 47
<211> LENGTH: 7
<212> TYPE: PRT
<213> ORGANISM: artificial sequence
<220> FEATURE:
<223> OTHER INFORMATION: antibody sequences

<400> SEQUENCE: 47

```
Asp Thr Ser Asn Leu Ala Ser
1               5
```

<210> SEQ ID NO 48
<211> LENGTH: 9
<212> TYPE: PRT

<213> ORGANISM: artificial sequence
<220> FEATURE:
<223> OTHER INFORMATION: antibody sequences

<400> SEQUENCE: 48

Gln Gln Trp Asn Ala Tyr Pro Leu Thr
1 5

<210> SEQ ID NO 49
<211> LENGTH: 856
<212> TYPE: PRT
<213> ORGANISM: artificial sequence
<220> FEATURE:
<223> OTHER INFORMATION: antibody sequences

<400> SEQUENCE: 49

Met Ala Ser Ala Asp Lys Asn Gly Gly Ser Val Ser Ser Val Ser Ser
1 5 10 15

Ser Arg Leu Gln Ser Arg Lys Pro Pro Asn Leu Ser Ile Thr Ile Pro
20 25 30

Pro Pro Glu Lys Glu Thr Gln Ala Pro Gly Glu Gln Asp Ser Met Leu
35 40 45

Pro Glu Gly Phe Gln Asn Arg Arg Leu Lys Lys Ser Gln Pro Arg Thr
50 55 60

Trp Ala Ala His Thr Thr Ala Cys Pro Pro Ser Phe Leu Pro Lys Arg
65 70 75 80

Lys Asn Pro Ala Tyr Leu Lys Ser Val Ser Leu Gln Glu Pro Arg Ser
85 90 95

Arg Trp Gln Glu Ser Ser Glu Lys Arg Pro Gly Phe Arg Arg Gln Ala
100 105 110

Ser Leu Ser Gln Ser Ile Arg Lys Gly Ala Ala Gln Trp Phe Gly Val
115 120 125

Ser Gly Asp Trp Glu Gly Gln Arg Gln Gln Trp Gln Arg Arg Ser Leu
130 135 140

His His Cys Ser Met Arg Tyr Gly Arg Leu Lys Ala Ser Cys Gln Arg
145 150 155 160

Asp Leu Glu Leu Pro Ser Gln Glu Ala Pro Ser Phe Gln Gly Thr Glu
165 170 175

Ser Pro Lys Pro Cys Lys Met Pro Lys Ile Val Asp Pro Leu Ala Arg
180 185 190

Gly Arg Ala Phe Arg His Pro Glu Glu Met Asp Arg Pro His Ala Pro
195 200 205

His Pro Pro Leu Thr Pro Gly Val Leu Ser Leu Thr Ser Phe Thr Ser
210 215 220

Val Arg Ser Gly Tyr Ser His Leu Pro Arg Arg Lys Arg Met Ser Val
225 230 235 240

Ala His Met Ser Leu Gln Ala Ala Ala Ala Leu Leu Lys Gly Arg Ser
245 250 255

Val Leu Asp Ala Thr Gly Gln Arg Cys Arg Val Val Lys Arg Ser Phe
260 265 270

Ala Phe Pro Ser Phe Leu Glu Glu Asp Val Val Asp Gly Ala Asp Thr
275 280 285

Phe Asp Ser Ser Phe Phe Ser Lys Glu Glu Met Ser Ser Met Pro Asp
290 295 300

Asp Val Phe Glu Ser Pro Pro Leu Ser Ala Ser Tyr Phe Arg Gly Ile
305 310 315 320

```
Pro His Ser Ala Ser Pro Val Ser Pro Asp Gly Val Gln Ile Pro Leu
                325                 330                 335

Lys Glu Tyr Gly Arg Ala Pro Val Pro Gly Pro Arg Arg Gly Lys Arg
            340                 345                 350

Ile Ala Ser Lys Val Lys His Phe Ala Phe Asp Arg Lys Lys Arg His
        355                 360                 365

Tyr Gly Leu Gly Val Val Gly Asn Trp Leu Asn Arg Ser Tyr Arg Arg
    370                 375                 380

Ser Ile Ser Ser Thr Val Gln Arg Gln Leu Glu Ser Phe Asp Ser His
385                 390                 395                 400

Arg Pro Tyr Phe Thr Tyr Trp Leu Thr Phe Val His Val Ile Ile Thr
                405                 410                 415

Leu Leu Val Ile Cys Thr Tyr Gly Ile Ala Pro Val Gly Phe Ala Gln
            420                 425                 430

His Val Thr Thr Gln Leu Val Leu Arg Asn Lys Gly Val Tyr Glu Ser
        435                 440                 445

Val Lys Tyr Ile Gln Gln Glu Asn Phe Trp Val Gly Pro Ser Ser Ile
    450                 455                 460

Asp Leu Ile His Leu Gly Ala Lys Phe Ser Pro Cys Ile Arg Lys Asp
465                 470                 475                 480

Gly Gln Ile Glu Gln Leu Val Leu Arg Glu Arg Asp Leu Glu Arg Asp
                485                 490                 495

Ser Gly Cys Cys Val Gln Asn Asp His Ser Gly Cys Ile Gln Thr Gln
            500                 505                 510

Arg Lys Asp Cys Ser Glu Thr Leu Ala Thr Phe Val Lys Trp Gln Asp
        515                 520                 525

Asp Thr Gly Pro Pro Met Asp Lys Ser Asp Leu Gly Gln Lys Arg Thr
    530                 535                 540

Ser Gly Ala Val Cys His Gln Asp Pro Arg Thr Cys Glu Glu Pro Ala
545                 550                 555                 560

Ser Ser Gly Ala His Ile Trp Pro Asp Asp Ile Thr Lys Trp Pro Ile
                565                 570                 575

Cys Thr Glu Gln Ala Arg Ser Asn His Thr Gly Phe Leu His Met Asp
            580                 585                 590

Cys Glu Ile Lys Gly Arg Pro Cys Cys Ile Gly Thr Lys Gly Ser Cys
        595                 600                 605

Glu Ile Thr Thr Arg Glu Tyr Cys Glu Phe Met His Gly Tyr Phe His
    610                 615                 620

Glu Glu Ala Thr Leu Cys Ser Gln Val His Cys Leu Asp Lys Val Cys
625                 630                 635                 640

Gly Leu Leu Pro Phe Leu Asn Pro Glu Val Pro Asp Gln Phe Tyr Arg
                645                 650                 655

Leu Trp Leu Ser Leu Phe Leu His Ala Gly Val Val His Cys Leu Val
            660                 665                 670

Ser Val Val Phe Gln Met Thr Ile Leu Arg Asp Leu Glu Lys Leu Ala
        675                 680                 685

Gly Trp His Arg Ile Ala Ile Ile Phe Ile Leu Ser Gly Ile Thr Gly
    690                 695                 700

Asn Leu Ala Ser Ala Ile Phe Leu Pro Tyr Arg Ala Glu Val Gly Pro
705                 710                 715                 720

Ala Gly Ser Gln Phe Gly Leu Leu Ala Cys Leu Phe Val Glu Leu Phe
                725                 730                 735

Gln Ser Trp Pro Leu Leu Glu Arg Pro Trp Lys Ala Phe Leu Asn Leu
```

```
            740                 745                 750

Ser Ala Ile Val Leu Phe Leu Phe Ile Cys Gly Leu Leu Pro Trp Ile
        755                 760                 765

Asp Asn Ile Ala His Ile Phe Gly Phe Leu Ser Gly Leu Leu Leu Ala
    770                 775                 780

Phe Ala Phe Leu Pro Tyr Ile Thr Phe Gly Thr Ser Asp Lys Tyr Arg
785                 790                 795                 800

Lys Arg Ala Leu Ile Leu Val Ser Leu Leu Ala Phe Ala Gly Leu Phe
                805                 810                 815

Ala Ala Leu Val Leu Trp Leu Tyr Ile Tyr Pro Ile Asn Trp Pro Trp
            820                 825                 830

Ile Glu His Leu Thr Cys Phe Pro Phe Thr Ser Arg Phe Cys Glu Lys
        835                 840                 845

Tyr Glu Leu Asp Gln Val Leu His
    850                 855


<210> SEQ ID NO 50
<211> LENGTH: 855
<212> TYPE: PRT
<213> ORGANISM: artificial sequence
<220> FEATURE:
<223> OTHER INFORMATION: antibody sequences

<400> SEQUENCE: 50

Met Ser Glu Ala Arg Arg Asp Ser Thr Ser Ser Leu Gln Arg Lys Lys
1               5                   10                  15

Pro Pro Trp Leu Lys Leu Asp Ile Pro Ser Ala Val Pro Leu Thr Ala
            20                  25                  30

Glu Glu Pro Ser Phe Leu Gln Pro Leu Arg Arg Gln Ala Phe Leu Arg
        35                  40                  45

Ser Val Ser Met Pro Ala Glu Thr Ala His Ile Ser Ser Pro His His
    50                  55                  60

Glu Leu Arg Arg Pro Val Leu Gln Arg Gln Thr Ser Ile Thr Gln Thr
65                  70                  75                  80

Ile Arg Arg Gly Thr Ala Asp Trp Phe Gly Val Ser Lys Asp Ser Asp
                85                  90                  95

Ser Thr Gln Lys Trp Gln Arg Lys Ser Ile Arg His Cys Ser Gln Arg
            100                 105                 110

Tyr Gly Lys Leu Lys Pro Gln Val Leu Arg Glu Leu Asp Leu Pro Ser
        115                 120                 125

Gln Asp Asn Val Ser Leu Thr Ser Thr Glu Thr Pro Pro Pro Leu Tyr
    130                 135                 140

Val Gly Pro Cys Gln Leu Gly Met Gln Lys Ile Ile Asp Pro Leu Ala
145                 150                 155                 160

Arg Gly Arg Ala Phe Arg Val Ala Asp Asp Thr Ala Glu Gly Leu Ser
                165                 170                 175

Ala Pro His Thr Pro Val Thr Pro Gly Ala Ala Ser Leu Cys Ser Phe
            180                 185                 190

Ser Ser Ser Arg Ser Gly Phe His Arg Leu Pro Arg Arg Arg Lys Arg
        195                 200                 205

Glu Ser Val Ala Lys Met Ser Phe Arg Ala Ala Ala Ala Leu Met Lys
    210                 215                 220

Gly Arg Ser Val Arg Asp Gly Thr Phe Arg Arg Ala Gln Arg Arg Ser
225                 230                 235                 240

Phe Thr Pro Ala Ser Phe Leu Glu Glu Asp Thr Thr Asp Phe Pro Asp
```

```
                245                 250                 255

Glu Leu Asp Thr Ser Phe Phe Ala Arg Glu Gly Ile Leu His Glu Glu
            260                 265                 270

Leu Ser Thr Tyr Pro Asp Glu Val Phe Glu Ser Pro Ser Glu Ala Ala
        275                 280                 285

Leu Lys Asp Trp Glu Lys Ala Pro Glu Gln Ala Asp Leu Thr Gly Gly
    290                 295                 300

Ala Leu Asp Arg Ser Glu Leu Glu Arg Ser His Leu Met Leu Pro Leu
305                 310                 315                 320

Glu Arg Gly Trp Arg Lys Gln Lys Glu Gly Ala Ala Ala Pro Gln Pro
                325                 330                 335

Lys Val Arg Leu Arg Gln Glu Val Val Ser Thr Ala Gly Pro Arg Arg
            340                 345                 350

Gly Gln Arg Ile Ala Val Pro Val Arg Lys Leu Phe Ala Arg Glu Lys
        355                 360                 365

Arg Pro Tyr Gly Leu Gly Met Val Gly Arg Leu Thr Asn Arg Thr Tyr
    370                 375                 380

Arg Lys Arg Ile Asp Ser Phe Val Lys Arg Gln Ile Glu Asp Met Asp
385                 390                 395                 400

Asp His Arg Pro Phe Phe Thr Tyr Trp Leu Thr Phe Val His Ser Leu
                405                 410                 415

Val Thr Ile Leu Ala Val Cys Ile Tyr Gly Ile Ala Pro Val Gly Phe
            420                 425                 430

Ser Gln His Glu Thr Val Asp Ser Val Leu Arg Asn Arg Gly Val Tyr
        435                 440                 445

Glu Asn Val Lys Tyr Val Gln Gln Glu Asn Phe Trp Ile Gly Pro Ser
    450                 455                 460

Ser Glu Ala Leu Ile His Leu Gly Ala Lys Phe Ser Pro Cys Met Arg
465                 470                 475                 480

Gln Asp Pro Gln Val His Ser Phe Ile Arg Ser Ala Arg Glu Arg Glu
                485                 490                 495

Lys His Ser Ala Cys Cys Val Arg Asn Asp Arg Ser Gly Cys Val Gln
            500                 505                 510

Thr Ser Glu Glu Glu Cys Ser Ser Thr Leu Ala Val Trp Val Lys Trp
        515                 520                 525

Pro Ile His Pro Ser Ala Pro Glu Leu Ala Gly His Lys Arg Gln Phe
    530                 535                 540

Gly Ser Val Cys His Gln Asp Pro Arg Val Cys Asp Glu Pro Ser Ser
545                 550                 555                 560

Glu Asp Pro His Glu Trp Pro Glu Asp Ile Thr Lys Trp Pro Ile Cys
                565                 570                 575

Thr Lys Asn Ser Ala Gly Asn His Thr Asn His Pro His Met Asp Cys
            580                 585                 590

Val Ile Thr Gly Arg Pro Cys Cys Ile Gly Thr Lys Gly Arg Cys Glu
        595                 600                 605

Ile Thr Ser Arg Glu Tyr Cys Asp Phe Met Arg Gly Tyr Phe His Glu
    610                 615                 620

Glu Ala Thr Leu Cys Ser Gln Val His Cys Met Asp Asp Val Cys Gly
625                 630                 635                 640

Leu Leu Pro Phe Leu Asn Pro Glu Val Pro Asp Gln Phe Tyr Arg Leu
                645                 650                 655

Trp Leu Ser Leu Phe Leu His Ala Gly Ile Leu His Cys Leu Val Ser
            660                 665                 670
```

```
Ile Cys Phe Gln Met Thr Val Leu Arg Asp Leu Glu Lys Leu Ala Gly
        675                 680                 685

Trp His Arg Ile Ala Ile Ile Tyr Leu Leu Ser Gly Val Thr Gly Asn
    690                 695                 700

Leu Ala Ser Ala Ile Phe Leu Pro Tyr Arg Ala Glu Val Gly Pro Ala
705                 710                 715                 720

Gly Ser Gln Phe Gly Ile Leu Ala Cys Leu Phe Val Glu Leu Phe Gln
                725                 730                 735

Ser Trp Gln Ile Leu Ala Arg Pro Trp Arg Ala Phe Phe Lys Leu Leu
            740                 745                 750

Ala Val Val Leu Phe Leu Phe Thr Phe Gly Leu Leu Pro Trp Ile Asp
        755                 760                 765

Asn Phe Ala His Ile Ser Gly Phe Ile Ser Gly Leu Phe Leu Ser Phe
    770                 775                 780

Ala Phe Leu Pro Tyr Ile Ser Phe Gly Lys Phe Asp Leu Tyr Arg Lys
785                 790                 795                 800

Arg Cys Gln Ile Ile Ile Phe Gln Val Val Phe Leu Gly Leu Leu Ala
                805                 810                 815

Gly Leu Val Val Leu Phe Tyr Val Tyr Pro Val Arg Cys Glu Trp Cys
            820                 825                 830

Glu Phe Leu Thr Cys Ile Pro Phe Thr Asp Lys Phe Cys Glu Lys Tyr
        835                 840                 845

Glu Leu Asp Ala Gln Leu His
    850                 855
```

<210> SEQ ID NO 51
<211> LENGTH: 827
<212> TYPE: PRT
<213> ORGANISM: artificial sequence
<220> FEATURE:
<223> OTHER INFORMATION: antibody sequences

<400> SEQUENCE: 51

```
Met Ala Ser Ala Asp Lys Asn Gly Ser Asn Leu Pro Ser Val Ser Gly
1               5                   10                  15

Ser Arg Leu Gln Ser Arg Lys Pro Pro Asn Leu Ser Ile Thr Ile Pro
            20                  25                  30

Pro Pro Glu Ser Gln Ala Pro Gly Glu Gln Asp Ser Met Leu Pro Glu
        35                  40                  45

Arg Arg Lys Asn Pro Ala Tyr Leu Lys Ser Val Ser Leu Gln Glu Pro
    50                  55                  60

Arg Gly Arg Trp Gln Glu Gly Ala Glu Lys Arg Pro Gly Phe Arg Arg
65                  70                  75                  80

Gln Ala Ser Leu Ser Gln Ser Ile Arg Lys Ser Thr Ala Gln Trp Phe
                85                  90                  95

Gly Val Ser Gly Asp Trp Glu Gly Lys Arg Gln Asn Trp His Arg Arg
            100                 105                 110

Ser Leu His His Cys Ser Val His Tyr Gly Arg Leu Lys Ala Ser Cys
        115                 120                 125

Gln Arg Glu Leu Glu Leu Pro Ser Gln Glu Val Pro Ser Phe Gln Gly
    130                 135                 140

Thr Glu Ser Pro Lys Pro Cys Lys Met Pro Lys Ile Val Asp Pro Leu
145                 150                 155                 160

Ala Arg Gly Arg Ala Phe Arg His Pro Asp Glu Val Asp Arg Pro His
                165                 170                 175
```

```
Ala Ala His Pro Pro Leu Thr Pro Gly Val Leu Ser Leu Thr Ser Phe
            180                 185                 190

Thr Ser Val Arg Ser Gly Tyr Ser His Leu Pro Arg Arg Lys Arg Ile
        195                 200                 205

Ser Val Ala His Met Ser Phe Gln Ala Ala Ala Ala Leu Leu Lys Gly
    210                 215                 220

Arg Ser Val Leu Asp Ala Thr Gly Gln Arg Cys Arg His Val Lys Arg
225                 230                 235                 240

Ser Phe Ala Tyr Pro Ser Phe Leu Glu Glu Asp Ala Val Asp Gly Ala
                245                 250                 255

Asp Thr Phe Asp Ser Ser Phe Phe Ser Lys Glu Glu Met Ser Ser Met
            260                 265                 270

Pro Asp Asp Val Phe Glu Ser Pro Pro Leu Ser Ala Ser Tyr Phe Arg
        275                 280                 285

Gly Val Pro His Ser Ala Ser Pro Val Ser Pro Asp Gly Val His Ile
    290                 295                 300

Pro Leu Lys Glu Tyr Ser Gly Gly Arg Ala Leu Gly Pro Gly Thr Gln
305                 310                 315                 320

Arg Gly Lys Arg Ile Ala Ser Lys Val Lys His Phe Ala Phe Asp Arg
                325                 330                 335

Lys Lys Arg His Tyr Gly Leu Gly Val Val Gly Asn Trp Leu Asn Arg
            340                 345                 350

Ser Tyr Arg Arg Ser Ile Ser Ser Thr Val Gln Arg Gln Leu Glu Ser
        355                 360                 365

Phe Asp Ser His Arg Pro Tyr Phe Thr Tyr Trp Leu Thr Phe Val His
    370                 375                 380

Ile Ile Ile Thr Leu Leu Val Ile Cys Thr Tyr Gly Ile Ala Pro Val
385                 390                 395                 400

Gly Phe Ala Gln His Val Thr Thr Gln Leu Val Leu Lys Asn Arg Gly
                405                 410                 415

Val Tyr Glu Ser Val Lys Tyr Ile Gln Gln Glu Asn Phe Trp Ile Gly
            420                 425                 430

Pro Ser Ser Ile Asp Leu Ile His Leu Gly Ala Lys Phe Ser Pro Cys
        435                 440                 445

Ile Arg Lys Asp Gln Gln Ile Glu Gln Leu Val Arg Arg Glu Arg Asp
    450                 455                 460

Ile Glu Arg Thr Ser Gly Cys Cys Val Gln Asn Asp Arg Ser Gly Cys
465                 470                 475                 480

Ile Gln Thr Leu Lys Lys Asp Cys Ser Glu Thr Leu Ala Thr Phe Val
                485                 490                 495

Lys Trp Gln Asn Asp Thr Gly Pro Ser Asp Lys Ser Asp Leu Ser Gln
            500                 505                 510

Lys Gln Pro Ser Ala Val Val Cys His Gln Asp Pro Arg Thr Cys Glu
        515                 520                 525

Glu Pro Ala Ser Ser Gly Ala His Ile Trp Pro Asp Asp Ile Thr Lys
    530                 535                 540

Trp Pro Ile Cys Thr Glu Gln Ala Gln Ser Asn His Thr Gly Leu Leu
545                 550                 555                 560

His Ile Asp Cys Lys Ile Lys Gly Arg Pro Cys Cys Ile Gly Thr Lys
                565                 570                 575

Gly Ser Cys Glu Ile Thr Thr Arg Glu Tyr Cys Glu Phe Met His Gly
            580                 585                 590
```

```
Tyr Phe His Glu Asp Ala Thr Leu Cys Ser Gln Val His Cys Leu Asp
        595                 600                 605

Lys Val Cys Gly Leu Leu Pro Phe Leu Asn Pro Glu Val Pro Asp Gln
    610                 615                 620

Phe Tyr Arg Ile Trp Leu Ser Leu Phe Leu His Ala Gly Ile Val His
625                 630                 635                 640

Cys Leu Val Ser Val Val Phe Gln Met Thr Ile Leu Arg Asp Leu Glu
                645                 650                 655

Lys Leu Ala Gly Trp His Arg Ile Ser Ile Ile Phe Ile Leu Ser Gly
            660                 665                 670

Ile Thr Gly Asn Leu Ala Ser Ala Ile Phe Leu Pro Tyr Arg Ala Glu
        675                 680                 685

Val Gly Pro Ala Gly Ser Gln Phe Gly Leu Leu Ala Cys Leu Phe Val
    690                 695                 700

Glu Leu Phe Gln Ser Trp Gln Leu Leu Glu Arg Pro Trp Lys Ala Phe
705                 710                 715                 720

Phe Asn Leu Ser Ala Ile Val Leu Phe Leu Phe Ile Cys Gly Leu Leu
                725                 730                 735

Pro Trp Ile Asp Asn Ile Ala His Ile Phe Gly Phe Leu Ser Gly Met
            740                 745                 750

Leu Leu Ala Phe Ala Phe Leu Pro Tyr Ile Thr Phe Gly Thr Ser Asp
        755                 760                 765

Lys Tyr Arg Lys Arg Ala Leu Ile Leu Val Ser Leu Leu Val Phe Ala
    770                 775                 780

Gly Leu Phe Ala Ser Leu Val Leu Trp Leu Tyr Ile Tyr Pro Ile Asn
785                 790                 795                 800

Trp Pro Trp Ile Glu Tyr Leu Thr Cys Phe Pro Phe Thr Ser Arg Phe
                805                 810                 815

Cys Glu Lys Tyr Glu Leu Asp Gln Val Leu His
            820                 825
```

<210> SEQ ID NO 52
<211> LENGTH: 360
<212> TYPE: DNA
<213> ORGANISM: artificial sequence
<220> FEATURE:
<223> OTHER INFORMATION: antibody sequences

<400> SEQUENCE: 52

```
caggtgaccc tgagggagag cggccccgcc ctggtgaagc ccacccagac cctgaccctg     60

acctgcacct tcagcggctt cagcctgagc accttcgccc tgggcgtggg ctggatcagg    120

cagccccccg gcaaggccct ggagtggctg gcccacatct ggtgggacga cgacaagtac    180

tacaaccccg ccctgaagag caggctgacc atcagcaagg acaccagcaa gaaccaggtg    240

gtgctgacca tcaccaacat ggaccccgtg gacaccgcca cctactactg cgccaggatc    300

accacctact actacggcat ggactactgg ggccagggca ccctggtgac cgtgagcagc    360
```

<210> SEQ ID NO 53
<211> LENGTH: 21
<212> TYPE: DNA
<213> ORGANISM: artificial sequence
<220> FEATURE:
<223> OTHER INFORMATION: antibody sequences

<400> SEQUENCE: 53

```
accttcgccc tgggcgtggg c                                               21
```

<210> SEQ ID NO 54
<211> LENGTH: 48
<212> TYPE: DNA
<213> ORGANISM: artificial sequence
<220> FEATURE:
<223> OTHER INFORMATION: antibody sequences

<400> SEQUENCE: 54
cacatctggt gggacgacga caagtactac aaccccgccc tgaagagc 48

<210> SEQ ID NO 55
<211> LENGTH: 30
<212> TYPE: DNA
<213> ORGANISM: artificial sequence
<220> FEATURE:
<223> OTHER INFORMATION: antibody sequences

<400> SEQUENCE: 55
atcaccacct actactacgg catggactac 30

<210> SEQ ID NO 56
<211> LENGTH: 321
<212> TYPE: DNA
<213> ORGANISM: artificial sequence
<220> FEATURE:
<223> OTHER INFORMATION: antibody sequences

<400> SEQUENCE: 56
gagatcgtga tgacccagag ccccgacttc cagagcgtga cccccaagga gaaggtgacc 60
atcacctgca gggccagcca gagcatcggc aaccacctgc actggtacca gcagaagccc 120
gacgccagcc ccaagctgct gatcaagtac gccagccaga gcatcagcgg cgtgcccagc 180
aggttcagcg gcagcggcag cggcaccgac ttcaccctga ccatcaacag cctggaggcc 240
gaggacgccg ccacctactt ctgccagcag agctaccagt ggcccctgac cttcggccag 300
ggcaccaagc tggagatcaa g 321

<210> SEQ ID NO 57
<211> LENGTH: 33
<212> TYPE: DNA
<213> ORGANISM: artificial sequence
<220> FEATURE:
<223> OTHER INFORMATION: antibody sequences

<400> SEQUENCE: 57
agggccagcc agagcatcgg caaccacctg cac 33

<210> SEQ ID NO 58
<211> LENGTH: 21
<212> TYPE: DNA
<213> ORGANISM: artificial sequence
<220> FEATURE:
<223> OTHER INFORMATION: antibody sequences

<400> SEQUENCE: 58
tacgccagcc agagcatcag c 21

<210> SEQ ID NO 59
<211> LENGTH: 27
<212> TYPE: DNA
<213> ORGANISM: artificial sequence
<220> FEATURE:
<223> OTHER INFORMATION: antibody sequences

<400> SEQUENCE: 59
cagcagagct accagtggcc cctgacc 27

<210> SEQ ID NO 60
<211> LENGTH: 360
<212> TYPE: DNA
<213> ORGANISM: artificial sequence
<220> FEATURE:
<223> OTHER INFORMATION: antibody sequences

<400> SEQUENCE: 60
caggtgaccc tgagggagag cggccccgcc ctggtgaagc ccacccagac cctgaccctg 60
acctgcacct tcagcggctt cagcctgagc accttcgccc tgggcgtggg ctggatcagg 120 cagcccccg gcaaggccct ggagtggctg gcccacatct ggtgggacga ggacaagtac 180
tacaaccccg ccctgaagag caggctgacc atcagcaagg acaccagcaa gaaccaggtg 240
gtgctgacca tcaccaacat ggaccccgtg gacaccgcca cctactactg cgccaggatc 300
accacctact actacggcat ggactactgg ggccagggca ccctggtgac cgtgagcagc 360

<210> SEQ ID NO 61
<211> LENGTH: 21
<212> TYPE: DNA
<213> ORGANISM: artificial sequence
<220> FEATURE:
<223> OTHER INFORMATION: antibody sequences

<400> SEQUENCE: 61
accttcgccc tgggcgtggg c 21

<210> SEQ ID NO 62
<211> LENGTH: 48
<212> TYPE: DNA
<213> ORGANISM: artificial sequence
<220> FEATURE:
<223> OTHER INFORMATION: antibody sequences

<400> SEQUENCE: 62
cacatctggt gggacgagga caagtactac aaccccgccc tgaagagc 48

<210> SEQ ID NO 63
<211> LENGTH: 30
<212> TYPE: DNA
<213> ORGANISM: artificial sequence
<220> FEATURE:
<223> OTHER INFORMATION: antibody sequences

<400> SEQUENCE: 63
atcaccacct actactacgg catggactac 30

<210> SEQ ID NO 64
<211> LENGTH: 321
<212> TYPE: DNA
<213> ORGANISM: artificial sequence
<220> FEATURE:
<223> OTHER INFORMATION: antibody sequences

<400> SEQUENCE: 64
gagatcgtga tgacccagag ccccgacttc cagagcgtga cccccaagga gaaggtgacc 60
atcacctgca gggccagcca gagcatcggc aaccacctgc actggtacca gcagaagccc 120
gacgccagcc ccaagctgct gatcaagtac gccagccaga gcatcagcgg cgtgcccagc 180
aggttcagcg gcagcggcag cggcaccgac ttcaccctga ccatcaacag cctggaggcc 240
gaggacgccg ccacctactt ctgccagcag agctacaact ggcccctgac cttcggccag 300
ggcaccaagc tggagatcaa g 321

<210> SEQ ID NO 65
<211> LENGTH: 33
<212> TYPE: DNA
<213> ORGANISM: artificial sequence
<220> FEATURE:
<223> OTHER INFORMATION: antibody sequences

<400> SEQUENCE: 65
agggccagcc agagcatcgg caaccacctg cac 33

<210> SEQ ID NO 66
<211> LENGTH: 21
<212> TYPE: DNA
<213> ORGANISM: artificial sequence
<220> FEATURE:
<223> OTHER INFORMATION: antibody sequences

<400> SEQUENCE: 66
tacgccagcc agagcatcag c 21

<210> SEQ ID NO 67
<211> LENGTH: 27
<212> TYPE: DNA
<213> ORGANISM: artificial sequence
<220> FEATURE:
<223> OTHER INFORMATION: antibody sequences

<400> SEQUENCE: 67
cagcagagct acaactggcc cctgacc 27

<210> SEQ ID NO 68
<211> LENGTH: 360
<212> TYPE: DNA
<213> ORGANISM: artificial sequence
<220> FEATURE:
<223> OTHER INFORMATION: antibody sequences

<400> SEQUENCE: 68
caggtgaccc tgagggagag cggccccgcc ctggtgaagc ccacccagac cctgaccctg 60
acctgcacct tcagcggctt cagcctgagc accttcgccc tgggcgtggg ctggatcagg 120
cagccccccg gcaaggccct ggagtggctg gcccacatct ggtgggacga ggacaagtac 180
tacaaccccg ccctgaagag caggctgacc atcagcaagg acaccagcaa gaaccaggtg 240
gtgctgacca tcaccaacat ggaccccgtg gacaccgcca cctactactg cgccaggatc 300
accacctact actacggcat ggactactgg ggccagggca ccctggtgac cgtgagcagc 360

<210> SEQ ID NO 69
<211> LENGTH: 21
<212> TYPE: DNA
<213> ORGANISM: artificial sequence
<220> FEATURE:
<223> OTHER INFORMATION: antibody sequences

<400> SEQUENCE: 69
accttcgccc tgggcgtggg c 21

<210> SEQ ID NO 70
<211> LENGTH: 48
<212> TYPE: DNA
<213> ORGANISM: artificial sequence
<220> FEATURE:
<223> OTHER INFORMATION: antibody sequences

<400> SEQUENCE: 70
cacatctggt gggacgagga caagtactac aaccccgccc tgaagagc 48

<210> SEQ ID NO 71
<211> LENGTH: 30
<212> TYPE: DNA
<213> ORGANISM: artificial sequence
<220> FEATURE:
<223> OTHER INFORMATION: antibody sequences

<400> SEQUENCE: 71
atcaccacct actactacgg catggactac 30

<210> SEQ ID NO 72
<211> LENGTH: 321
<212> TYPE: DNA
<213> ORGANISM: artificial sequence
<220> FEATURE:
<223> OTHER INFORMATION: antibody sequences

<400> SEQUENCE: 72
gagatcgtga tgacccagag ccccgacttc cagagcgtga cccccaagga gaaggtgacc 60
atcacctgca gggccagcca gagcatcggc aaccacctgc actggtacca gcagaagccc 120
gacgccagcc ccaagctgct gatcaagtac gccagccaga gcatcagcgg cgtgcccagc 180
aggttcagcg gcagcggcag cggcaccgac ttcaccctga ccatcaacag cctggaggcc 240
gaggacgccg ccacctactt ctgccagcag agctaccagt ggcccctgac cttcggccag 300
ggcaccaagc tggagatcaa g 321

<210> SEQ ID NO 73
<211> LENGTH: 33
<212> TYPE: DNA
<213> ORGANISM: artificial sequence
<220> FEATURE:
<223> OTHER INFORMATION: antibody sequences

<400> SEQUENCE: 73
agggccagcc agagcatcgg caaccacctg cac 33

<210> SEQ ID NO 74
<211> LENGTH: 21
<212> TYPE: DNA
<213> ORGANISM: artificial sequence
<220> FEATURE:
<223> OTHER INFORMATION: antibody sequences

<400> SEQUENCE: 74
tacgccagcc agagcatcag c 21

<210> SEQ ID NO 75
<211> LENGTH: 27
<212> TYPE: DNA
<213> ORGANISM: artificial sequence
<220> FEATURE:
<223> OTHER INFORMATION: antibody sequences

<400> SEQUENCE: 75
cagcagagct accagtggcc cctgacc 27

<210> SEQ ID NO 76

<211> LENGTH: 369
<212> TYPE: DNA
<213> ORGANISM: artificial sequence
<220> FEATURE:
<223> OTHER INFORMATION: antibody sequences

<400> SEQUENCE: 76
caggtgaccc tgagggagag cggccccgcc ctggtgaagc ccacccagac cctgaccctg 60
acctgcacct tcagcggctt cagcctgagc accttcggca tgggcgtggg ctggatcagg 120 cagcccccg gcaaggccct ggagtggctg gcccacatct ggtgggacga cgagaagtac 180
tacaacagcg ccctgaagag caggctgacc atcagcaagg acaccagcaa gaaccaggtg 240
gtgctgacca tcaccaacat ggaccccgtg gacaccgcca cctactactg cgccaggatc 300
agcaactacg gcagcaacta ctggtacttc aacgtgtggg gccagggcac cctggtgacc 360
gtgagcagc 369

<210> SEQ ID NO 77
<211> LENGTH: 21
<212> TYPE: DNA
<213> ORGANISM: artificial sequence
<220> FEATURE:
<223> OTHER INFORMATION: antibody sequences

<400> SEQUENCE: 77
accttcggca tgggcgtggg c 21

<210> SEQ ID NO 78
<211> LENGTH: 48
<212> TYPE: DNA
<213> ORGANISM: artificial sequence
<220> FEATURE:
<223> OTHER INFORMATION: antibody sequences

<400> SEQUENCE: 78
cacatctggt gggacgacga gaagtactac aacagcgccc tgaagagc 48

<210> SEQ ID NO 79
<211> LENGTH: 39
<212> TYPE: DNA
<213> ORGANISM: artificial sequence
<220> FEATURE:
<223> OTHER INFORMATION: antibody sequences

<400> SEQUENCE: 79
atcagcaact acggcagcaa ctactggtac ttcaacgtg 39

<210> SEQ ID NO 80
<211> LENGTH: 318
<212> TYPE: DNA
<213> ORGANISM: artificial sequence
<220> FEATURE:
<223> OTHER INFORMATION: antibody sequences

<400> SEQUENCE: 80
gccatccagc tgacccagag ccccagcagc ctgagcgcca gcgtgggcga cagggtgacc 60
atcacctgca gggccagcag cagcgtgagc tacatgtact ggtaccagca gaagcccggc 120
aaggccccca aggtgctgat ctacgacacc agcaacctgg ccagcggcgt gcccagcagg 180
ttcagcggca gcggcagcgg caccgactac accctgacca tcagcagcct gcagcccgag 240
gacttcgcca cctactactg ccagcagtgg aacgcctacc ccctgacctt cggccagggc 300
accaagctgg agatcaag 318

<210> SEQ ID NO 81
<211> LENGTH: 30
<212> TYPE: DNA
<213> ORGANISM: artificial sequence
<220> FEATURE:
<223> OTHER INFORMATION: antibody sequences

<400> SEQUENCE: 81
agggccagca gcagcgtgag ctacatgtac 30

<210> SEQ ID NO 82
<211> LENGTH: 21
<212> TYPE: DNA
<213> ORGANISM: artificial sequence
<220> FEATURE:
<223> OTHER INFORMATION: antibody sequences

<400> SEQUENCE: 82
gacaccagca acctggccag c 21

<210> SEQ ID NO 83
<211> LENGTH: 27
<212> TYPE: DNA
<213> ORGANISM: artificial sequence
<220> FEATURE:
<223> OTHER INFORMATION: antibody sequences

<400> SEQUENCE: 83
cagcagtgga acgcctaccc cctgacc 27

<210> SEQ ID NO 84
<211> LENGTH: 369
<212> TYPE: DNA
<213> ORGANISM: artificial sequence
<220> FEATURE:
<223> OTHER INFORMATION: antibody sequences

<400> SEQUENCE: 84
caggtgaccc tgagggagag cggccccgcc ctggtgaagc ccacccagac cctgaccctg 60
acctgcacct tcagcggctt cagcctgagc accttcggca ggggcgtggg ctggatcagg 120
cagccccccg gcaaggccct ggagtggctg gcccacatct ggtgggacga cgagaagtac 180
tacaacagcg ccctgaagag caggctgacc atcagcaagg acaccagcaa gaaccaggtg 240
gtgctgacca tcaccaacat ggaccccgtg gacaccgcca cctactactg cgccaggatc 300
cagaactacg gcagcaacta ctggtacttc gacgtgtggg gccagggcac cctggtgacc 360
gtgagcagc 369

<210> SEQ ID NO 85
<211> LENGTH: 21
<212> TYPE: DNA
<213> ORGANISM: artificial sequence
<220> FEATURE:
<223> OTHER INFORMATION: antibody sequences

<400> SEQUENCE: 85
accttcggca ggggcgtggg c 21

<210> SEQ ID NO 86
<211> LENGTH: 48
<212> TYPE: DNA
<213> ORGANISM: artificial sequence
<220> FEATURE:

<223> OTHER INFORMATION: antibody sequences

<400> SEQUENCE: 86
cacatctggt gggacgacga gaagtactac aacagcgccc tgaagagc 48

<210> SEQ ID NO 87
<211> LENGTH: 39
<212> TYPE: DNA
<213> ORGANISM: artificial sequence
<220> FEATURE:
<223> OTHER INFORMATION: antibody sequences

<400> SEQUENCE: 87
atccagaact acggcagcaa ctactggtac ttcgacgtg 39

<210> SEQ ID NO 88
<211> LENGTH: 318
<212> TYPE: DNA
<213> ORGANISM: artificial sequence
<220> FEATURE:
<223> OTHER INFORMATION: antibody sequences

<400> SEQUENCE: 88
gccatccagc tgacccagag ccccagcagc ctgagcgcca gcgtgggcga cagggtgacc 60
atcacctgca gggccagcag caggatcagc tacatgttct ggtaccagca gaagcccggc 120 aaggcccccca aggtgctgat ctacgacacc agcaacctgg ccagcggcgt gcccagcagg 180
ttcagcggca gcggcagcgg caccgactac accctgacca tcagcagcct gcagcccgag 240
gacttcgcca cctactactg ccagcagtgg aacagctacc ccctgacctt cggccagggc 300
accaagctgg agatcaag 318

<210> SEQ ID NO 89
<211> LENGTH: 30
<212> TYPE: DNA
<213> ORGANISM: artificial sequence
<220> FEATURE:
<223> OTHER INFORMATION: antibody sequences

<400> SEQUENCE: 89
agggccagca gcaggatcag ctacatgttc 30

<210> SEQ ID NO 90
<211> LENGTH: 21
<212> TYPE: DNA
<213> ORGANISM: artificial sequence
<220> FEATURE:
<223> OTHER INFORMATION: antibody sequences

<400> SEQUENCE: 90
gacaccagca acctggccag c 21

<210> SEQ ID NO 91
<211> LENGTH: 27
<212> TYPE: DNA
<213> ORGANISM: artificial sequence
<220> FEATURE:
<223> OTHER INFORMATION: antibody sequences

<400> SEQUENCE: 91
cagcagtgga acagctaccc cctgacc 27

<210> SEQ ID NO 92
<211> LENGTH: 369

<212> TYPE: DNA
<213> ORGANISM: artificial sequence
<220> FEATURE:
<223> OTHER INFORMATION: antibody sequences

<400> SEQUENCE: 92
caggtgaccc tgagggagag cggccccgcc ctggtgaagc ccacccagac cctgaccctg 60
acctgcacct tcagcggctt cagcctgagc accttcggca ggggcgtggg ctggatcagg 120
cagccccccg gcaaggccct ggagtggctg gcccacatct ggtgggacga cgagaagtac 180
tacaacagcg ccctgaagag caggctgacc atcagcaagg acaccagcaa gaaccaggtg 240
gtgctgacca tcaccaacat ggaccccgtg gacaccgcca cctactactg cgccaggatc 300
cagaactacg gcagcaacta ctggtacttc gacgtgtggg gccagggcac cctggtgacc 360
gtgagcagc 369

<210> SEQ ID NO 93
<211> LENGTH: 21
<212> TYPE: DNA
<213> ORGANISM: artificial sequence
<220> FEATURE:
<223> OTHER INFORMATION: antibody sequences

<400> SEQUENCE: 93
accttcggca ggggcgtggg c 21

<210> SEQ ID NO 94
<211> LENGTH: 48
<212> TYPE: DNA
<213> ORGANISM: artificial sequence
<220> FEATURE:
<223> OTHER INFORMATION: antibody sequences

<400> SEQUENCE: 94
cacatctggt gggacgacga gaagtactac aacagcgccc tgaagagc 48

<210> SEQ ID NO 95
<211> LENGTH: 39
<212> TYPE: DNA
<213> ORGANISM: artificial sequence
<220> FEATURE:
<223> OTHER INFORMATION: antibody sequences

<400> SEQUENCE: 95
atccagaact acggcagcaa ctactggtac ttcgacgtg 39

<210> SEQ ID NO 96
<211> LENGTH: 318
<212> TYPE: DNA
<213> ORGANISM: artificial sequence
<220> FEATURE:
<223> OTHER INFORMATION: antibody sequences

<400> SEQUENCE: 96
gccatccagc tgacccagag ccccagcagc ctgagcgcca gcgtgggcga cagggtgacc 60
atcacctgca gggccagcag caggatcagc tacatgttct ggtaccagca gaagcccggc 120
aaggccccca aggtgctgat ctacgacacc agcaacctgg ccagcggcgt gcccagcagg 180
ttcagcggca gcggcagcgg caccgactac accctgacca tcagcagcct gcagcccgag 240
gacttcgcca cctactactg ccagcagtgg aacgcctacc ccctgacctt cggccagggc 300
accaagctgg agatcaag 318

<210> SEQ ID NO 97
<211> LENGTH: 30
<212> TYPE: DNA
<213> ORGANISM: artificial sequence
<220> FEATURE:
<223> OTHER INFORMATION: antibody sequences

<400> SEQUENCE: 97
agggccagca gcaggatcag ctacatgttc 30

<210> SEQ ID NO 98
<211> LENGTH: 21
<212> TYPE: DNA
<213> ORGANISM: artificial sequence
<220> FEATURE:
<223> OTHER INFORMATION: antibody sequences

<400> SEQUENCE: 98
gacaccagca acctggccag c 21

<210> SEQ ID NO 99
<211> LENGTH: 27
<212> TYPE: DNA
<213> ORGANISM: artificial sequence
<220> FEATURE:
<223> OTHER INFORMATION: antibody sequences

<400> SEQUENCE: 99
cagcagtgga acgcctaccc cctgacc 27

<210> SEQ ID NO 100
<211> LENGTH: 360
<212> TYPE: RNA
<213> ORGANISM: artificial sequence
<220> FEATURE:
<223> OTHER INFORMATION: antibody sequences

<400> SEQUENCE: 100
caggugaccc ugagggagag cggccccgcc cuggugaagc ccacccagac ccugacccug 60
accugcaccu ucagcggcuu cagccugagc accuucgccc ugggcguggg cuggaucagg 120 cagcccccg gcaaggcccu ggaguggcug gcccacaucu ggugggacga cgacaaguac 180
uacaaccccg cccugaagag caggcugacc aucagcaagg acaccagcaa gaaccaggug 240
gugcugacca ucaccaacau ggaccccgug gacaccgcca ccuacuacug cgccaggauc 300
accaccuacu acuacggcau ggacuacugg ggccagggca cccuggugac cgugagcagc 360

<210> SEQ ID NO 101
<211> LENGTH: 21
<212> TYPE: RNA
<213> ORGANISM: artificial sequence
<220> FEATURE:
<223> OTHER INFORMATION: antibody sequences

<400> SEQUENCE: 101
accuucgccc ugggcguggg c 21

<210> SEQ ID NO 102
<211> LENGTH: 48
<212> TYPE: RNA
<213> ORGANISM: artificial sequence
<220> FEATURE:
<223> OTHER INFORMATION: antibody sequences

<400> SEQUENCE: 102
cacaucuggu gggacgacga caaguacuac aaccccgccc ugaagagc 48

<210> SEQ ID NO 103
<211> LENGTH: 30
<212> TYPE: RNA
<213> ORGANISM: artificial sequence
<220> FEATURE:
<223> OTHER INFORMATION: antibody sequences

<400> SEQUENCE: 103
aucaccaccu acuacuacgg cauggacuac 30

<210> SEQ ID NO 104
<211> LENGTH: 321
<212> TYPE: RNA
<213> ORGANISM: artificial sequence
<220> FEATURE:
<223> OTHER INFORMATION: antibody sequences

<400> SEQUENCE: 104
gagaucguga ugacccagag ccccgacuuc cagagcguga cccccaagga gaaggugacc 60
aucaccugca gggccagcca gagcaucggc aaccaccugc acugguacca gcagaagccc 120
gacgccagcc ccaagcugcu gaucaaguac gccagccaga gcaucagcgg cgugcccagc 180
agguucagcg gcagcggcag cggcaccgac uucacccuga ccaucaacag ccuggaggcc 240
gaggacgccg ccaccuacuu cugccagcag agcuaccagu ggccccugac cuucggccag 300
ggcaccaagc uggagaucaa g 321

<210> SEQ ID NO 105
<211> LENGTH: 33
<212> TYPE: RNA
<213> ORGANISM: artificial sequence
<220> FEATURE:
<223> OTHER INFORMATION: antibody sequences

<400> SEQUENCE: 105
agggccagcc agagcaucgg caaccaccug cac 33

<210> SEQ ID NO 106
<211> LENGTH: 21
<212> TYPE: RNA
<213> ORGANISM: artificial sequence
<220> FEATURE:
<223> OTHER INFORMATION: antibody sequences

<400> SEQUENCE: 106
uacgccagcc agagcaucag c 21

<210> SEQ ID NO 107
<211> LENGTH: 27
<212> TYPE: RNA
<213> ORGANISM: artificial sequence
<220> FEATURE:
<223> OTHER INFORMATION: antibody sequences

<400> SEQUENCE: 107
cagcagagcu accaguggcc ccugacc 27

<210> SEQ ID NO 108
<211> LENGTH: 360
<212> TYPE: RNA
<213> ORGANISM: artificial sequence
<220> FEATURE:

<223> OTHER INFORMATION: antibody sequences

<400> SEQUENCE: 108
caggugaccc ugagggagag cggccccgcc cuggugaagc ccacccagac ccugacccug 60
accugcaccu ucagcggcuu cagccugagc accuucgccc ugggcguggg cuggaucagg 120 cagcccccg gcaaggcccu ggaguggcug gcccacaucu ggugggacga ggacaaguac 180
uacaaccccg cccugaagag caggcugacc aucagcaagg acaccagcaa gaaccaggug 240
gugcugacca ucaccaacau ggaccccgug gacaccgcca ccuacuacug cgccaggauc 300
accaccuacu acuacggcau ggacuacugg ggccagggca cccugguggac cgugagcagc 360

<210> SEQ ID NO 109
<211> LENGTH: 21
<212> TYPE: RNA
<213> ORGANISM: artificial sequence
<220> FEATURE:
<223> OTHER INFORMATION: antibody sequences

<400> SEQUENCE: 109
accuucgccc ugggcguggg c 21

<210> SEQ ID NO 110
<211> LENGTH: 48
<212> TYPE: RNA
<213> ORGANISM: artificial sequence
<220> FEATURE:
<223> OTHER INFORMATION: antibody sequences

<400> SEQUENCE: 110
cacaucuggu gggacgagga caaguacuac aaccccgccc ugaagagc 48

<210> SEQ ID NO 111
<211> LENGTH: 30
<212> TYPE: RNA
<213> ORGANISM: artificial sequence
<220> FEATURE:
<223> OTHER INFORMATION: antibody sequences

<400> SEQUENCE: 111
aucaccaccu acuacuacgg cauggacuac 30

<210> SEQ ID NO 112
<211> LENGTH: 321
<212> TYPE: RNA
<213> ORGANISM: artificial sequence
<220> FEATURE:
<223> OTHER INFORMATION: antibody sequences

<400> SEQUENCE: 112
gagaucguga ugacccagag ccccgacuuc cagagcguga cccccaagga gaaggugacc 60
aucaccugca gggccagcca gagcaucggc aaccaccugc acugguacca gcagaagccc 120
gacgccagcc ccaagcugcu gaucaaguac gccagccaga gcaucagcgg cgugcccagc 180
agguucagcg gcagcggcag cggcaccgac uucacccuga ccaucaacag ccuggaggcc 240
gaggacgccg ccaccuacuu cugccagcag agcuacaacu ggccccugac cuucggccag 300
ggcaccaagc uggagaucaa g 321

<210> SEQ ID NO 113
<211> LENGTH: 33
<212> TYPE: RNA
<213> ORGANISM: artificial sequence
<220> FEATURE:
<223> OTHER INFORMATION: antibody sequences

<400> SEQUENCE: 113
agggccagcc agagcaucgg caaccaccug cac 33

<210> SEQ ID NO 114
<211> LENGTH: 21
<212> TYPE: RNA
<213> ORGANISM: artificial sequence
<220> FEATURE:
<223> OTHER INFORMATION: antibody sequences

<400> SEQUENCE: 114
uacgccagcc agagcaucag c 21

<210> SEQ ID NO 115
<211> LENGTH: 27
<212> TYPE: RNA
<213> ORGANISM: artificial sequence
<220> FEATURE:
<223> OTHER INFORMATION: antibody sequences

<400> SEQUENCE: 115
cagcagagcu acaacuggcc ccugacc 27

<210> SEQ ID NO 116
<211> LENGTH: 360
<212> TYPE: RNA
<213> ORGANISM: artificial sequence
<220> FEATURE:
<223> OTHER INFORMATION: antibody sequences

<400> SEQUENCE: 116
caggugaccc ugagggagag cggccccgcc cuggugaagc ccacccagac ccugacccug 60
accugcaccu ucagcggcuu cagccugagc accuucgccc ugggcguggg cuggaucagg 120 cagcccccg gcaaggcccu ggaguggcug gcccacaucu ggugggacga ggacaaguac 180
uacaaccccg cccugaagag caggcugacc aucagcaagg acaccagcaa gaaccaggug 240
gugcugacca ucaccaacau ggaccccgug gacaccgcca ccuacuacug cgccaggauc 300
accaccuacu acuacggcau ggacuacugg ggccagggca cccuggugac cgugagcagc 360

<210> SEQ ID NO 117
<211> LENGTH: 21
<212> TYPE: RNA
<213> ORGANISM: artificial sequence
<220> FEATURE:
<223> OTHER INFORMATION: antibody sequences

<400> SEQUENCE: 117
accuucgccc ugggcguggg c 21

<210> SEQ ID NO 118
<211> LENGTH: 48
<212> TYPE: RNA
<213> ORGANISM: artificial sequence
<220> FEATURE:
<223> OTHER INFORMATION: antibody sequences

<400> SEQUENCE: 118
cacaucuggu gggacgagga caaguacuac aaccccgccc ugaagagc 48

<210> SEQ ID NO 119

<211> LENGTH: 30
<212> TYPE: RNA
<213> ORGANISM: artificial sequence
<220> FEATURE:
<223> OTHER INFORMATION: antibody sequences

<400> SEQUENCE: 119
aucaccaccu acuacuacgg cauggacuac 30

<210> SEQ ID NO 120
<211> LENGTH: 321
<212> TYPE: RNA
<213> ORGANISM: artificial sequence
<220> FEATURE:
<223> OTHER INFORMATION: antibody sequences

<400> SEQUENCE: 120
gagaucguga ugacccagag ccccgacuuc cagagcguga cccccaagga gaaggugacc 60
aucaccugca gggccagcca gagcaucggc aaccaccugc acugguacca gcagaagccc 120
gacgccagcc ccaagcugcu gaucaaguac gccagccaga gcaucagcgg cgugcccagc 180
agguucagcg gcagcggcag cggcaccgac uucacccuga ccaucaacag ccuggaggcc 240
gaggacgccg ccaccuacuu cugccagcag agcuaccagu ggccccugac cuucggccag 300
ggcaccaagc uggagaucaa g 321

<210> SEQ ID NO 121
<211> LENGTH: 33
<212> TYPE: RNA
<213> ORGANISM: artificial sequence
<220> FEATURE:
<223> OTHER INFORMATION: antibody sequences

<400> SEQUENCE: 121
agggccagcc agagcaucgg caaccaccug cac 33

<210> SEQ ID NO 122
<211> LENGTH: 21
<212> TYPE: RNA
<213> ORGANISM: artificial sequence
<220> FEATURE:
<223> OTHER INFORMATION: antibody sequences

<400> SEQUENCE: 122
uacgccagcc agagcaucag c 21

<210> SEQ ID NO 123
<211> LENGTH: 27
<212> TYPE: RNA
<213> ORGANISM: artificial sequence
<220> FEATURE:
<223> OTHER INFORMATION: antibody sequences

<400> SEQUENCE: 123
cagcagagcu accaguggcc ccugacc 27

<210> SEQ ID NO 124
<211> LENGTH: 369
<212> TYPE: RNA
<213> ORGANISM: artificial sequence
<220> FEATURE:
<223> OTHER INFORMATION: antibody sequences

<400> SEQUENCE: 124
caggugaccc ugagggagag cggccccgcc cuggugaagc ccacccagac ccugacccug 60
accugcaccu ucagcggcuu cagccugagc accuucggca ugggcguggg cuggaucagg 120
cagccccccg gcaaggcccu ggaguggcug gcccacaucu ggugggacga cgagaaguac 180
uacaacagcg cccugaagag caggcugacc aucagcaagg acaccagcaa gaaccaggug 240
gugcugacca ucaccaacau ggaccccgug gacaccgcca ccuacuacug cgccaggauc 300
agcaacuacg gcagcaacua cugguacuuc aacgugug gg gccagggcac ccuggugacc 360
gugagcagc 369

<210> SEQ ID NO 125
<211> LENGTH: 21
<212> TYPE: RNA
<213> ORGANISM: artificial sequence
<220> FEATURE:
<223> OTHER INFORMATION: antibody sequences

<400> SEQUENCE: 125
accuucggca ugggcguggg c 21

<210> SEQ ID NO 126
<211> LENGTH: 48
<212> TYPE: RNA
<213> ORGANISM: artificial sequence
<220> FEATURE:
<223> OTHER INFORMATION: antibody sequences

<400> SEQUENCE: 126
cacaucuggu gggacgacga gaaguacuac aacagcgccc ugaagagc 48

<210> SEQ ID NO 127
<211> LENGTH: 39
<212> TYPE: RNA
<213> ORGANISM: artificial sequence
<220> FEATURE:
<223> OTHER INFORMATION: antibody sequences

<400> SEQUENCE: 127
aucagcaacu acggcagcaa cuacugguac uucaacgug 39

<210> SEQ ID NO 128
<211> LENGTH: 318
<212> TYPE: RNA
<213> ORGANISM: artificial sequence
<220> FEATURE:
<223> OTHER INFORMATION: antibody sequences

<400> SEQUENCE: 128
gccauccagc ugacccagag ccccagcagc cugagcgcca gcgugggcga cagggugacc 60
aucaccugca gggccagcag cagcgugagc uacauguacu gguaccagca gaagcccggc 120
aaggccccca aggugcugau cuacgacacc agcaaccugg ccagcggcgu gcccagcagg 180
uucagcggca gcggcagcgg caccgacuac acccugacca ucagcagccu gcagcccgag 240
gacuucgcca ccuacuacug ccagcagugg aacgccuacc cccugaccuu cggccagggc 300
accaagcugg agaucaag 318

<210> SEQ ID NO 129
<211> LENGTH: 30
<212> TYPE: RNA
<213> ORGANISM: artificial sequence
<220> FEATURE:
<223> OTHER INFORMATION: antibody sequences

<400> SEQUENCE: 129
agggccagca gcagcgugag cuacauguac 30

<210> SEQ ID NO 130
<211> LENGTH: 21
<212> TYPE: RNA
<213> ORGANISM: artificial sequence
<220> FEATURE:
<223> OTHER INFORMATION: antibody sequences

<400> SEQUENCE: 130
gacaccagca accuggccag c 21

<210> SEQ ID NO 131
<211> LENGTH: 27
<212> TYPE: RNA
<213> ORGANISM: artificial sequence
<220> FEATURE:
<223> OTHER INFORMATION: antibody sequences

<400> SEQUENCE: 131
cagcagugga acgccuaccc ccugacc 27

<210> SEQ ID NO 132
<211> LENGTH: 369
<212> TYPE: RNA
<213> ORGANISM: artificial sequence
<220> FEATURE:
<223> OTHER INFORMATION: antibody sequences

<400> SEQUENCE: 132
caggugaccc ugagggagag cggccccgcc cuggugaagc ccacccagac ccugacccug 60
accugcaccu ucagcggcuu cagccugagc accuucggca ggggcguggg cuggaucagg 120 cagcccccg gcaaggcccu ggaguggcug gcccacaucu ggugggacga cgagaaguac 180
uacaacagcg cccugaagag caggcugacc aucagcaagg acaccagcaa gaaccaggug 240
gugcugacca ucaccaacau ggaccccgug gacaccgcca ccuacuacug cgccaggauc 300
cagaacuacg gcagcaacua cugguacuuc gacgugugg gccagggcac ccuggugacc 360
gugagcagc 369

<210> SEQ ID NO 133
<211> LENGTH: 21
<212> TYPE: RNA
<213> ORGANISM: artificial sequence
<220> FEATURE:
<223> OTHER INFORMATION: antibody sequences

<400> SEQUENCE: 133
accuucggca ggggcguggg c 21

<210> SEQ ID NO 134
<211> LENGTH: 48
<212> TYPE: RNA
<213> ORGANISM: artificial sequence
<220> FEATURE:
<223> OTHER INFORMATION: antibody sequences

<400> SEQUENCE: 134
cacaucuggu gggacgacga gaaguacuac aacagcgccc ugaagagc 48

<210> SEQ ID NO 135
<211> LENGTH: 39

<212> TYPE: RNA
<213> ORGANISM: artificial sequence
<220> FEATURE:
<223> OTHER INFORMATION: antibody sequences

<400> SEQUENCE: 135
auccagaacu acggcagcaa cuacugguac uucgacgug 39

<210> SEQ ID NO 136
<211> LENGTH: 318
<212> TYPE: RNA
<213> ORGANISM: artificial sequence
<220> FEATURE:
<223> OTHER INFORMATION: antibody sequences

<400> SEQUENCE: 136
gccauccagc ugacccagag ccccagcagc cugagcgcca gcgugggcga cagggugacc 60
aucaccugca gggccagcag caggaucagc uacauguucu gguaccagca gaagcccggc 120
aaggccccca aggugcugau cuacgacacc agcaaccugg ccagcggcgu gcccagcagg 180
uucagcggca gcggcagcgg caccgacuac acccugacca ucagcagccu gcagcccgag 240
gacuucgcca ccuacuacug ccagcagugg aacagcuacc cccugaccuu cggccagggc 300
accaagcugg agaucaag 318

<210> SEQ ID NO 137
<211> LENGTH: 30
<212> TYPE: RNA
<213> ORGANISM: artificial sequence
<220> FEATURE:
<223> OTHER INFORMATION: antibody sequences

<400> SEQUENCE: 137
agggccagca gcaggaucag cuacauguuc 30

<210> SEQ ID NO 138
<211> LENGTH: 21
<212> TYPE: RNA
<213> ORGANISM: artificial sequence
<220> FEATURE:
<223> OTHER INFORMATION: antibody sequences

<400> SEQUENCE: 138
gacaccagca accuggccag c 21

<210> SEQ ID NO 139
<211> LENGTH: 27
<212> TYPE: RNA
<213> ORGANISM: artificial sequence
<220> FEATURE:
<223> OTHER INFORMATION: antibody sequences

<400> SEQUENCE: 139
cagcagugga acagcuaccc ccugacc 27

<210> SEQ ID NO 140
<211> LENGTH: 369
<212> TYPE: RNA
<213> ORGANISM: artificial sequence
<220> FEATURE:
<223> OTHER INFORMATION: antibody sequences

<400> SEQUENCE: 140
caggugaccc ugagggagag cggccccgcc cuggugaagc ccacccagac ccugacccug 60

```
accugcaccu ucagcggcuu cagccugagc accuucggca ggggcguggg cuggaucagg    120

cagccccccg gcaaggcccu ggaguggcug gcccacaucu ggugggacga cgagaaguac    180

uacaacagcg cccugaagag caggcugacc aucagcaagg acaccagcaa gaaccaggug    240

gugcugacca ucaccaacau ggaccccgug gacaccgcca ccuacuacug cgccaggauc    300

cagaacuacg gcagcaacua cugguacuuc gacguguggg gccagggcac ccuggugacc    360

gugagcagc                                                            369
```

```
<210> SEQ ID NO 141
<211> LENGTH: 21
<212> TYPE: RNA
<213> ORGANISM: artificial sequence
<220> FEATURE:
<223> OTHER INFORMATION: antibody sequences

<400> SEQUENCE: 141

accuucggca ggggcguggg c                                               21
```

```
<210> SEQ ID NO 142
<211> LENGTH: 48
<212> TYPE: RNA
<213> ORGANISM: artificial sequence
<220> FEATURE:
<223> OTHER INFORMATION: antibody sequences

<400> SEQUENCE: 142

cacaucuggu gggacgacga gaaguacuac aacagcgccc ugaagagc                  48
```

```
<210> SEQ ID NO 143
<211> LENGTH: 39
<212> TYPE: RNA
<213> ORGANISM: artificial sequence
<220> FEATURE:
<223> OTHER INFORMATION: antibody sequences

<400> SEQUENCE: 143

auccagaacu acggcagcaa cuacugguac uucgacgug                            39
```

```
<210> SEQ ID NO 144
<211> LENGTH: 318
<212> TYPE: RNA
<213> ORGANISM: artificial sequence
<220> FEATURE:
<223> OTHER INFORMATION: antibody sequences

<400> SEQUENCE: 144

gccauccagc ugacccagag ccccagcagc cugagcgcca gcgugggcga cagggugacc     60

aucaccugca gggccagcag caggaucagc uacauguucu gguaccagca gaagcccggc    120

aaggccccca aggugcugau cuacgacacc agcaaccugg ccagcggcgu gcccagcagg    180

uucagcggca gcggcagcgg caccgacuac acccugacca ucagcagccu gcagcccgag    240

gacuucgcca ccuacuacug ccagcagugg aacgccuacc cccugaccuu cggccagggc    300

accaagcugg agaucaag                                                  318
```

```
<210> SEQ ID NO 145
<211> LENGTH: 30
<212> TYPE: RNA
<213> ORGANISM: artificial sequence
<220> FEATURE:
<223> OTHER INFORMATION: antibody sequences

<400> SEQUENCE: 145
```

-continued

```
agggccagca gcaggaucag cuacauguuc                              30


<210> SEQ ID NO 146
<211> LENGTH: 21
<212> TYPE: RNA
<213> ORGANISM: artificial sequence
<220> FEATURE:
<223> OTHER INFORMATION: antibody sequences

<400> SEQUENCE: 146

gacaccagca accuggccag c                                       21


<210> SEQ ID NO 147
<211> LENGTH: 27
<212> TYPE: RNA
<213> ORGANISM: artificial sequence
<220> FEATURE:
<223> OTHER INFORMATION: antibody sequences

<400> SEQUENCE: 147

cagcagugga acgccuaccc ccugacc                                 27


<210> SEQ ID NO 148
<211> LENGTH: 20
<212> TYPE: DNA
<213> ORGANISM: artificial sequence
<220> FEATURE:
<223> OTHER INFORMATION: primer

<400> SEQUENCE: 148

aagcatgcta tcctgctcgc                                         20


<210> SEQ ID NO 149
<211> LENGTH: 22
<212> TYPE: DNA
<213> ORGANISM: artificial sequence
<220> FEATURE:
<223> OTHER INFORMATION: primer

<400> SEQUENCE: 149

tcaatgagct ctttatgggg ca                                      22


<210> SEQ ID NO 150
<211> LENGTH: 22
<212> TYPE: DNA
<213> ORGANISM: artificial sequence
<220> FEATURE:
<223> OTHER INFORMATION: primer

<400> SEQUENCE: 150

aaggtctcca tcccctcagg tc                                      22
```

HUMANIZED ANTIBODIES AGAINST iRhom2

CROSS-REFERENCE TO RELATED APPLICATIONS

This application is a national stage filing under U.S.C. § 371 of PCT International Application PCT/EP2022/054853, filed Feb. 25, 2022, which claims the benefit of European Patent Application No. 21165682.2, filed Mar. 29, 2021, and European Patent Application No. 21160030.9, filed Mar. 1, 2021, the entirety of each of which is hereby incorporated by reference.

SEQUENCE LISTING

The instant application contains a Sequence Listing which has been submitted electronically in ASCII format and is hereby incorporated by reference in its entirety. Said ASCII copy, created on Dec. 31, 2023, is named 18279715_1_1.txt and is 71,269 bytes in size.

FIELD OF THE INVENTION

The present application relates to humanized antibodies against iRhom2.

BACKGROUND

ADAM metallopeptidase domain 17 (ADAM17) (NCBI reference of human ADAM17: NP_003174), also called TACE (tumor necrosis factor-α-converting enzyme), is an enzyme that belongs to the ADAM protein family of disintegrins and metalloproteases. It is an 824-amino acid polypeptide.

ADAM17 is understood to be involved in the processing of tumor necrosis factor alpha (TNF-α) at the surface of the cell, and from within the intracellular membranes of the trans-Golgi network. This process, which is also known as 'shedding', involves the cleavage and release of a soluble ectodomain from membrane-bound pro-proteins (such as pro-TNF-α), and is of known physiological importance. ADAM17 was the first 'sheddase' to be identified, and is also understood to play a role in the release of a variety of membrane-anchored cytokines, cell adhesion molecules, receptors, ligands, and enzymes.

Cloning of the TNF-α gene revealed it to encode a 26 kDa type II transmembrane pro-polypeptide that becomes inserted into the cell membrane during its translocation in the endoplasmic reticulum. At the cell surface, pro-TNF-α is biologically active and is able to induce immune responses via juxtacrine intercellular signaling. However, pro-TNF-α can undergo proteolytic cleavage at its Ala76-Val77 amide bond, which releases a soluble 17 kDa extracellular domain (ectodomain) from the pro-TNF-α molecule. This soluble ectodomain is the cytokine commonly known as TNF-α, which is of pivotal importance in paracrine signaling of this molecule. This proteolytic liberation of soluble TNF-α is catalyzed by ADAM17.

ADAM17 also modulates the MAP kinase signaling pathway by regulating the cleavage of the EGFR ligand amphiregulin in the mammary gland. ADAM17 is important for activating several ligands of the EGFR, TGFα, AREG, EREG, HB-EGF, Epigen. Moreover, ADAM17 has a role in shedding of L-selectin, a cellular adhesion molecule.

Recently, ADAM17 was discovered as a crucial mediator of resistance formation to radiotherapy. It was also shown that radiotherapy activates ADAM17 in non-small cell lung cancer, which results in shedding of multiple survival factors, growth factor pathway activation, and radiotherapy-induced treatment resistance.

Since ADAM17 seems to be a crucial factor for the release of different pathogenic and non-pathogenic factors, including TNFα, it has come into the focus as therapeutic target molecule. For that reason, different attempts have been made to develop inhibitors of ADAM17.

However, so far, no such inhibitor has proven clinically successful.

It is hence one object of the present invention to provide a new approach which allows the control, regulation, reduction or inhibition of ADAM17 activity.

It is another object of the present invention to provide a new approach that allows the treatment of inflammatory diseases.

These and other objects are solved by the features of the independent claims. The dependent claims disclose embodiments of the invention which may be preferred under particular circumstances. Likewise, the specification discloses further embodiments of the invention which may be preferred under particular circumstances.

SUMMARY OF THE INVENTION

The present invention provides, among others, humanized antibodies that bind to human iRhom2. In one embodiment, these antibodies inhibit and/or reduce TACE/ADAM17 activity when bound to human iRhom2.

BRIEF DESCRIPTION OF THE FIGURES

FIG. 1 provides results for antibody affinity determination by FACS (fluorescence activated cell sorting) scatchard analyses on genetically engineered murine L929 cell populations expressing a T7-tagged full length (FL) wild type (WT) human iRhom2, ectopically expressed by L929-2041-hiR2-FL-WT-T7 (SEQ ID NO 49). These results demonstrate that the KD values for binding of the humanized antibodies 16-B-03, 16-B-05, 16-B-07, 23-B-04, 42-B-02 and 42-B-04 to L929-2041-hiR2-FL-WT-T7 cells are in the subnanomolar to low nanomolar range.

FIG. 17*b* -17*f* summarizes the results of FACS analyses of all antibodies of the invention on the entire panel of 128 engineered functional MEF populations ectopically expressing human iRhom2 variants with single amino acid substitutions or deletions within the large extracellular loop (AA502 to AA594 of human iRhom2). The data reveal related patterns of amino acid positions relevant for iRhom2 binding of the antibodies of the invention.

DETAILED DESCRIPTION

Figure 2A:
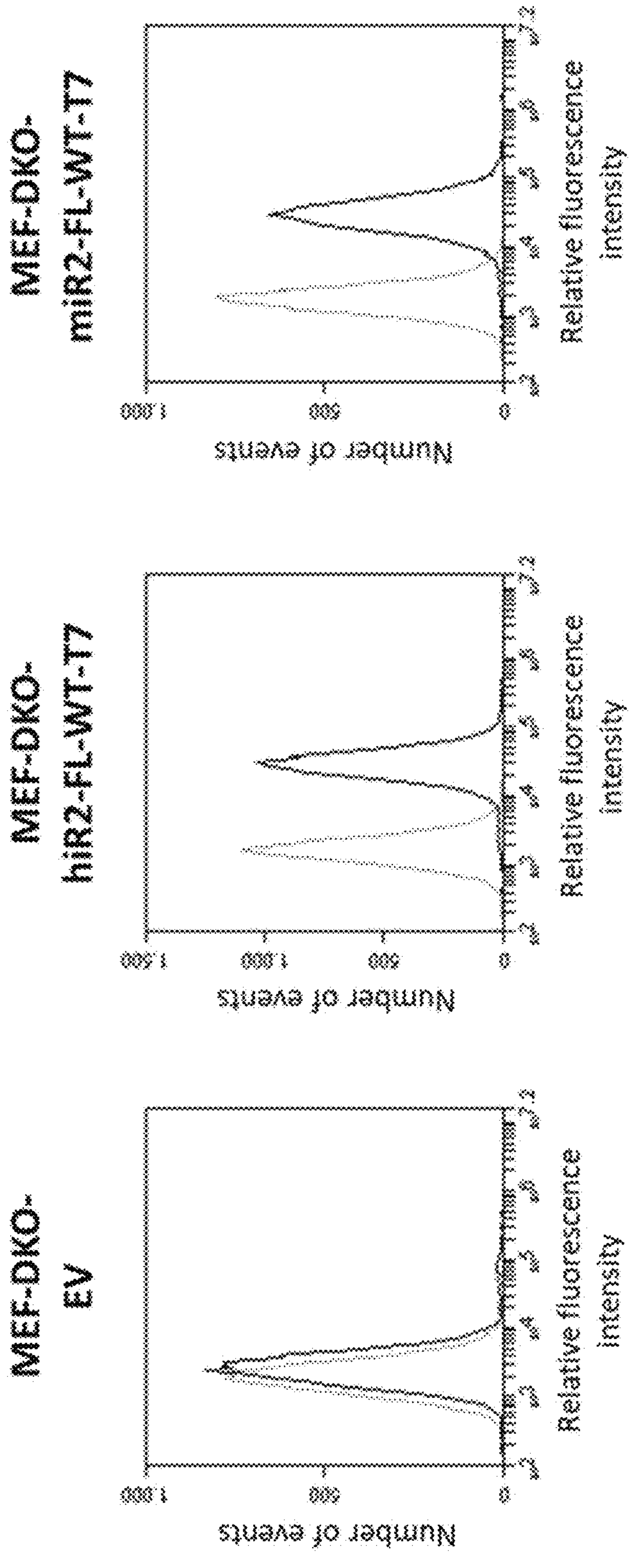
FIG. 2*a* depicts results from FACS analyses on genetically engineered mouse embryonic fibroblast (MEF) populations, demonstrating that T7-tagged variants of human and mouse iRhom2 full length wild type ectopically expressed by MEF-DKO-hiR2-FL-WT-T7 (SEQ ID NO 49) and MEF-DKO-miR2-FL-WT-T7 (SEQ ID NO 51) cells, respectively, are localized on the surface of these cells. Stainings: gray=secondary antibody only; black=anti-T7-antibody

According to one aspect of the invention, a humanized antibody binding iRhom2, or a target-binding fragment or derivative thereof retaining target binding capacities, is provided which a) comprises a set of three heavy chain and three light chain complementarity determining regions (CDR) comprised in the one of the following heavy chain/light variable domain sequence pairs
   SEQ ID NOs 1 and 5;
   SEQ ID NOs 9 and 13;
   SEQ ID NOs 17 and 21;
   SEQ ID NOs 25 and 29;
   SEQ ID NOs 33 and 37 or
   SEQ ID NOs 41 and 45,
b) comprises a set of three heavy chain and three light chain complementarity determining regions (CDR) selected from
   SEQ ID NOs 2, 3, 4, 6, 7 and 8,
   SEQ ID NOs 10, 11, 12, 14, 15 and 16,
   SEQ ID NOs 18, 19, 20, 22, 23 and 24,
   SEQ ID NOs 26, 27, 28, 30, 31 and 32,
   SEQ ID NOs 34, 35, 36, 38, 39 and 40, or
   SEQ ID NOs 42, 43, 44, 46, 47 and 48,
c) comprises the set of heavy chain/light chain complementarity determining regions (CDR) of b), with the proviso that at least one of the CDRs has up to 3 amino acid substitutions relative to the respective SEQ ID NOs, and/or
d) comprises the set of heavy chain/light chain complementarity determining regions (CDR) of b) or c), with the proviso that at least one of the CDRs has a sequence identity of ≥66% to the respective CDRs comprised in the SEQ ID NOS, The CDRs are embedded in a suitable protein framework, preferably a variable domain framework, so as to be capable to bind to human iRhom2.

In one embodiment, the CDRs are determined according to the definition of Kabat, Chothia or MacCallum, preferably wherein the CDRs are determined according to the numbering set forth in Table 1.

Methods for the production and/or selection of humanised mAbs are known in the art. For example, U.S. Pat. No. 6,331,415 by Genentech describes the production of chimeric antibodies, while U.S. Pat. No. 6,548,640 by Medical Research Council describes CDR grafting techniques and U.S. Pat. No. 5,859,205 by Celltech describes the production of humanised antibodies.

Humanized antibodies are antibodies in which the complementarity determining regions stem from a parent antibody taken from a non human species and are grafted into the framework (at least the variable domain) of a human antibody, like e.g. of an IgG1, IgG2 or IgG4. The humanized antibody binds the same target as the parent antibody, but, due to its grafting into a human framework, has reduced immunogenicity (like e.g HAMA response). For this reason, a humanized antibody is structurally different from its parent (e.g. murine) antibody.

In humanization, the step of grafting the CDRs into a human framework is often followed by a step of affinity maturation, to reacquire affinity that was lost in the grafting process. This process further modifies the sequence of the human antibody, including its CDRs.

In one embodiment the CDRs are embedded in a suitable protein framework so as to be capable inhibit or reduce TACE/ADAM17 activity.

Inactive Rhomboid family member 2 (iRhom2) is a protein that in humans is encoded by the RHBDF2 gene. It is a transmembrane protein consisting of about 850 amino acids, having seven transmembrane domains.

iRhom2 comes in different isoforms. The experiments made herein have been established with the isoform defined as NCBI reference NP_078875.4. However, the teachings are transferable, without limitation, to other isoforms of iRhom2, as shown in the following table:

| mRNA | protein | name |
|---|---|---|
| NM_024599.5 | NP_078875.4 | inactive rhomboid protein 2 transcript variant 1/isoform 1 |
| NM_001005498.3 | NP_001005498.2 | inactive rhomboid protein 2 transcript variant 2/isoform 2 |

As used herein, the term "inhibits and/or reduces TACE/ADAM17 activity is meant to describe an effect caused by an antibody or fragment that blocks or reduces the activity of TACE/ADAM17, as measured e.g. in a respective shedding assay (see., e.g., FIG. 8 and example 6).

ADAM metallopeptidase domain 17 (ADAM17), also called TACE (tumor necrosis factor-α-converting enzyme), is an enzyme that belongs to the ADAM protein family of disintegrins and metalloproteases. ADAM17 is understood to be involved in the processing of tumor necrosis factor alpha (TNF-α) at the surface of the cell, and from within the intracellular membranes of the trans-Golgi network. This process, which is also known as 'shedding', involves the cleavage and release of a soluble ectodomain from membrane-bound pro-proteins (such as pro-TNF-α), and is of known physiological importance. ADAM17 was the first 'sheddase' to be identified, and it is also understood to play a role in the release of a diverse variety of membrane-anchored cytokines, cell adhesion molecules, receptors, ligands, and enzymes.

Cloning of the TNF-α gene revealed it to encode a 26 kDa type II transmembrane pro-polypeptide that becomes inserted into the cell membrane during its maturation. At the cell surface, pro-TNF-α is biologically active, and is able to induce immune responses via juxtacrine intercellular signaling. However, pro-TNF-α can undergo a proteolytic cleavage at its Ala76-Val77 amide bond, which releases a soluble 17 kDa extracellular domain (ectodomain) from the pro-TNF-α molecule. This soluble ectodomain is the cytokine commonly known as TNF-α, which is of pivotal importance in paracrine signaling. This proteolytic liberation of soluble TNF-α is catalyzed by ADAM17.

Recently, ADAM17 was discovered as a crucial mediator of resistance to radiotherapy. It was also shown that radiotherapy activates ADAM17 in non-small cell lung cancer, which results in shedding of multiple survival factors, growth factor pathway activation, and radiotherapy-induced treatment resistance.

ADAM17 also regulates the MAP kinase signaling pathway by regulating shedding of the EGFR ligand amphiregulin in the mammary gland. ADAM17 also has a role in the shedding of L-selectin, a cellular adhesion molecule.

As used herein, the term "CDR" or "complementarity determining region" is intended to mean the non-contiguous antigen combining sites found within the variable region of both heavy and light chain polypeptides. These particular regions have been described by Kabat et al. (1977), Kabat et al. (1991), Chothia et al. (1987) and MacCallum et al., (1996) where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR definitions | | | |
|---|---|---|---|
| | Kabat | Chothia | MacCallum |
| VH CDR1 | 31-35 | 26-32 | 30-35 |
| VH CDR2 | 50-65 | 53-55 | 47-58 |
| VH CDR3 | 95-102 | 96-101 | 93-101 |
| VL CDR1 | 24-34 | 26-32 | 30-36 |
| VL CDR2 | 50-56 | 50-52 | 46-55 |
| VL CDR3 | 89-97 | 91-96 | 89-96 |

As used herein, the term "framework" when used in reference to an antibody variable domain is entered to mean all amino acid residues outside the CDR regions within the variable domain of an antibody. Therefore, a variable domain framework is between about 100-120 amino acids in length but is intended to reference only those amino acids outside of the CDRs.

As used herein, the term "capable to bind to target X" has to be understood as meaning that respective binding domain binds the target with a $K_D$ of 10-4 or smaller. $K_D$ is the equilibrium dissociation constant, a ratio of $k_{off}/k_{on}$, between the antibody or fragment and its antigen. $K_D$ and affinity are inversely related. The $K_D$ value relates to the concentration of antibody or fragment (the amount of antibody or fragment needed for a particular experiment) and so the lower the $K_D$ value (lower concentration) and thus the higher the affinity of the binding domain. The following table shows typical $K_D$ ranges of monoclonal antibodies

TABLE 2

| $K_D$ and Molar Values | |
|---|---|
| $K_D$ value | Molar range |
| $10^{-4}$ to $10^{-6}$ | Micromolar (μM) |
| $10^{-7}$ to $10^{-9}$ | Nanomolar (nM) |
| $10^{-10}$ to $10^{-12}$ | Picomolar (pM) |
| $10^{-13}$ to $10^{-15}$ | Femtomolar (fM) |

Preferably, the antibody or fragment has up to 2 amino acid substitutions, and more preferably up to 1 amino acid substitution.

Preferably, at least one of the CDRs of the antibody or fragment has a sequence identity of ≥67%; ≥68%; ≥69%; ≥70%; ≥71%; ≥72%; ≥73%; ≥74%; ≥75%; ≥76%; ≥77%; ≥78%; ≥79%; ≥80%; ≥81%; ≥82%; ≥83%; ≥84%; ≥85%; ≥86%; ≥87%; ≥88%; 89%; ≥90%; ≥91%; ≥92%; ≥93%; ≥94%; ≥95%; ≥96%; ≥97%; ≥98%; ≥99%, and most preferably 100% to the respective SEQ ID NO.

"Percentage of sequence identity" as used herein, is determined by comparing two optimally aligned biosequences (amino acid sequences or polynucleotide sequences) over a comparison window, wherein the portion of the corresponding sequence in the comparison window may comprise additions or deletions (i.e., gaps) as compared to the reference sequence, which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The disclosure provides polypeptides that are substantially identical to the polypeptides exemplified herein. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

Preferably, at least one of the CDRs has been subject to CDR sequence modification, including affinity maturation reduction of immunogenicity Affinity maturation in the process by which the affinity of a given antibody is increased in vitro. Like the natural counterpart, in vitro affinity maturation is based on the principles of mutation and selection. It has successfully been used to optimize antibodies, antibody fragments or other peptide molecules like antibody mimetics. Random mutations inside the CDRs are introduced using radiation, chemical mutagens or error-prone PCR. In addition, the genetic diversity can be increased by chain shuffling. Two or three rounds of mutation and selection using display methods like phage display usually results in antibody fragments with affinities in the low nanomolar range. For principles see Eylenstein et al. (2016) or US20050169925A1, the content of which is incorporated herein by reference for enablement purposes.

Engineered antibodies contain murine-sequence derived CDR regions that have been engrafted, along with any necessary framework back-mutations, into sequence-derived V regions. Hence, the CDRs themselves can cause immunogenic reactions when the humanized antibody is administered to a patient. Methods of reducing immunogenicity caused by CDRs are disclosed in Harding et al. (2010), or US2014227251A1, the content of which is incorporated herein by reference for enablement purposes.

According to one embodiment of the invention, the antibody or fragment comprises a) the heavy chain/light chain variable domain (HCVD/LCVD) pairs set forth in the following pairs of SEQ ID NOs:
   1 and 5;
   9 and 13;
   17 and 21;
   25 and 29;
   33 and 37 and/or
   41 and 45
b) the heavy chain/light chain variable domains (HCVD/LCVD) pairs of a), with the proviso that
   the HCVD has a sequence identity of ≥80% to the respective SEQ ID NO, and/or
   the LCVD has a sequence identity of ≥80% to the respective SEQ ID NO,
c) the heavy chain/light chain variable domains (VD) pairs of a) or b), with the proviso that at least one of the HCVD or LCVD has up to 10 amino acid substitutions relative to the respective SEQ ID NO, said antibody or fragment still being capable to bind to human iRhom2 and/or to inhibit or reduce TACE/ADAM17 activity.

A "variable domain" when used in reference to an antibody or a heavy or light chain thereof is intended to mean the portion of an antibody which confers antigen binding onto the molecule and which is not the constant region. The term is intended to include functional fragments thereof which maintain some of all of the binding function of the whole variable region. Variable region binding fragments include, for example, functional fragments such as Fab, $F(ab)_2$, Fv, single chain Fv (scfv) and the like. Such functional fragments are well known to those skilled in the art. Accordingly, the use of these terms in describing functional fragments of a heteromeric variable region is intended to correspond to the definitions well known to those skilled in the art. Such terms are described in, for example, Huston et al., (1993) or Plückthun and Skerra (1990).

Preferably, the HCVD and/or LCVD has a sequence identity of ≥81%; ≥82%; ≥83%; ≥84%; ≥85%; ≥86%; ≥87%; ≥88%; ≥89%; ≥90%; ≥91%; ≥92%; ≥93%; ≥94%; ≥95%; ≥96%; ≥97%; ≥98%; ≥99%; or most preferably 100% to the respective SEQ ID NO.

According to one embodiment of the invention, at least one amino acid substitution is a conservative amino acid substitution.

A "conservative amino acid substitution", as used herein, has a smaller effect on antibody function than a non-conservative substitution. Although there are many ways to classify amino acids, they are often sorted into six main groups on the basis of their structure and the general chemical characteristics of their R groups.

In some embodiments, a "conservative amino acid substitution" is one in which the amino acid residue is replaced with an amino acid residue having a similar side chain. For example, families of amino acid residues having similar side chains have been defined in the art. These families include amino acids with

- basic side chains (e.g., lysine, arginine, histidine),
- acidic side chains (e.g., aspartic acid, glutamic acid),
- uncharged polar side chains (e.g., glycine, asparagine, glutamine, serine, threonine, tyrosine, cysteine),
- nonpolar side chains (e.g., alanine, valine, leucine, isoleucine, proline, phenylalanine, methionine, tryptophan),
- beta-branched side chains (e.g., threonine, valine, isoleucine) and
- aromatic side chains (e.g., tyrosine, phenylalanine, tryptophan, histidine).

Other conserved amino acid substitutions can also occur across amino acid side chain families, such as when substituting an asparagine for aspartic acid in order to modify the charge of a peptide.

Conservative changes can further include substitution of chemically homologous non-natural amino acids (i.e. a synthetic non-natural hydrophobic amino acid in place of leucine, a synthetic non-natural aromatic amino acid in place of tryptophan).

According to one embodiment of the invention, the antibody or fragment has at least one of

- target binding affinity of ≥50% to human iRhom2 compared to that of the antibody or fragment according to any one of the aforementioned claims, and/or.
- ≥50% of the inhibiting or reducing effect on TACE/ADAM17 activity of the antibody or fragment according to any one of the aforementioned claims.

As used herein the term "binding affinity" is intended to mean the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction. For example, a bivalent heteromeric variable region binding fragment can exhibit altered or optimized binding affinity due to its valency.

A suitable method for measuring the affinity of a binding agent is through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates ($k_{on}$) and disassociation rates ($k_{off}$).

Measurements of $k_{on}$ and $k_{off}$ values can be advantageous because they can identify altered variable regions or optimized variable regions that are therapeutically more efficacious. For example, an altered variable region, or heteromeric binding fragment thereof, can be more efficacious because it has, for example, a higher $k_{on}$ valued compared to variable regions and heteromeric binding fragments that exhibit similar binding affinity. Increased efficacy is conferred because molecules with higher $k_{on}$ values can specifically bind and inhibit their target at a faster rate. Similarly, a molecule of the invention can be more efficacious because it exhibits a lower $k_{off}$ value compared to molecules having similar binding affinity. Increased efficacy observed with molecules having lower $k_{off}$ rates can be observed because, once bound, the molecules are slower to dissociate from their target. Although described with reference to the altered variable regions and optimized variable regions of the invention including, heteromeric variable region binding fragments thereof, the methods described above for measuring associating and disassociation rates are applicable to essentially any antibody or fragment or fragment thereof for identifying more effective binders for therapeutic or diagnostic purposes.

Another suitable method for measuring the affinity of a binding agent is through surface is by FACS/scatchard analysis. See inter alia example 1 for a respective description. Methods for measuring the affinity, including association and disassociation rates using surface plasmon resonance are well known in the arts and can be found described in, for example, Jonsson and Malmquist, (1992) and Wu et al. (1998). Moreover, one apparatus well known in the art for measuring binding interactions is a BIAcore 2000 instrument which is commercially available through Pharmacia Biosensor, (Uppsala, Sweden).

Preferably said target binding affinity is ≥51%, ≥52%, ≥53%, ≥54%, ≥55%, ≥56%, ≥57%, ≥58%, ≥59%, ≥60%, ≥61%, ≥62%, ≥63%, ≥64%, ≥65%, ≥66%, ≥67%, ≥68%, ≥69%, ≥70%, ≥71%, ≥72%, ≥73%, ≥74%, ≥75%, ≥76%, ≥77%, ≥78%, ≥79%, ≥80%, ≥81%, ≥82%, ≥83%, ≥84%, ≥85%, ≥86%, ≥87%, ≥88%, ≥89%, ≥90%, ≥91%, ≥92%, ≥93%, ≥94%, ≥95%, ≥96%, ≥97%, ≥98%, and most preferably ≥99% compared to that of the reference binding agent.

As used herein, the quantification of the inhibiting or reducing effect on TACE/ADAM17 activity, compared to a benchmark binding agent, is determined with a suitable assay to determine the TNFα shedding effect, as, e.g., described, e.g., in FIG. 8 and example 6.

According to another aspect of the invention, a humanized antibody is provided that binds to human iRhom2, and competes for binding to human iRhom2 with a) an antibody according to the above description, and/or
b) an antibody selected from the group consisting of clones 16-B-03; 16-B-05; 16-B-07; 23-B-04; 42-B-02; and/or 42-B-04.

According to another aspect of the invention, a humanized antibody is provided that binds to essentially the same, or the same region on human iRhom2 as a) an antibody according to the above description, and/or
b) an antibody selected from the group consisting of clones 16-B-03; 16-B-05; 16-B-07; 23-B-04; 42-B-02; and/or 42-B-04.

Clones 16-B-03; 16-B-05; 16-B-07; 23-B-04; 42-B-02; and 42-B-04 are identified in the sequence table herein.

As used herein, the term "region shall be undertstood to mean an extracellular region, a domain, a subdomain, or a secondary structure (e.g. loop), or preferably an epitope.

As regards the format or structure of such antibody or fragment, the same preferred embodiments as set forth above apply. In one embodiment, said antibody or fragment is a monoclonal antibody, or a target-binding fragment or derivative thereof retaining target binding capacities, or an antibody mimetic.

As used herein, the term "competes for binding" is used in reference to one of the antibodies defined by the sequences as above, meaning that the actual antibody or fragment as an activity which binds to the same target, or target epitope or domain or subdomain, as does said sequence defined antibody or fragment, and is a variant of the latter. The efficiency (e.g., kinetics or thermodynamics) of binding may be the same as or greater than or less than the efficiency of the latter. For example, the equilibrium binding constant for binding to the substrate may be different for the two antibodies.

Such competition for binding can be suitably measured with a competitive binding assay. Such assays are disclosed in Finco et al. 2011, the content of which is incorporated herein by reference for enablement purposes, and their meaning for interpretation of a patent claim is disclosed in Deng et al 2018, the content of which is incorporated herein by reference for enablement purposes.

In order to test for this characteristic, suitable epitope mapping technologies are available, including, inter alia, X-ray co-crystallography and cryogenic electron microscopy (cryo-EM)
Array-based oligo-peptide scanning
Site-directed mutagenesis mapping
High-throughput shotgun mutagenesis epitope mapping
Hydrogen-deuterium exchange.
Cross-linking-coupled mass spectrometry These methods are, inter alia, disclosed and discussed in Banik et al (2010), and DeLisser (1999), the content of which is herein incorporated by reference for enablement purposes.

According to one embodiment, the antibody or fragment, when bound to human iRhom2, binds at least within a region of Loop 1 thereof.Loop 1 of Rhom2 comprises amino acid residues 474-660 of SEQ ID NO 49.

In another embodiment, the antibody or fragment does not bind to the juxtamembrane domain (JMD) located on the N-terminal side of Loop 1.

According to one embodiment of the invention, the inhibition or reduction of TACE/ADAM17 activity is caused by interference of the antibody or fragment with iRhom2-mediated TACE/ADAM17 activation or TACE/ADAM17 interaction with other proteins including substrate molecules.

According to one embodiment of the invention, the antibody or fragment, when bound to human iRhom2, inhibits or reduces induced TNFα shedding.

According to one embodiment of the invention, the antibody or fragment, when bound to human iRhom2, inhibits or reduces induced IL-6R shedding.

According to one embodiment of the invention, the antibody or fragment, when bound to human iRhom2, inhibits or reduces induced HB-EGF shedding.

Tumor necrosis factor alpha (TNFα) shedding or release, as used herein, refers to a process in which membrane-anchored tumor necrosis factor alpha (mTNFα/pro-TNFα) upon cleavage is released into the environment to become soluble TNFα (sTNFα or simply TNFα). This process is, inter alia, triggered by TACE/ADAM17.

Release or shedding of Interleukin 6 receptor (IL-6R) refers to a process in which soluble IL-6R is produced by proteolytic cleavage of the membrane-bound IL-6R on the cell surface at a proteolytic site close to its transmembrane domain by TACE/ADAM17

Release or shedding of Heparin-binding EGF-like growth factor (HB-EGF) refers to a cleavage process in which the soluble form of HB-EGF is generated and set free from the cell surface. Heparin-binding EGF-like growth factor, an epidermal growth factor with an affinity for heparin, is synthesized as a membrane-anchored mitogenic and chemotactic glycoprotein. First identified in the conditioned media of human macrophage-like cells, HB-EGF is an 87-amino acid glycoprotein that displays highly regulated gene expression.

Suitable Assays to determine the TNFα shedding effect are described, e.g., in FIG. 8 and example 6. Suitable Assays to determine the release or shedding of IL-6R and/or HB- EGF are described, e.g., in FIG. 10 and example 8 or in FIG. 12 and example 10, respectively.

According to one embodiment of the invention, the human iRhom2 to which the antibody or fragment binds comprises a) the amino acid sequence set forth in SEQ ID NO 49, or b) an amino acid sequence that has at least 80% sequence identity with SEQ ID NO 49, with the proviso that said sequence maintains iRhom2 activity.

In some embodiments, human iRhom2 comprises an amino acid sequence that has ≥81%, preferably ≥82%, more preferably ≥83%, ≥84%, ≥85%, ≥86%, ≥87%, ≥88%, ≥89%, ≥90%, ≥91%, ≥92%, ≥93%, ≥94%, ≥95%, ≥96%, ≥97%, ≥98 or most preferably ≥99% sequence identity with SEQ ID NO 49.

SEQ ID NO 49 represents the amino acid sequence of inactive rhomboid protein 2 (iRhom2) isoform 1 [*Homo sapiens*], accessible under NCBI reference NP_078875.4. Generally, different variants and isoforms of iRhom2 exist. Likewise, mutants comprising conservative or silent amino acid substitutions exist, or may exist, which maintain full or at least substantial iRhom2 activity. These isoforms, variants and mutants are encompassed by the identity range specified above, meaning however that dysfunctional, non-active variants and mutants are excluded.

According to one embodiment of the invention, the antibody or fragment is a monoclonal antibody, or a target-binding fragment or derivative thereof retaining target binding capacities According to one embodiment of the invention, the antibody or fragment according is in at least one of the formats selected from the group consisting of: IgG, scFv, Fab, and (Fab)2.

As used herein, the term "monoclonal antibody (mAb)" shall refer to an antibody composition having a homogenous antibody population, i.e., a homogeneous population consisting of a whole immunoglobulin, or a fragment or derivative thereof retaining target binding capacities.

Particularly preferred, such antibody is an IgG antibody, or a fragment or derivative thereof retaining target binding capacities. Immunoglobulin G (IgG) is a type of antibody. Representing approximately 75% of serum antibodies in humans, IgG is the most common type of antibody found in blood circulation. IgG molecules are created and released by plasma B cells. Each IgG has two antigen binding sites.

IgG antibodies are large molecules with a molecular weight of about 150 kDa made of four peptide chains. It contains two identical class y heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding site. The Fc regions of IgGs bear a highly conserved N-glycosylation site. The N-glycans attached to this site are predominantly core-fucosylated diantennary structures of the complex type. In addition, small amounts of these N-glycans also bear bisecting GlcNAc and α-2,6-linked sialic acid residues.

There are four IgG subclasses (IgG1, 2, 3, and 4) in humans, named in order of their abundance in serum (IgG1 being the most abundant).

As used herein, the term "fragment" shall refer to fragments of such antibody retaining target binding capacities, e.g.

a CDR (complementarity determining region)

a hypervariable region, a variable domain (Fv)

an IgG or IgM heavy chain (consisting of VH, CH1, hinge, CH2 and CH3 regions)

an IgG or IgM light chain (consisting of VL and CL regions), and/or a Fab and/or $F(ab)_2$.

As used herein, the term "derivative" shall refer to protein constructs being structurally different from, but still having some structural relationship to, the common antibody concept, e.g., scFv, Fab and/or $F(ab)_2$, as well as bi-, tri- or higher specific antibody constructs, and further retaining target binding capacities. All these items are explained below.

Other antibody derivatives known to the skilled person are Diabodies, Camelid Antibodies, Nanobodies, Domain Antibodies, bivalent homodimers with two chains consisting of scFvs, IgAs (two IgG structures joined by a J chain and a secretory component), shark antibodies, antibodies consisting of new world primate framework plus non-new world primate CDR, dimerized constructs comprising CH3+VL+VH, and antibody conjugates (e.g. antibody or fragments or derivatives linked to a toxin, a cytokine, a radioisotope or a label). These types are well described in the literature and can be used by the skilled person on the basis of the present disclosure, without adding further inventive activity.

Methods for the production of a hybridoma cell are disclosed in Köhler & Milstein (1975).

Methods for the production and/or selection of fully human mAbs are known in the art. These can involve the use of a transgenic animal which is immunized with the respective protein or peptide, or the use of a suitable display technique, like yeast display, phage display, B-cell display or ribosome display, where antibodies from a library are screened against human iRhom2 in a stationary phase.

In vitro antibody libraries are, among others, disclosed in U.S. Pat. No. 6,300,064 by MorphoSys and U.S. Pat. No. 6,248,516 by MRC/Scripps/Stratagene. Phage Display techniques are for example disclosed in U.S. Pat. No. 5,223,409 by Dyax. Transgenic mammal platforms are for example described in EP1480515A2 by TaconicArtemis.

IgG, IgM, scFv, Fab and/or $F(ab)_2$ are antibody formats well known to the skilled person. Related enabling techniques are available from the respective textbooks.

As used herein, the term "Fab" relates to an IgG/IgM fragment comprising the antigen binding region, said fragment being composed of one constant and one variable domain from each heavy and light chain of the antibody As used herein, the term "$F(ab)_2$" relates to an IgG/IgM fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually serine(S) or glycine (G). This chimeric molecule retains the specificity of the original immunoglobulin, despite removal of the constant regions and the introduction of a linker peptide.

Modified antibody formats are for example bi- or trispecific antibody constructs, antibody-based fusion proteins, immunoconjugates and the like. These types are well described in the literature and can be used by the skilled person on the basis of the present disclosure, with adding further inventive activity.

As used herein, the term "antibody mimetic" relates to an organic molecule, most often a protein that specifically binds to a target protein, similar to an antibody, but is not structurally related to antibodies. Antibody mimetics are usually artificial peptides or proteins with a molar mass of about 3 to 20 kDa. The definition encompasses, inter alia, Affibody molecules, Affilins, Affimers, Affitins, Alphabodies, Anticalins, Avimers, DARPins, Fynomers, Kunitz domain peptides, Monobodies, and nanoCLAMPs.

In one or more embodiments, the antibody or fragment is an isolated antibody, or a target-binding fragment or derivative thereof retaining target binding capacities, or an isolated antibody mimetic In one or more embodiments, the antibody is an engineered or recombinant antibody, or a target binding fragment or derivative thereof retaining target binding capacities, or an engineered or recombinant antibody mimetic.

According to one embodiment of the invention, the antibody or fragment is an antibody in at least one of the formats selected from the group consisting of: IgG, scFv, Fab, and (Fab)2.

According to one embodiment of the invention, the antibody or fragment is not cross-reactive with human iRhom1. The sequence of human iRhom 1 is disclosed herein as SEQ ID NO 50.

According to another aspect of the invention, a nucleic acid is provided that encodes for at least one chain of the binding agent according to the above description.

In one embodiment, a nucleic acid, or a pair of nucleic acids, is provided which encodes for the heavy chain and the light chain, respectively, of the binding agent, in case the latter is a monoclonal antibody having a heteromeric structure of at least one light chain and one heavy chain.

Such nucleic acid can be also be used for pharmaceutic purposes. The nucleic acid can be an RNA molecule, or an RNA derivative comprising, e.g., modified nucleotides, like pseudouridine (Y) or N-1 Methyl Pseudouridine (m1Ψ) to provide stability and reduce immunogenicity (see, e.g., U.S. Pat. Nos. 8,278,036 and 9,428,535, the contents of which are incorporated herein for enablement purposes). In another embodiment, the RNA comprises the most GC-rich codon is selected to provide stability and reduce immunogenicity (see e.g. EP1392341 the content of which is incorporated herein for enablement purposes). The mRNA can for example be delivered in suitable liposomes and comprises either specific sequences or modified uridine nucleosides to avoid immune responses and/or improve folding and translation efficiency, sometimes comprising cap modifications at the 5'- and/or 3' terminus to target them to specific cell types. In several embodiments, the respective RNA sequences are selected from SEQ ID NO 100-SEQ ID NO 147. See the table below to find out which RNA is encoding for which antibody sequence.

The nucleic acid can likewise be a DNA molecule. In such case, the molecule can be a cDNA that is optionally integrated into a suitable vector, e.g., an attenuated, non pathogenic virus, or is provided as one or more plasmids. Such plasmids can for example be administered to a patient by means of an electroporation device as e.g. disclosed in patent EP3397337B1, the content of which is incorporated herein for enablement purposes. In several embodiments, the respective DNA sequences are selected from SEQ ID NO 52-SEQ ID NO 99. See the table below to find out which cDNA is encoding for which antibody sequence.

Generally, due to the degeneracy of the genetic code, there is a large number of different nucleic acids that have the capacity to encode for such chain. The skilled person is perfectly able to determine if a given nucleic acid satisfies the above criterion. On the other hand, the skilled person is perfectly able to reverse engineer, from a given amino acid sequence, based on codon usage tables, a suitable nucleic acid encoding therefore. For this purpose, software tools such as "reverse translate" provided the online tool by "sequence manipulation suite", (bioinformatics.org/sms2/rev_trans.html) can be used. Hence, there are plenty of alternative DNA and RNA sequences that encode for the protein sequences as claimed. These alternative sequences shall be deemed to fall under the scope of the present invention.

According to another aspect of the invention, the use of the antibody or fragment or nucleic acid according to the above description is provided (for the manufacture of a medicament) in the treatment of a human or animal subject being diagnosed for, suffering from or being at risk of developing an inflammatory condition, or for the prevention of such condition.

In order to diagnose am inflammatory condition, the patient may have a physical exam and may also be asked about medical history. A practitioner may look for inflammation in the joints, joint stiffness and loss of function in the joint. In addition, the practitioner may order X-rays and/or Blood tests to detect inflammatory markers, like e.g. serum hs-CRP, IL-6, TNF-α, and IL-10, erythrocyte sedimentation rate, plasma viscosity, fibrinogen, and/or ferritin, as compared to healthy controls.

According to another aspect of the invention, a pharmaceutical composition comprising the antibody or fragment or nucleic acid according to the above description, and optionally one or more pharmaceutically acceptable excipients, is provided.

According to another aspect of the invention, a combination comprising (i) the antibody or fragment or the nucleic acid or the pharmaceutical composition according to the above description and (ii) one or more therapeutically active compounds is provided.

According to another aspect of the invention, a method for treating or preventing an inflammatory condition is provided, which method comprises administration, to a human or animal subject, of (i) the antibody or fragment according to the above description (ii) the nucleic acid according to the above description, (iii) the pharmaceutical composition according to the above description, or (iv) the combination according to the above description is provided in a therapeutically sufficient dose.

According to another aspect of the invention, a therapeutic kit of parts comprising:

a) the antibody or fragment according to the above description, the nucleic acid according to the above description, the pharmaceutical composition according to the above description, or the combination according to the above description b) an apparatus for administering the composition, composition or combination, and c) instructions for use.

is provided.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'->3'.

General Methods of Antibody Humanization

Humanisation by CDR grafting is a proven, successful technique to take antibodies originating from murine, other xenogenic species or hybridomas and reduce the potential immunogenicity whilst retaining the binding and functional activity of the Parental antibody. Commonly starting from a chimeric antibody, the aim is to remove the foreign framework regions (FR) in the variable domains that can evoke an immune response. The solution to the problem is to "graft" the complementarity determining regions (CDRs) of the murine antibody onto a human Acceptor framework However, CDR-grafting alone can lead to a significant reduction or complete loss of binding affinity, as a set of supporting framework residues in the Vernier zone are important for maintaining the conformation of the CDRs. This problem can be solved by reintroducing murine residues into the human framework; such substitutions are commonly called back-mutations.

As the most significant property of a therapeutic antibody is the activity, it is important that substitutions proposed during the humanisation do not affect the affinity or stability of the antibody. A large amount of information has been collected in the last 20 years on humanisation and grafting of the CDRs; the biophysical properties of antibodies, the conformation of the CDR-loops and for the frameworks which along with advance in protein modelling (makes it possible to accurately humanise antibodies with retained binding affinity and stability.

The humanisation procedure was performed as outlined below:

1) Parental antibody domains and regions identified
2) Critical positions and potential Post-translational modifications (PTMs) were identified Antibody Fv's have a number of critical positions that make up the VH/VL inter chain interface or are responsible for the discrete set of canonical structures that has been defined for 5 of the CDRs: these positions should be considered in detail before substitutions are proposed for them.

Post-translational modifications (PTMs) can cause problems during the development of a therapeutic protein such as increased heterogeneity, reduced bioactivity, reduced stability, immunogenicity, fragmentation and aggregation. The potential impact of PTMs depends on their location and in some cases on solvent exposure. The sequences were analysed for the following potential PTMs: Asparagine deamidation, Aspartate isomerisation, free Cysteine thiol group, N-glycosylation, oxidation of Methionine and Tryptophane.

3) Based on the sequence analysis and the critical positions optimal Acceptor human germline sequences were selected for each chain.

Based on the Parental antibody sequence alignment to the human germlines, the closest matching entries were identified. The identification of the optimal human germlines as Acceptor was based on the ordered criteria listed below:

Sequence identity across the whole V gene (framework+CDRs)
Identical or compatible inter-chain interface residues
Support loops with the Parental CDRs canonical conformations 4) A 3D structural model of the Parental mouse Fv regions was constructed
5) Following a close inspection of the molecular model an initial assessment of the possibility to substitute each position was made. Positions were categorised as Neutral Contributing or Critical. Also single mutations in order to destroy potential PTMs were identified.
6) The CDR-grafting was performed by analysing positions differing between the Parental and Acceptor sequences. All substitutions in Neutral positions were performed.

For the design phase of a humanized antibody, the procedure is more accurately defined as germlining-replacing amino acids in the Parental framework that differ from the chosen Acceptor with the corresponding human amino acid.

7) Combinations of the different humanized VH and VL versions were produced, purified and tested for binding and biological activity.
8) The selection of the best humanized heavy and light chain combination between the different versions was performed by assessing the following criteria:
   a) The level of transient expression of the humanized versions produced in mammalian cells (HEK 293 or preferably CHO) as human IgG1/Kappa (as compared to the chimeric version). Using tissue culture supernatant from transfected cells before harvest for purification using ELISA or measurement by protein A using Octet label-free detection systems.
   b) The binding capacity (EC50 by ELISA or FACS; or preferably Kd by Biacore or Octet) as compared to the chimeric human IgG1/Kappa version (chimeric meaning the combination of the parental murine VH and VL fused to human constant regions).
   c) The biological activity of the humanized versions in a relevant in vitro cellular assay compared with that of the reference chimeric antibody.
   d) The cross-reactivity with relevant orthologue species (in vitro binding activity).
   e) A determination of the biophysical properties of the humanized versions as compared with chimeric:
      SEC-HPLC profile to determine the level of high molecular weight aggregates,
      SDS-PAGE under non-reducing and reducing conditions,
      Analysis by differential scanning calorimetry (DSC) using Microcal™ VP-capillary DSC system to determine the Tm of Fab, CH2 and CH3.

General Methods of Antibody Production

To produce the recombinant antibody material, target DNA sequence was designed, optimized and synthesized. The complete sequence was sub-cloned into an expression vector and the transfection grade plasmid was maxi-prepared for CHO cell expression. CHO cells were grown in CHO TF expression medium (Xell AG, Germany) and transfected with recombinant plasmids encoding target protein. The cell culture supernatant collected on day 11 post-transfection was used for purification. Cell culture broth was centrifuged and filtrated. Filtered cell culture supernatant was loaded onto MabSelect PrismA (Thermo Fisher, USA) affinity purification columns at an appropriate flowrate. After washing and elution with appropriate buffers, the eluted fractions were pooled and buffer exchanged to final formulation buffer. The purified protein was analyzed by SDS-PAGE analysis for molecular weight and purity measurements.

Example 1: Affinity Determination of the Humanized Antibodies of the Invention

In this study, affinity measurements of the humanized antibodies 16-B-03, 16-B-05, 16-B-07, 23-B-04, 42-B-02 and 42-B-04 of the invention were performed by indirect FACS scatchard analysis on L920-2041-hiR2-FL-WT-T7 cells, a murine cell line expressing human iRhom2.

Generation of L929-2041-hiR2-FL-WT-T7

In order to generate a cell system that is suited for comparable and reliable binding analyses of the antibodies, L929 (NCTC clone 929) mouse fibroblast cells (ATCC, USA) were genetically modified to knock-out the mouse iRhom2 gene. The resulting L929 mouse iRhom2 knock-out cell line was afterwards infected with different human iRhom2 constructs to obtain cell line derivatives, stably expressing different human iRhom2 proteins, that allow for binding analyses to different iRhom2 variants in the same genetic background.

In brief, mRhbdf2.3 IVT gRNA (AAGCATGCTATCCTGCTCGC) was synthesized at Thermo Fisher Scientific GeneArt GmbH, Regensburg, Germany. One day post seeding in 24 well plates, L929 parental cells were transfected according to GeneArt CRISPR Nuclease mRNA user guide (Thermo Fisher Scientific, USA) with the gRNA/GeneArt Platinium Cas9 Nucelase (Thermo Fisher Scientific, USA) mix using Lipofectamine CRISPRMAX Transfection Reagent (Thermo Fisher Scientific, USA). 3 days post transfection, cells were lysed and DNA was extracted for amplification of specific PCR products using the mRhbdf2.3 fwd (TCAATGAGCTCTTTATGGGGCA)/mRhbdf2.3 rev (AAGGTCTCCATCCCCTCAGGTC) 5primer pair (Thermo Fisher Scientific, USA). For selection of positive wells, GeneArt Genomic Cleavage Detection Kit (Thermo Fisher Scientific, USA) was applied to those samples that had a prominent single band of the correct size in an Invitrogen 2% E-Gel Size Select agarose gel (Thermo Fisher Scientific, USA). Cleavage assay PCR products were also analyzed on Invitrogen 2% E-Gel Size Select agarose gels. Two rounds of subsequent sub cloning of the identified polyclonal L929 population using limited dilution technique were performed, using the Cleavage Detection Kit for identification of positive sub clones. Thereby, the most promising positive sub clone identified in the first round, named 1029, was further sub cloned in the second round to obtain the final clone, named 2041. The monoclonal cell population derived from this sub clone is named L929-2041 and was used for subsequent infection (according to the procedure described in Example 3) with the human iRhom2 construct hiR2-FL-WT-T7 for the generation of the cell lines L929-2041-hiR2-FL-WT-T7.

FACS Scatchard Analyses on L929-2041-hiR2-FL-T7

In brief, L929-2041-hiR2-FL-T7 were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $3\times10^5$ cells per well. In order to pellet cells and remove supernatants, the plates were centrifuged at 1,500 rpm and 4° C. for 3 minutes. For primary staining, cells were resuspended in 100 µl per well of either FACS buffer alone (controls) or serial two-fold dilutions (in total 22 concentrations) of the humanized antibodies 16-B-03, 16-B-05, 16-B-07, 23-B-04, 42-B-02 and 42-B-04 of the invention in FACS buffer starting at 160 µg/ml and incubated on ice for 1 hour. Afterwards, plates were centrifuged at 1,500 rpm and 4° C. for 3 minutes and washed twice with 200 µl per well of FACS buffer. For secondary staining, cells were spun down and resuspended in 100 µl per well of PE-conjugated goat anti-human IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 µl per well of FACS buffer. Finally, cells were resuspended in 150 µl per well of FACS buffer and analyzed using a BD Accuri™ C6 Plus flow cytometer (Becton Dickinson, Germany). Applying Prism8 software (GraphPad Sowtware, USA), the respective KD value for each of the antibodies of the invention were calculated.

FIG. 1 shows representative results of this study, demonstrating that the KD values for binding of the humanized antibodies 16-B-03, 16-B-05, 16-B-07, 23-B-04, 42-B-02 and 42-B-04 of the invention to L929-2041-hiR2-FL-T7cells are in the subnanomolar to low nanomolar range.

Example 2: Generation of iRhom1/2−/− Double Knockout Mouse Embryonic Fibroblasts For various purposes, in particular binding studies, described in some of the following examples, cell systems expressing defined levels of particular iRhom variants of interest against a background lacking any endogenous iRhom1 or iRhom2 protein were required. For this purpose, mouse embryonic fibroblasts (MEFs) from double knockout (DKO) mice homozygously negative for both mouse iRhom1 and mouse iRhom2 (iRhom1/2−/−) were established. This example describes the mouse strains used for the establishment of iRhom 1/2−/− DKO MEFs and the generation of an immortalized iRhom1/2−/− DKO MEF cell line.

Mouse Strains Used for the Establishment of iRhom 1/2−/− DKO MEFs

In brief, the Rhbdf2tm1b (KOMP) Wtsi mouse strain on a C57BL/6N background (C57BL/6N-Rhbdf2tm 1b (KOMP) Wtsi) was obtained from the Knockout Mouse Project (KOMP) Repository at the University of California, Davis, USA (Rhbdf2 is an alternative name for iRhom2). Heterozygous male Rhbdf2tm 1b mice were mated with wild type female mice of a 129Sv/J genetic background to produce heterozygous offspring of mixed genetic background (129Sv/J-C57BL/6N). These heterozygous mice were mated with one another to generate male and female offspring that were homozygous for the deletion of the Rhbdf2 gene (Rhbdf2−/−mice, 129Sv/J-C57BL/6N). The resulting homozygous Rhbdf2 knockout mouse colony was further expanded by breeding of Rhbdf−/− male and female mice to generate sufficient numbers of mice. Homozygous Rhbdf2−/−mice are viable and fertile with no evident spontaneous pathological phenotypes.

Rhbdf1 knockout mice were obtained from the European Conditional Mouse Mutagenesis Program (EUCOMM) of the International Knockout Mouse Consortium (IKMC). The generation of these animals is described in Li et al., PNAS, 2015, doi: 10.1073/pnas.1505649112.

Homozygous Rhbdf1−/−mice are viable and fertile with no evident spontaneous pathological phenotypes.

For the generation of DKO mice for Rhbdf1 and Rhbdf2 (Rhbdf1/2−/−mice), Rhbdf1−/−mice were mated with Rhbdf2−/−mice to generate Rhbdf1+/−Rhbdf2+/−doubly heterozygous mice. These were mated with Rhbdf2−/−mice to produce Rhbdf1+/−Rhbdf2−/− animals, which were mated with one another to generate E14.5 embryos lacking both Rhbdf genes (Rhbdf1/2−/− DKO embryos) at the expected Mendelian ratios (1/4 of all embryos) for production of E13.5 Rhbdf1/2−/− DKO MEFs, as described below.

Generation of an Immortalized iRhom1/2−/− DKO MEF Cell Line

In brief, pregnant Rhbdf1+/−Rhbdf2−/− females were sacrificed at E13.5. The uterine horns were removed into a dish with ice-cold PBS. Using fine tip forceps, the embryos were released from maternal tissue and each embryo was removed from placenta. Each embryo was then decapitated with a sharp scalpel and all internal organs such as liver, heart, lung and intestines were removed. A 0.5 mm section of the tail was removed and transferred to a 1.5 ml Eppendorf tube for isolation of genomic DNA and subsequent PCR genotyping to confirm the correct genotype of the embryo. Afterwards, the remaining embryonic tissue was washed once with PBS and transferred into a tissue culture dish with 2 mL of 0.25% trypsin/EDTA. The tissue was extensively minced with two sterile scalpels, and the trypsin/cell mixture was incubated at 37° C. for 15 minutes. Trypsinization was stopped by the addition of FCS-containing growth medium. To generate a single cell suspension, the mixture was pipetted up and down, first five times with a 10 mL serum pipet, then five times with a 5 mL serum pipet and finally several times with a fire-polished Pasteur pipet to further dissociate any remaining cell clusters. Subsequently, cells obtained from one embryo were plated on two 10 cm tissue culture plates. The next day, the medium was replaced by fresh medium and the cells were allowed to grow until they reached 90% confluency. Finally, cells were expanded and stocked for future usage.

For immortalization of primary Rhbdf1/2−/− DKO MEFs, cells were transduced with a retroviral system using the pMSCV expression system (Clontech, USA). Briefly, a pMSCV-Zeo-SV40 was generated as follows: the sequences coding for the puromycin resistance were removed from plasmid pMSCV-puro (Clontech, USA) and replaced with the sequences conferring the Zeocin resistance from pcDNA3.1 (+) Zeo vector (Thermo Fisher Scientific, USA). The retroviral packaging cell line GP2-293 (Clontech, USA) was used in combination with the envelope vector pVSV-G (Clontech, USA) and the pMSCV-Zeo-SV40 plasmid to produce a retrovirus encoding the SV40 large T-antigen. The virus was filtered and added to primary Rhbdf1/2−/− DKO MEFs plated at 50% confluency for 24 hours. Afterwards, transduced Rhbdf1/2−/− DKO MEFs were allowed to grow in growth medium without selection pressure for 24 hours and were then shifted to growth medium containing 100 μg/ml of Zeocin. Cells were passaged when confluent and after ten passages were stocked for future usage.

Example 3: Evaluation of Mouse Cross-Reactivity of the Humanized Antibodies of the Invention Next, immortalized iRhom1/2−/− DKO MEFs were reconstituted with a tagged form of human iRhom2 to test target recognition of humanized antibodies of the invention. Additionally, iRhom 1/2−/− DKO MEFs stably expressing a tagged form of mouse iRhom2 were generated in order to determine cross-reactivity of the humanized antibodies 16-B-03, 16-B-05, 16-B-07, 23-B-04, 42-B-02 and 42-B-04 of the invention with the mouse orthologue of iRhom2.

Generation of iRhom 1/2−/− DKO MEFs Stably Expressing T7-Tagged Human or Mouse iRhom2

In brief, on day 1, Phoenix-ECO cells (American Type Culture Collection, USA) were seeded on 6-well tissue culture plates (Greiner, Germany) in standard growth medium at $8\times10^5$ cells per well and kept overnight at 37° C., 5% $CO_2$. On day 2, the medium was replaced by fresh medium supplemented with chloroquine (Sigma-Aldrich, USA) at a final concentration of 25 μM. Applying the calcium phosphate method, cells were transfected with 2 μg/ml of pMSCV (Clontech, USA) empty vector, pMSCV-hiR2-FL-WT-T7 encoding human iRhom2 full length wild type C-terminally tagged with 3 consecutive copies of the T7 epitope (MASMTGGQQMG) or pMSCV-miR2-FL-WT-T7 encoding mouse iRhom2 full length wild type C-terminally tagged with 3 consecutive copies of the T7 epitope, and were kept at 37° C., 5% $CO_2$. After 7 hours, the transfections were stopped by replacing cell supernatants with standard growth medium lacking chloroquine, and cells were incubated at 37° C., 5% $CO_2$ to allow virus production overnight. In parallel, immortalized iRhom 1/2−/− DKO MEFs as target cells for retroviral infection were seeded on 6-well tissue culture plates (Greiner, Germany) in standard growth medium at $1\times10^5$ cells per well and were also kept overnight at 37° C., 5% $CO_2$. On day 3, the supernatants of Phoenix-ECO cells releasing pMSCV, pMSCV-hiR2-FL-WT-T7 or pMSCV-miR2-FL-WT-T7 ecotrophic virus were collected, filtered with 0.45 μm CA filters, and supplemented with 4 μg/ml of polybrene (Sigma-Aldrich, USA). Upon removal of medium from the immortalized iRhom1/2−/− DKO MEFs, the virus containing supernatants were added to the target cells for 4 hours at 37° C., 5% $CO_2$ for first infection. Simultaneously, Phoenix-ECO cells were re-incubated with fresh medium, which, after another 4 hours, was filtered and used for the second infection of the respective target cell populations, again in the presence of 4 μg/ml of polybrene. Likewise, a third, but overnight infection cycle was performed. On day 4, virus containing cell supernatants were replaced by fresh standard growth medium. From day 5 onwards, cells were grown in the presence of 2 mg/ml of geneticin (G418, Thermo Fisher Scientific, USA) for the selection of immortalized MEF-DKO-EV control cells stably infected with pMSCV empty vector, MEF-DKO-hiR2-FL-WT-T7 cells stably expressing human iRhom2 full length wild type C-terminally tagged with 3 consecutive copies of the T7 epitope, and MEF-DKO-miR2-FL-WT-T7 cells stably expressing mouse iRhom2 full length wild type C-terminally tagged with 3 consecutive copies of the T7 epitope. Upon propagation, cells were stocked for future usage.

FACS Analyses for Test System Validation and Antibody Characterization

In brief, immortalized MEF-DKO-EV control cells, MEF-DKO-hiR2-FL-WT-T7 cells and MEF-DKO-miR2-FL-WT-T7 cells were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $3\times10^5$ cells per well. To pellet cells and remove supernatants, the plates were centrifuged at 1,500 rpm and 4° C. for 3 minutes. For primary staining, cells were resuspended in 100 μl per well of either FACS buffer alone (controls), mouse monoclonal anti-T7 IgG (Merck Millipore, USA) at 3 μg/ml FACS buffer or the humanized antibodies 16-B-03, 16-B-05, 16-B-07, 23-B-04, 42-B-02 and 42-B-04 of the invention also at 3 μg/ml FACS buffer and incubated on ice for 1 hour. Afterwards, plates were centrifuged at 1,500 rpm and 4° C. for 3 minutes and washed twice with 200 μl per well of FACS buffer. For secondary staining of previous anti T7 staining, cells were spun down and resuspended in 100 μl per well of PE-conjugated goat anti-mouse IgG F(ab') 2 detection fragment (Dianova, Germany) diluted 1:100 in FACS buffer. For secondary staining of previous staining with humanized antibodies of invention, cells were spun down and resuspended in 100 μl per well of PE-conjugated goat anti-human IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 μl per well of FACS buffer. Finally, cells were resuspended in 150 μl per well of FACS buffer and analyzed using a BD Accuri™ C6 Plus flow cytometer (Becton Dickinson, Germany).

Figure 2B:
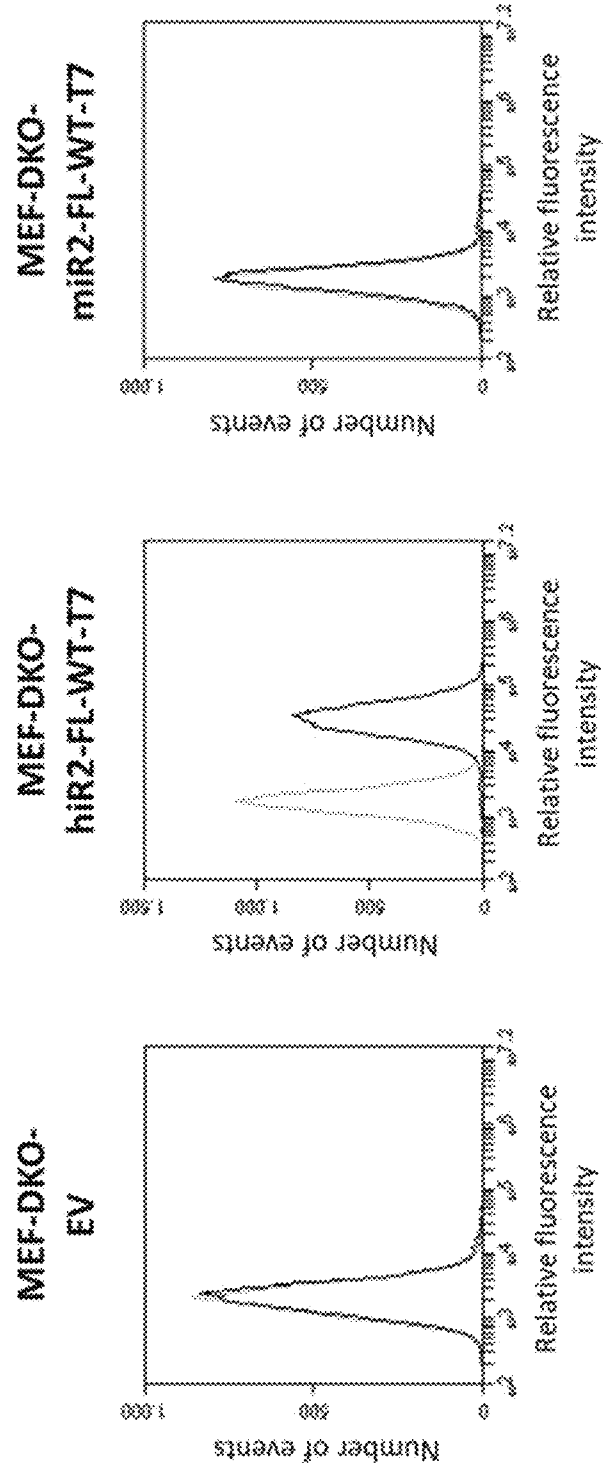
FIG. 2*b* shows results from FACS analyses for the determination of mouse cross-reactivity of the antibodies of the invention, demonstrating that the humanized antibody 16-B-03 as a representative example of the antibodies of the invention clearly recognizes the human iRhom2 variant ectopically expressed by MEF-DKO-hiR2-FL-WT-T7, but not the mouse iRhom2 variant ectopically expressed by MEF-DKO-miR2-FL-WT-T7 cells and, thus, is not cross-reactive with mouse iRhom2. Stainings: gray=secondary antibody only; black=antibody 16-B-03

FIGS. 2*a* & 2b show representative results of this experiment. As compared to control samples incubated with anti-mouse IgG or anti human IgG secondary antibody only (2a & 2b, gray), co-incubation with anti-T7 tag antibody (FIG. 2*a*, black) results in very little background staining of MEF-DKO-EV control cells (FIG. 2*a*, left). In contrast, binding analyses of the anti-T7 tag antibody on both MEF-DKO-hiR2-FL-WT-T7 (FIG. 2*a*, middle) and MEF-DKO-miR2-FL-WT-T7 (FIG. 2*a*, right) cells reveal a strong increase in relative fluorescence intensity, demonstrating both the ectopically expressed human and the mouse iRhom2 variant to be localized on the surface of these genetically engineered cell populations and, thus, validating them as suitable test systems for characterizing the antibodies of the invention. Co-incubation of these cell populations with humanized antibody 16-B-03 as a representative example of the humanized antibodies of the invention (FIG. 2*b*, black) leads to no background staining of MEF-DKO-EV control cells at all (FIG. 2*b*, left), while the strong shift in relative fluorescence intensity, similar to the one observed with the anti-T7 tag antibody, on MEF-DKO-hiR2-FL-WT-T7 cells demonstrates strong binding of the humanized antibody 16-B-03 of the invention to the human iRhom2 variant (FIG. 2*b*, middle). In contrast, no significant binding of the humanized antibody 16-B-03 of the invention to MEF-DKO-miR2-FL-WT-T7 cells is detectable (FIG. 2*b*, right), providing evidence that the mouse iRhom2 variant, whose presence on the cell surface is verified with the anti-T7 tag antibody (FIG. 2*a*, right), is not being recognized by the humanized antibody 16-B-03 of the invention. Similar results were obtained with the humanized antibodies 16-B-05, 16-B-07, 23-B-04, 42-B-02, 42-B-04 of the invention, demonstrating that none of these humanized antibodies of the invention are cross-reactive with mouse iRhom2.

Example 4: Assessment of Binding Specificity of the Humanized Antibodies of the Invention Due to the sequence homology of the human iRhom2 protein versus its closely related family member human iRhom1 (referring to the NCBI reference sequence NP_078875.4. for human iRhom2 and the NCBI reference sequence NP_071895.3 for human iRhom1, the amino acid sequence identity for the extracellular loops 1, 2, 3 and the C-terminal tail of human iRhom2 versus human iRhom1 are calculated as 67.4%, 100.00%, 80.00% and 63.64%, respectively), the binding specificity of the humanized antibodies 16-B-03, 16-B-05, 16-B-07, 23-B-04, 42-B-02, 42-B-04 of the invention for human iRhom2 versus human iRhom1 was assessed as a next step. For this purpose, iRhom 1/2−/− DKO MEFs stably expressing a tagged form of human iRhom 1 were generated.

Generation of iRhom 1/2−/− DKO MEFs Stably Expressing T7-Tagged Human iRhom1

In brief, on day 1, Phoenix-ECO cells (American Type Culture Collection, USA) were seeded on 6-well tissue culture plates (Greiner, Germany) in standard growth medium at $8\times10^5$ cells per well and kept overnight at 37° C., 5% $CO_2$. On day 2, the medium was replaced by fresh medium supplemented with chloroquine (Sigma-Aldrich, USA) at a final concentration of 25 μM. Applying the calcium phosphate method, cells were transfected with 2 μg/ml of pMSCV-hiR1-FL-WT-T7 (SEQ ID NO 50) encoding human iRhom1 full length wild type C-terminally tagged with 3 consecutive copies of the T7 epitope, and were kept at 370C, 5% $CO_2$. After 7 hours, the transfections were stopped by replacing cell supernatants with standard growth medium lacking chloroquine, and cells were incubated at 37° C., 5% $CO_2$ to allow virus production overnight. In parallel, immortalized iRhom 1/2−/− DKO MEFs as target cells for retroviral infection were seeded on 6-well tissue culture plates (Greiner, Germany) in standard growth medium at $1\times10^5$ cells per well and were also kept overnight at 37° C., 5% $CO_2$. On day 3, the supernatants of Phoenix-ECO cells releasing pMSCV-hiR1-FL-WT-T7 ecotrophic virus were collected, filtered with 0.45 μm CA filters, and supplemented with 4 μg/ml of polybrene (Sigma-Aldrich, USA). Upon removal of medium from the immortalized iRhom1/2−/− DKO MEFs, these supernatants were added to the target cells for 4 hours at 37° C., 5% $CO_2$ for first infection. Simultaneously, Phoenix-ECO cells were re-incubated with fresh medium, which, after another 4 hours, was filtered and used for the second infection of the respective target cell populations, again in the presence of 4 μg/ml of polybrene. Likewise, a third, but overnight infection cycle was performed. On day 4, virus containing cell supernatants were replaced by fresh standard growth medium. From day 5 onwards, cells were grown in the presence of 2 mg/ml of geneticin (G418, Thermo Fisher Scientific, USA) for the selection of immortalized MEF-DKO-hiR1-FL-WT-T7 cells stably expressing human iRhom1 full length wild type C-terminally tagged with 3 consecutive copies of the T7 epitope. Upon propagation, cells were stocked for future usage.

FACS Analyses for Test System Validation and Antibody Characterization

In brief, in addition to immortalized MEF-DKO-EV control cells and MEF-DKO-hiR2-FL-WT-T7 cells (as already described in example 3), MEF-DKO-hiR1-FL-WT-T7 cells were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $3\times10^5$ cells per well. To pellet cells and remove supernatants, the plates were centrifuged at 1,500 rpm and 4° C. for 3 minutes. For primary staining, cells were resuspended in 100 μl per well of either FACS buffer alone (controls), mouse monoclonal anti-T7 IgG (Merck Millipore, USA) at 3 μg/ml FACS buffer or the humanized antibodies 16-B-03, 16-B-05, 16-B-07, 23-B-04, 42-B-02, 42-B-04 of the invention also at 3 μg/ml FACS buffer and incubated on ice for 1 hour. Afterwards, plates were centrifuged at 1,500 rpm and 4° C. for 3 minutes and washed twice with 200 μl per well of FACS buffer. For secondary staining of previous anti T7 staining, cells were spun down and resuspended in 100 μl per well of PE-conjugated goat anti-mouse IgG F(ab') 2 detection fragment (Dianova, Germany) diluted 1:100 in FACS buffer. For secondary staining of previous staining with humanized antibodies of invention, cells were spun down and resuspended in 100 μl per well of PE-conjugated goat anti-human IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 μl per well of FACS buffer. Finally, cells were resuspended in 150 μl per well of FACS buffer and analyzed using a BD Accuri™ C6 Plus flow cytometer (Becton Dickinson, Germany).

Figure 3A:
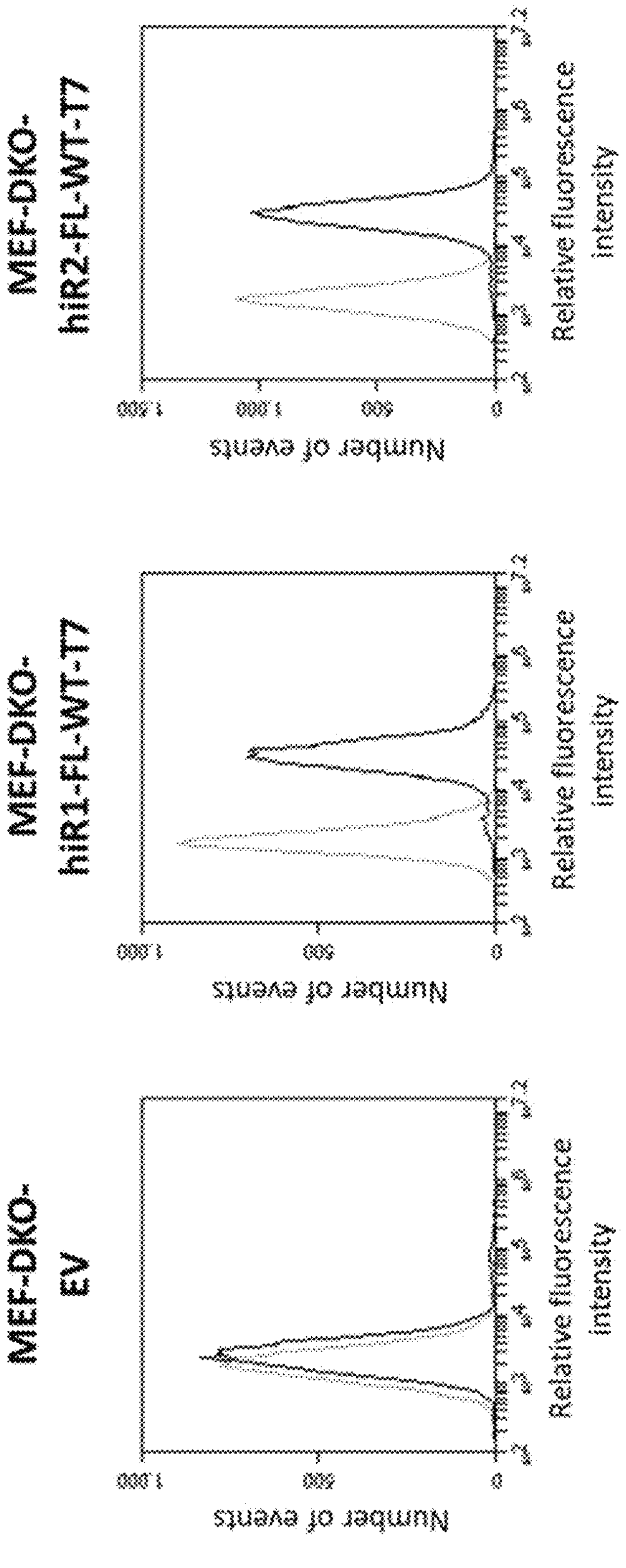
FIG. 3*a* depicts results from FACS analyses on genetically engineered MEF populations, demonstrating that T7-tagged variants of human iRhom1 full length wild type ectopically expressed by MEF-DKO-hiR1-FL-WT-T7 (SEQ ID NO 50) and human iRhom2 full length wild type ectopically expressed by MEF-DKO-hiR2-FL-WT-T7 (SEQ ID NO 49) cells, respectively, are localized on the surface of these cells. Stainings: gray=secondary antibody only; black=anti-T7-antibody
Figure 3B:
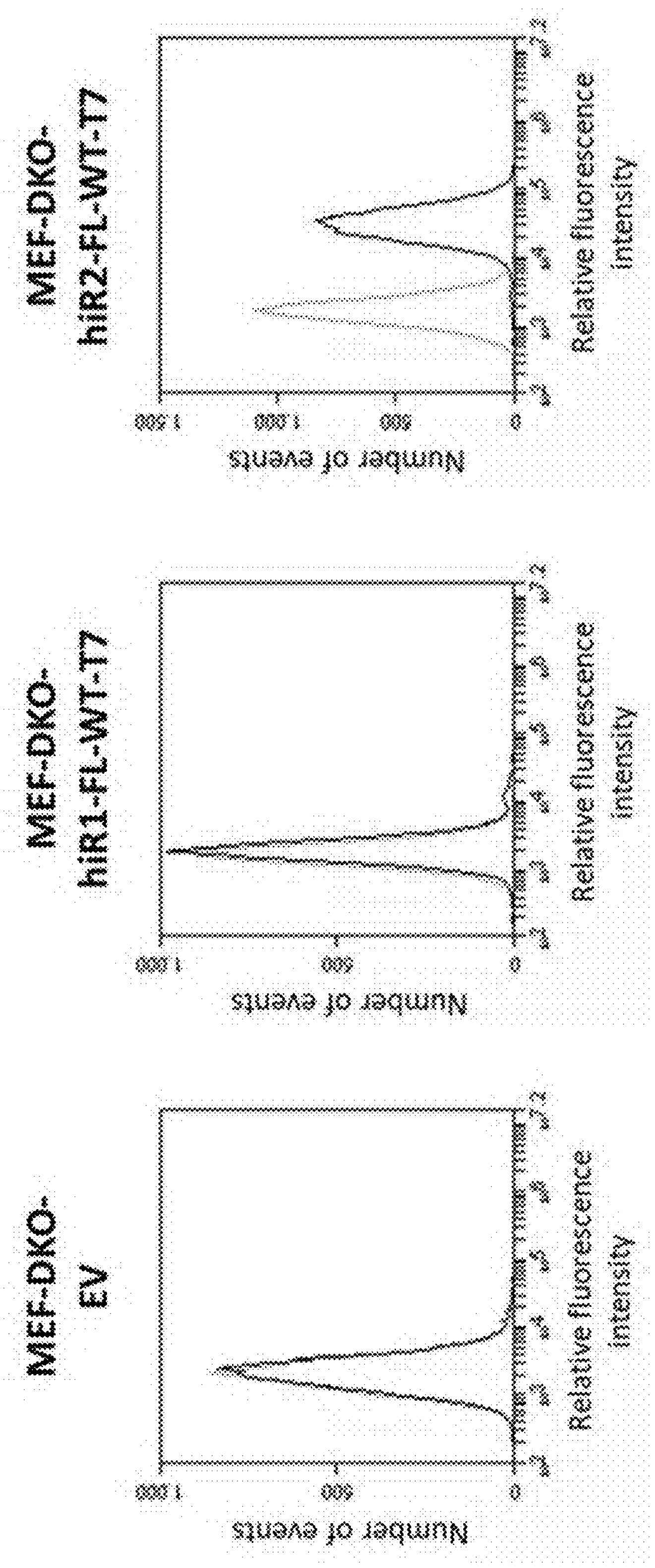
FIG. 3*b* shows results from FACS analyses for the determination of specificity of the antibodies of the invention, demonstrating that the humanized antibody 16-B-03 as a representative example of the antibodies of the invention—in contrast to the human iRhom2 variant ectopically expressed by MEF-DKO-hiR2-FL-WT-T7 (SEQ ID NO 49) cells-does not recognize the closely related human iRhom1 variant ectopically expressed by MEF-DKO-hiR1-FL-WT-T7 (SEQ ID NO 50) cells and, thus, is specific for human iRhom2. Stainings: gray=secondary antibody only; black=antibody 16-B-03

FIGS. 3*a* & 3b show representative results of these analyses. When compared to the stainings of MEF-DKO-EV control cells (FIG. 3*a*, left; identical to FIG. 2*a*, left) and MEF-DKO-hiR2-FL-WT-T7 (FIG. 3*a*, right; identical to FIG. 2*a*, middle), the strong increase in relative fluorescence intensity obtained on MEF-DKO-hiR1-FL-WT-T7 with the anti-T7 tag antibody (FIG. 3*a*, middle) demonstrates that, similarly to the human iRhom2 variant, the human iRhom1 variant is also located on the surface of this genetically engineered cell population and, thus, validates it as a suitable test systems for characterizing the antibodies of the invention. In this context, while binding of the antibody 16-B-03 as a representative example of the humanized antibodies of the invention to the human iRhom2 variant expressed on MEF-DKO-hiR2-FL-WT-T7 cells (FIG. 3*b*, right; identical to FIG. 2*b*, middle) was already shown in example 3, no significant binding of the humanized antibody 16-B-03 of the invention to MEF-DKO-hiR1-FL-WT-T7 cells is detectable (FIG. 3*b*, middle), providing evidence that the human iRhom1 variant, whose presence on the cell surface is verified with the anti-T7 tag antibody (FIG. 3*a*, middle), is not being recognized by the humanized antibody 16-B-03 of the invention. Similar results were obtained with the humanized antibodies 16-B-05, 16-B-07, 23-B-04, 42-B-02, 42-B-04 of the invention, demonstrating that none of these humanized antibodies of the invention recognizes human iRhom1.

Example 5: Evaluation of Cross-Reactivity of the Antibodies of the Invention to Different Species Next, iRhom1/2−/− DKO MEFs stably expressing a tagged form of rhesus monkey, cynomolgus monkey, dog or rabbit iRhom2 were generated in order to determine cross-reactivity of the antibodies of the invention with the respective orthologue of iRhom2. iRhom1/2−/− DKO MEFs stably expressing a tagged form of rhesus monkey, cynomolgus monkey, dog or rabbit iRhom 1 were generated to confirm specificity for iRhom2 versus iRhom1 of these species.

Generation of iRhom 1/2−/− DKO MEFs Stably Expressing T7-Tagged Rhesus Monkey, Cynomolgus Monkey, Dog or Rabbit iRhom2

In brief, on day 1, Phoenix-ECO cells (American Type Culture Collection, USA) were seeded on 6-well tissue culture plates (Greiner, Germany) in standard growth medium at $8\times10^5$ cells per well and kept overnight at 37° C., 5% $CO_2$. On day 2, the medium was replaced by fresh medium supplemented with chloroquine (Sigma-Aldrich, USA) at a final concentration of 25 μM. Applying the calcium phosphate method, cells were transfected with 2 μg/ml of pMSCV (Clontech, USA) empty vector, pMSCV-rhesus-iR2-FL-WT-T7 encoding rhesus monkey iRhom2 full length wild type C-terminally tagged with 3 consecutive copies of the T7 epitope, pMSCV-cyno-iR2-FL-WT-T7 encoding cynomolgus monkey iRhom2 full length wild type C-terminally tagged with 3 consecutive copies of the T7 epitope, pMSCV-dog-iR2-FL-WT-T7 encoding dog iRhom2 full length wild type C-terminally tagged with 3 consecutive copies of the T7 epitope or pMSCV-rabbit-iR2-FL-WT-T7 encoding rabbit iRhom2 full length wild type C-terminally tagged with 3 consecutive copies of the T7 epitope, respectively, and were kept at 37° C., 5% $CO_2$. After 7 hours, the transfections were stopped by replacing cell supernatants with standard growth medium lacking chloroquine, and cells were incubated at 37° C., 5% $CO_2$ to allow virus production overnight. In parallel, immortalized iRhom 1/2−/− DKO MEFs as target cells for retroviral infection were seeded on 6-well tissue culture plates (Greiner, Germany) in standard growth medium at $1\times10^5$ cells per well and were also kept overnight at 37° C., 5% $CO_2$. On day 3, the supernatants of Phoenix-ECO cells releasing pMSCV, pMSCV-rhesus-iR2-FL-WT-T7, pMSCV-cyno-iR2-FL-WT-T7, pMSCV-dog-iR2-FL-WT-T7 or pMSCV-rabbit-iR2-FL-WT-T7 ecotrophic virus, respectively were collected, filtered with 0.45 μm CA filters, and supplemented with 4 μg/ml of polybrene (Sigma-Aldrich, USA). Upon removal of medium from the immortalized iRhom1/2−/− DKO MEFs, the virus containing supernatants were added to the target cells for 4 hours at 37° C., 5% $CO_2$ for first infection. Simultaneously, Phoenix-ECO cells were re-incubated with fresh medium, which, after another 4 hours, was filtered and used for the second infection of the respective target cell populations, again in the presence of 4 μg/ml of polybrene. Likewise, a third, but overnight infection cycle was performed. On day 4, virus containing cell supernatants were replaced by fresh standard growth medium. From day 5 onwards, cells were grown in the presence of 2 mg/ml of geneticin (G418, Thermo Fisher Scientific, USA) for the selection of immortalized MEF-DKO-EV control cells stably infected with pMSCV empty vector, pMSCV-rhesus-iR2-FL-WT-T7 cells stably expressing rhesus monkey iRhom2 full length wild type C-terminally tagged with 3 consecutive copies of the T7 epitope, pMSCV-cyno-iR2-FL-WT-T7 cells stably expressing cynomolgus monkey iRhom2 full length wild type C-terminally tagged with 3 consecutive copies of the T7 epitope, pMSCV-dog-iR2-FL-WT-T7 cells stably expressing dog iRhom2 full length wild type C-terminally tagged with 3 consecutive copies of the T7 epitope or pMSCV-rabbit-iR2-FL-WT-T7 cells stably expressing rabbit iRhom2 full length wild type C-terminally tagged with 3 consecutive copies of the T7 epitope, respectively. Upon propagation, cells were stocked for future usage. In parallel, iRhom1/2−/− DKO MEFs stably expressing a tagged form of rhesus monkey, cynomolgus monkey, dog or rabbit iRhom1 were generated in an analogous manner.

FACS Analyses for Test System Validation and Antibody Characterization

In brief, immortalized MEF-DKO-EV control cells, MEF-DKO-rhesus-iR2-FL-WT-T7 cells, MEF-DKO-cyno-iR2-FL-WT-T7 cells, MEF-DKO-dog-iR2-FL-WT-T7 cells and MEF-DKO-rabbit-iR2-FL-WT-T7 cells, as well as their respective iRhom 1 counterparts, were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $3\times10^5$ cells per well. To pellet cells and remove supernatants, the plates were centrifuged at 1,500 rpm and 4° C. for 3 minutes. For primary staining, cells were resuspended in 100 μl per well of either FACS buffer alone (controls), mouse monoclonal anti-T7 IgG (Merck Millipore, USA) at 3 μg/ml FACS buffer or the antibodies of the invention also at 3 μg/ml FACS buffer and incubated on ice for 1 hour. Afterwards, plates were centrifuged at 1,500 rpm and 4° C. for 3 minutes and washed twice with 200 μl per well of FACS buffer. For secondary staining of previous anti T7 staining, cells were spun down and resuspended in 100 μl per well of PE-conjugated goat anti-mouse IgG F(ab') 2 detection fragment (Dianova, Germany) diluted 1:100 in FACS buffer. For secondary staining of previous staining with humanized antibodies of invention, cells were spun down and resuspended in 100 μl per well of PE-conjugated goat anti-human IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 μl per well of FACS buffer. Finally, cells were resuspended in 150 μl per well of FACS buffer and analyzed using a BD Accuri™ C6 Plus flow cytometer (Becton Dickinson, Germany).

Figure 4A:
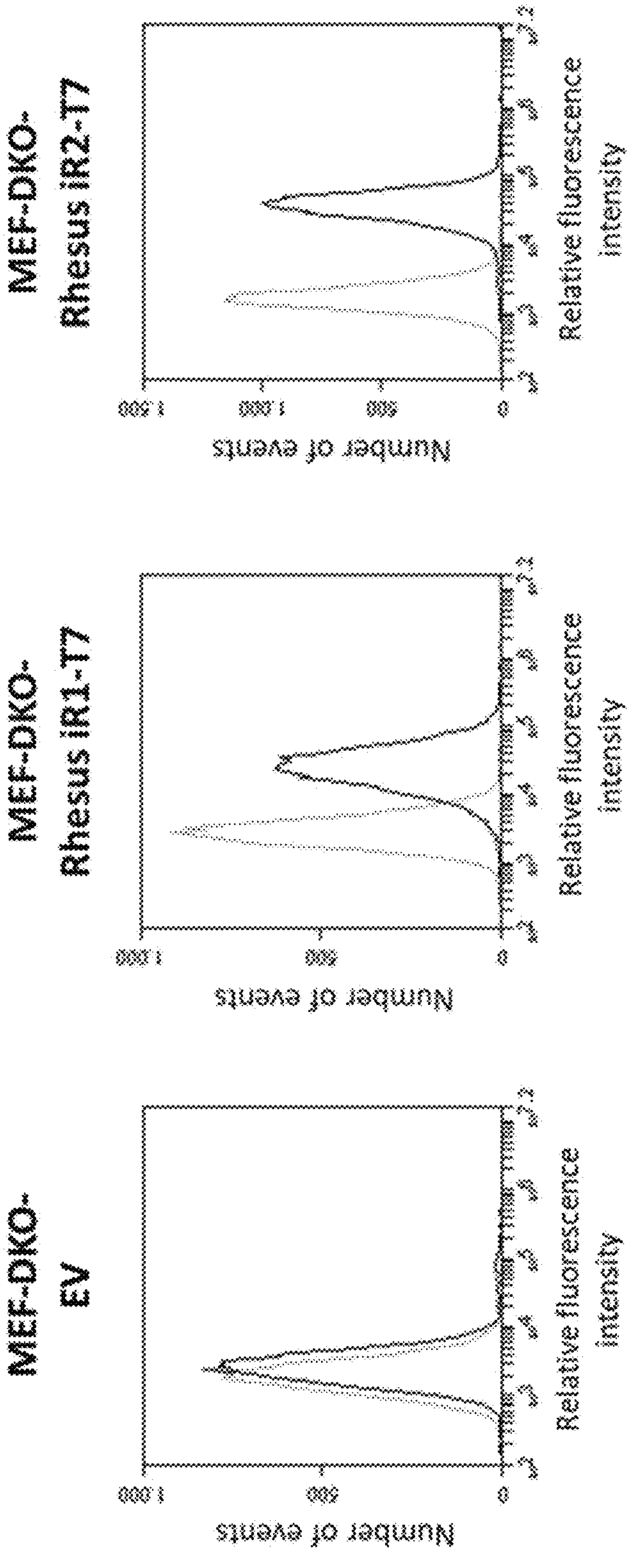
FIG. 4*a* depicts results from FACS analyses on genetically engineered MEF populations, demonstrating that also a T7-tagged version of rhesus monkey iRhom1 full length wild type ectopically expressed by MEF-DKO-Rhesus-iR1-FL-WT-T7 (UniProt Identifier: F6ZPC8) cells as well as a T7-tagged version of rhesus monkey iRhom2 full length wild type ectopically expressed by MEF-DKO-Rhesus-iR2-FL-WT-T7 (UniProt Identifier: F6Y4X6) cells, respectively, are localized on the surface of these cells. Stainings: gray=secondary antibody only; black=anti-T7-antibody
Figure 4B:
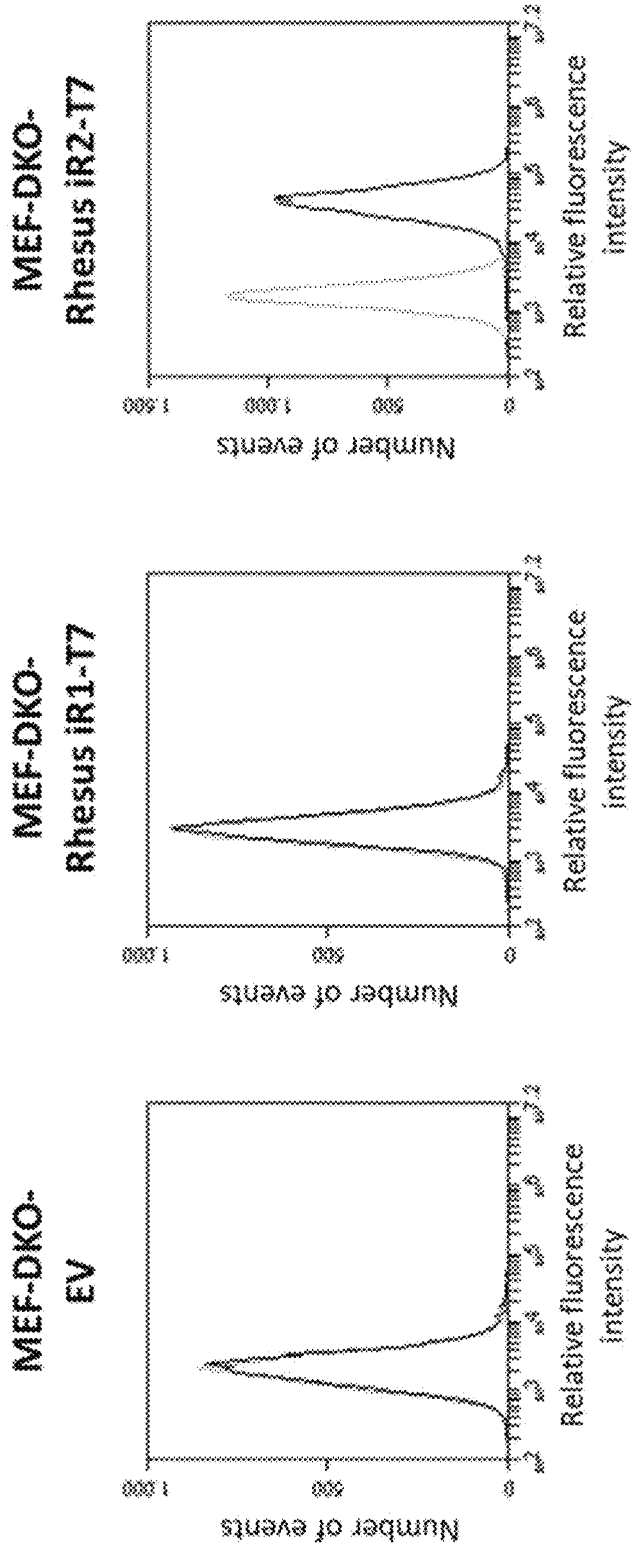
FIG. 4*b* shows results from FACS analyses for the determination of the cross-reactivity of the antibodies of the invention with rhesus monkey, demonstrating that the humanized antibody 16-B-03 as a representative example of antibodies of the invention 16-B-03, 16-B-05, 16-B-07, 23-B-04, 42-B-02 and 42-B-04 clearly recognizes the rhesus monkey iRhom2 variant ectopically expressed by MEF-DKO-Rhesus-iR2-FL-WT-T7, but not the rhesus monkey iRhom1 variant ectopically expressed by MEF-DKO-Rhesus-iR1-FL-WT-T7 cells and, thus, is cross-reactive with rhesus monkey iRhom2 but does not bind to rhesus monkey iRhom1. Stainings: gray=secondary antibody only; black=antibody 16-B-03

FIGS. 4*a* & 4b show representative results of cross-reactivity analysis to rhesus monkey. When compared to the stainings of MEF-DKO-EV control cells (FIG. 4*a*, left; identical to FIG. 2*a*, left), MEF-DKO-Rhesus-iR1-FL-WT-T7 (FIG. 4*a*, middle) and MEF-DKO-Rhesus-iR2-FL-WT-T7 (FIG. 4*a*, right), the strong increase in relative fluorescence intensity obtained on MEF-DKO-Rhesus-iR1-FL-WT-T7 and MEF-DKO-Rhesus-iR2-FL-WT-T7 with the anti-T7 tag antibody demonstrates that, similarly to the human iRhom1 and 2 variants, the rhesus monkey iRhom1 and 2 variants are also located on the surface of this genetically engineered cell population and, thus, validates it as a suitable test systems for characterizing the antibodies of the invention. Strong binding of the antibody 16-B-03 as a representative example of the humanized antibodies of the invention to the rhesus monkey iRhom2 variant expressed on MEF-DKO-Rhesus-iR2-FL-WT-T7 cells (FIG. 4*b*, right) compared to no significant binding to MEF-DKO-Rhesus-iR1-FL-WT-T7 cells is detectable (FIG. 4*b*, middle). This provides evidence that the rhesus monkey iRhom2 variant is specifically recognized by the humanized antibody 16-B-03 of the invention, compared to no recognition of rhesus monkey iRhom1, whose presence on the cell surface is verified with the anti-T7 tag antibody (FIG. 4*a*, middle). Similar results were obtained with the humanized antibodies 16-B-05, 16-B-07, 23-B-04, 42-B-02, 42-B-04 of the invention, demonstrating that all these humanized antibodies of the invention recognize rhesus monkey iRhom2 but do not recognize rhesus monkey iRhom1.

Figure 5A:
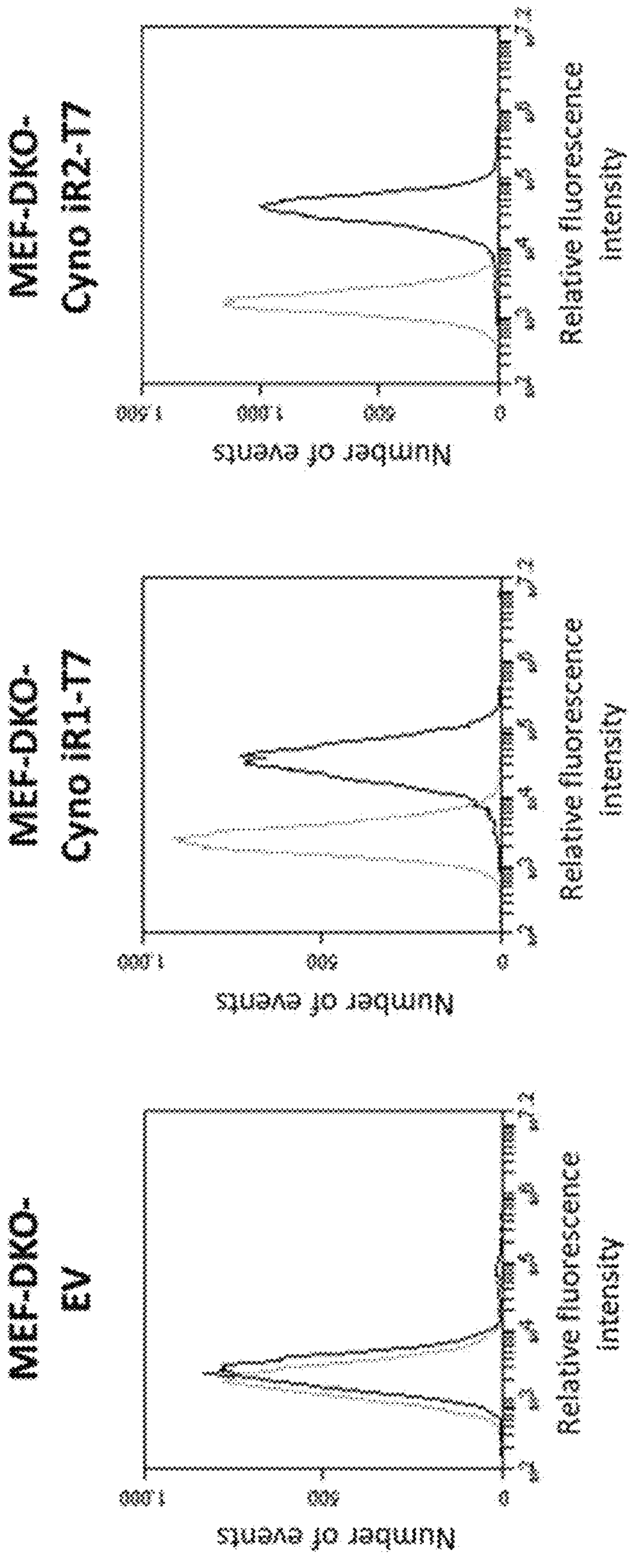
FIG. 5*a* depicts results from FACS analyses on genetically engineered MEF populations, demonstrating that also a T7-tagged version of cynomolgus monkey iRhom 1 full length wild type ectopically expressed by MEF-DKO-Cyno-iR1-FL-WT-T7 (UniProt Identifier: A0A2K5TUM2) cells as well as a T7-tagged version of cynomolgus monkey iRhom2 full length wild type ectopically expressed by MEF-DKO-Cyno-iR2-FL-WT-T7 (UniProt Identifier: A0A2K5TX07) cells, respectively, are localized on the surface of these cells Stainings: gray=secondary antibody only; black=anti-T7-antibody
Figure 5B:
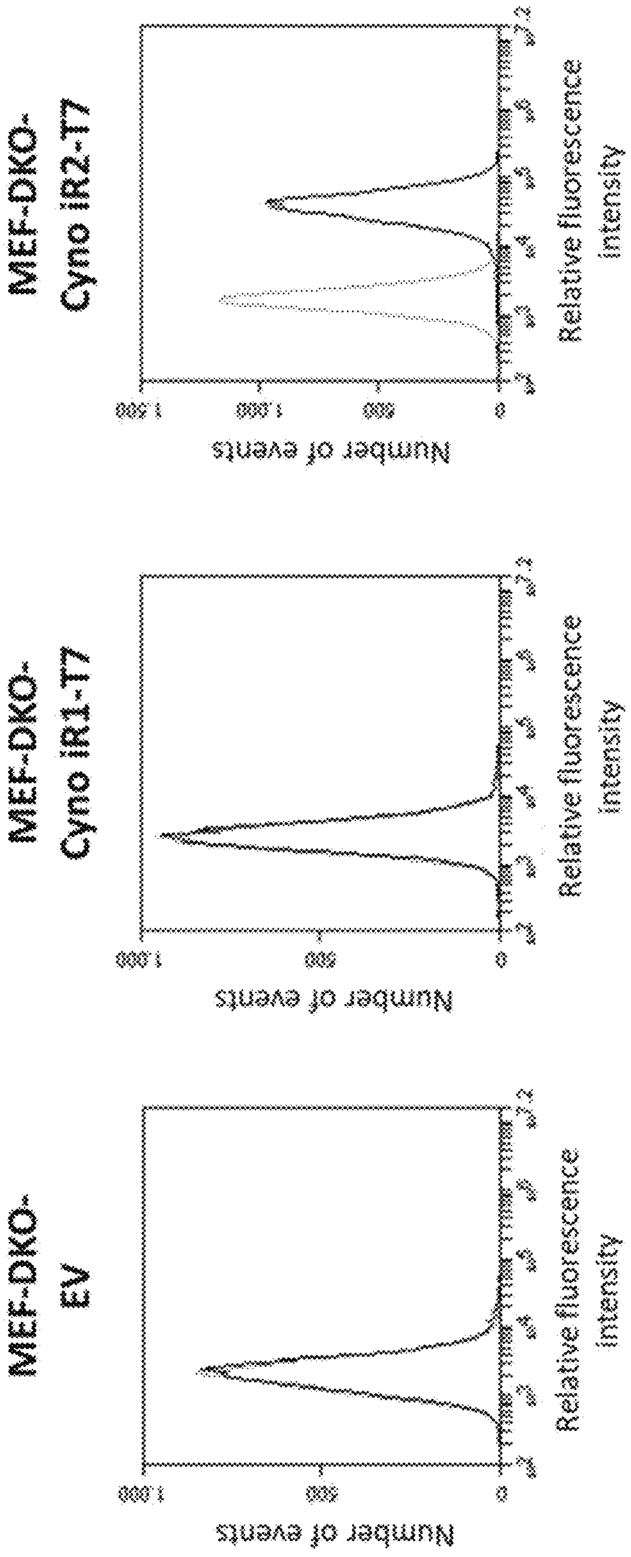
FIG. 5*b* shows results from FACS analyses for the determination of the cross-reactivity of the antibodies of the invention with cynomolgus monkey, demonstrating that the humanized antibody 16-B-03 as a representative example of antibodies of the invention 16-B-03, 16-B-05, 16-B-07, 23-B-04, 42-B-02 and 42-B-04 clearly recognizes the cynomolgus monkey iRhom2 variant ectopically expressed by MEF-DKO-Cyno-iR2-FL-WT-T7, but not the cynomolgus monkey iRhom1 variant ectopically expressed by MEF-DKO-Cyno-iR1-FL-WT-T7 cells and, thus, is cross-reactive with cynomolgus monkey iRhom2 but does not bind to cynomolgus monkey iRhom1. Stainings: gray=secondary antibody only; black=antibody 16-B-03

FIGS. 5*a* & 5b show representative results of cross-reactivity analysis to cynomolgus monkey. When compared to the stainings of MEF-DKO-EV control cells (FIG. 5*a*, left; identical to FIG. 2*a*, left), MEF-DKO-Cyno-iR1-FL-WT-T7 (FIG. 5*a*, middle) and MEF-DKO-Cyno-iR2-FL-WT-T7 (FIG. 5*a*, right), the strong increase in relative fluorescence intensity obtained on MEF-DKO-Cyno-iR1-FL-WT-T7 and MEF-DKO-Cyno-iR2-FL-WT-T7 with the anti-T7 tag antibody demonstrates that, similarly to the human iRhom 1 and 2 variants, the cynomolgus monkey iRhom 1 and 2 variants are also located on the surface of this genetically engineered cell population and, thus, validates it as a suitable test systems for characterizing the antibodies of the invention. Strong binding of the antibody 16-B-03 as a representative example of the humanized antibodies of the invention to the cynomolgus monkey iRhom2 variant expressed on MEF-DKO-Cyno-iR2-FL-WT-T7 cells (FIG. 5*b*, right) compared to no significant binding to MEF-DKO-Cyno-iR1-FL-WT-T7 cells is detectable (FIG. 5*b*, middle). This provides evidence that the cynomolgus monkey iRhom2 variant is specifically recognized by the humanized antibody 16-B-03 of the invention, compared to no recognition of cynomolgus monkey iRhom1, whose presence on the cell surface is verified with the anti-T7 tag antibody (FIG. 5*a*, middle). Similar results were obtained with the humanized antibodies 16-B-05, 16-B-07, 23-B-04, 42-B-02, 42-B-04 of the invention, demonstrating that all these humanized antibodies of the invention recognize cynomolgus monkey iRhom2 but do not recognize cynomolgus monkey iRhom1.

Figure 6A:
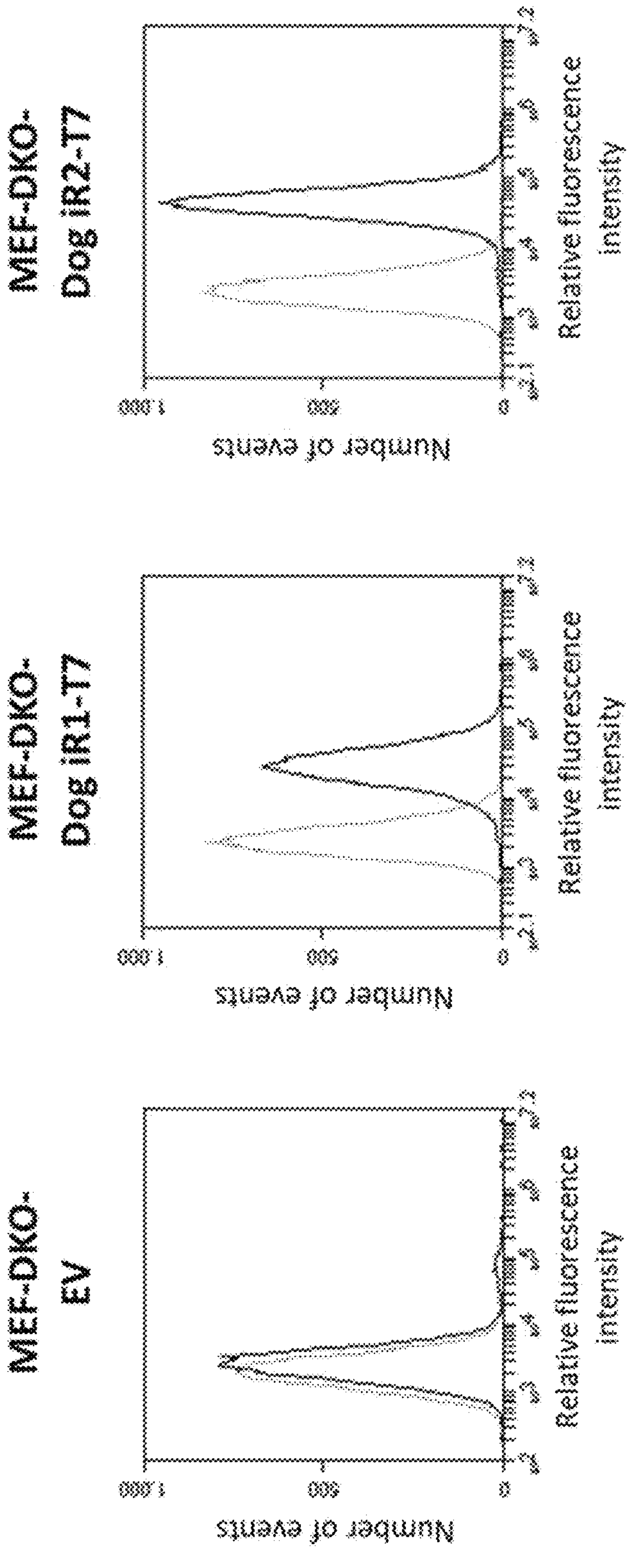
FIG. 6*a* depicts results from FACS analyses on genetically engineered MEF populations, demonstrating that also a T7-tagged version of dog iRhom1 full length wild type ectopically expressed by MEF-DKO-Dog-iR1-FL-WT-T7 (UniProt Identifier: A0A5F4CNN3) cells as well as a T7-tagged version of dog iRhom2 full length wild type ectopically expressed by MEF-DKO-Dog-iR2-FL-WT-T7 (UniProt Identifier: Q00M95) cells, respectively, are localized on the surface of these cells Stainings: gray=secondary antibody only; black=anti-T7-antibody
Figure 6B:
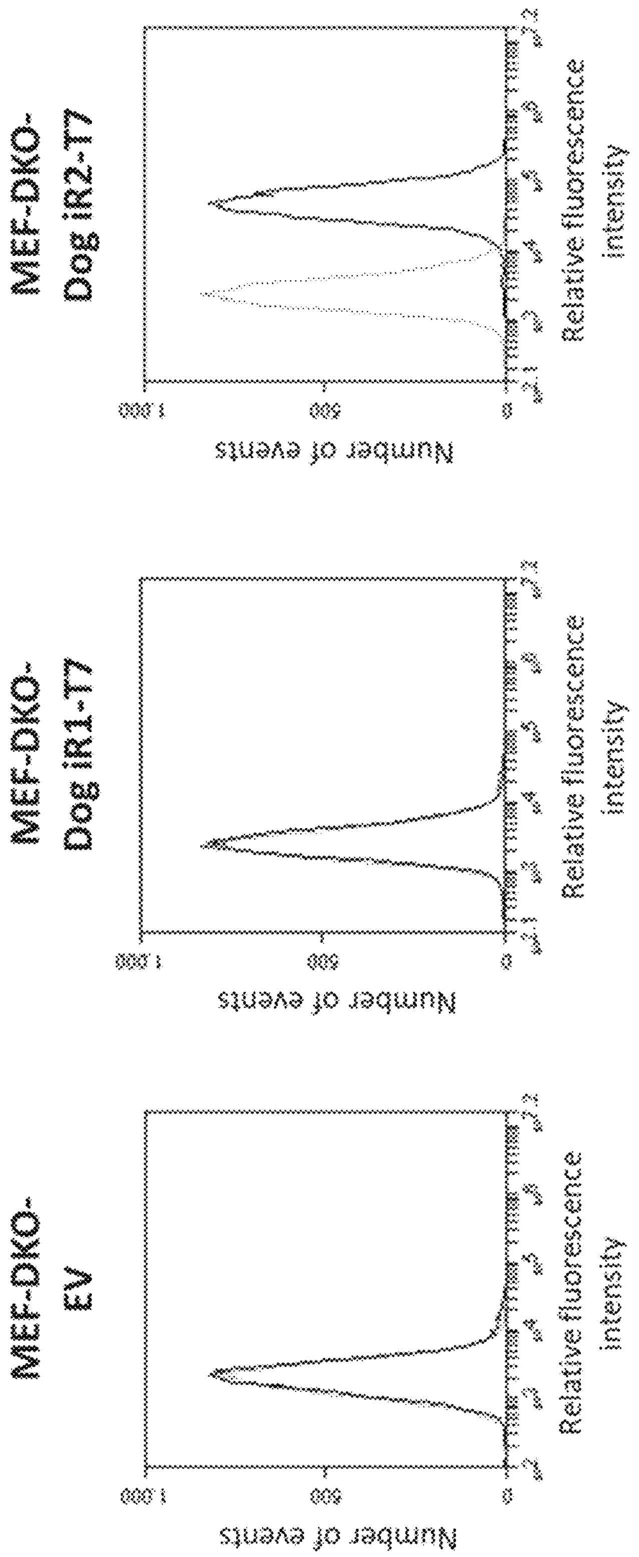
FIG. 6*b* shows results from FACS analyses for the determination of the cross-reactivity of the antibodies of the invention with dog, demonstrating that the humanized antibody 16-B-03 as a representative example of antibodies of the invention 16-B-03, 16-B-05, 16-B-07, 23-B-04, 42-B-02 and 42-B-04 clearly recognizes the dog iRhom2 variant ectopically expressed by MEF-DKO-Dog-iR2-FL-WT-T7, but not the dog iRhom1 variant ectopically expressed by MEF-DKO-Dog-iR1-FL-WT-T7 cells and, thus, is cross-reactive with dog iRhom2 but does not bind to dog iRhom 1. Stainings: gray=secondary antibody only; black=antibody 16-B-03

FIGS. 6*a* & 6b show representative results of cross-reactivity analysis to dog. When compared to the stainings of MEF-DKO-EV control cells (FIG. 6*a*, left; identical to FIG. 2*a*, left), MEF-DKO-Dog-iR1-FL-WT-T7 (FIG. 6*a*, middle) and MEF-DKO-Dog-iR2-FL-WT-T7 (FIG. 6*a*, right), the strong increase in relative fluorescence intensity obtained on MEF-DKO-Dog-iR1-FL-WT-T7 and MEF-DKO-Dog-iR2-FL-WT-T7 with the anti-T7 tag antibody demonstrates that, similarly to the human iRhom1 and 2 variants, the dog iRhom1 and 2 variants are also located on the surface of this genetically engineered cell population and, thus, validates it as a suitable test systems for characterizing the antibodies of the invention. Strong binding of the antibody 16-B-03 as a representative example of the humanized antibodies of the invention to the dog iRhom2 variant expressed on MEF-DKO-Dog-iR2-FL-WT-T7 cells (FIG. 6*b*, right) compared to no significant binding to MEF-DKO-Dog-iR1-FL-WT-T7 cells is detectable (FIG. 6*b*, middle). This provides evidence that the dog iRhom2 variant is specifically recognized by the humanized antibody 16-B-03 of the invention, compared to no recognition of dog iRhom1, whose presence on the cell surface is verified with the anti-T7 tag antibody (FIG. 6*a*, middle). Similar results were obtained with the humanized antibodies 16-B-05, 16-B-07, 23-B-04, 42-B-02, 42-B-04 of the invention, demonstrating that all these humanized antibodies of the invention recognize dog iRhom2 but do not recognize dog iRhom1.

Figure 7A:
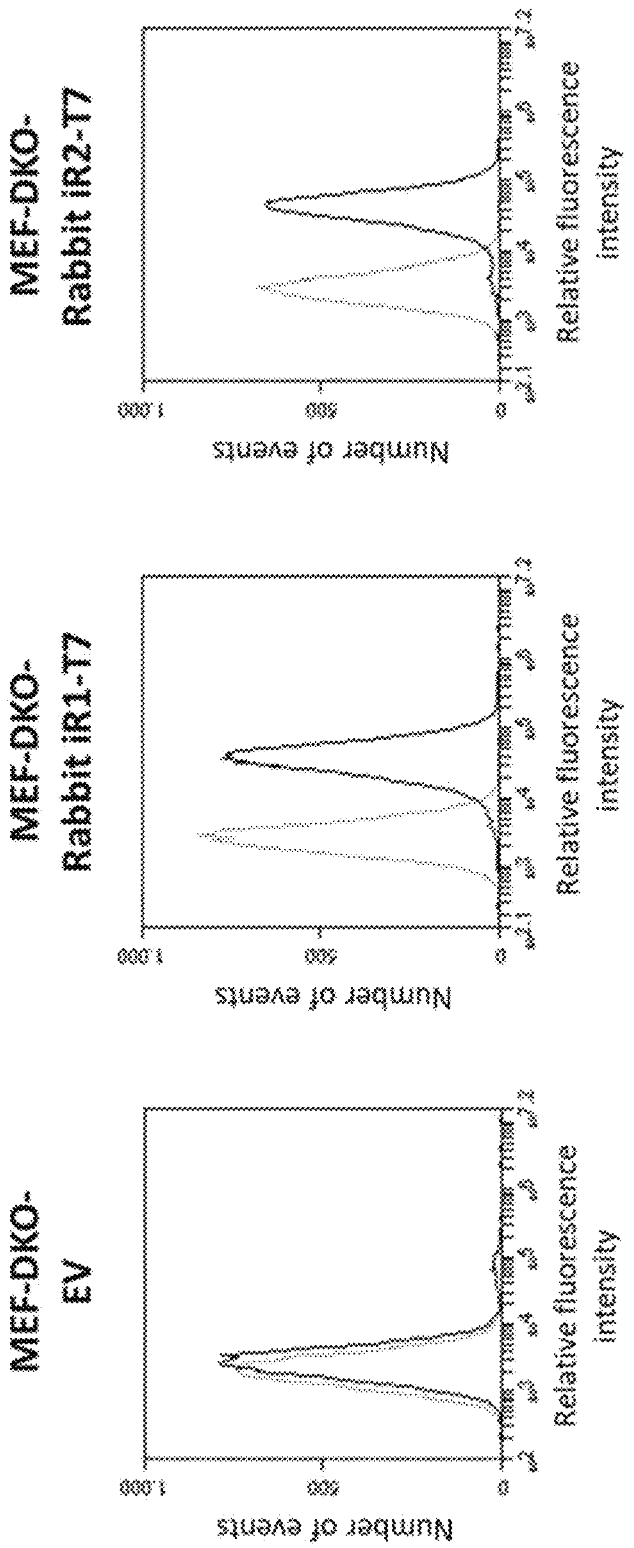
FIG. 7*a* depicts results from FACS analyses on genetically engineered MEF populations, demonstrating that also a T7-tagged version of rabbit iRhom1 full length wild type ectopically expressed by MEF-DKO-Rabbit-iR1-FL-WT-T7 (UniProt Identifier: B8K128) cells as well as a T7-tagged version of rabbit iRhom2 full length wild type ectopically expressed by MEF-DKO-Rabbit-iR2-FL-WT-T7 (UniProt Identifier: GIT7M2) cells, respectively, are localized on the surface of these cells Stainings: gray=secondary antibody only; black=anti-T7-antibody
Figure 7B:
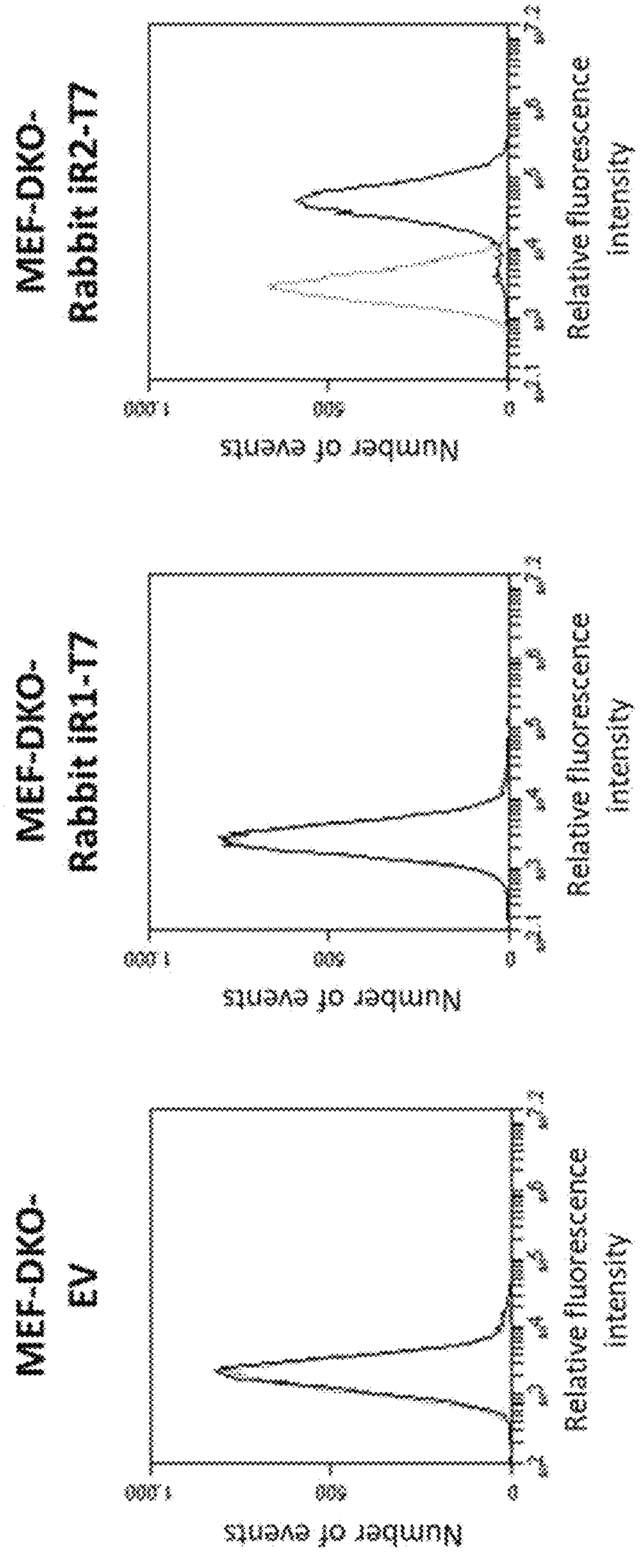
FIG. 7*b* shows results from FACS analyses for the determination of the cross-reactivity of the antibodies of the invention with rabbit, demonstrating that the humanized antibody 16-B-03 as a representative example of antibodies of the invention 16-B-03, 16-B-05, 16-B-07, 23-B-04, 42-B-02 and 42-B-04 clearly recognizes the rabbit iRhom2 variant ectopically expressed by MEF-DKO-Rabbit-iR2-FL-WT-T7, but not the rabbit iRhom1 variant ectopically expressed by MEF-DKO-Rabbit-iR1-FL-WT-T7 cells and, thus, is cross-reactive with rabbit iRhom2 but does not bind to rabbit iRhom1. Stainings: gray=secondary antibody only; black=antibody 16-B-03.

FIGS. 7*a* & 7b show representative results of cross-reactivity analysis to rabbit. When compared to the stainings of MEF-DKO-EV control cells (FIG. 7*a*, left; identical to FIG. 2*a*, left), MEF-DKO-Rabbit-iR1-FL-WT-T7 (FIG. 7*a*, middle) and MEF-DKO-Rabbit-iR2-FL-WT-T7 (FIG. 7*a*, right), the strong increase in relative fluorescence intensity obtained on MEF-DKO-Rabbit-iR1-FL-WT-T7 and MEF-DKO-Rabbit-iR2-FL-WT-T7 with the anti-T7 tag antibody demonstrates that, similarly to the human iRhom1 and 2 variants, the rabbit iRhom1 and 2 variants are also located on the surface of this genetically engineered cell population and, thus, validates it as a suitable test systems for characterizing the antibodies of the invention. Strong binding of the antibody 16-B-03 as a representative example of the humanized antibodies of the invention to the rabbit iRhom2 variant expressed on MEF-DKO-Rabbit-iR2-FL-WT-T7 cells (FIG. 7*b*, right) compared to no significant binding to MEF-DKO-Rabbit-iR1-FL-WT-T7 cells is detectable (FIG. 7*b*, middle). This provides the evidence that the rabbit iRhom2 variant is specifically recognized by the humanized antibody 16-B-03 of the invention, compared to no recognition of rabbit iRhom1, whose presence on the cell surface is verified with the anti-T7 tag antibody (FIG. 7*a*, middle). Similar results were obtained with the humanized antibodies 16-B-05, 16-B-07, 23-B-04, 42-B-02, 42-B-04 of the invention, demonstrating that all these humanized antibodies of the invention recognize rabbit iRhom2 but do not recognize rabbit iRhom1.

Example 6: Analysis of Inhibitory Effects of the Antibodies of the Invention on LPS-Induced TNFα Shedding In Vitro In the following study, ELISA-based TNFα release assays were performed to verify the inhibitory effects of the humanized antibodies of the invention on LPS-induced release of endogenous TNFα from human THP-1 monocytic cells.

The ELISA-based TNFα release assay that was used in this example is described below.

In brief, on day 1, Nunc black MaxiSorp® 96-well plates (Thermo Fisher Scientific, USA) were coated overnight with 100 μl per well of mouse anti-human TNFα capture antibody (provided as part of the DuoSet ELISA kit) at 4 μg/ml TBS at 4° C. On day 2, the capture antibody solution was removed and MaxiSorp® plates were blocked with 300 μl per well of TBS, 1% BSA at room temperature for 1-2 hours. Meanwhile, 20,000 THP-1 (American Type Culture Collection, USA) cells in 80 μl of normal growth medium were seeded in each well of Greiner CELLSTAR V-bottom 96-well plates (Greiner Bio-One, Germany) and pre-incubated with 20 μl per well of standard growth medium supplemented with Batimastat (BB94, Abcam, UK) at 50 μM as positive control (for a final concentration of 10 μM in the resulting 100 μl sample volume), human IgG antibody (BioLegend, USA) at 15 μg/ml as isotype control (for a final concentration of 3 μg/ml in the resulting 100 μl sample volume) or humanized antibodies of the invention at 15 μg/ml (for a final concentration of 3 μg/ml in the resulting 100 μl sample volume) at 37° C., 5% $CO_2$ for 30 minutes. In case of stimulation controls, 20 μl of standard growth medium without test articles were added. Subsequently, cells (except those for unstimulated controls) were stimulated with 20 μl per well of LPS (Sigma-Aldrich, USA) at 300 ng/ml in growth medium for a final concentration of 50 ng/ml at 37° C., 5% $CO_2$ for 2 hours. Afterwards, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human TNFα protein (provided as part of the DuoSet ELISA kit) diluted in TBS at defined concentrations were added to the plate as standard references. Thereafter, 100 μl biotinylated goat anti-human TNFα detection antibody (provided as part of the DuoSet ELISA kit) at 50 ng/ml TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 8A:
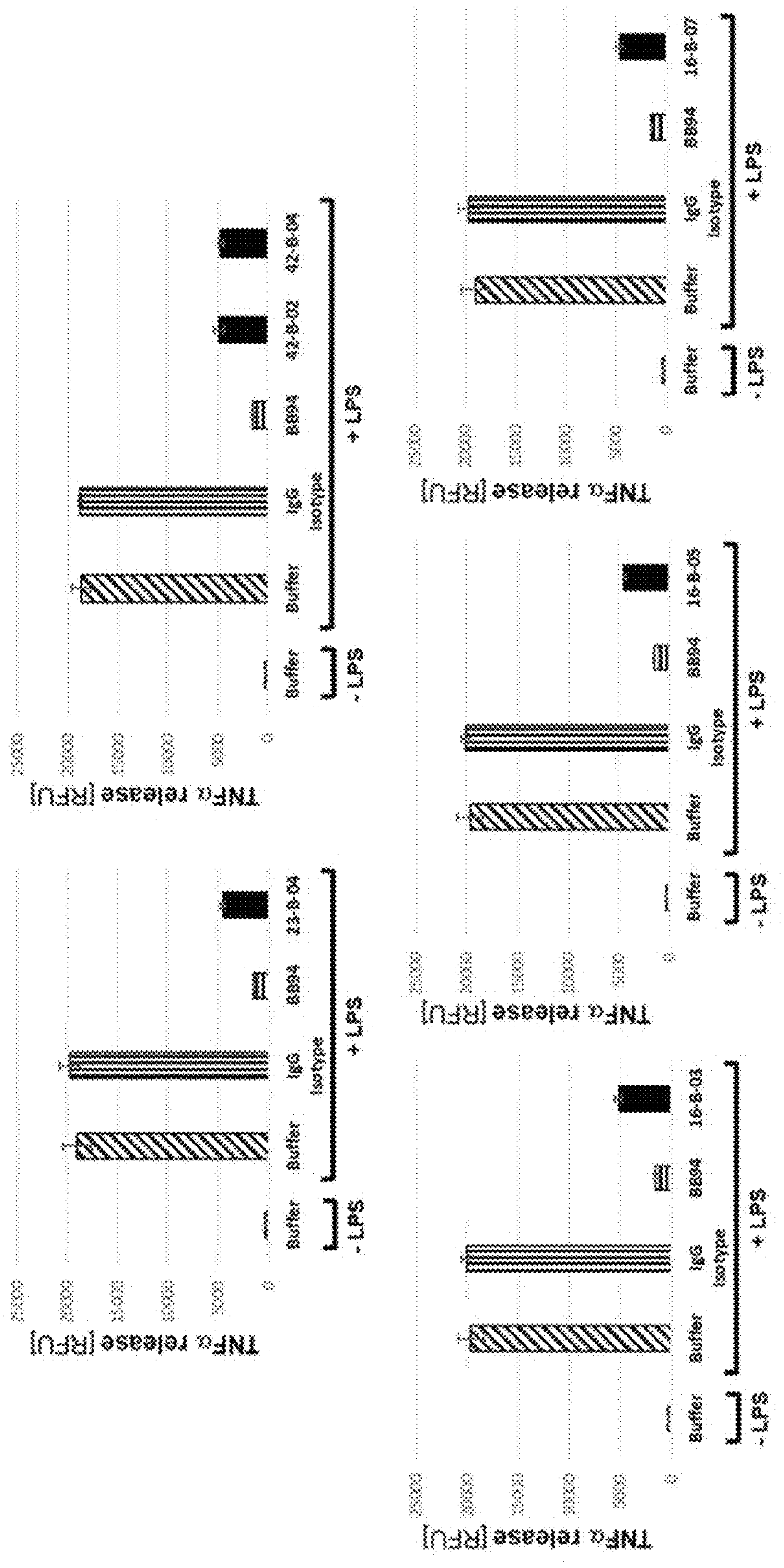
FIG. 8*a* shows results from TNFα release assays, demonstrating the humanized antibodies 16-B-03, 16-B-05, 16-B-07, 23-B-04, 42-B-02 and 42-B-04 of the invention to interfere with LPS-induced shedding of TNFα in THP-1 cells. The data illustrate the effects of test articles in absolute numbers of released TNFα.
Figure 8B:
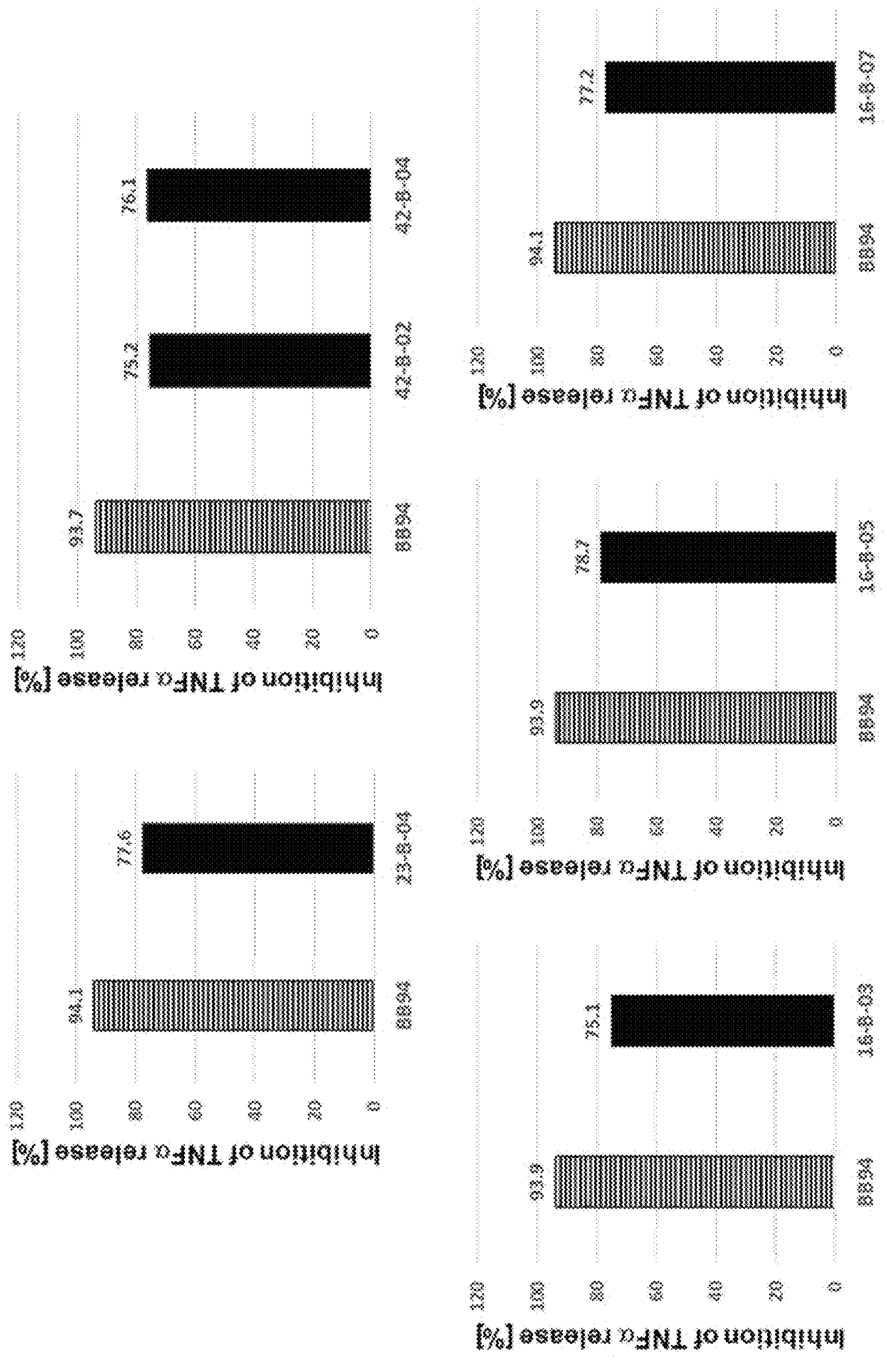
FIG. 8*b* refers to the results depicted in FIG. 8*a* and illustrates the effects of test articles on TNFα release in percent inhibition.

FIG. 8 shows representative results of this experiment demonstrating the effects of test articles on LPS-induced release of TNFα from THP-1 cells in absolute numbers (FIG. 8*a*) and percent inhibition (FIG. 8*b*). While Batimastat (BB94) as a small molecule inhibitor of metalloproteinases serves as positive control and results in strong inhibition of LPS-induced release of TNFα, the presence of IgG isotype control has no significant effect on TNFα shedding. In contrast, an equal concentration of the humanized antibodies 16-B-03, 16-B-05, 16-B-07, 23-B-04, 42-B-02 and 42-B-04 of the invention inhibits LPS-induced release of TNFα from THP-1 cells by 75.1%, 78.7%, 77.2%, 77.6%, 75.2% and 76.1%, respectively.

Example 7: Analysis of Inhibitory Effects of the Antibodies of the Invention on PMA-Induced TNFα Shedding In Vitro In contrast to Example 6, where the inhibitory effects of the antibodies of the invention on LPS-induced release of endogenous TNFα from human THP-1 cells were tested, this analysis was conducted to verify the inhibitory effects of the antibodies of the invention on PMA-induced release of endogenous TNFα from human monocytic U-937 cells.

The ELISA-based TNFα release assay that was used in this example is described below.

In brief, on day 1, Nunc black MaxiSorp® 96-well plates (Thermo Fisher Scientific, USA) were coated overnight with 100 μl per well of mouse anti-human TNFα capture antibody (provided as part of the DuoSet ELISA kit) at 4 μg/ml TBS at 4° C. On day 2, the capture antibody solution was removed and MaxiSorp® plates were blocked with 300 μl per well of TBS, 1% BSA at room temperature for 1-2 hours. Meanwhile, 75,000 U-937 (European Collection of Authenticated Cell Cultures, UK) cells in 80 μl of normal growth medium were seeded in each well of Greiner CELLSTAR V-bottom 96-well plates (Greiner Bio-One, Germany) and pre-incubated with 20 μl per well of standard growth medium supplemented with Batimastat (BB94, Abcam, UK) at 50 μM as positive control (for a final concentration of 10 μM in the resulting 100 μl sample volume), human IgG antibody (BioLegend, USA) at 50 μg/ml as isotype control (for a final concentration of 10 μg/ml in the resulting 100 μl sample volume) or antibodies of the invention at 16.66 μg/ml (for a final concentration of 3.33 μg/ml in the resulting 100 μl sample volume) at 37° C., 5% $CO_2$for 30 minutes. In case of stimulation controls, 20 μl of standard growth medium without test articles were added. Subsequently, cells (except those for unstimulated controls) were stimulated with 20 μl per well of PMA (Sigma-Aldrich, USA) at 150 ng/ml in growth medium for a final concentration of 25 ng/ml at 37° C., 5% $CO_2$ for 1 hour. Afterwards, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human TNFα protein (provided as part of the DuoSet ELISA kit) diluted in TBS at defined concentrations were added to the plate as standard references. Thereafter, 100 μl biotinylated goat anti-human TNFα detection antibody (provided as part of the DuoSet ELISA kit) at 50 ng/ml TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 µl streptavidin-AP (R&D Systems, USA) diluted 1:10,000 in TBS were added to each well and, again protected from direct light, plates were incubated at room temperature for 30 minutes. Following another round of 4 times washing with 350 µl TBS-T (Carl Roth, Germany) per well on a 96-head plate washer (Tecan Group, Switzerland) and careful removal of all buffer traces after the fourth cycle, 100 µl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 9A:
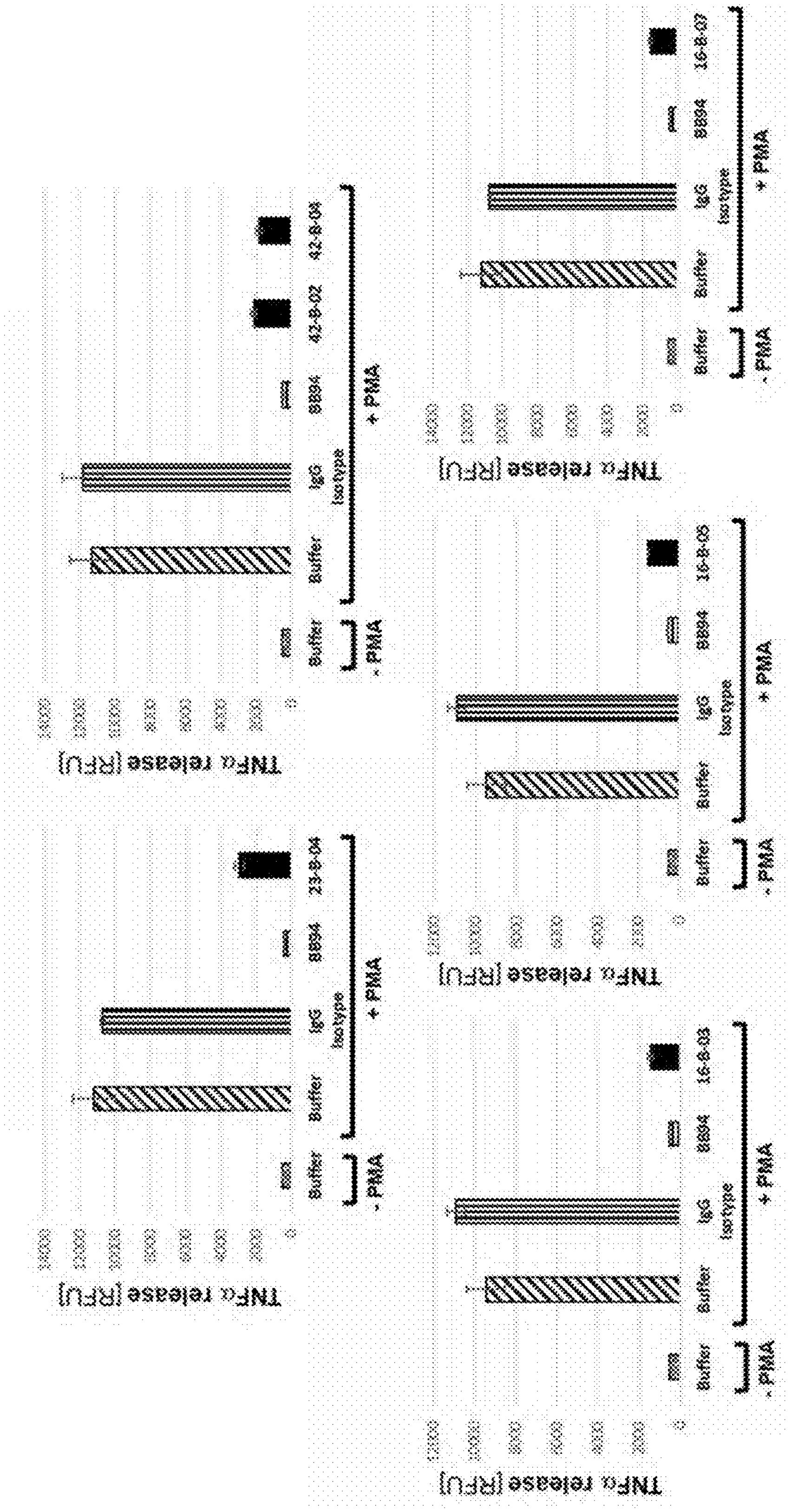
FIG. 9*a* shows results from TNFα release assays, demonstrating the humanized antibodies 16-B-03, 16-B-05, 16-B-07, 23-B-04, 42-B-02 and 42-B-04 of the invention to interfere with PMA-induced shedding of TNFα in U937 cells. The data illustrate the effects of test articles in absolute numbers of released TNFα.
Figure 9B:
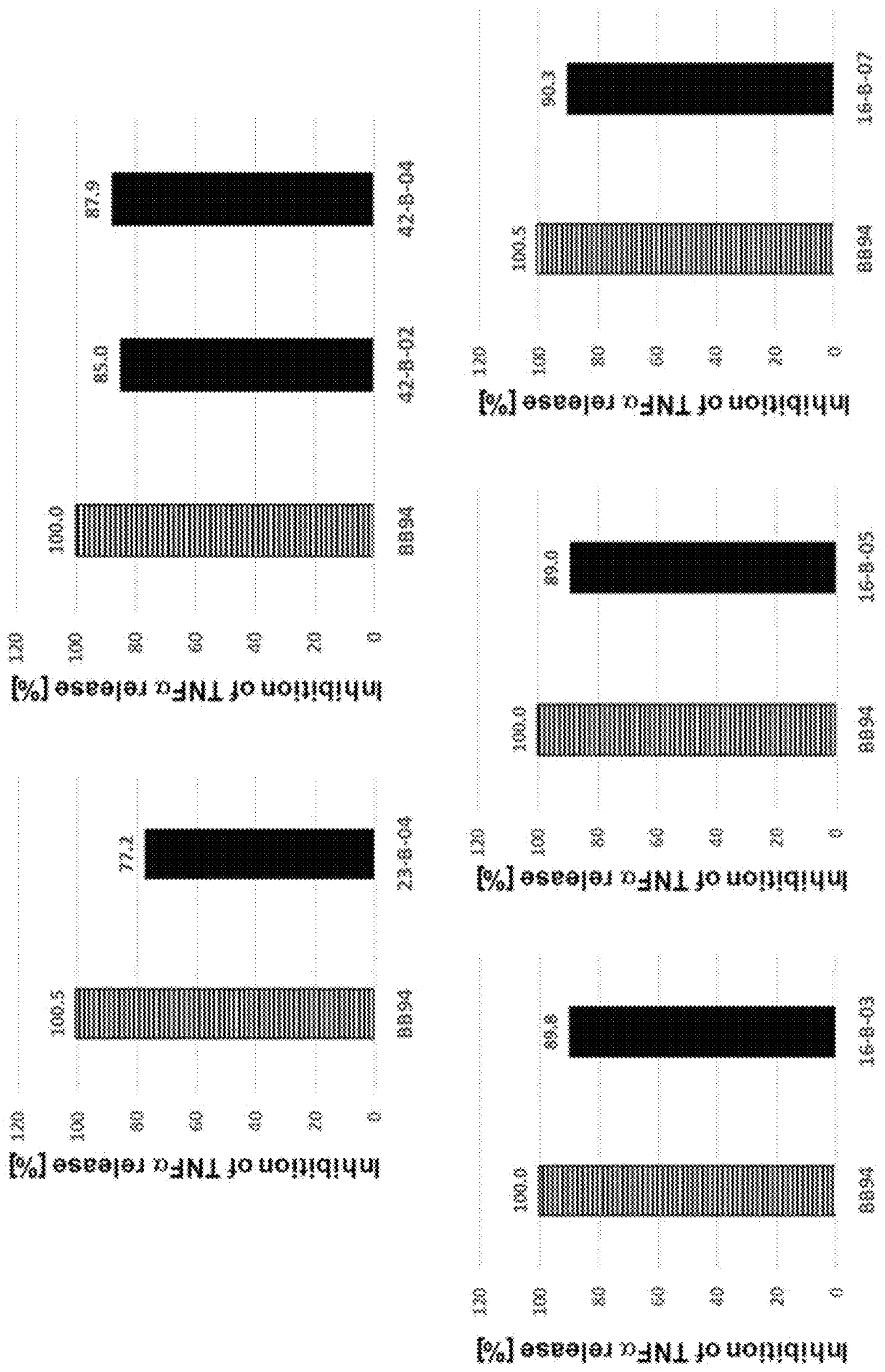
FIG. 9*b* refers to the results depicted in FIG. 9*a* and illustrates the effects of test articles on TNFα release in percent inhibition.

FIG. 9 shows representative results of this experiment demonstrating the effects of test articles on PMA-induced release of TNFα from U-937 cells in absolute numbers (FIG. 9*a*) and percent inhibition (FIG. 9*b*). While Batimastat (BB94) as a small molecule inhibitor of metalloproteinases serves as positive control and results in strong inhibition of PMA-induced release of TNFα, the presence of IgG isotype control has no significant effect on TNFα shedding. In contrast, the humanized antibodies 16-B-03, 16-B-05, 16-B-07, 23-B-04, 42-B-02 and 42-B-04 of the invention inhibit PMA-induced release of TNFα from U-937 cells by 89.8%, 89.0%, 90.3%, 77.2%, 85.0% and 87.9%, respectively.

Example 8: Analysis of Inhibitory Effects of the Antibodies of the Invention on PMA-Induced Interleukin 6 Receptor (IL-6R) Shedding In Vitro In the following study, ELISA-based IL-6R release assays were performed to analyze the inhibitory effects of the antibodies of the invention on PMA-induced release of endogenous IL-6R from human THP-1 monocytic cells.

The ELISA-based IL-6R release assay that was used in this example is described below.

In brief, on day 1, Nunc black MaxiSorp® 96-well plates (Thermo Fisher Scientific, USA) were coated overnight with 100 µl per well of mouse anti-human IL-6R capture antibody (provided as part of the DuoSet ELISA kit) at 2 µg/ml TBS at 4° C. On day 2, the capture antibody solution was removed and MaxiSorp® plates were blocked with 300 µl per well of TBS, 1% BSA at room temperature for 1-2 hours. Meanwhile, 40,000 THP-1 (American Type Culture Collection, USA) cells in 80 µl of normal growth medium were seeded in each well of Greiner CELLSTAR V-bottom 96-well plates (Greiner Bio-One, Germany) and pre-incubated with 20 µl per well of standard growth medium supplemented with Batimastat (BB94, Abcam, UK) at 50 µM as positive control (for a final concentration of 10 µM in the resulting 100 µl sample volume), human IgG antibody (BioLegend, USA) at 15 µg/ml as isotype control (for a final concentration of 3 µg/ml in the resulting 100 µl sample volume) or antibodies of the invention at 15 µg/ml (for a final concentration of 3 µg/ml in the resulting 100 µl sample volume) at 37° C., 5% $CO_2$ for 30 minutes. In case of stimulation controls, 20 µl of standard growth medium without test articles were added. Subsequently, cells (except those for unstimulated controls) were stimulated with 20 µl per well of PMA (Sigma-Aldrich, USA) at 150 ng/ml in growth medium for a final concentration of 25 ng/ml at 37° C., 5% $CO_2$ for 1 hour. Afterwards, the 96-well plates were centrifuged to pellet cells. In parallel, blocking buffer was removed from the MaxiSorp® plates and plates were washed 4 times with 350 µl TBS-T (Carl Roth, Germany) per well on a 96-head plate washer (Tecan Group, Switzerland). To avoid drying-up, 30 µl TBS were added to each well of the MaxiSorp® plates immediately, followed by the transfer of 70 µl cell-free supernatant per sample. Additionally, 100 µl recombinant human IL-6R protein (provided as part of the DuoSet ELISA kit) diluted in TBS at defined concentrations were added to the plate as standard references. Thereafter, 100 µl biotinylated goat anti-human IL-6R detection antibody (provided as part of the DuoSet ELISA kit) at 100 ng/ml TBS were added per well and, protected from direct light, plates were incubated at room temperature for 2 hours. After 4 times washing with 350 µl TBS-T (Carl Roth, Germany) per well on a 96-head plate washer (Tecan Group, Switzerland) and careful removal of all buffer traces after the fourth cycle, 100 µl streptavidin-AP (R&D Systems, USA) diluted 1:10,000 in TBS were added to each well and, again protected from direct light, plates were incubated at room temperature for 30 minutes. Following another round of 4 times washing with 350 µl TBS-T (Carl Roth, Germany) per well on a 96-head plate washer (Tecan Group, Switzerland) and careful removal of all buffer traces after the fourth cycle, 100 µl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 10A:
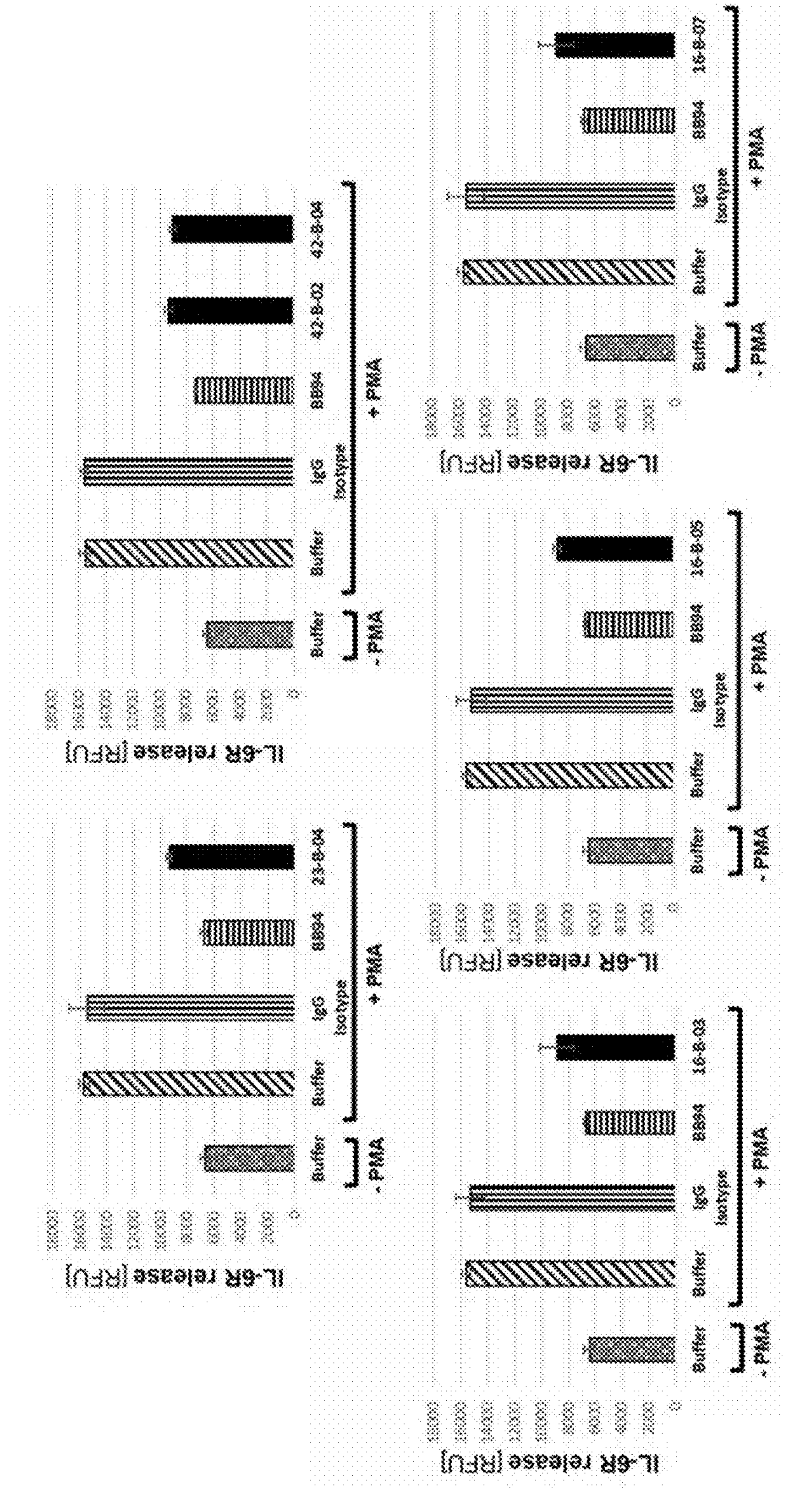
FIG. 10*a* shows results from IL-6R release assays, demonstrating the humanized antibodies 16-B-03, 16-B-05, 16-B-07, 23-B-04, 42-B-02 and 42-B-04 of the invention to interfere with PMA-induced shedding of IL-6R in THP-1 cells. The data illustrate the effects of test articles in absolute numbers of released IL-6R.
Figure 10B:
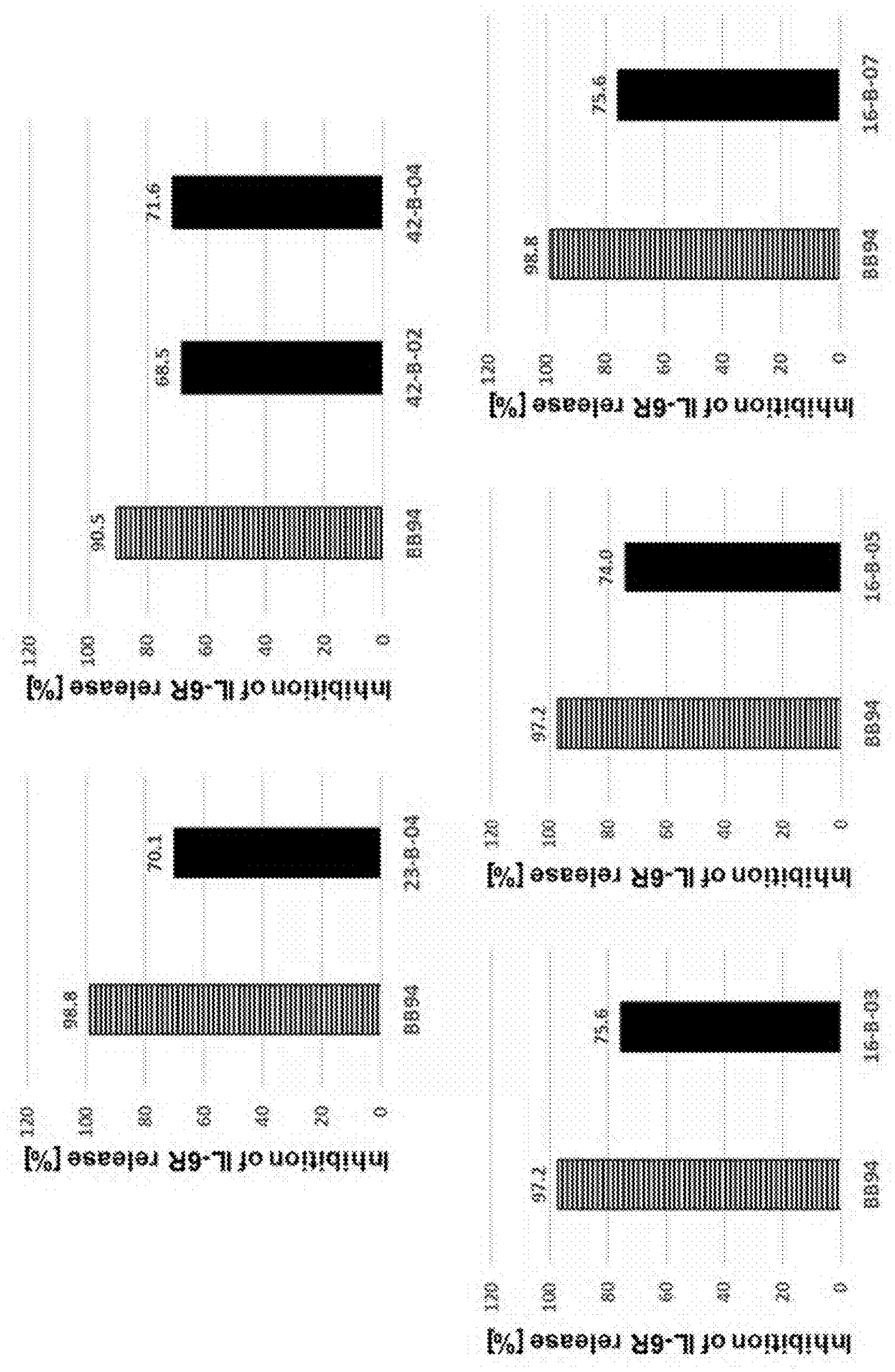
FIG. 10*b* refers to the results depicted in FIG. 10*a* and illustrates the effects of test articles on IL-6R release in percent inhibition.

FIGS. 10*a* & 10b show representative results of this experiment demonstrating the effects of test articles on PMA-induced release of IL-6R from THP-1 cells in absolute numbers (FIG. 10*a*) and percent inhibition (FIG. 10*b*). While Batimastat (BB94) as a small molecule inhibitor of metalloproteinases serves as positive control and results in strong inhibition of PMA-induced release of IL-6R, the presence of IgG isotype control has no significant effect on IL-6R shedding. In contrast, an equal concentration of the humanized antibodies 16-B-03, 16-B-05, 16-B-07, 23-B-04, 42-B-02 and 42-B-04 of the invention inhibits PMA-induced release of IL-6R from THP-1 cells by 75.6%, 74.0%, 75.6%, 70.1%, 68.5% and 71.6%, respectively.

Example 9: Analysis of Inhibitory Effects of the Antibodies of the Invention on PMA-Induced Interleukin 6 Receptor (IL-6R) Shedding In Vitro Complementary to Example 8 described above, ELISA-based IL-6R release assays were performed to verify the inhibitory effects of the antibodies of the invention on PMA-induced release of endogenous IL-6R from human U-937 cells.

The ELISA-based IL-6R release assay that was used in this example is described below.

In brief, on day 1, Nunc black MaxiSorp® 96-well plates (Thermo Fisher Scientific, USA) were coated overnight with 100 µl per well of mouse anti-human IL-6R capture antibody (provided as part of the DuoSet ELISA kit) at 2 µg/ml TBS at 4° C. On day 2, the capture antibody solution was removed and MaxiSorp® plates were blocked with 300 µl per well of TBS, 1% BSA at room temperature for 1-2 hours. Meanwhile, 75,000 U-937 (European Collection of Authenticated Cell Cultures, UK) cells in 80 µl of normal growth medium were seeded in each well of Greiner CELLSTAR V-bottom 96-well plates (Greiner Bio-One, Germany) and pre-incubated with 20 µl per well of standard growth medium supplemented with Batimastat (BB94, Abcam, UK)

at 50 μM as positive control (for a final concentration of 10 μM in the resulting 100 μl sample volume), human IgG antibody (BioLegend, USA) at 50 μg/ml as isotype control (for a final concentration of 10 μg/ml in the resulting 100 μl sample volume) or antibodies of the invention at 16.66 μg/ml (for a final concentration of 3.33 μg/ml in the resulting 100 μl sample volume) at 37° C., 5% $CO_2$ for 30 minutes. In case of stimulation controls, 20 μl of standard growth medium without test articles were added. Subsequently, cells (except those for unstimulated controls) were stimulated with 20 μl per well of PMA (Sigma-Aldrich, USA) at 150 ng/ml in growth medium for a final concentration of 25 ng/ml at 37° C., 5% $CO_2$ for 1 hour. Afterwards, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human IL-6R protein (provided as part of the DuoSet ELISA kit) diluted in TBS at defined concentrations were added to the plate as standard references. Thereafter, 100 μl biotinylated goat anti-human IL-6R detection antibody (provided as part of the DuoSet ELISA kit) at 100 ng/ml TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 11A:
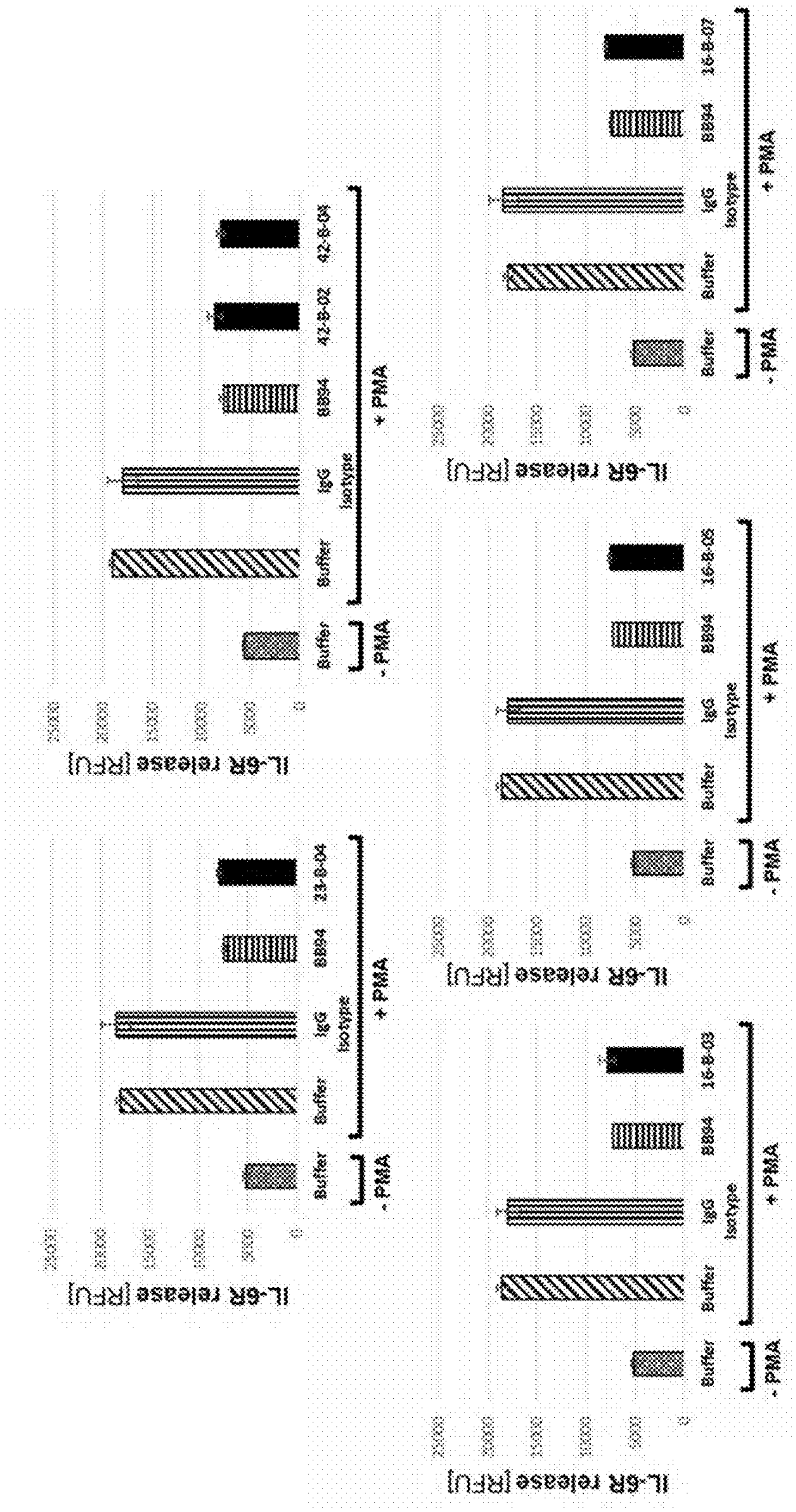
FIG. 11*a* shows results from IL-6R release assays, demonstrating the humanized antibodies 16-B-03, 16-B-05, 16-B-07, 23-B-04, 42-B-02 and 42-B-04 of the invention to interfere with PMA-induced shedding of IL-6R in U937 cells. The data illustrate the effects of test articles in absolute numbers of released IL-6R.
Figure 11B:
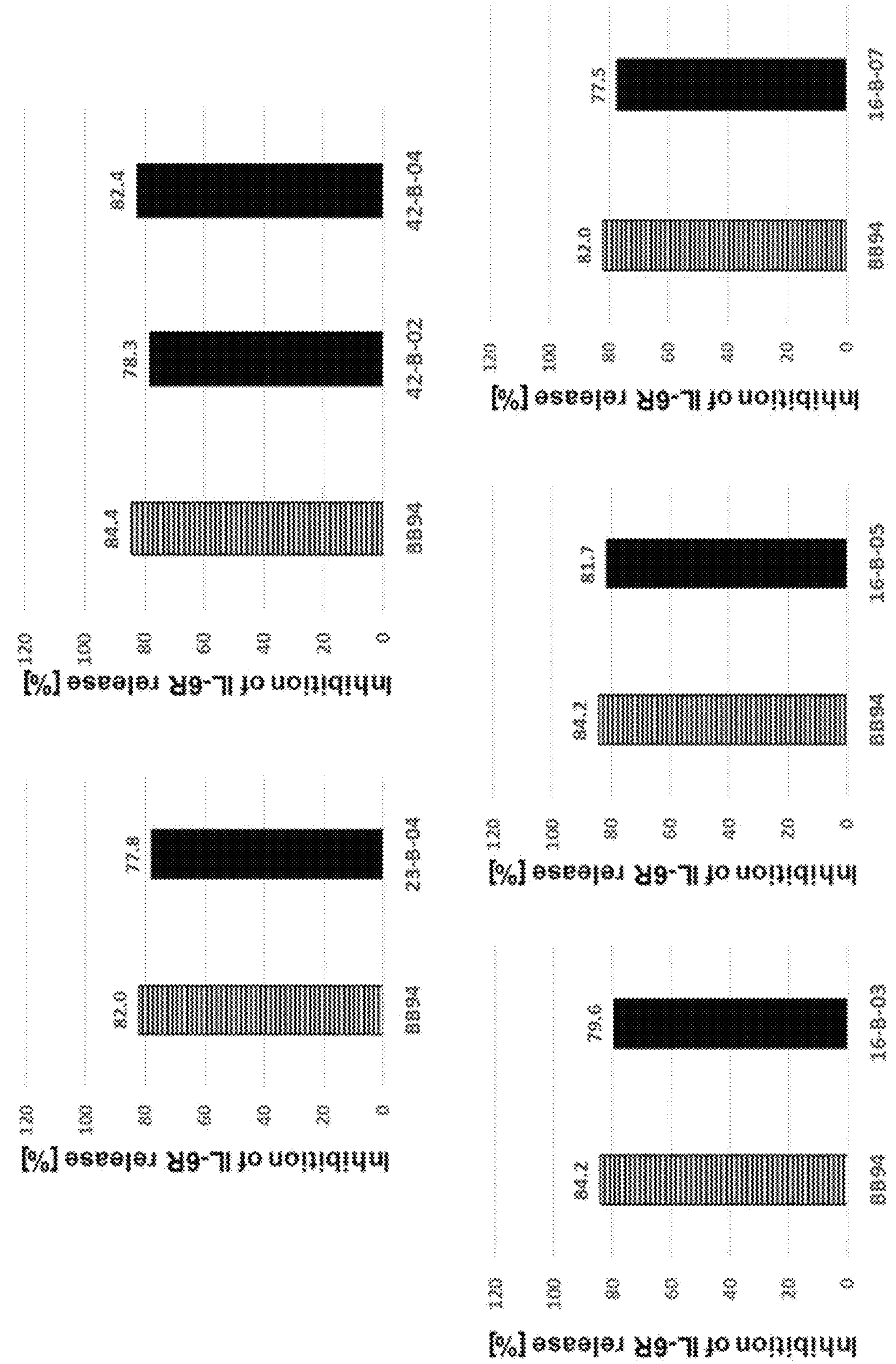
FIG. 11*b* refers to the results depicted in FIG. 11*a* and illustrates the effects of test articles on IL-6R release in percent inhibition.

FIG. 11 shows representative results of this experiment demonstrating the effects of test articles on PMA-induced release of IL-6R from U-937 cells in absolute numbers (FIG. 11*a*) and percent inhibition (FIG. 11*b*). While Batimastat (BB94) as a small molecule inhibitor of metalloproteinases serves as positive control and results in strong inhibition of PMA-induced release of IL-6R, the presence of IgG isotype control has no significant effect on IL-6R shedding. In contrast, the humanized antibodies 16-B-03, 16-B-05, 16-B-07, 23-B-04, 42-B-02 and 42-B-04 of the invention inhibit PMA-induced release of IL-6R from U-937 cells by 79.6%, 81.7%, 77.5%, 77.8%, 78.3% and 82.4%, respectively.

Example 10: Analysis of Inhibitory Effects of the Antibodies of the Invention on PMA-Induced Heparin-Binding EGF-Like Growth Factor (HB-EGF) Shedding In Vitro In the following study, ELISA-based HB-EGF release assays were performed to analyze the inhibitory effects of the antibodies of the invention on PMA-induced release of endogenous HB-EGF from human THP-1 monocytic cells.

The ELISA-based HB-EGF release assay that was used in this example is described below.

In brief, on day 1, Nunc black MaxiSorp® 96-well plates (Thermo Fisher Scientific, USA) were coated overnight with 100 μl per well of rat anti-human HB-EGF capture antibody (provided as part of the DuoSet ELISA kit) at 2 μg/ml TBS at 4° C. 40,000 THP-1 (American Type Culture Collection, USA) cells in 80 μl of normal growth medium were seeded in each well of Greiner CELLSTAR V-bottom 96-well plates (Greiner Bio-One, Germany) and pre-incubated with 20 μl per well of standard growth medium supplemented with Batimastat (BB94, Abcam, UK) at 50 μM as positive control (for a final concentration of 10 μM in the resulting 100 μl sample volume), human IgG antibody (BioLegend, USA) at 15 μg/ml as isotype control (for a final concentration of 3 μg/ml in the resulting 100 μl sample volume) or antibodies of the invention at 15 μg/ml (for a final concentration of 3 μg/ml in the resulting 100 μl sample volume) at 37° C., 5% $CO_2$ for 30 minutes. In case of stimulation controls, 20 μl of standard growth medium without test articles were added. Subsequently, cells (except those for unstimulated controls) were stimulated with 20 μl per well of PMA (Sigma-Aldrich, USA) at 150 ng/ml in growth medium for a final concentration of 25 ng/ml at 37° C., 5% $CO_2$ for 24 hours. On day 2, the capture antibody solution was removed and MaxiSorp® plates were blocked with 300 μl per well of TBS, 1% BSA at room temperature for 1-2 hours. Afterwards, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human HB-EGF protein (provided as part of the DuoSet ELISA kit) diluted in TBS at defined concentrations were added to the plate as standard references. Thereafter, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl biotinylated goat anti-human HB-EGF detection antibody (provided as part of the DuoSet ELISA kit) at 50 ng/ml TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 12A:
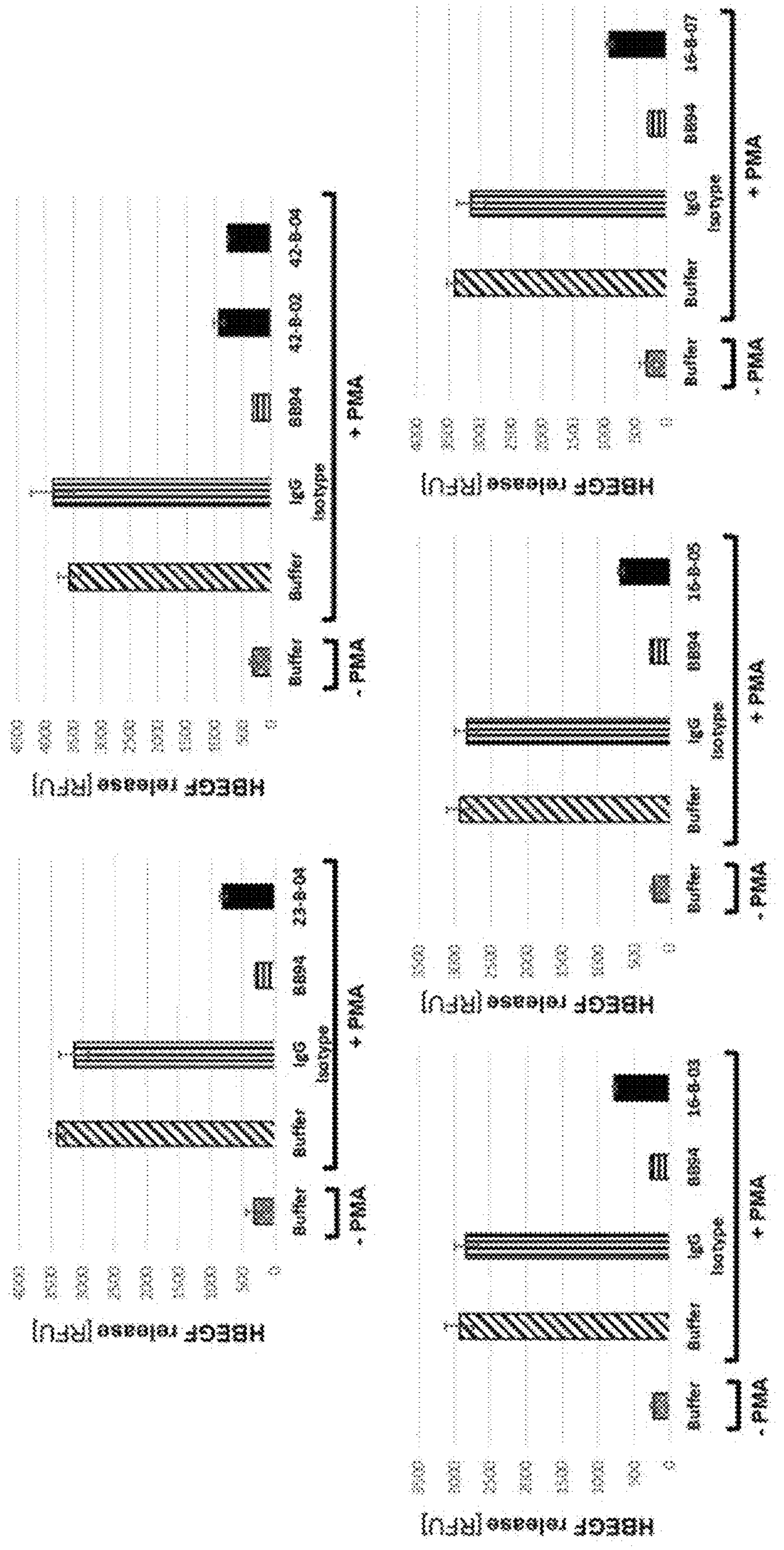
FIG. 12*a* shows results from HB-EGF release assays, demonstrating the humanized antibodies 16-B-03, 16-B-05, 16-B-07, 23-B-04, 42-B-02 and 42-B-04 of the invention to interfere with PMA-induced shedding of HB-EGF in THP-1 cells. The data illustrate the effects of test articles in absolute numbers of released HB-EGF.
Figure 12B:
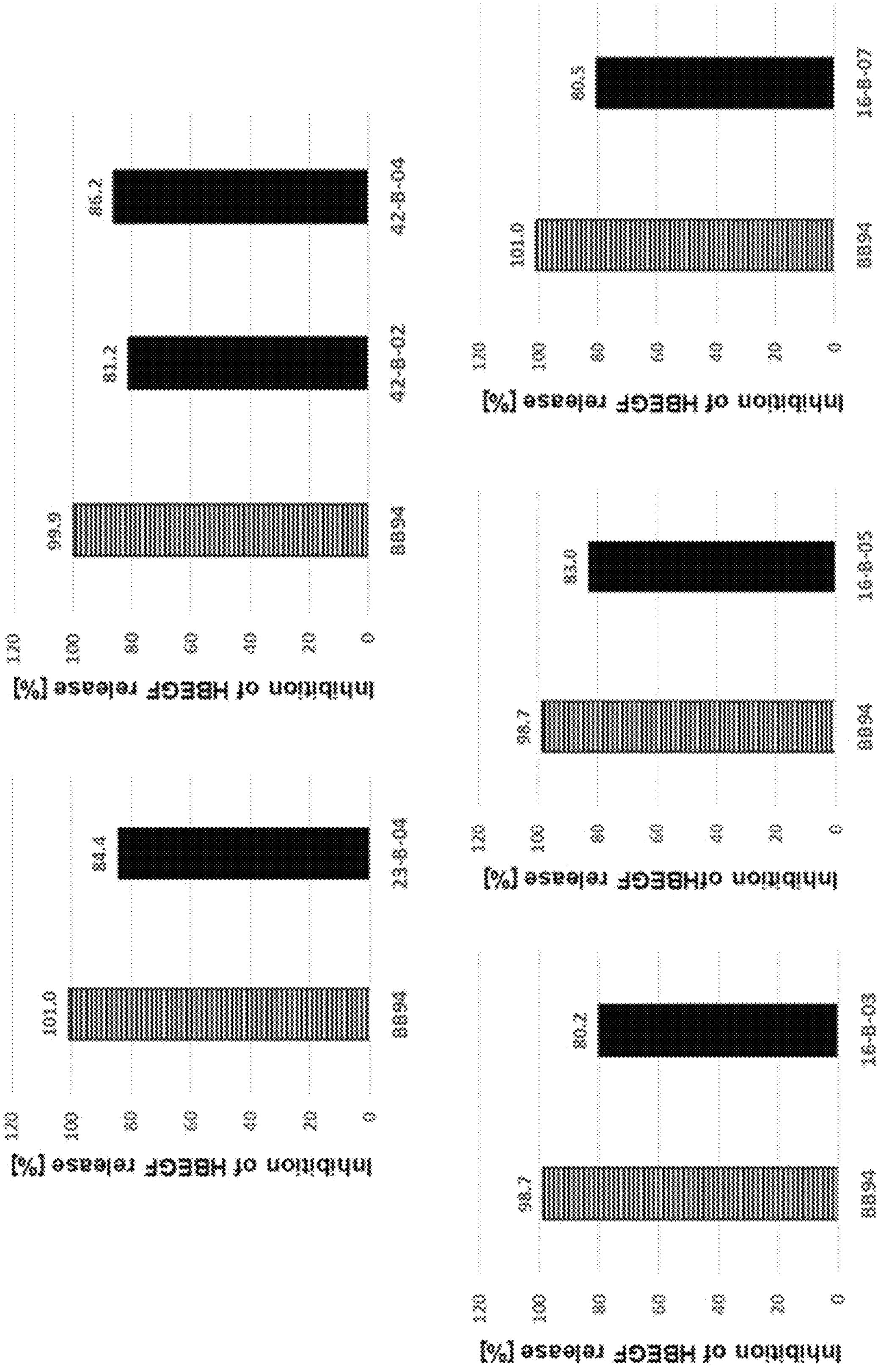
FIG. 12*b* refers to the results depicted in FIG. 12*a* and illustrates the effects of test articles on HB-EGF release in percent inhibition.

FIG. 12 shows representative results of this experiment demonstrating the effects of test articles on PMA-induced release of HB-EGF from THP-1 cells in absolute numbers (FIG. 12*a*) and percent inhibition (FIG. 12*b*). While Batimastat (BB94) as a small molecule inhibitor of metalloproteinases serves as positive control and results in strong inhibition of PMA-induced release of HB-EGF, the presence of human IgG isotype control has no significant effect on HB-EGF shedding. In contrast, an equal concentration of the humanized antibodies 16-B-03, 16-B-05, 16-B-07, 23-B-04, 42-B-02 and 42-B-04 of the invention inhibits PMA-induced release of HB-EGF from THP-1 cells by 80.2%, 83.0%, 80.5%, 84.4%, 81.2% and 86.2%, respectively.

Example 11: Analysis of Inhibitory Effects of the Antibodies of the Invention on PMA-Induced HB-EGF Shedding In Vitro Complementary to Example 10 described above, ELISA-based HB-EGF release assays were performed to verify the inhibitory effects of the antibodies of the invention on PMA-induced release of endogenous HB-EGF from human U-937 cells.

The ELISA-based HB-EGF release assay that was used in this example is identical with the one described in Example 10, with the only difference, that U-937 (European Collection of Authenticated Cell Cultures, UK) cells (80,000cells/well) were used instead of THP-1 (American Type Culture Collection, USA) cells.

Figure 13A:
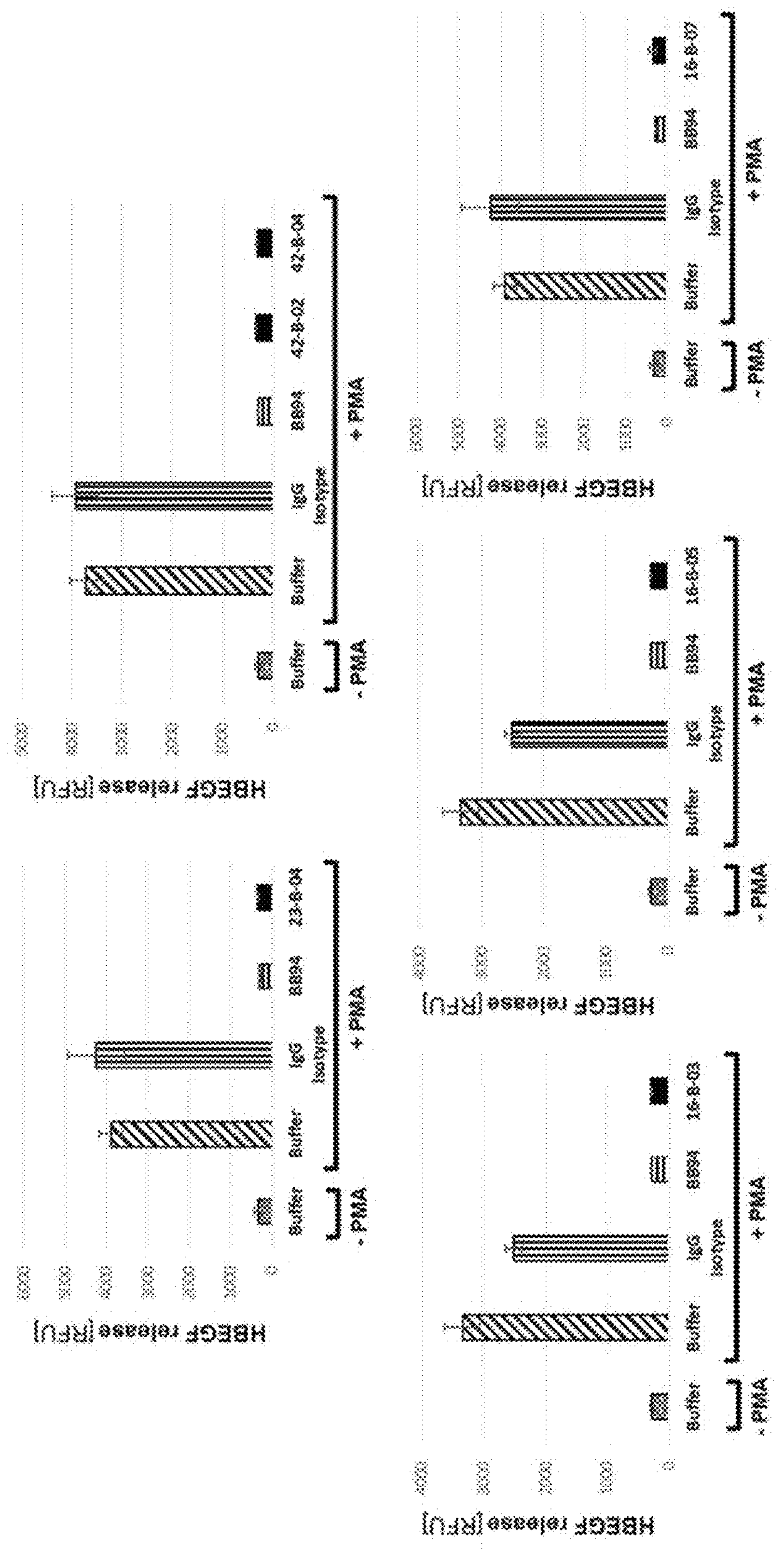
FIG. 13*a* shows results from HB-EGF release assays, demonstrating the humanized antibodies 16-B-03, 16-B-05, 16-B-07, 23-B-04, 42-B-02 and 42-B-04 of the invention to interfere with PMA-induced shedding of HB-EGF in U937 cells. The data illustrate the effects of test articles in absolute numbers of released HB-EGF.
Figure 13B:
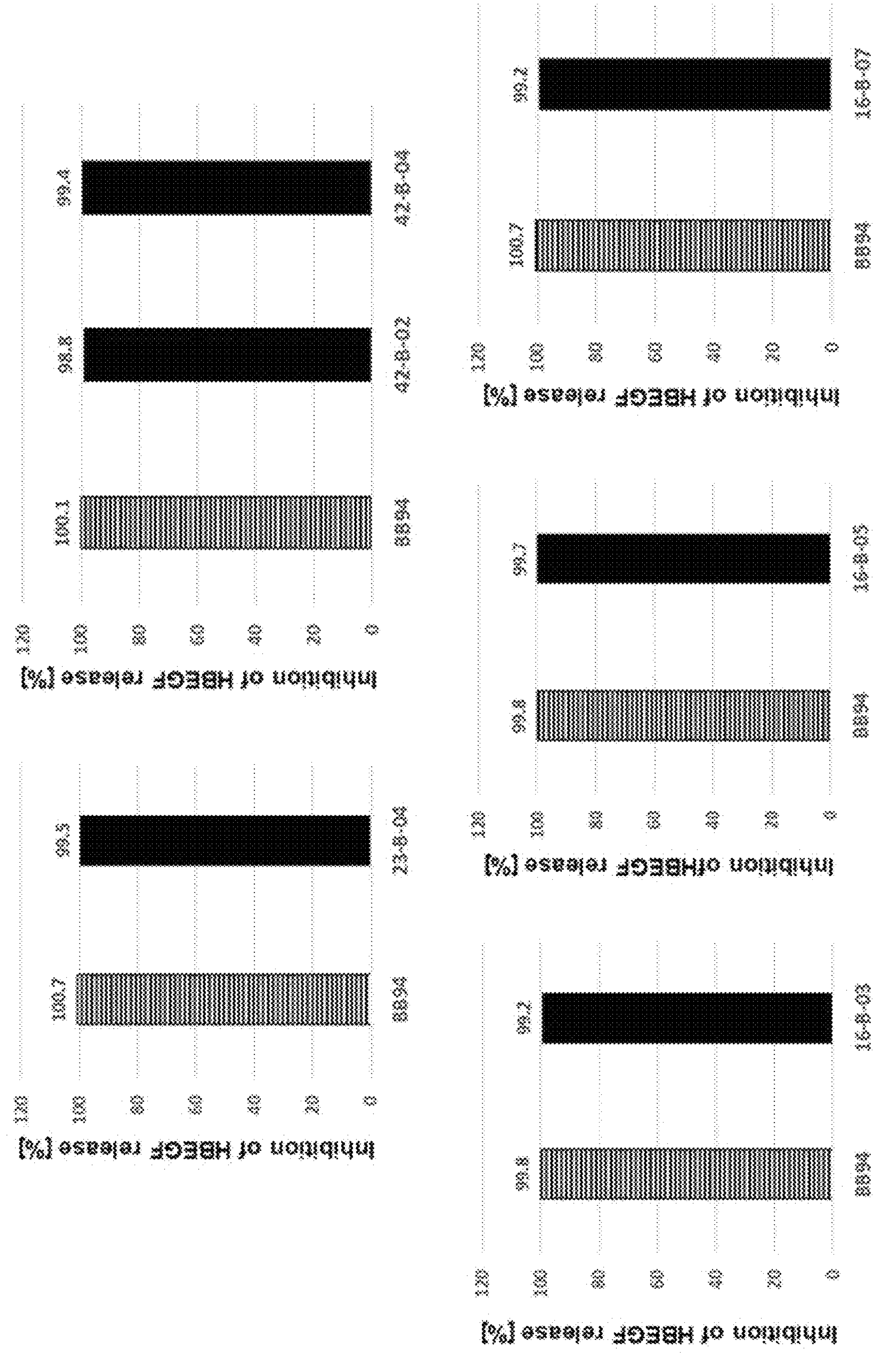
FIG. 13*b* refers to the results depicted in FIG. 13*a* and illustrates the effects of test articles on HB-EGF release in percent inhibition.

FIG. 13 shows representative results of this experiment demonstrating the effects of test articles on PMA-induced release of HB-EGF from U-937 cells in absolute numbers (FIG. 13*a*) and percent inhibition (FIG. 13*b*). While Batimastat (BB94) as a small molecule inhibitor of metalloproteinases serves as positive control and results in strong inhibition of PMA-induced release of HB-EGF, the presence of human IgG isotype control has almost no effect on HB-EGF shedding. In contrast, an equal concentration of the humanized antibodies 16-B-03, 16-B-05, 16-B-07, 23-B-04, 42-B-02 and 42-B-04 of the invention inhibits PMA-induced release of HB-EGF from U-937 cells by 99.2%, 99.7%, 99.2%, 99.5%, 98.8% and 99.4%, respectively.

Example 12: Analysis of Inhibitory Effects of the Antibodies of the Invention on PMA-Induced Transforming Growth Factor Alpha (TGFα) Shedding In Vitro In the following study, ELISA-based TGFα release assays were performed to analyze the inhibitory effects of the antibodies of the invention on PMA-induced release of endogenous TGFα from human PC3 prostate cancer cells.

The ELISA-based TGFα release assay that was used in this example is described below.

In brief, on day 1, Nunc black MaxiSorp® 96-well plates (Thermo Fisher Scientific, USA) were coated overnight with 100 μl per well of goat anti-human TGFα capture antibody (provided as part of the DuoSet ELISA kit) at 0.4 μg/ml TBS at 4° C. 80,000 PC3 (European Collection of Authenticated Cell Cultures, UK) cells in 100 μl of normal growth medium were seeded in each well of F-bottom 96-well cell culture plates (Corning, USA) and incubated at 37° C., 5% $CO_2$ overnight. On day 2, the capture antibody solution was removed and MaxiSorp® plates were blocked with 300 μl per well of TBS, 1% BSA at room temperature for 1-2 hours. Meanwhile, cells were washed once with PBS and pre-incubated in 80 μl of OptiMEM medium with 20 μl per well of OptiMEM medium supplemented with Batimastat (BB94, Abcam, UK) at 50 μM as positive control (for a final concentration of 10 μM in the resulting 100 μl sample volume), human IgG antibody (BioLegend, USA) at 50 μg/ml as isotype control (for a final concentration of 10 μg/ml in the resulting 100 μl sample volume) or antibodies of the invention at 50 μg/ml (for a final concentration of 10 μg/ml in the resulting 100 μl sample volume) at 37° C., 5% $CO_2$ for 30 minutes. In case of stimulation controls, 20 μl of OptiMEM medium without test articles were added. Subsequently, cells (except those for unstimulated controls) were stimulated with 20 μl per well of PMA (Sigma-Aldrich, USA) at 150 ng/ml in OptiMEM for a final concentration of 25 ng/ml at 37° C., 5% $CO_2$ for 2 hours. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 20 μl TBS were added to each well of the MaxiSorp® plates immediately, followed by the transfer of 80 μl cell-free supernatant per sample. Additionally, 100 μl recombinant human TGFα protein (provided as part of the DuoSet ELISA kit) diluted in TBS at defined concentrations were added to the plate as standard references. Thereafter, 100 μl biotinylated goat anti-human TGFα detection antibody (provided as part of the DuoSet ELISA kit) at 37.5 ng/ml in TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 14A:
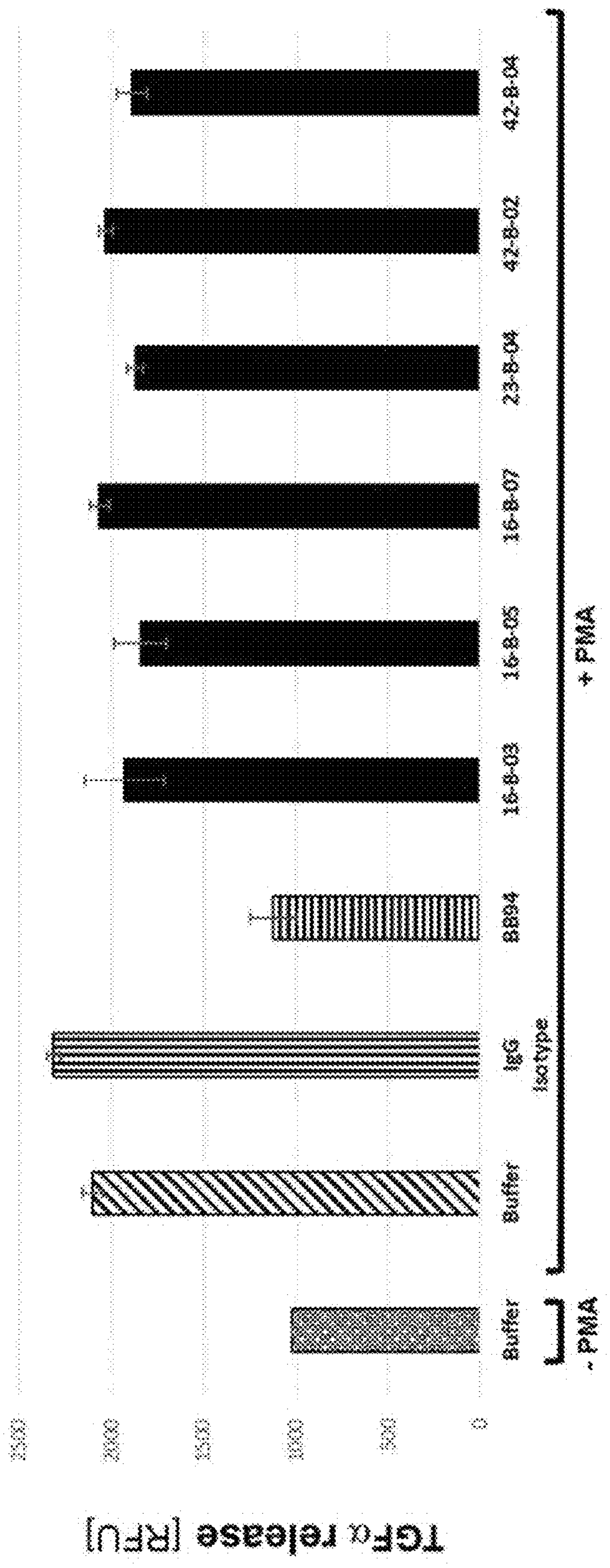
FIG. 14*a* shows results from TGFα release assays, demonstrating the humanized antibodies 16-B-03, 16-B-05, 16-B-07, 23-B-04, 42-B-02 and 42-B-04 of the invention to weakly interfere with PMA-induced shedding of TGFα in PC3 cells. The data illustrate the effects of test articles in absolute numbers of released TGFα.
Figure 14B:
FIG. 14*b* refers to the results depicted in FIG. 14*a* and illustrates the effects of test articles on TGFα release in percent inhibition.

FIG. 14 shows representative results of this experiment demonstrating the effects of test articles on PMA-induced release of TGFα from PC3 cells in absolute numbers (FIG. 14*a*) and percent inhibition (FIG. 14*b*). While Batimastat (BB94) as a small molecule inhibitor of metalloproteinases serves as positive control and results in 90.7% inhibition of PMA-induced release of TGFα, the presence of IgG isotype control has no inhibitory effect on TGFα shedding. Only a very moderate effect on TGFα shedding was detected in the presence of equal concentrations of the humanized antibodies 16-B-03, 16-B-05, 16-B-07, 23-B-04, 42-B-02 and 42-B-04 of the invention which inhibit PMA-induced release of TGFα from PC3 cells by 15.9%, 23.8%, 3.3%, 21.3%, 6.4% and 19.5%, respectively.

Example 13: Assessment of Binding Specificity of the Antibodies of the Invention in Cell Lines Endogenously Expressing iRhom2

In this study, binding specificity analyses of the humanized antibody 42-B-02 as a representative example of the antibodies of the invention in cell lines endogenously expressing iRhom2 were performed. The studies were conducted on RPMI-8226 cells, a human B lymphocytic cell line endogenously expressing iRhom2 but being endogenously negative for iRhom1, on THP-1 cells, a human monocytic cell line endogenously expressing both iRhom2 and iRhom1 and on RH-30 cells, a human fibroblastic cell line endogenously negative for iRhom2 but endogenously expressing iRhom1.

In brief, human RPMI-8226 cells (Deutsche Sammlung von Mikroorganismen und Zellkulturen, Germany), THP-1 cells (American Type Culture Collection, USA) and RH-30 cells (Deutsche Sammlung von Mikroorganismen und Zellkulturen, Germany) were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $2\times10^5$ cells per well. In order to pellet cells and remove supernatants, the plates were centrifuged at 1,500 rpm and 4° C. for 3 minutes. For primary staining, cells were resuspended in 100 μl per well of either FACS buffer alone (controls) or 3 μg/ml of the antibodies of the invention in FACS buffer and incubated on ice for 1 hour. Afterwards, plates were centrifuged at 1,500 rpm and 4° C. for 3 minutes and washed twice with 200 μl per well of FACS buffer. For secondary staining, cells were spun down and resuspended in 100 μl per well of PE-conjugated goat anti-human IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 μl per well of FACS buffer. Finally, cells were resuspended in 150 μl per well of FACS buffer and analyzed using a BD Accuri™ C6 Plus flow cytometer (Becton Dickinson, Germany).

Figure 15:
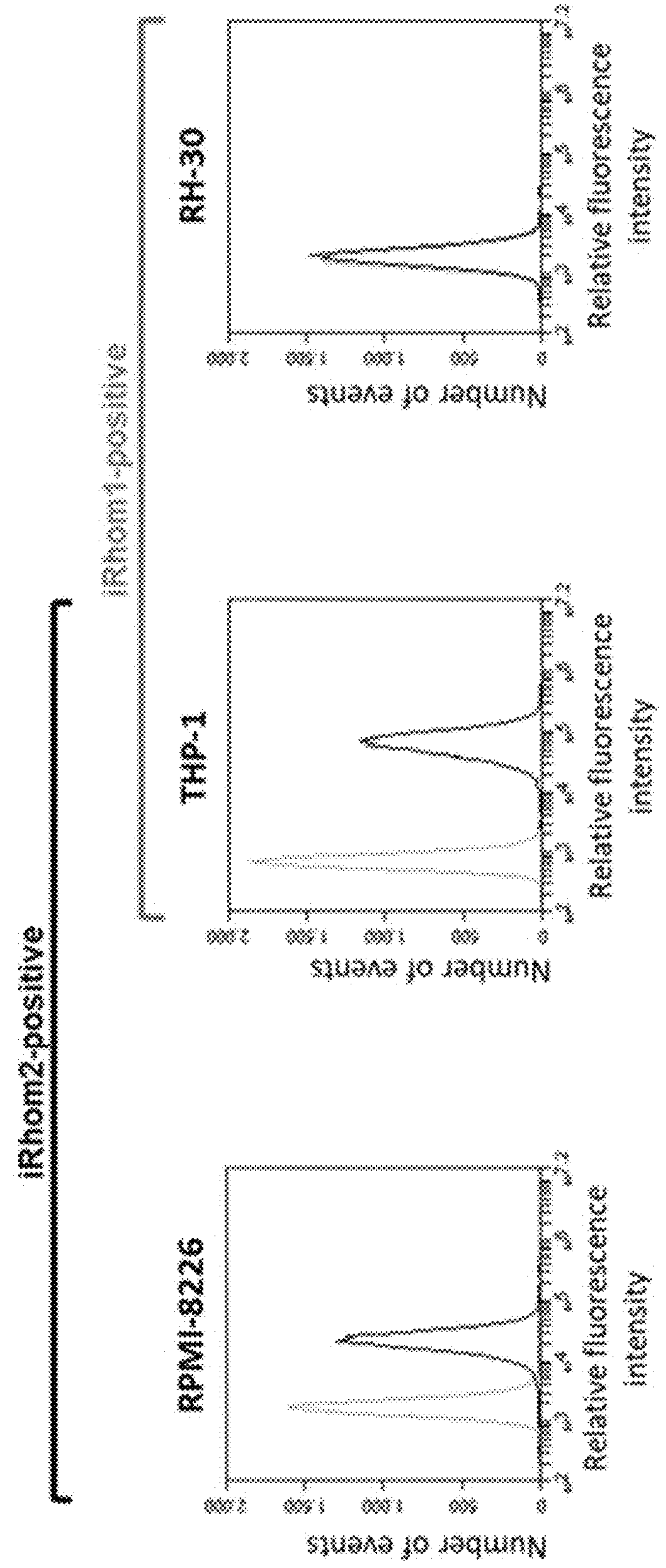
FIG. 15 shows results from FACS analyses for the determination of specificity of the antibodies of the invention, demonstrating that the humanized antibody 42-B-02 as a representative example of the antibodies of the invention binds to RPMI-8226 (left panel) and THP-1 cells (middle panel), both of which express iRhom2 endogenously, but does not bind to RH-30 cells (right panel), which do not express iRhom2 endogenously and, thus, is specifically recognizing endogenous human iRhom2. The analyzed antibodies result from transient expression of the respective heavy chain/kappa light chain pairs in CHO cells. Stainings: gray=secondary antibody only; black=humanized antibody 42-B-02

FIG. 15 shows representative results of this study. As compared to control samples incubated with secondary antibody only (gray), co-incubation of both RPMI-8226 and THP-1 cells, both of which express iRhom2 endogenously, with humanized antibody 42-B-02 as a representative example of the antibodies of the invention (left & middle, black) leads to a strong shift in relative fluorescence intensity in both cell lines, demonstrating a strong binding of the humanized antibody 42-B-02 of the invention to the two human cell lines endogenously positive for iRhom2. In contrast, no binding of the humanized antibody 42-B-02 as a representative example of the antibodies of the invention (right, black) to RH-30 cells, which do not express iRhom2, is detectable, providing evidence that endogenously expressed iRhom2 is specifically recognized by the humanized antibody 42-B-02 of the invention.

Example 14: Epitope Mapping of the Antibodies of the Invention Based on Single Amino Acid Substitutions or Deletions in the Large Extracellular Loop Nowadays, several methods to map epitopes recognized by antibodies are available, including X-ray co-crystallography, array-based oligo-peptide scanning, hydrogen-deuterium exchange or cross-linking-coupled mass spectrometry. Genetic approaches such as site-directed mutagenesis or high-throughput shotgun mutagenesis allow epitope mapping at single amino acid resolution. However, amino acid substitutions at random positions of the protein or substitutions by non-related amino acids bear the risk of causing conformational changes and/or functional loss of the protein and, thus, may result in misinterpretations as to whether the substituted amino acid contributes to an antibody epitope. An elegant and generally accepted way to circumvent these risks is to replace individual amino acids of a given protein by the homologous amino acids of a structurally related protein, i.e. an orthologue or a closely related family member, provided these related proteins are not being recognized by the antibodies of interest. As described earlier, both is true for all humanized anti-human iRhom2 antibodies of the invention, since they were demonstrated to be neither cross-reactive with the mouse orthologue (example 3) nor to bind to the closely related family member human iRhom1 (example 4). Additionally, replacement of individual amino acids of a given protein by the amino acid alanine represents a widely used approach to map epitopes.

Thus, in an approach to identify single amino acids that contribute to binding of the antibodies of the invention, plasmids for a set of 137 human iRhom2 variants with either mouse iRhom2-related single amino acid substitutions, human iRhom1-related single amino acid substitutions or single amino acid substitutions to alanine were designed. These 137 substitutions reflect amino acids in the large extracellular loop 1 (AA502 to AA594 of human iRhom2), that are either non-identical in human iRhom2 versus mouse iRhom2, non-identical in human iRhom2 versus human iRhom1 or where the respective amino acid in human iRhom2 was replaced by alanine. Instead of the amino acid of human iRhom2, the amino acid at the corresponding position of mouse iRhom2 or human iRhom1 was introduced or the amino acid of human iRhom2 was replaced by alanine. In case no corresponding amino acid exists in mouse iRhom2 or human iRhom1, the respective amino acid of human iRhom2 was deleted, resulting in the variants hiR2-FL-Q502R-T7, hiR2-FL-N503A-T7, hiR2-FL-D504A-T7, hiR2-FL-H505R-T7, hiR2-FL-H505A-T7, hiR2-FL-S506A-T7, hiR2-FL-G507A-T7, hiR2-FL-C508A-T7, hiR2-FL-I509V-T7, hiR2-FL-I509A-T7, hiR2-FL-Q510A-T7, hiR2-FL-T511A-T7, hiR2-FL-Q512L-T7, hiR2-FL-Q512S-T7, hiR2-FL-Q512A-T7, hiR2-FL-R513K-T7, hiR2-FL-R513E-T7, hiR2-FL-R513A-T7, hiR2-FL-K514E-T7, hiR2-FL-K514A-T7, hiR2-FL-D515E-T7, hiR2-FL-D515A-T7, hiR2-FL-C516A-T7, hiR2-FL-S517A-T7, hiR2-FL-E518S-T7, hiR2-FL-E518A-T7, hiR2-FL-T519A-T7, hiR2-FL-L520A-T7, hiR2-FL-A521S-T7, hiR2-FL-T522V-T7, hiR2-FL-T522A-T7, hiR2-FL-F523W-T7, hiR2-FL-F523A-T7, hiR2-FL-V524A-T7, hiR2-FL-K525A-T7, hiR2-FL-W526A-T7, hiR2-FL-Q527P-T7, hiR2-FL-Q527A-T7, hiR2-FL-D528N-T7, hiR2-FL-D528I-T7, hiR2-FL-D528A-T7, hiR2-FL-D529H-T7, hiR2-FL-D529A-T7, hiR2-FL-T530P-T7, hiR2-FL-T530A-T7, hiR2-FL-G531S-T7, hiR2-FL-G531A-T7, hiR2-FL-P532A-T7, hiR2-FL-P533--T7, hiR2-FL-P533A-T7, hiR2-FL-M534S-T7, hiR2-FL-M534--T7, hiR2-FL-M534A-T7, hiR2-FL-D535--T7, hiR2-FL-D535A-T7, hiR2-FL-K536--T7, hiR2-FL-K536A-T7, hiR2-FL-S537E-T7, hiR2-FL-S537A-T7, hiR2-FL-D538L-T7, hiR2-FL-D538A-T7, hiR2-FL-L539A-T7, hiR2-FL-G540S-T7, hiR2-FL-G540A-T7, hiR2-FL-Q541H-T7, hiR2-FL-Q541A-T7, hiR2-FL-K542A-T7, hiR2-FL-R543Q-T7, hiR2-FL-R543A-T7, hiR2-FL-T544P-T7, hiR2-FL-T544Q-T7, hiR2-FL-T544A-T7, hiR2-FL-S545F-T7, hiR2-FL-S545A-T7, hiR2-FL-G546A-T7, hiR2-FL-A547V-T7, hiR2-FL-A547S-T7, hiR2-FL-V548A-T7, hiR2-FL-C549A-T7, hiR2-FL-H550A-T7, hiR2-FL-Q551A-T7, hiR2-FL-D552A-T7, hiR2-FL-P553A-T7, hiR2-FL-R554A-T7, hiR2-FL-T555V-T7, hiR2-FL-T555A-T7, hiR2-FL-C556A-T7, hiR2-FL-E557D-T7, hiR2-FL-E557A-T7, hiR2-FL-E558A-T7, hiR2-FL-P559A-T7, hiR2-FL-A560S-T7, hiR2-FL-S561A-T7, hiR2-FL-S562E-T7, hiR2-FL-S562A-T7, hiR2-FL-G563D-T7, hiR2-FL-G563A-T7, hiR2-FL-A564P-T7, hiR2-FL-A564S-T7, hiR2-FL-H565A-T7, hiR2-FL-I566E-T7, hiR2-FL-1566A-T7, hiR2-FL-W567A-T7, hiR2-FL-P568A-T7, hiR2-FL-D569E-T7, hiR2-FL-D569A-T7, hiR2-FL-D570A-T7, hiR2-FL-1571A-T7, hiR2-FL-T572A-T7, hiR2-FL-K573A-T7, hiR2-FL-W574A-T7, hiR2-FL-P575A-T7, hiR2-FL-1576A-T7, hiR2-FL-C577A-T7, hiR2-FL-T578A-T7, hiR2-FL-E579K-T7, hiR2-FL-E579A-T7, hiR2-FL-Q580N-T7, hiR2-FL-Q580A-T7, hiR2-FL-A581S-T7, hiR2-FL-R582A-T7, hiR2-FL-S583G-T7, hiR2-FL-S583A-T7, hiR2-FL-N584A-T7, hiR2-FL-H585A-T7, hiR2-FL-T586A-T7, hiR2-FL-G587N-T7, hiR2-FL-G587A-T7, hiR2-FL-F588H-T7, hiR2-FL-F588A-T7, hiR2-FL-L589P-T7, hiR2-FL-L589A-T7, hiR2-FL-H590A-T7, hiR2-FL-M591A-T7, hiR2-FL-D592A-T7, hiR2-FL-C593A-T7 and hiR2-FL-E594V-T7.

This example describes the generation of iRhom1/2−/− DKO MEF populations expressing the 137 single amino acid substitution or deletion variants as well as their characterization in terms of cell surface localization and functional activity as indicators of proper protein conformation. Subsequently, binding analyses of the humanized antibodies 16-B-03, 16-B-05, 16-B-07, 23-B-04, 42-B-02 and 42-B-04 of the invention on the entire panel of 137 engineered MEF populations expressing human iRhom2 variants with single amino acid substitutions or deletions are described.

Generation of iRhom 1/2−/− DKO MEFs Stably Expressing 137 T7-Tagged Human iRhom2 Variants with Single Amino Acid Substitutions or Deletions In brief, on day 1, Phoenix-ECO cells (American Type Culture Collection, USA) were seeded on 6-well tissue culture plates (Greiner, Germany) in standard growth medium at $8\times10^5$ cells per well and kept overnight at 37° C., 5% $CO_2$. On day 2, the medium was replaced by fresh medium supplemented with chloroquine (Sigma-Aldrich, USA) at a final concentration of 25 μM. Applying the calcium phosphate method, cells were transfected with 2 μg/ml of pMSCV-hiR2-FL-Q502R-T7, pMSCV-hiR2-FL-N503A-T7, pMSCV-hiR2-FL-D504A-T7, pMSCV-hiR2-FL-H505R-T7, pMSCV-hiR2-FL-H505A-T7, pMSCV-hiR2-FL-S506A-T7, pMSCV-hiR2-FL-G507A-T7, pMSCV-hiR2-FL-C508A-T7, pMSCV-hiR2-FL-I509V-T7, pMSCV-hiR2-FL-I509A-T7, pMSCV-hiR2-FL-Q510A-T7, pMSCV-hiR2-FL-T511A-T7, pMSCV-hiR2-FL-Q512L-T7, pMSCV-hiR2-FL-Q512S-T7, pMSCV-hiR2-FL-Q512A-T7, pMSCV-hiR2-FL-R513K-T7, pMSCV-hiR2-FL-R513E-T7, pMSCV-hiR2-FL-R513A-T7, pMSCV-hiR2-FL-K514E-T7, pMSCV-hiR2-FL-K514A-T7, pMSCV-hiR2-FL-D515E-T7, pMSCV-hiR2-FL-D515A-T7, pMSCV-hiR2-FL-C516A-T7, pMSCV-hiR2-FL-S517A-T7, pMSCV-hiR2-FL-E518S-T7, pMSCV-hiR2-FL-E518A-T7, pMSCV-hiR2-FL-T519A-T7, pMSCV-hiR2-FL-L520A-T7, pMSCV-hiR2-FL-A521S-T7, pMSCV-hiR2-FL-T522V-T7, pMSCV-hiR2-FL-T522A-T7, pMSCV-hiR2-FL-F523W-T7, pMSCV-hiR2-FL-K525A-T7, pMSCV-hiR2-FL-Q527A-T7, pMSCV-hiR2-FL-D528A-T7, pMSCV-hiR2-FL-T530P-T7, pMSCV-hiR2-FL-G531A-T7, pMSCV-hiR2-FL-P533A-T7, pMSCV-hiR2-FL-M534A-T7, pMSCV-hiR2-FL-K536--T7, pMSCV-hiR2-FL-S537A-T7, pMSCV-hiR2-FL-L539A-T7, pMSCV-hiR2-FL-Q541H-T7, pMSCV-hiR2-FL-R543Q-T7, pMSCV-hiR2-FL-T544Q-T7, pMSCV-hiR2-FL-S545A-T7, pMSCV-hiR2-FL-A547S-T7, pMSCV-hiR2-FL-H550A-T7, pMSCV-hiR2-FL-P553A-T7, pMSCV-hiR2-FL-T555A-T7, pMSCV-hiR2-FL-E557A-T7, pMSCV-hiR2-FL-A560S-T7, pMSCV-hiR2-FL-S562A-T7, pMSCV-hiR2-FL-A564P-T7, pMSCV-hiR2-FL-1566E-T7, pMSCV-hiR2-FL-P568A-T7, pMSCV-hiR2-FL-D570A-T7, pMSCV-hiR2-FL-K573A-T7, pMSCV-hiR2-FL-1576A-T7, pMSCV-hiR2-FL-E579K-T7, pMSCV-hiR2-FL-Q580A-T7, pMSCV-hiR2-FL-S583G-T7, pMSCV-hiR2-FL-F523A-T7, pMSCV-hiR2-FL-W526A-T7, pMSCV-hiR2-FL-D528N-T7, pMSCV-hiR2-FL-D529H-T7, pMSCV-hiR2-FL-T530A-T7, pMSCV-hiR2-FL-P532A-T7, pMSCV-hiR2-FL-M534S-T7, pMSCV-hiR2-FL-D535--T7, pMSCV-hiR2-FL-K536A-T7, pMSCV-hiR2-FL-D538L-T7, pMSCV-hiR2-FL-G540S-T7, pMSCV-hiR2-FL-Q541A-T7, pMSCV-hiR2-FL-R543A-T7, pMSCV-hiR2-FL-T544A-T7, pMSCV-hiR2-FL-G546A-T7, pMSCV-hiR2-FL-V548A-T7, pMSCV-hiR2-FL-Q551A-T7, pMSCV-hiR2-FL-R554A-T7, pMSCV-hiR2-FL-C556A-T7, pMSCV-hiR2-FL-E558A-T7, pMSCV-hiR2-FL-S561A-T7, pMSCV-hiR2-FL-G563D-T7, pMSCV-hiR2-FL-A564S-T7, pMSCV-hiR2-FL-1566A-T7, pMSCV-hiR2-FL-D569E-T7, pMSCV-hiR2-FL-I571A-T7, pMSCV-hiR2-FL-W574A-T7, pMSCV-hiR2-FL-C577A-T7, pMSCV-hiR2-FL-E579A-T7, pMSCV-hiR2-FL-A581S-T7, pMSCV-hiR2-FL-S583A-T7, pMSCV-hiR2-FL-V524A-T7, pMSCV-hiR2-FL-Q527P-T7, pMSCV-hiR2-FL-D528I-T7, pMSCV-hiR2-FL-D529A-T7, pMSCV-hiR2-FL-G531S-T7, pMSCV-hiR2-FL-P533--T7, pMSCV-hiR2-FL-M534--T7, pMSCV-hiR2-FL-D535A-T7, pMSCV-hiR2-FL-S537E-T7, pMSCV-hiR2-FL-D538A-T7, pMSCV-hiR2-FL-G540A-T7, pMSCV-hiR2-FL-K542A-T7, pMSCV-hiR2-FL-T544P-T7, pMSCV-hiR2-FL-S545F-T7, pMSCV-hiR2-FL-A547V-T7, pMSCV-hiR2-FL-C549A-T7, pMSCV-hiR2-FL-D552A-T7, pMSCV-hiR2-FL-T555V-T7, pMSCV-hiR2-FL-E557D-T7, pMSCV-hiR2-FL-P559A-T7, pMSCV-hiR2-FL-S562E-T7, pMSCV-hiR2-FL-G563A-T7, pMSCV-hiR2-FL-H565A-T7, pMSCV-hiR2-FL-W567A-T7, pMSCV-hiR2-FL-D569A-T7, pMSCV-hiR2-FL-T572A-T7, pMSCV-hiR2-FL-P575A-T7, pMSCV-hiR2-FL-T578A-T7, pMSCV-hiR2-FL-Q580N-T7, pMSCV-hiR2-FL-R582A-T7, pMSCV-hiR2-FL-N584A-T7, pMSCV-hiR2-FL-H585A-T7, pMSCV-hiR2-FL-T586A-T7, pMSCV-hiR2-FL-G587N-T7, pMSCV-hiR2-FL-G587A-T7, pMSCV-hiR2-FL-F588A-T7, pMSCV-hiR2-FL-F588H-T7, pMSCV-hiR2-FL-L589P-T7, pMSCV-hiR2-FL-L589A-T7, pMSCV-hiR2-FL-H590A-T7, pMSCV-hiR2-FL-M591A-T7, pMSCV-hiR2-FL-D592A-T7, pMSCV-hiR2-FL-C593A-T7 and pMSCV-hiR2-FL-E594V-T7 encoding human iRhom2 full length single amino acid substitutions C-terminally tagged with 3 consecutive copies of the T7 epitope (MASMTGGQQMG), and were kept at 37° C., 5% $CO_2$. After 7 hours, the transfections were stopped by replacing cell supernatants with standard growth medium lacking chloroquine, and cells were incubated at 37° C., 5% $CO_2$ to allow virus production overnight. In parallel, immortalized iRhom 1/2−/− DKO MEFs as target cells for retroviral infection were seeded on 6-well tissue culture plates (Greiner, Germany) in standard growth medium at $1\times10^5$ cells per well and were also kept overnight at 37° C., 5% $CO_2$. On day 3, the supernatants of Phoenix-ECO cells releasing pMSCV-hiR2-FL-Q502R-T7, pMSCV-hiR2-FL-N503A-T7, pMSCV-hiR2-FL-D504A-T7, pMSCV-hiR2-FL-H505R-T7, pMSCV-hiR2-FL-H505A-T7, pMSCV-hiR2-FL-S506A-T7, pMSCV-hiR2-FL-G507A-T7, pMSCV-hiR2-FL-C508A-T7, pMSCV-hiR2-FL-1509V-T7, pMSCV-hiR2-FL-I509A-T7, pMSCV-hiR2-FL-Q510A-T7, pMSCV-hiR2-FL-T511A-T7, pMSCV-hiR2-FL-Q512L-T7, pMSCV-hiR2-FL-Q512S-T7, pMSCV-hiR2-FL-Q512A-T7, pMSCV-hiR2-FL-R513K-T7, pMSCV-hiR2-FL-pMSCV-hiR2-FL-K514E-T7, R513E-T7, pMSCV-hiR2-FL-R513A-T7, pMSCV-hiR2-FL-K514A-T7, pMSCV-hiR2-FL-D515E-T7, pMSCV-hiR2-FL-D515A-T7, pMSCV-hiR2-FL-C516A-T7, pMSCV-hiR2-FL-S517A-T7, pMSCV-hiR2-FL-E518S-T7, pMSCV-hiR2-FL-E518A-T7, pMSCV-hiR2-FL-T519A-T7, pMSCV-hiR2-FL-L520A-T7, pMSCV-hiR2-FL-A521S-T7, pMSCV-hiR2-FL-T522V-T7, pMSCV-hiR2-FL-T522A-T7, pMSCV-hiR2-FL-F523W-T7, pMSCV-hiR2-FL-F523A-T7, pMSCV-hiR2-FL-V524A-T7, pMSCV-hiR2-FL-K525A-T7, pMSCV-hiR2-FL-W526A-T7, pMSCV-hiR2-FL-Q527P-T7, pMSCV-hiR2-FL-Q527A-T7, pMSCV-hiR2-FL-D528N-T7, pMSCV-hiR2-FL-D528I-T7, pMSCV-hiR2-FL-D528A-T7, pMSCV-hiR2-FL-D529H-T7, pMSCV-hiR2-FL-D529A-T7, pMSCV-hiR2-FL-T530P-T7, pMSCV-hiR2-FL-T530A-T7, pMSCV-hiR2-FL-G531S-T7, pMSCV-hiR2-FL-G531A-T7, pMSCV-hiR2-FL-P532A-T7, pMSCV-hiR2-FL-P533--T7, pMSCV-hiR2-FL-P533A-T7, pMSCV-hiR2-FL-M534S-T7, pMSCV-hiR2-FL-M534--T7, pMSCV-hiR2-FL-M534A-T7, pMSCV-hiR2-FL-D535--T7, pMSCV-hiR2-FL-D535A-T7, pMSCV-hiR2-FL-K536--T7, pMSCV-hiR2-FL-K536A-T7, pMSCV-hiR2-FL-S537E-T7, pMSCV-hiR2-FL-S537A-T7, pMSCV-hiR2-FL-D538L-T7, pMSCV-hiR2-FL-D538A-T7, pMSCV-hiR2-FL-L539A-T7, pMSCV-hiR2-FL-G540S-T7, pMSCV-hiR2-FL-G540A-T7, pMSCV-hiR2-FL-Q541H-T7, pMSCV-hiR2-FL-Q541A-T7, pMSCV-hiR2-FL-K542A-T7, pMSCV-hiR2-FL-R543Q-T7, pMSCV-hiR2-FL-R543A-T7, pMSCV-hiR2-FL-T544P-T7, pMSCV-hiR2-FL-T544Q-T7, pMSCV-hiR2-FL-T544A-T7, pMSCV-hiR2-FL-S545F-T7, pMSCV-hiR2-FL-S545A-T7, pMSCV-hiR2-FL-G546A-T7, pMSCV-hiR2-FL-A547V-T7, pMSCV-hiR2-FL-A547S-T7, pMSCV-hiR2-FL-V548A-T7, pMSCV-hiR2-FL-C549A-T7, pMSCV-hiR2-FL-H550A-T7, pMSCV-hiR2-FL-Q551A-T7, pMSCV-hiR2-FL-D552A-T7, pMSCV-hiR2-FL-P553A-T7, pMSCV-hiR2-FL-R554A-T7, pMSCV-hiR2-FL-T555V-T7, pMSCV-hiR2-FL-T555A-T7, pMSCV-hiR2-FL-C556A-T7, pMSCV-hiR2-FL-E557D-T7, pMSCV-hiR2-FL-E557A-T7, pMSCV-hiR2-FL-E558A-T7, pMSCV-hiR2-FL-P559A-T7, pMSCV-hiR2-FL-A560S-T7, pMSCV-hiR2-FL-S561A-T7, pMSCV-hiR2-FL-S562E-T7, pMSCV-hiR2-FL-S562A-T7, pMSCV-hiR2-FL-G563D-T7, pMSCV-hiR2-FL-G563A-T7, pMSCV-hiR2-FL-A564P-T7, pMSCV-hiR2-FL-A564S-T7, pMSCV-hiR2-FL-H565A-T7, pMSCV-hiR2-FL-I566E-T7, pMSCV-hiR2-FL-1566A-T7, pMSCV-hiR2-FL-W567A-T7, pMSCV-hiR2-FL-P568A-T7, pMSCV-hiR2-FL-D569E-T7, pMSCV-hiR2-FL-D569A-T7, pMSCV-hiR2-FL-D570A-T7, pMSCV-hiR2-FL-1571A-T7, pMSCV-hiR2-FL-T572A-T7, pMSCV-hiR2-FL-K573A-T7, pMSCV-hiR2-FL-W574A-T7, pMSCV-hiR2-FL-P575A-T7, pMSCV-hiR2-FL-1576A-T7, pMSCV-hiR2-FL-C577A-T7, pMSCV-hiR2-FL-T578A-T7, pMSCV-hiR2-FL-E579K-T7, pMSCV-hiR2-FL-E579A-T7, pMSCV-hiR2-FL-Q580N-T7, pMSCV-hiR2-FL-Q580A-T7, pMSCV-hiR2-FL-A581S-T7, pMSCV-hiR2-FL-R582A-T7, pMSCV-hiR2-FL-S583G-T7, pMSCV-hiR2-FL-S583A-T7, pMSCV-hiR2-FL-N584A-T7, pMSCV-hiR2-FL-H585A-T7, pMSCV-hiR2-FL-T586A-T7, pMSCV-hiR2-FL-G587N-T7, pMSCV-hiR2-FL-G587A-T7, pMSCV-hiR2-FL-F588H-T7, pMSCV-hiR2-FL-F588A-T7, pMSCV-hiR2-FL-L589P-T7, pMSCV-hiR2-FL-L589A-T7, pMSCV-hiR2-FL-H590A-T7, pMSCV-hiR2-FL-M591A-T7, pMSCV-hiR2-FL-D592A-T7, pMSCV-hiR2-FL-C593A-T7 and pMSCV-hiR2-FL-E594V-T7 ecotrophic virus were collected, filtered with 0.45 μm CA filters, and supplemented with 4 μg/ml of polybrene (Sigma-Aldrich, USA). Upon removal of medium from the immortalized iRhom1/2−/− DKO MEFs, these supernatants were added to the target cells for 4 hours at 37° C., 5% $CO_2$ for first infection. Simultaneously, Phoenix-ECO cells were re-incubated with fresh medium, which, after another 4 hours, was filtered and used for the second infection of the respective target cell populations, again in the presence of 4 μg/ml of polybrene. Likewise, a third, but overnight infection cycle was performed. On day 4, virus containing cell supernatants were replaced by fresh standard growth medium. From day 5 onwards, cells were grown in the presence of 2 mg/ml of geneticin (G418, Thermo Fisher Scientific, USA) for the selection of immortalized MEF-DKO-hiR2-FL-Q502R-T7, MEF-DKO-hiR2-FL-N503A-T7, MEF-DKO-hiR2-FL-D504A-T7, MEF-DKO-hiR2-FL-H505R-T7, MEF-DKO-hiR2-FL-H505A-T7, MEF-DKO-hiR2-FL-S506A-T7, MEF-DKO-hiR2-FL-G507A-T7, MEF-DKO-hiR2-FL-C508A-T7, MEF-DKO-hiR2-FL-I509V-T7, MEF-DKO-hiR2-FL-I509A-T7, MEF-DKO-hiR2-FL-Q510A-T7, MEF-DKO-hiR2-FL-T511A-T7, MEF-DKO-hiR2-FL-Q512L-T7, MEF-DKO-hiR2-FL-Q512S-T7, MEF-DKO-hiR2-FL-Q512A-T7, MEF-DKO-hiR2-FL-R513K-T7, MEF-DKO-hiR2-FL-R513E-T7, MEF-DKO-hiR2-FL-R513A-T7, MEF-DKO-hiR2-FL-K514E-T7, MEF-DKO-hiR2-FL-K514A-T7, MEF-DKO-hiR2-FL-D515E-T7, MEF-DKO-hiR2-FL-D515A-T7, MEF-DKO-hiR2-FL-C516A-T7, MEF-DKO-hiR2-FL-S517A-T7, MEF-DKO-hiR2-FL-E518S-T7, MEF-DKO-hiR2-FL-E518A-T7, MEF-DKO-hiR2-FL-T519A-T7, MEF-DKO-hiR2-FL-L520A-T7, MEF-DKO-hiR2-FL-A521S-T7, MEF-DKO-hiR2-FL-T522V-T7, MEF-DKO-hiR2-FL-T522A-T7, MEF-DKO-hiR2-FL-F523W-T7, MEF-DKO-hiR2-FL-F523A-T7, MEF-DKO-hiR2-FL-V524A-T7, MEF-DKO-hiR2-FL-K525A-T7, MEF-DKO-hiR2-FL-W526A-T7, MEF-DKO-hiR2-FL-Q527P-T7, MEF-DKO-hiR2-FL-Q527A-T7, MEF-DKO-hiR2-FL-D528N-T7, MEF-DKO-hiR2-FL-D528I-T7, MEF-DKO-hiR2-FL-D528A-T7, MEF-DKO-hiR2-FL-D529H-T7, MEF-DKO-hiR2-FL-D529A-T7, MEF-DKO-hiR2-FL-T530P-T7, MEF-DKO-hiR2-FL-T530A-T7, MEF-DKO-hiR2-FL-G531S-T7, MEF-DKO-hiR2-FL-G531A-T7, MEF-DKO-hiR2-FL-P532A-T7, MEF-DKO-hiR2-FL-P533--T7, MEF-DKO-hiR2-FL-P533A-T7, MEF-DKO-hiR2-FL-M534S-T7, MEF-DKO-hiR2-FL-M534--T7, MEF-DKO-hiR2-FL-M534A-T7, MEF-DKO-hiR2-FL-D535--T7, MEF-DKO-hiR2-FL-D535A-T7, MEF-DKO-hiR2-FL-K536--T7, MEF-DKO-hiR2-FL-K536A-T7, MEF-DKO-hiR2-FL-S537E-T7, MEF-DKO-hiR2-FL-S537A-T7, MEF-DKO-hiR2-FL-D538L-T7, MEF-DKO-hiR2-FL-D538A-T7, MEF-DKO-hiR2-FL-L539A-T7, MEF-DKO-hiR2-FL-G540S-T7, MEF-DKO-hiR2-FL-G540A-T7, MEF-DKO-hiR2-FL-Q541H-T7, MEF-DKO-hiR2-FL-Q541A-T7, MEF-DKO-hiR2-FL-K542A-T7, MEF-DKO-hiR2-FL-R543Q-T7, MEF-DKO-hiR2-FL-R543A-T7, MEF-DKO-hiR2-FL-T544P-T7, MEF-DKO-hiR2-FL-T544Q-T7, MEF-DKO-hiR2-FL-T544A-T7, MEF-DKO-hiR2-FL-S545F-T7, MEF-DKO-hiR2-FL-S545A-T7, MEF-DKO-hiR2-FL-G546A-T7, MEF-DKO-hiR2-FL-A547V-T7, MEF-DKO-hiR2-FL-A547S-T7, MEF-DKO-hiR2-FL-V548A-T7, MEF-DKO-hiR2-FL-C549A-T7, MEF-DKO-hiR2-FL-H550A-T7, MEF-DKO-hiR2-FL-Q551A-T7, MEF-DKO-hiR2-FL-D552A-T7, MEF-DKO-hiR2-FL-P553A-T7, MEF-DKO-hiR2-FL-R554A-T7, MEF-DKO-hiR2-FL-T555V-T7, MEF-DKO-hiR2-FL-T555A-T7, MEF-DKO-hiR2-FL-C556A-T7, MEF-DKO-hiR2-FL-E557D-T7, MEF-DKO-hiR2-FL-E557A-T7, MEF-DKO-hiR2-FL-E558A-T7, MEF-DKO-hiR2-FL-P559A-T7, MEF-DKO-hiR2-FL-A560S-T7, MEF-DKO-hiR2-FL-S561A-T7, MEF-DKO-hiR2-FL-S562E-T7, MEF-DKO-hiR2-FL-S562A-T7, MEF-DKO-hiR2-FL-G563D-T7, MEF-DKO-hiR2-FL-G563A-T7, MEF-DKO-hiR2-FL-A564P-T7, MEF-DKO-hiR2-FL- A564S-T7, MEF-DKO-hiR2-FL-H565A-T7, MEF-DKO-hiR2-FL-1566E-T7, MEF-DKO-hiR2-FL-1566A-T7, MEF-DKO-hiR2-FL-W567A-T7, MEF-DKO-hiR2-FL-P568A-T7, MEF-DKO-hiR2-FL-D569E-T7, MEF-DKO-hiR2-FL-D569A-T7, MEF-DKO-hiR2-FL-D570A-T7, MEF-DKO-hiR2-FL-1571A-T7, MEF-DKO-hiR2-FL-T572A-T7, MEF-DKO-hiR2-FL-K573A-T7, MEF-DKO-hiR2-FL-W574A-T7, MEF-DKO-hiR2-FL-P575A-T7, MEF-DKO-hiR2-FL-I576A-T7, MEF-DKO-hiR2-FL-C577A-T7, MEF-DKO-hiR2-FL-T578A-T7, MEF-DKO-hiR2-FL-E579K-T7, MEF-DKO-hiR2-FL-E579A-T7, MEF-DKO-hiR2-FL-Q580N-T7, MEF-DKO-hiR2-FL-Q580A-T7, MEF-DKO-hiR2-FL-A581S-T7, MEF-DKO-hiR2-FL-R582A-T7, MEF-DKO-hiR2-FL-S583G-T7, MEF-DKO-hiR2-FL-S583A-T7, MEF-DKO-hiR2-FL-N584A-T7, MEF-DKO-hiR2-FL-H585A-T7, MEF-DKO-hiR2-FL-T586A-T7, MEF-DKO-hiR2-FL-G587N-T7, MEF-DKO-hiR2-FL-G587A-T7, MEF-DKO-hiR2-FL-F588H-T7, MEF-DKO-hiR2-FL-F588A-T7, MEF-DKO-hiR2-FL-L589P-T7, MEF-DKO-hiR2-FL-L589A-T7, MEF-DKO-hiR2-FL-H590A-T7, MEF-DKO-hiR2-FL-M591A-T7, MEF-DKO-hiR2-FL-D592A-T7, MEF-DKO-hiR2-FL-C593A-T7 and MEF-DKO-hiR2-FL-E594V-T7 cells stably expressing human iRhom2 full length single amino acid substitutions C-terminally tagged with 3 consecutive copies of the T7 epitope. Upon propagation, cells were stocked for future usage.

FACS Analyses for Test System Validation

In brief, immortalized MEF-DKO-hiR2-FL-WT-T7 cells and MEF-DKO-hiR2-FL-Q502R-T7, MEF-DKO-hiR2-FL-N503A-T7, MEF-DKO-hiR2-FL-D504A-T7, MEF-DKO-hiR2-FL-H505R-T7, MEF-DKO-hiR2-FL-H505A-T7, MEF-DKO-hiR2-FL-S506A-T7, MEF-DKO-hiR2-FL-G507A-T7, MEF-DKO-hiR2-FL-C508A-T7, MEF-DKO-hiR2-FL-I509V-T7, MEF-DKO-hiR2-FL-I509A-T7, MEF-DKO-hiR2-FL-Q510A-T7, MEF-DKO-hiR2-FL-T511A-T7, MEF-DKO-hiR2-FL-Q512L-T7, MEF-DKO-hiR2-FL-Q512S-T7, MEF-DKO-hiR2-FL-Q512A-T7, MEF-DKO-hiR2-FL-R513K-T7, MEF-DKO-hiR2-FL-R513E-T7, MEF-DKO-hiR2-FL-R513A-T7, MEF-DKO-hiR2-FL-K514E-T7, MEF-DKO-hiR2-FL-K514A-T7, MEF-DKO-hiR2-FL-D515E-T7, MEF-DKO-hiR2-FL-D515A-T7, MEF-DKO-hiR2-FL-C516A-T7, MEF-DKO-hiR2-FL-S517A-T7, MEF-DKO-hiR2-FL-E518S-T7, MEF-DKO-hiR2-FL-E518A-T7, MEF-DKO-hiR2-FL-T519A-T7, MEF-DKO-hiR2-FL-L520A-T7, MEF-DKO-hiR2-FL-A521S-T7, MEF-DKO-hiR2-FL-T522V-T7, MEF-DKO-hiR2-FL-T522A-T7, MEF-DKO-hiR2-FL-F523W-T7, MEF-DKO-hiR2-FL-F523A-T7, MEF-DKO-hiR2-FL-V524A-T7, MEF-DKO-hiR2-FL-K525A-T7, MEF-DKO-hiR2-FL-W526A-T7, MEF-DKO-hiR2-FL-Q527P-T7, MEF-DKO-hiR2-FL-Q527A-T7, MEF-DKO-hiR2-FL-D528N-T7, MEF-DKO-hiR2-FL-D528I-T7, MEF-DKO-hiR2-FL-D528A-T7, MEF-DKO-hiR2-FL-D529H-T7, MEF-DKO-hiR2-FL-D529A-T7, MEF-DKO-hiR2-FL-T530P-T7, MEF-DKO-hiR2-FL-T530A-T7, MEF-DKO-hiR2-FL-G531S-T7, MEF-DKO-hiR2-FL-G531A-T7, MEF-DKO-hiR2-FL-P532A-T7, MEF-DKO-hiR2-FL-P533--T7, MEF-DKO-hiR2-FL-P533A-T7, MEF-DKO-hiR2-FL-M534S-T7, MEF-DKO-hiR2-FL-M534--T7, MEF-DKO-hiR2-FL-M534A-T7, MEF-DKO-hiR2-FL-D535--T7, MEF-DKO-hiR2-FL-D535A-T7, MEF-DKO-hiR2-FL-K536--T7, MEF-DKO-hiR2-FL-K536A-T7, MEF-DKO-hiR2-FL-S537E-T7, MEF-DKO-hiR2-FL-S537A-T7, MEF-DKO-hiR2-FL-D538L-T7, MEF-DKO-hiR2-FL-D538A-T7, MEF-DKO-hiR2-FL-L539A-T7, MEF-DKO-hiR2-FL-G540S-T7, MEF-DKO-hiR2-FL-G540A-T7, MEF-DKO-hiR2-FL-Q541H-T7, MEF-DKO-hiR2-FL-Q541A-T7, MEF-DKO-hiR2-FL-K542A-T7, MEF-DKO-hiR2-FL-R543Q-T7, MEF-DKO-hiR2-FL-R543A-T7, MEF-DKO-hiR2-FL-T544P-T7, MEF-DKO-hiR2-FL-T544Q-T7, MEF-DKO-hiR2-FL-T544A-T7, MEF-DKO-hiR2-FL-S545F-T7, MEF-DKO-hiR2-FL-S545A-T7, MEF-DKO-hiR2-FL-G546A-T7, MEF-DKO-hiR2-FL-A547V-T7, MEF-DKO-hiR2-FL-A547S-T7, MEF-DKO-hiR2-FL-V548A-T7, MEF-DKO-hiR2-FL-C549A-T7, MEF-DKO-hiR2-FL-H550A-T7, MEF-DKO-hiR2-FL-Q551A-T7, MEF-DKO-hiR2-FL-D552A-T7, MEF-DKO-hiR2-FL-P553A-T7, MEF-DKO-hiR2-FL-R554A-T7, MEF-DKO-hiR2-FL-T555V-T7, MEF-DKO-hiR2-FL-T555A-T7, MEF-DKO-hiR2-FL-C556A-T7, MEF-DKO-hiR2-FL-E557D-T7, MEF-DKO-hiR2-FL-E557A-T7, MEF-DKO-hiR2-FL-E558A-T7, MEF-DKO-hiR2-FL-P559A-T7, MEF-DKO-hiR2-FL-A560S-T7, MEF-DKO-hiR2-FL-S561A-T7, MEF-DKO-hiR2-FL-S562E-T7, MEF-DKO-hiR2-FL-S562A-T7, MEF-DKO-hiR2-FL-G563D-T7, MEF-DKO-hiR2-FL-G563A-T7, MEF-DKO-hiR2-FL-A564P-T7, MEF-DKO-hiR2-FL-A564S-T7, MEF-DKO-hiR2-FL-H565A-T7, MEF-DKO-hiR2-FL-1566E-T7, MEF-DKO-hiR2-FL-1566A-T7, MEF-DKO-hiR2-FL-W567A-T7, MEF-DKO-hiR2-FL-P568A-T7, MEF-DKO-hiR2-FL-D569E-T7, MEF-DKO-hiR2-FL-D569A-T7, MEF-DKO-hiR2-FL-D570A-T7, MEF-DKO-hiR2-FL-I571A-T7, MEF-DKO-hiR2-FL-T572A-T7, MEF-DKO-hiR2-FL-K573A-T7, MEF-DKO-hiR2-FL-W574A-T7, MEF-DKO-hiR2-FL-P575A-T7, MEF-DKO-hiR2-FL-1576A-T7, MEF-DKO-hiR2-FL-C577A-T7, MEF-DKO-hiR2-FL-T578A-T7, MEF-DKO-hiR2-FL-E579K-T7, MEF-DKO-hiR2-FL-E579A-T7, MEF-DKO-hiR2-FL-Q580N-T7, MEF-DKO-hiR2-FL-Q580A-T7, MEF-DKO-hiR2-FL-A581S-T7, MEF-DKO-hiR2-FL-R582A-T7, MEF-DKO-hiR2-FL-S583G-T7, MEF-DKO-hiR2-FL-S583A-T7, MEF-DKO-hiR2-FL-N584A-T7, MEF-DKO-hiR2-FL-H585A-T7, MEF-DKO-hiR2-FL-T586A-T7, MEF-DKO-hiR2-FL-G587N-T7, MEF-DKO-hiR2-FL-G587A-T7, MEF-DKO-hiR2-FL-F588H-T7, MEF-DKO-hiR2-FL-F588A-T7, MEF-DKO-hiR2-FL-L589P-T7, MEF-DKO-hiR2-FL-L589A-T7, MEF-DKO-hiR2-FL-H590A-T7, MEF-DKO-hiR2-FL-M591A-T7, MEF-DKO-hiR2-FL-D592A-T7, MEF-DKO-hiR2-FL-C593A-T7 and MEF-DKO-hiR2-FL-E594V-T7 cells were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $1\times10^5$ cells per well. To pellet cells and remove supernatants, the plates were centrifuged at 1,500 rpm and 4° C. for 3 minutes. For primary staining, cells were resuspended in 100 μl per well of either FACS buffer alone (controls) or mouse monoclonal anti-T7 IgG (Merck Millipore, USA) at 3 μg/ml FACS buffer and incubated on ice for 1 hour. Afterwards, plates were centrifuged at 1,500 rpm and 4° C. for 3 minutes and washed twice with 200 μl per well of FACS buffer. For secondary staining, cells were spun down and resuspended in 100 μl per well of PE-conjugated goat anti-mouse IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 μl per well of FACS buffer. Finally, cells were resuspended in 150 μl per well of FACS buffer and analyzed using a BD Accuri™ C6 Plus flow cytometer (Becton Dickinson, Germany).

Figure 16A:
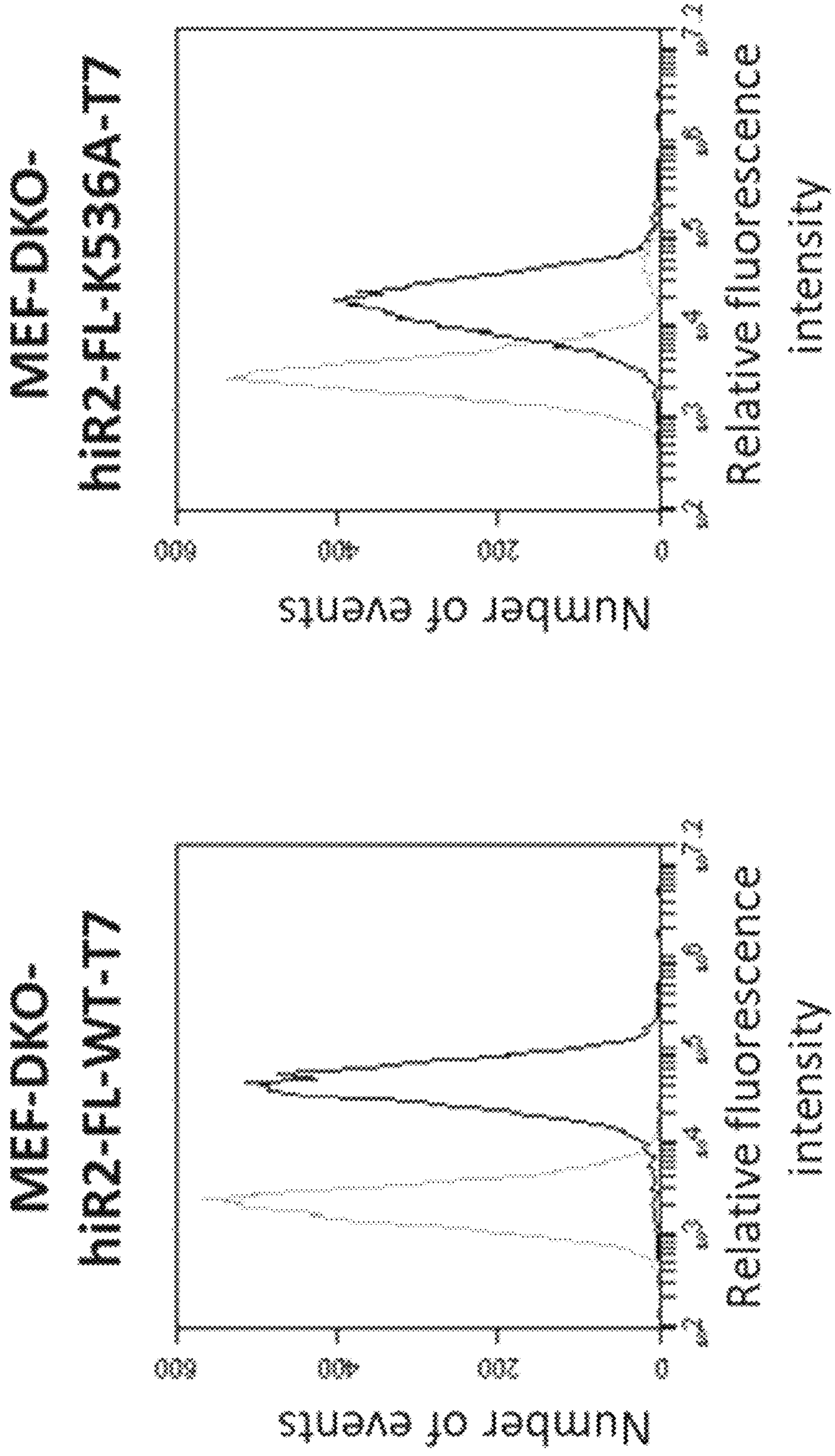
FIG. 16*a* depicts results from FACS analyses on MEF populations with single amino acid substitutions or deletions within the large extracellular loop (AA502 to AA594 of human iRhom2) that were genetically engineered for epitope determination. The data demonstrate that-similarly to the T7-tagged variant of human iRhom2 full length wild type ectopically expressed by MEF-DKO-hiR2-FL-WT-T7—also the T7-tagged human iRhom2 variant hiR2-FL-K536 Å ectopically expressed by MEF-DKO-hiR2-FL-K536A-T7 cells is localized on the surface of these cells. Stainings: gray=secondary antibody only; black=anti-T7-antibody

FIG. 16*a* shows representative results of this experiment exemplarily for the human iRhom2 variant hiR2-FL-K536A-T7. Binding analyses of anti-T7 tag antibody (black) and anti-mouse IgG secondary antibody (gray) on MEF-DKO-hiR2-FL-WT-T7 (left) and MEF-DKO-hiR2-FL-K536A-T7 cells (right) reveal a strong increase in relative fluorescence intensity. This demonstrates that, similarly to human iRhom2 wild type (left), the human iRhom2 variant hiR2-FL-K536A-T7 is well expressed and localized on the surface of these cells (right). Similar results were obtained for the expression and localization of the human iRhom2 full length single amino acid substitutions expressed on MEF-DKO-hiR2-FL-Q502R-T7, MEF-DKO-hiR2-FL-N503A-T7, MEF-DKO-hiR2-FL-D504A-T7, MEF-DKO-hiR2-FL-H505R-T7, MEF-DKO-hiR2-FL-H505A-T7, MEF-DKO-hiR2-FL-S506A-T7, MEF-DKO-hiR2-FL-G507A-T7, MEF-DKO-hiR2-FL-C508A-T7, MEF-DKO-hiR2-FL-1509V-T7, MEF-DKO-hiR2-FL-1509A-T7, MEF-DKO-hiR2-FL-Q510A-T7, MEF-DKO-hiR2-FL-T511A-T7, MEF-DKO-hiR2-FL-Q512L-T7, MEF-DKO-hiR2-FL-Q512S-T7, MEF-DKO-hiR2-FL-Q512A-T7, MEF-DKO-hiR2-FL-R513K-T7, MEF-DKO-hiR2-FL-R513E-T7, MEF-DKO-hiR2-FL-R513A-T7, MEF-DKO-hiR2-FL-K514E-T7, MEF-DKO-hiR2-FL-K514A-T7, MEF-DKO-hiR2-FL-D515E-T7, MEF-DKO-hiR2-FL-D515A-T7, MEF-DKO-hiR2-FL-C516A-T7, MEF-DKO-hiR2-FL-S517A-T7, MEF-DKO-hiR2-FL-E518S-T7, MEF-DKO-hiR2-FL-E518A-T7, MEF-DKO-hiR2-FL-T519A-T7, MEF-DKO-hiR2-FL-L520A-T7, MEF-DKO-hiR2-FL-A521S-T7, MEF-DKO-hiR2-FL-T522V-T7, MEF-DKO-hiR2-FL-T522A-T7, MEF-DKO-hiR2-FL-F523W-T7, MEF-DKO-hiR2-FL-F523A-T7, MEF-DKO-hiR2-FL-V524A-T7, MEF-DKO-hiR2-FL-K525A-T7, MEF-DKO-hiR2-FL-W526A-T7, MEF-DKO-hiR2-FL-Q527P-T7, MEF-DKO-hiR2-FL-Q527A-T7, MEF-DKO-hiR2-FL-D528N-T7, MEF-DKO-hiR2-FL-D528I-T7, MEF-DKO-hiR2-FL-D528A-T7, MEF-DKO-hiR2-FL-D529H-T7, MEF-DKO-hiR2-FL-D529A-T7, MEF-DKO-hiR2-FL-T530P-T7, MEF-DKO-hiR2-FL-T530A-T7, MEF-DKO-hiR2-FL-G531S-T7, MEF-DKO-hiR2-FL-G531A-T7, MEF-DKO-hiR2-FL-P532A-T7, MEF-DKO-hiR2-FL-P533--T7, MEF-DKO-hiR2-FL-P533A-T7, MEF-DKO-hiR2-FL-M534S-T7, MEF-DKO-hiR2-FL-M534--T7, MEF-DKO-hiR2-FL-M534A-T7, MEF-DKO-hiR2-FL-D535--T7, MEF-DKO-hiR2-FL-D535A-T7, MEF-DKO-hiR2-FL-K536--T7, MEF-DKO-hiR2-FL-K536A-T7, MEF-DKO-hiR2-FL-S537E-T7, MEF-DKO-hiR2-FL-S537A-T7, MEF-DKO-hiR2-FL-D538L-T7, MEF-DKO-hiR2-FL-D538A-T7, MEF-DKO-hiR2-FL-L539A-T7, MEF-DKO-hiR2-FL-G540S-T7, MEF-DKO-hiR2-FL-G540A-T7, MEF-DKO-hiR2-FL-Q541H-T7, MEF-DKO-hiR2-FL-Q541A-T7, MEF-DKO-hiR2-FL-K542A-T7, MEF-DKO-hiR2-FL-R543Q-T7, MEF-DKO-hiR2-FL-R543A-T7, MEF-DKO-hiR2-FL-T544P-T7, MEF-DKO-hiR2-FL-T544Q-T7, MEF-DKO-hiR2-FL-T544A-T7, MEF-DKO-hiR2-FL-S545F-T7, MEF-DKO-hiR2-FL-S545A-T7, MEF-DKO-hiR2-FL-G546A-T7, MEF-DKO-hiR2-FL-A547V-T7, MEF-DKO-hiR2-FL-A547S-T7, MEF-DKO-hiR2-FL-V548A-T7, MEF-DKO-hiR2-FL-C549A-T7, MEF-DKO-hiR2-FL-H550A-T7, MEF-DKO-hiR2-FL-Q551A-T7, MEF-DKO-hiR2-FL-D552A-T7, MEF-DKO-hiR2-FL-P553A-T7, MEF-DKO-hiR2-FL-R554A-T7, MEF-DKO-hiR2-FL-T555V-T7, MEF-DKO-hiR2-FL-T555A-T7, MEF-DKO-hiR2-FL-C556A-T7, MEF-DKO-hiR2-FL-E557D-T7, MEF-DKO-hiR2-FL-E557A-T7, MEF-DKO-hiR2-FL-E558A-T7, MEF-DKO-hiR2-FL-P559A-T7, MEF-DKO-hiR2-FL-A560S-T7, MEF-DKO-hiR2-FL-S561A-T7, MEF-DKO-hiR2-FL-S562E-T7, MEF-DKO-hiR2-FL-S562A-T7, MEF-DKO-hiR2-FL-G563D-T7, MEF-DKO-hiR2-FL-G563A-T7, MEF-DKO-hiR2-FL-A564P-T7, MEF-DKO-hiR2-FL-A564S-T7, MEF-DKO-hiR2-FL-H565A-T7, MEF-DKO-hiR2-FL-I566E-T7, MEF-DKO-hiR2-FL-1566A-T7, MEF-DKO-hiR2-FL-W567A-T7, MEF-DKO-hiR2-FL-P568A-T7, MEF-DKO-hiR2-FL-D569E-T7, MEF-DKO-hiR2-FL-D569A-T7, MEF-DKO-hiR2-FL-D570A-T7, MEF-DKO-hiR2-FL-1571A-T7, MEF-DKO-hiR2-FL-T572A-T7, MEF-DKO-hiR2-FL-K573A-T7, MEF-DKO-hiR2-FL-W574A-T7, MEF-DKO-hiR2-FL-P575A-T7, MEF-DKO-hiR2-FL-1576A-T7, MEF-DKO-hiR2-FL-C577A-T7, MEF-DKO-hiR2-FL-T578A-T7, MEF-DKO-hiR2-FL-E579K-T7, MEF-DKO-hiR2-FL-E579A-T7, MEF-DKO-hiR2-FL-Q580N-T7, MEF-DKO-hiR2-FL-Q580A-T7, MEF-DKO-hiR2-FL-A581S-T7, MEF-DKO-hiR2-FL-R582A-T7, MEF-DKO-hiR2-FL-S583G-T7, MEF-DKO-hiR2-FL-S583A-T7, MEF-DKO-hiR2-FL-N584A-T7, MEF-DKO-hiR2-FL-H585A-T7, MEF-DKO-hiR2-FL-T586A-T7, MEF-DKO-hiR2-FL-G587N-T7, MEF-DKO-hiR2-FL-G587A-T7, MEF-DKO-hiR2-FL-F588H-T7, MEF-DKO-hiR2-FL-F588A-T7, MEF-DKO-hiR2-FL-L589P-T7, MEF-DKO-hiR2-FL-L589A-T7, MEF-DKO-hiR2-FL-H590A-T7, MEF-DKO-hiR2-FL-M591A-T7, MEF-DKO-hiR2-FL-D592A-T7, MEF-DKO-hiR2-FL-C593A-T7 and MEF-DKO-hiR2-FL-E594V-T7 cells.

TGFα ELISA for Test System Validation

To test all 137 human iRhom2 variants with single amino acid substitutions or deletions, the respective MEF-DKO cell lines stably expressing these variants, generated as described in the example above, were subjected to TGFα shedding ELISA analysis. In order to demonstrate the functionality of all variants as an indicator that these variants are properly folded, PMA-induced release of nucleofected TGFα was assessed. As the cells used in this analysis are rescue variants of iRhom 1/2−/− double knockout mouse embryonic fibroblasts (described in Example 2), that are rescued by the respective human iRhom2 variant with a single amino acid substitution or deletion, the iRhom2 variant stably expressed is the only iRhom protein expressed in these cells at all and is therefore the only contributing iRhom to the shedding TGFα in these cells.

In brief, on day 1, Nunc black MaxiSorp® 96-well plates (Thermo Fisher Scientific, USA) were coated overnight with 100 μl per well of mouse anti-human TGFα capture antibody (provided as part of the DuoSet ELISA kit) at 400 ng/ml in TBS at 4° C. After MEF-DKO-hiR2-FL-Q502R-T7, MEF-DKO-hiR2-FL-N503A-T7, MEF-DKO-hiR2-FL-D504A-T7, MEF-DKO-hiR2-FL-H505R-T7, MEF-DKO-hiR2-FL-H505A-T7, MEF-DKO-hiR2-FL-S506A-T7, MEF-DKO-hiR2-FL-G507A-T7, MEF-DKO-hiR2-FL-C508A-T7, MEF-DKO-hiR2-FL-I509V-T7, MEF-DKO-hiR2-FL-I509A-T7, MEF-DKO-hiR2-FL-Q510A-T7, MEF-DKO-hiR2-FL-T511A-T7, MEF-DKO-hiR2-FL-Q512L-T7, MEF-DKO-hiR2-FL-Q512S-T7, MEF-DKO-hiR2-FL-Q512A-T7, MEF-DKO-hiR2-FL-R513K-T7, MEF-DKO-hiR2-FL-R513E-T7, MEF-DKO-hiR2-FL-R513A-T7, MEF-DKO-hiR2-FL-K514E-T7, MEF-DKO-hiR2-FL-K514A-T7, MEF-DKO-hiR2-FL-D515E-T7, MEF-DKO-hiR2-FL-D515A-T7, MEF-DKO-hiR2-FL-C516A-T7, MEF-DKO-hiR2-FL-S517A-T7, MEF-DKO-hiR2-FL-E518S-T7, MEF-DKO-hiR2-FL-E518A-T7, MEF-DKO-hiR2-FL-T519A-T7, MEF-DKO-hiR2-FL-L520A-T7, MEF-DKO-hiR2-FL-A521S-T7, MEF-DKO-hiR2-FL-T522V-T7, MEF-DKO-hiR2-FL-T522A-T7, MEF-DKO-hiR2-FL-F523W-T7, MEF-DKO-hiR2-FL- F523A-T7, MEF-DKO-hiR2-FL-V524A-T7, MEF-DKO-hiR2-FL-K525A-T7, MEF-DKO-hiR2-FL-W526A-T7, MEF-DKO-hiR2-FL-Q527P-T7, MEF-DKO-hiR2-FL-Q527A-T7, MEF-DKO-hiR2-FL-D528N-T7, MEF-DKO-hiR2-FL-D528I-T7, MEF-DKO-hiR2-FL-D528A-T7, MEF-DKO-hiR2-FL-D529H-T7, MEF-DKO-hiR2-FL-D529A-T7, MEF-DKO-hiR2-FL-T530P-T7, MEF-DKO-hiR2-FL-T530A-T7, MEF-DKO-hiR2-FL-G531S-T7, MEF-DKO-hiR2-FL-G531A-T7, MEF-DKO-hiR2-FL-P532A-T7, MEF-DKO-hiR2-FL-P533--T7, MEF-DKO-hiR2-FL-P533A-T7, MEF-DKO-hiR2-FL-M534S-T7, MEF-DKO-hiR2-FL-M534--T7, MEF-DKO-hiR2-FL-M534A-T7, MEF-DKO-hiR2-FL-D535--T7, MEF-DKO-hiR2-FL-D535A-T7, MEF-DKO-hiR2-FL-K536--T7, MEF-DKO-hiR2-FL-K536A-T7, MEF-DKO-hiR2-FL-S537E-T7, MEF-DKO-hiR2-FL-S537A-T7, MEF-DKO-hiR2-FL-D538L-T7, MEF-DKO-hiR2-FL-D538A-T7, MEF-DKO-hiR2-FL-L539A-T7, MEF-DKO-hiR2-FL-G540S-T7, MEF-DKO-hiR2-FL-G540A-T7, MEF-DKO-hiR2-FL-Q541H-T7, MEF-DKO-hiR2-FL-Q541A-T7, MEF-DKO-hiR2-FL-K542A-T7, MEF-DKO-hiR2-FL-R543Q-T7, MEF-DKO-hiR2-FL-R543A-T7, MEF-DKO-hiR2-FL-T544P-T7, MEF-DKO-hiR2-FL-T544Q-T7, MEF-DKO-hiR2-FL-T544A-T7, MEF-DKO-hiR2-FL-S545F-T7, MEF-DKO-hiR2-FL-S545A-T7, MEF-DKO-hiR2-FL-G546A-T7, MEF-DKO-hiR2-FL-A547V-T7, MEF-DKO-hiR2-FL-A547S-T7, MEF-DKO-hiR2-FL-V548A-T7, MEF-DKO-hiR2-FL-C549A-T7, MEF-DKO-hiR2-FL-H550A-T7, MEF-DKO-hiR2-FL-Q551A-T7, MEF-DKO-hiR2-FL-D552A-T7, MEF-DKO-hiR2-FL-P553A-T7, MEF-DKO-hiR2-FL-R554A-T7, MEF-DKO-hiR2-FL-T555V-T7, MEF-DKO-hiR2-FL-T555A-T7, MEF-DKO-hiR2-FL-C556A-T7, MEF-DKO-hiR2-FL-E557D-T7, MEF-DKO-hiR2-FL-E557A-T7, MEF-DKO-hiR2-FL-E558A-T7, MEF-DKO-hiR2-FL-P559A-T7, MEF-DKO-hiR2-FL-A560S-T7, MEF-DKO-hiR2-FL-S561A-T7, MEF-DKO-hiR2-FL-S562E-T7, MEF-DKO-hiR2-FL-S562A-T7, MEF-DKO-hiR2-FL-G563D-T7, MEF-DKO-hiR2-FL-G563A-T7, MEF-DKO-hiR2-FL-A564P-T7, MEF-DKO-hiR2-FL-A564S-T7, MEF-DKO-hiR2-FL-H565A-T7, MEF-DKO-hiR2-FL-I566E-T7, MEF-DKO-hiR2-FL-1566A-T7, MEF-DKO-hiR2-FL-W567A-T7, MEF-DKO-hiR2-FL-P568A-T7, MEF-DKO-hiR2-FL-D569E-T7, MEF-DKO-hiR2-FL-D569A-T7, MEF-DKO-hiR2-FL-D570A-T7, MEF-DKO-hiR2-FL-1571A-T7, MEF-DKO-hiR2-FL-T572A-T7, MEF-DKO-hiR2-FL-K573A-T7, MEF-DKO-hiR2-FL-W574A-T7, MEF-DKO-hiR2-FL-P575A-T7, MEF-DKO-hiR2-FL-1576A-T7, MEF-DKO-hiR2-FL-C577A-T7, MEF-DKO-hiR2-FL-T578A-T7, MEF-DKO-hiR2-FL-E579K-T7, MEF-DKO-hiR2-FL-E579A-T7, MEF-DKO-hiR2-FL-Q580N-T7, MEF-DKO-hiR2-FL-Q580A-T7, MEF-DKO-hiR2-FL-A581S-T7, MEF-DKO-hiR2-FL-R582A-T7, MEF-DKO-hiR2-FL-S583G-T7, MEF-DKO-hiR2-FL-S583A-T7, MEF-DKO-hiR2-FL-N584A-T7, MEF-DKO-hiR2-FL-H585A-T7, MEF-DKO-hiR2-FL-T586A-T7, MEF-DKO-hiR2-FL-G587N-T7, MEF-DKO-hiR2-FL-G587A-T7, MEF-DKO-hiR2-FL-F588H-T7, MEF-DKO-hiR2-FL-F588A-T7, MEF-DKO-hiR2-FL-L589P-T7, MEF-DKO-hiR2-FL-L589A-T7, MEF-DKO-hiR2-FL-H590A-T7, MEF-DKO-hiR2-FL-M591A-T7, MEF-DKO-hiR2-FL-D592A-T7, MEF-DKO-hiR2-FL-C593A-T7 and MEF-DKO-hiR2-FL-E594V-T7 cells were electroporated with the hTGFx-FL-WT construct in a pcDNA3.1 vector backbone, using an 4D-Nucleofector System (Lonza, Switzerland), approximately 33,000 MEF-DKO cells carrying the human iRhom2 variant with the single amino acid substitution or deletion were seeded in 100 μl of normal growth medium in each well of F-bottom 96-well cell culture plates (Thermo Fisher Scientific, USA). On day 2, the capture antibody solution was removed and MaxiSorp® plates were blocked with 300 μl per well of TBS, 1% BSA at room temperature for at least 1 hour. Meanwhile, the cells were washed once with PBS and afterwards 80 μl of OptiMEM medium (Thermo Fisher Scientific, USA) was added per well.

Subsequently, cells (except those for unstimulated controls) were stimulated with 20 μl per well of PMA (Sigma-Aldrich, USA) at a final concentration of 25 ng/ml at 37° C., 5% $CO_2$ for 1 hour. 20 μl of OptiMEM medium was added to the unstimulated control cells. Afterwards, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Thereafter, 100 μl biotinylated goat anti-human TGFα detection antibody (provided as part of the DuoSet ELISA kit) at 37.5 ng/ml in TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 16B:
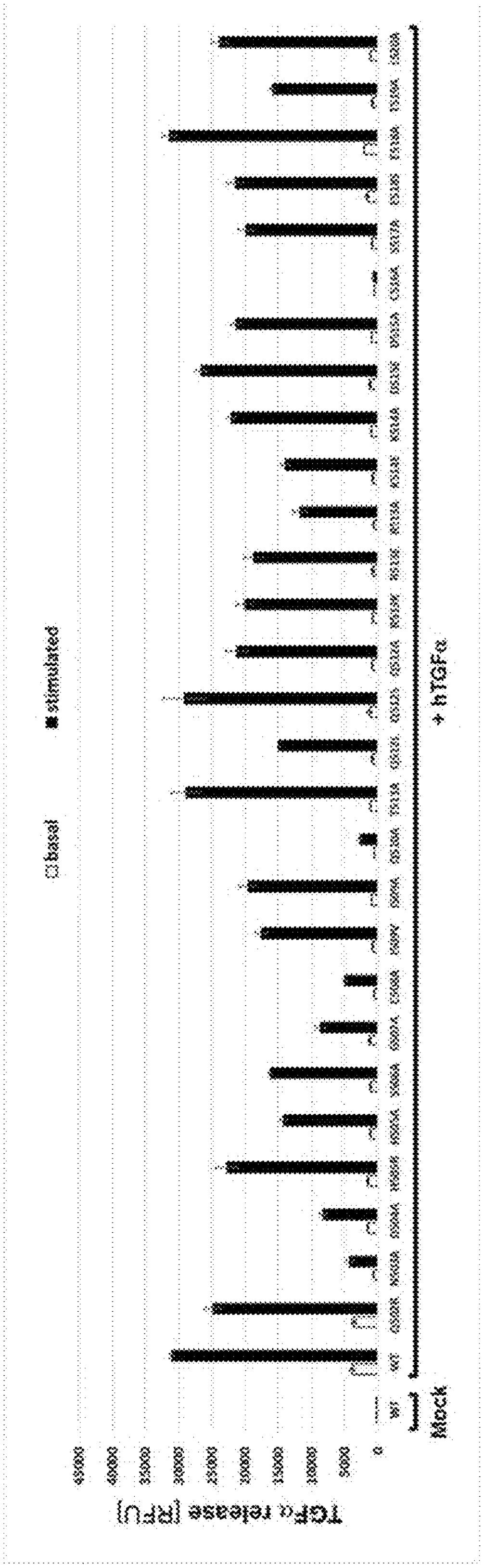
FIGS. 16*b* -16*f* shows results from TGFα release assays (shedding assays), demonstrating that all 137 human iRhom2 variants with single amino acid substitutions or deletions within the large extracellular loop (AA502 to AA594 of human iRhom2), except for the human iRhom2 variants hiR2-FL-C516A, hiR2-FL-F523A, hiR2-FL-C549A, hiR2-FL-D552A, hiR2-FL-C556A, hiR2-FL-P559A, hiR2-FL-W567A, hiR2-FL-W574A and hiR2-FL-C577A, are functionally active and can support PMA-stimulated shedding of TGFα to varying degrees, indicating that these variants are most likely properly folded.
Figure 16C:
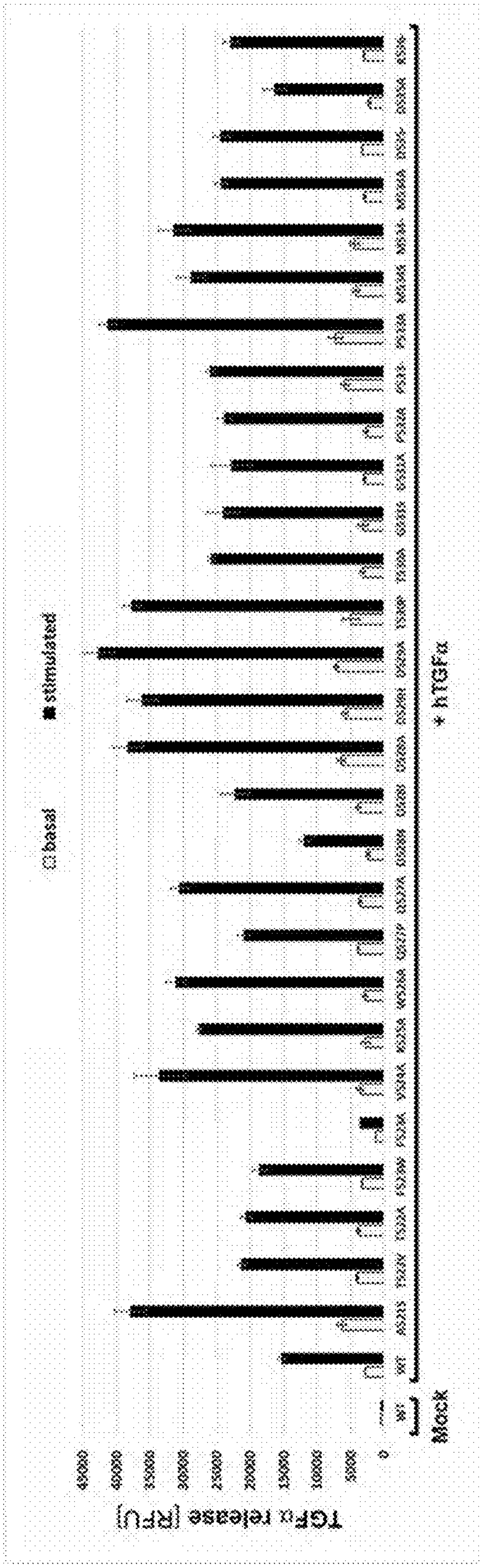
Figure 16D:
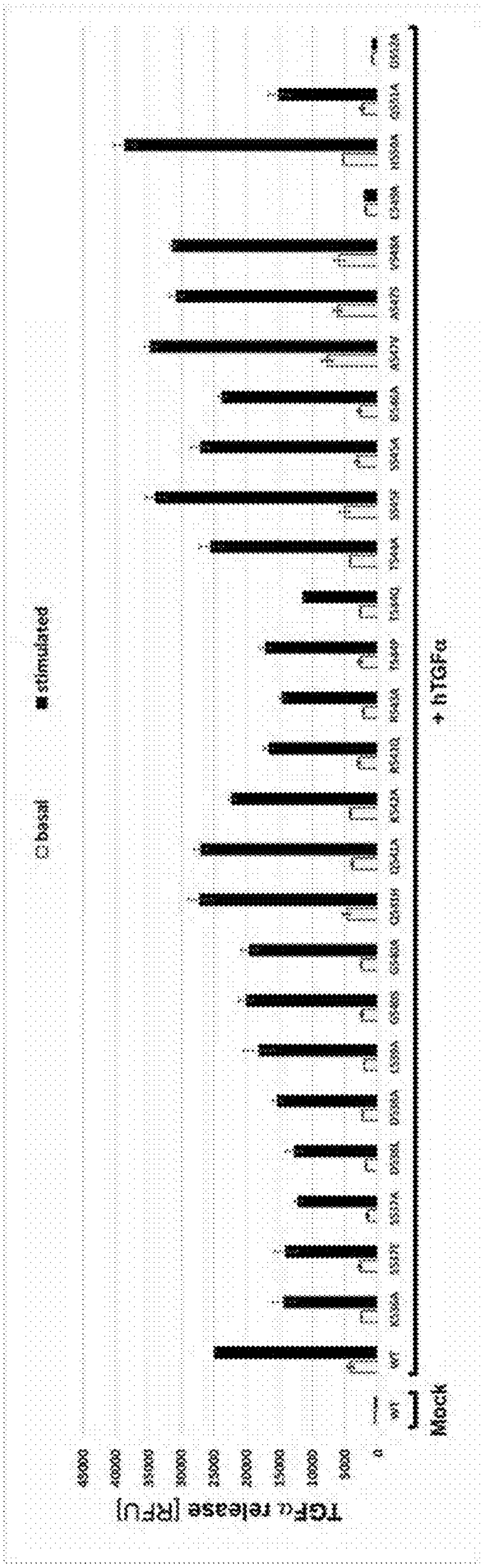
Figure 16E:
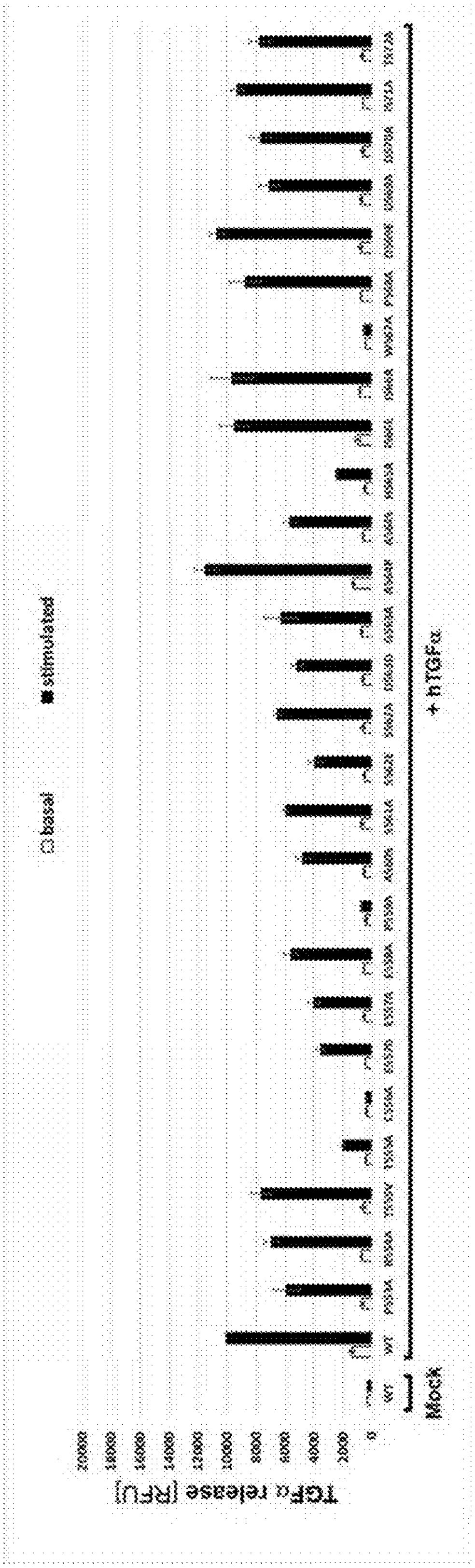
Figure 16F:
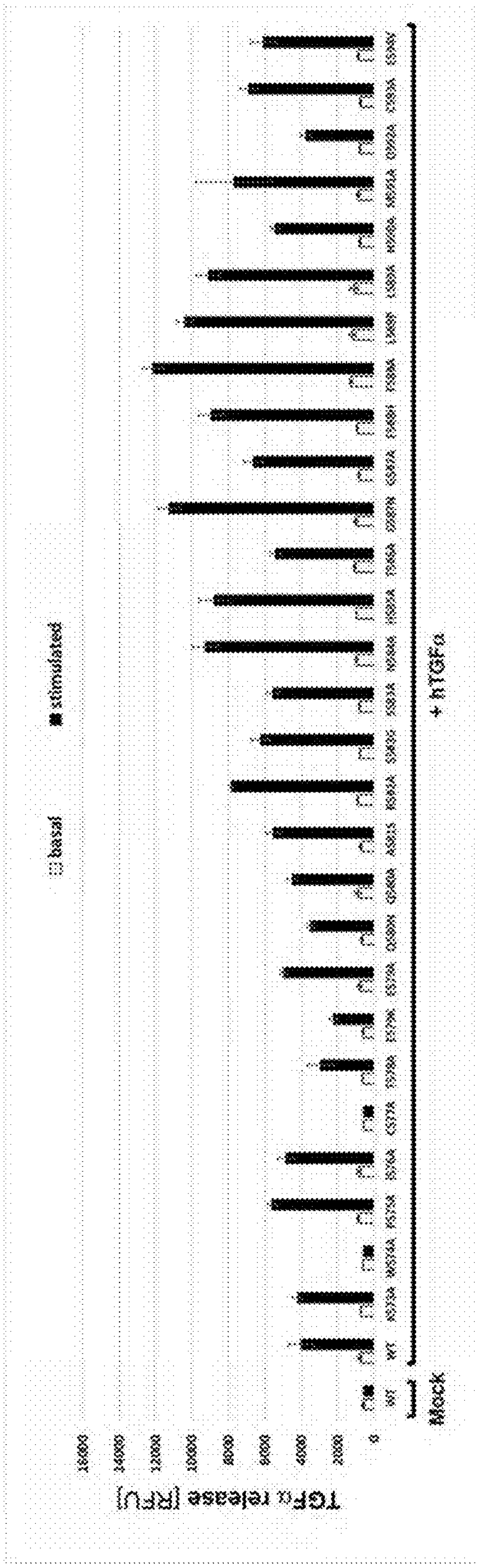

FIG. 16*b* shows results from these TGFα release assays demonstrating that 128 of the 137 human iRhom2 variants with single amino acid substitutions or deletions are functionally active as TGFα shedding can be induced with PMA, indicating that these variants are properly folded, in contrast to the empty vector electroporated (Mock) negative control population, where no PMA-induced shedding of TGFα is detectable. The human iRhom2 variants hiR2-FL-C516A-T7, hiR2-FL-F523A-T7, hiR2-FL-C549A-T7, hiR2-FL-D552A-T7, hiR2-FL-C556A-T7, hiR2-FL-P559A-T7, hiR2-FL-W567A-T7, hiR2-FL-W574A-T7 and hiR2-FL-C577A-T7 showed no or almost no functionality and were therefore excluded from further analyses.

FACS Analyses to Characterize Binding of the Purified Antibodies of the Invention for the Purpose of Epitope Mapping In brief, immortalized MEF-DKO-hiR2-FL-Q502R-T7, MEF-DKO-hiR2-FL-N503A-T7, MEF-DKO-hiR2-FL-D504A-T7, MEF-DKO-hiR2-FL-H505R-T7, MEF-DKO-hiR2-FL-H505A-T7, MIEF-DKO-hiR2-FL-S506A-T7, MEF-DKO-hiR2-FL-G507A-T7, MEF-DKO-hiR2-FL-C508A-T7, MEF-DKO-hiR2-FL-I509V-T7, MEF-DKO-hiR2-FL-I509A-T7, MEF-DKO-hiR2-FL-Q510A-T7, MEF-DKO-hiR2-FL-T511A-T7, MEF-DKO-hiR2-FL-Q512L-T7, MEF-DKO-hiR2-FL-Q512S-T7, MEF-DKO-hiR2-FL-Q512A-T7, MEF-DKO-hiR2-FL-R513K-T7, MEF-DKO-hiR2-FL-R513E-T7, MEF-DKO-hiR2-FL-R513A-T7, MEF-DKO-hiR2-FL-K514E-T7, MEF-DKO-hiR2-FL-K514A-T7, MEF-DKO-hiR2-FL-D515E-T7, MEF-DKO-hiR2-FL-D515A-T7, MEF-DKO-hiR2-FL-C516A-T7, MEF-DKO-hiR2-FL-S517A-T7, MEF-DKO-hiR2-FL-E518S-T7, MEF-DKO-hiR2-FL-E518A-T7, MEF-DKO-hiR2-FL-T519A-T7, MEF-DKO-hiR2-FL-L520A-T7, MEF-DKO-hiR2-FL-A521S-T7, MEF-DKO-hiR2-FL-T522V-T7, MEF-DKO-hiR2-FL-T522A-T7, MEF-DKO-hiR2-FL-F523W-T7, MEF-DKO-hiR2-FL-F523A-T7, MEF-DKO-hiR2-FL-V524A-T7, MEF-DKO-hiR2-FL-K525A-T7, MEF-DKO-hiR2-FL-W526A-T7, MEF-DKO-hiR2-FL-Q527P-T7, MEF-DKO-hiR2-FL-Q527A-T7, MEF-DKO-hiR2-FL-D528N-T7, MEF-DKO-hiR2-FL-D528I-T7, MEF-DKO-hiR2-FL-D528A-T7, MEF-DKO-hiR2-FL-D529H-T7, MEF-DKO-hiR2-FL-D529A-T7, MEF-DKO-hiR2-FL-T530P-T7, MEF-DKO-hiR2-FL-T530A-T7, MEF-DKO-hiR2-FL-G531S-T7, MEF-DKO-hiR2-FL-G531A-T7, MEF-DKO-hiR2-FL-P532A-T7, MEF-DKO-hiR2-FL-P533--T7, MEF-DKO-hiR2-FL-P533A-T7, MEF-DKO-hiR2-FL-M534S-T7, MEF-DKO-hiR2-FL-M534--T7, MEF-DKO-hiR2-FL-M534A-T7, MEF-DKO-hiR2-FL-D535--T7, MEF-DKO-hiR2-FL-D535A-T7, MEF-DKO-hiR2-FL-K536--T7, MEF-DKO-hiR2-FL-K536A-T7, MEF-DKO-hiR2-FL-S537E-T7, MEF-DKO-hiR2-FL-S537A-T7, MEF-DKO-hiR2-FL-D538L-T7, MEF-DKO-hiR2-FL-D538A-T7, MEF-DKO-hiR2-FL-L539A-T7, MEF-DKO-hiR2-FL-G540S-T7, MEF-DKO-hiR2-FL-G540A-T7, MEF-DKO-hiR2-FL-Q541H-T7, MEF-DKO-hiR2-FL-Q541A-T7, MEF-DKO-hiR2-FL-K542A-T7, MEF-DKO-hiR2-FL-R543Q-T7, MEF-DKO-hiR2-FL-R543A-T7, MEF-DKO-hiR2-FL-T544P-T7, MEF-DKO-hiR2-FL-T544Q-T7, MEF-DKO-hiR2-FL-T544A-T7, MEF-DKO-hiR2-FL-S545F-T7, MEF-DKO-hiR2-FL-S545A-T7, MEF-DKO-hiR2-FL-G546A-T7, MEF-DKO-hiR2-FL-A547V-T7, MEF-DKO-hiR2-FL-A547S-T7, MEF-DKO-hiR2-FL-V548A-T7, MEF-DKO-hiR2-FL-C549A-T7, MEF-DKO-hiR2-FL-H550A-T7, MEF-DKO-hiR2-FL-Q551A-T7, MEF-DKO-hiR2-FL-D552A-T7, MEF-DKO-hiR2-FL-P553A-T7, MEF-DKO-hiR2-FL-R554A-T7, MEF-DKO-hiR2-FL-T555V-T7, MEF-DKO-hiR2-FL-T555A-T7, MEF-DKO-hiR2-FL-C556A-T7, MEF-DKO-hiR2-FL-E557D-T7, MEF-DKO-hiR2-FL-E557A-T7, MEF-DKO-hiR2-FL-E558A-T7, MEF-DKO-hiR2-FL-P559A-T7, MEF-DKO-hiR2-FL-A560S-T7, MEF-DKO-hiR2-FL-S561A-T7, MEF-DKO-hiR2-FL-S562E-T7, MEF-DKO-hiR2-FL-S562A-T7, MEF-DKO-hiR2-FL-G563D-T7, MEF-DKO-hiR2-FL-G563A-T7, MEF-DKO-hiR2-FL-A564P-T7, MEF-DKO-hiR2-FL-A564S-T7, MEF-DKO-hiR2-FL-H565A-T7, MEF-DKO-hiR2-FL-1566E-T7, MEF-DKO-hiR2-FL-1566A-T7, MEF-DKO-hiR2-FL-W567A-T7, MEF-DKO-hiR2-FL-P568A-T7, MEF-DKO-hiR2-FL-D569E-T7, MEF-DKO-hiR2-FL-D569A-T7, MEF-DKO-hiR2-FL-D570A-T7, MEF-DKO-hiR2-FL-1571A-T7, MEF-DKO-hiR2-FL-T572A-T7, MEF-DKO-hiR2-FL-K573A-T7, MEF-DKO-hiR2-FL-W574A-T7, MEF-DKO-hiR2-FL-P575A-T7, MEF-DKO-hiR2-FL-I576A-T7, MEF-DKO-hiR2-FL-C577A-T7, MEF-DKO-hiR2-FL-T578A-T7, MEF-DKO-hiR2-FL-E579K-T7, MEF-DKO-hiR2-FL-E579A-T7, MEF-DKO-hiR2-FL-Q580N-T7, MEF-DKO-hiR2-FL-Q580A-T7, MEF-DKO-hiR2-FL-A581S-T7, MEF-DKO-hiR2-FL-R582A-T7, MEF-DKO-hiR2-FL-S583G-T7, MEF-DKO-hiR2-FL-S583A-T7, MEF-DKO-hiR2-FL-N584A-T7, MEEF-DKO-hiR2-FL-H585A-T7, MEF-DKO-hiR2-FL-T586A-T7, MEF-DKO-hiR2-FL-G587N-T7, MEF-DKO-hiR2-FL-G587A-T7, MEF-DKO-hiR2-FL-F588H-T7, MEF-DKO-hiR2-FL-F588A-T7, MEF-DKO-hiR2-FL-L589P-T7, MEF-DKO-hiR2-FL-L589A-T7, MEF-DKO-hiR2-FL-H590A-T7, MEF-DKO-hiR2-FL-M591A-T7, MEF-DKO-hiR2-FL-D592A-T7, MEF-DKO-hiR2-FL-C593A-T7 and MEF-DKO-hiR2-FL-E594V-T7 cells were harvested with 10 mM EDTA in PBS, washed and resuspended in FACS buffer (PBS, 3% FBS, 0.05% sodium azide), and seeded in Nunc U-bottom 96-well plates (Thermo Fisher Scientific, USA) at approximately $1\times10^5$ cells per well. To pellet cells and remove supernatants, the plates were centrifuged at 1,500 rpm and 4° C. for 3 minutes. For primary staining, cells were resuspended in 100 µl per well of either FACS buffer alone (controls) or the humanized antibodies 16-B-03, 16-B-05, 16-B-07, 23-B-04, 42-B-02 and 42-B-04 of the invention at 3 µg/ml in FACS buffer and incubated on ice for 1 hour. Afterwards, plates were centrifuged at 1,500 rpm and 4° C. for 3 minutes and washed twice with 200 µl per well of FACS buffer. For secondary staining, cells were spun down and resuspended in 100 µl per well of PE-conjugated goat anti-human IgG F(ab') 2 detection fragment (Dianova, Germany) diluted 1:100 in FACS buffer. Protected from light, the cell suspensions were incubated on ice for 1 hour. Plates were then centrifuged at 1,500 rpm and 4° C. for 3 minutes and washed three times with 200 µl per well of FACS buffer. Finally, cells were resuspended in 150 µl per well of FACS buffer and analyzed using a BD Accuri™ C6 Plus flow cytometer (Becton Dickinson, Germany).

Figure 17A:
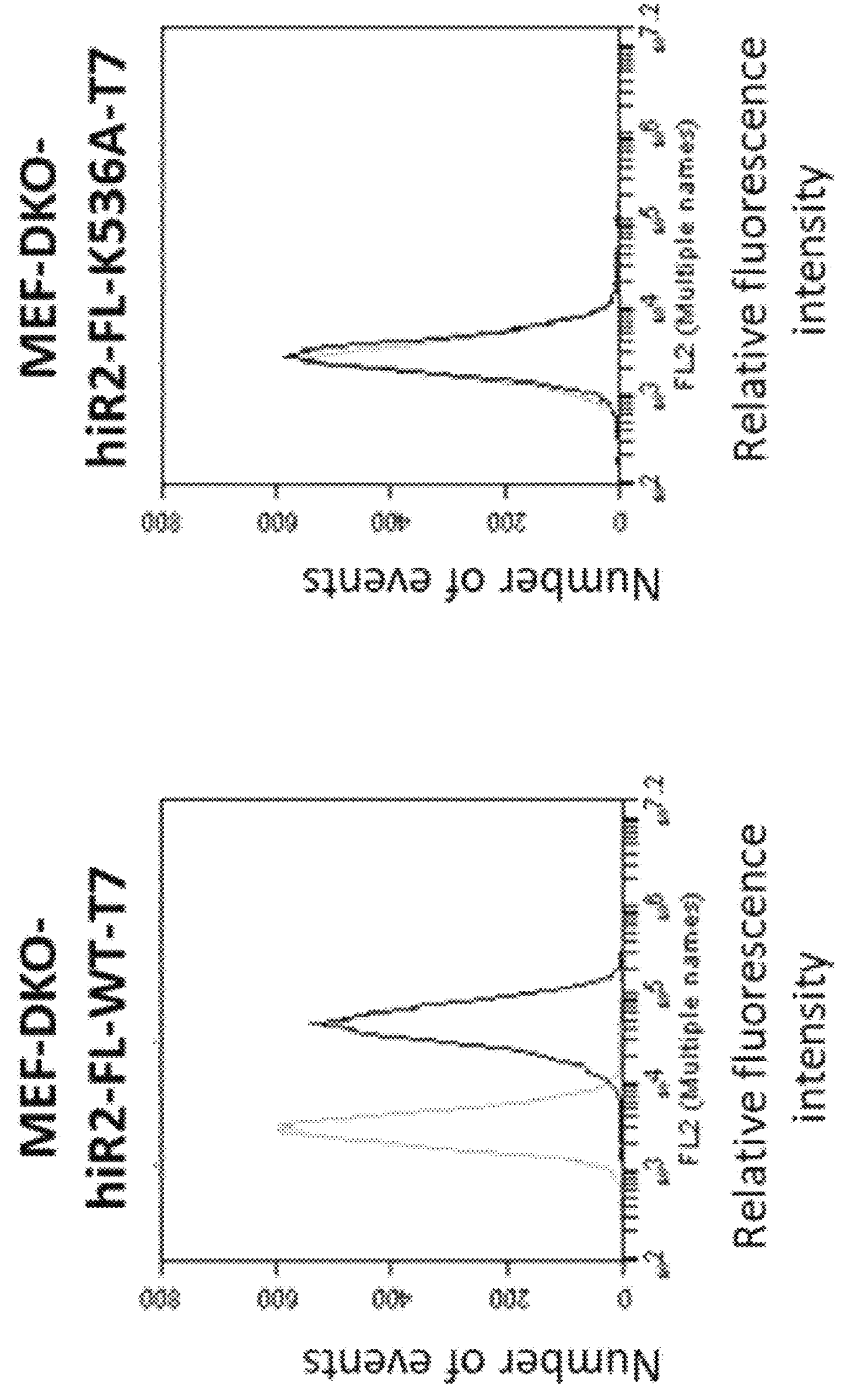
FIG. 17*a* depicts results from FACS analyses for epitope determination of the antibodies of the invention. Exemplary for the entire panel of 128 functional human iRhom2 variants with single amino acid substitutions or deletions within the large extracellular loop (AA502 to AA594 of human iRhom2), data for the analysis of MEF-DKO-hiR2-FL-K536A-T7 cells ectopically expressing the human iRhom2 variant hiR2-FL-K536A are shown. The data demonstrate that the substitution of the single amino acid leucine 536 in human iRhom2 by alanine strongly impairs and, thus, contributes to binding of the humanized antibody 42-B-02 as a representative example of the antibodies of the invention. Stainings: gray=secondary antibody only; black=humanized antibody 42-B-02

FIG. 17*a* shows representative results of this experiment. Exemplarily for the entire panel of 128 functional human iRhom2 variants with single amino acid substitutions or deletions, data for the analysis of cells expressing the human iRhom2 variant hiR2-FL-K536A-T7 are shown. Binding analyses of the humanized antibody 42-B-02 as a representative example of the antibodies of the invention (black) as well as anti-mouse IgG secondary antibody (gray) on MEF-DKO-hiR2-FL-WT-T7 cells (left) and MEF-DKO-hiR2-FL-K536A-T7 cells (right) demonstrate that the substitution of the single amino acid lysine 536 of human iRhom2 by alanine strongly impairs and, thus, contributes to binding of the humanized antibody 42-B-02 of the invention (right). Binding to MEF-DKO-hiR2-FL-WT-T7 cells (left) serves as positive control for the humanized antibody 42-B-02.

FIG. 17*b* summarizes—in extension of FIG. 17*a*—the results of FACS analyses of the humanized antibodies 16-B-03, 16-B-05, 16-B-07, 23-B-04, 42-B-02 and 42-B-04 of the invention on the entire panel of 128 engineered functional MEF populations expressing human iRhom2 variants with single amino acid substitutions or deletions. Binding of each antibody to human iRhom2 wild type is considered 100 percent. A respective drop of antibody binding to any variant by 30-59% is indicated by cells held in light gray (and marked with "1"), an impaired binding by 60-95% is illustrated by cells colored in gray (and marked with "2"), and a loss of binding by ≥95% is highlighted by dark gray cells (marked with "3"). These data reveal related patterns of amino acid positions relevant for binding of humanized antibodies 16-B-03, 16-B-05, 16-B-07, 23-B-04, 42-B-02 and 42-B-04 of the invention.

Example 15: Analysis of Inhibitory Effects of the Antibodies of the Invention on LPS-Induced TNFα Shedding in Primary Human Material from Healthy Donors In Vitro In the following study, ELISA-based TNFα release assays were performed to analyze the inhibitory effects of the antibodies of the invention on LPS-induced release of endogenous TNF& from primary human material obtained from healthy donors using peripheral blood mononuclear cells (PBMCs).

The ELISA-based TNFα release assay that was used in this example is described below.

In brief, on day 1, Nunc black MaxiSorp® 96-well plates (Thermo Fisher Scientific, USA) were coated overnight with 100 μl per well of mouse anti-human TNFα capture antibody (provided as part of the DuoSet ELISA kit) at 4 μg/ml TBS at 4° C. On day 2, the capture antibody solution was removed and MaxiSorp® plates were blocked with 300 μl per well of TBS, 1% BSA at room temperature for 3 hours. Meanwhile, 20,000 PBMC from healthy donors (ReachBio Research Labs, USA) cells in 80 μl of normal growth medium were seeded in each well of Greiner CELLSTAR V-bottom 96-well plates (Greiner Bio-One, Germany) and pre-incubated with 20 μl per well of standard growth medium supplemented with Batimastat (BB94, Abcam, UK) at 50 μM as positive control (for a final concentration of 10 μM in the resulting 100 μl sample volume), human IgG 1 kappa antibody (BioLegend, USA) at 15 μg/ml as isotype control (for a final concentration of 3 μg/ml in the resulting 100 μl sample volume) or antibodies of the invention at 15 μg/ml (for a final concentration of 3 μg/ml in the resulting 100 μl sample volume) at 37° C., 5% $CO_2$ for 30 minutes. In case of stimulation controls, 20 μl of standard growth medium without test articles were added. Subsequently, cells (except those for unstimulated controls) were stimulated with 20 μl per well of LPS (Sigma-Aldrich, USA) at 0.06 ng/ml in growth medium for a final concentration of 0.01 ng/ml at 37° C., 5% $CO_2$ for 2 hours. Afterwards, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human TNFα protein (provided as part of the DuoSet ELISA kit) diluted in TBS at defined concentrations were added to the plate as standard references. Thereafter, 100 μl biotinylated goat anti-human TNFα detection antibody (provided as part of the DuoSet ELISA kit) at 50 ng/ml TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 18A:
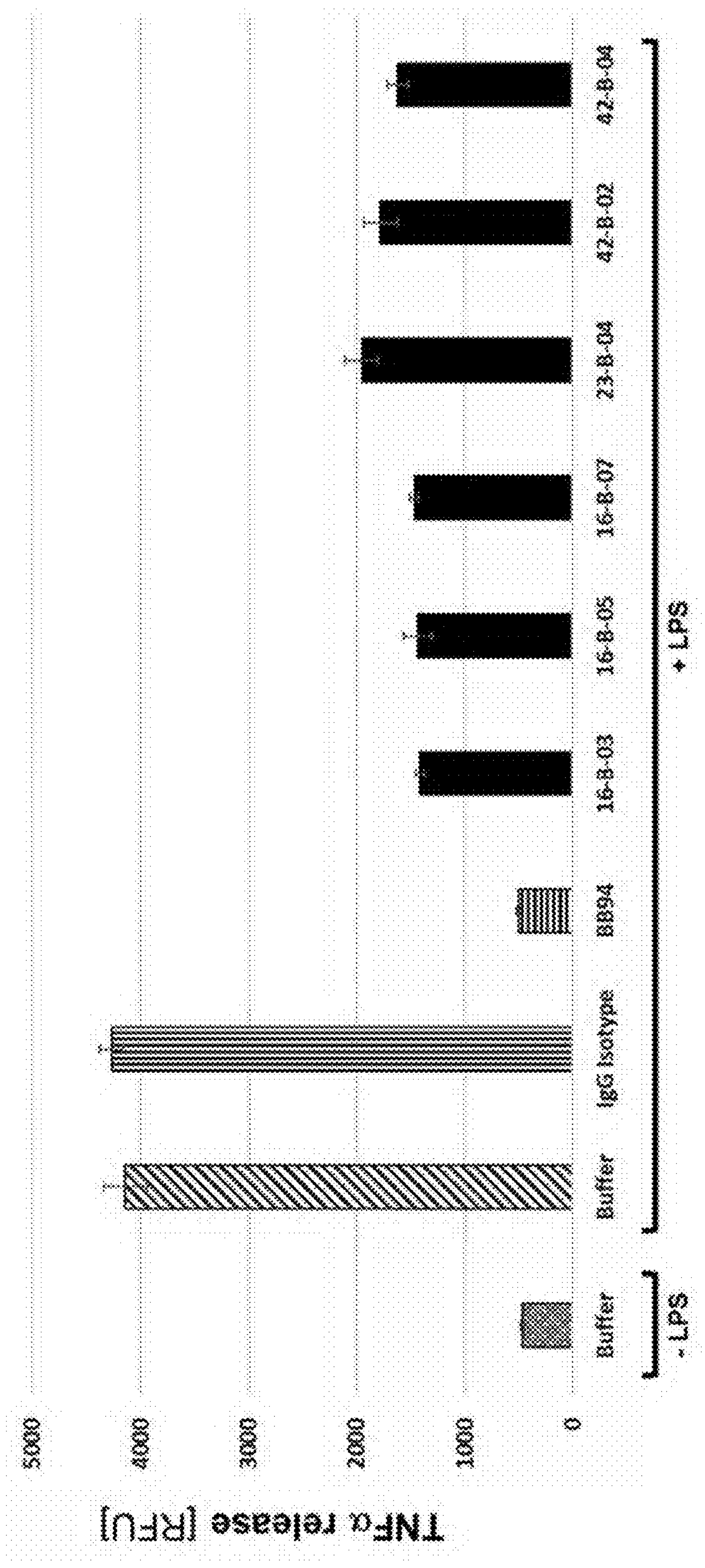
FIG. 18*a* shows results from TNFα release assays, demonstrating all antibodies of the invention to interfere with LPS-induced shedding of TNFα in human peripheral blood mononuclear cells (PBMCs) isolated from healthy donors. The data illustrate the effects of test articles in absolute numbers of released TNFα. The analyzed humanized antibodies result from transient expression of the respective heavy chain/kappa light chain pairs in CHO cells.
Figure 18B:
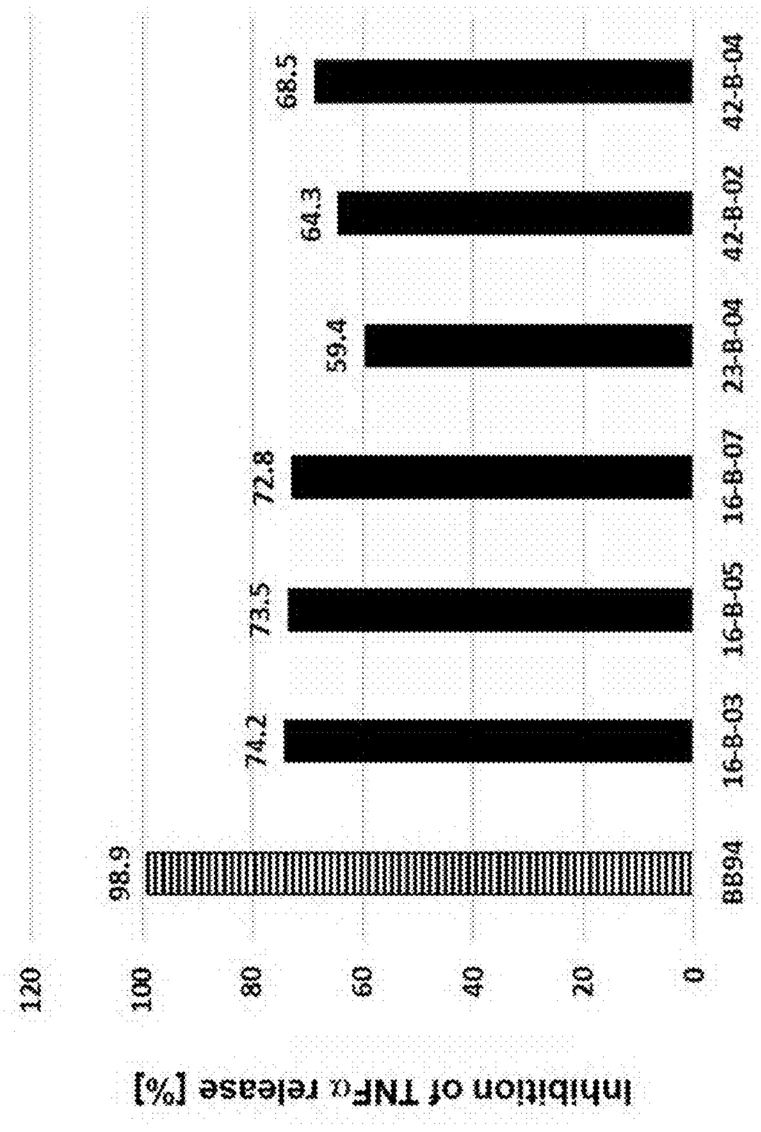
FIG. 18*b* refers to the results depicted in FIG. 18*a* and illustrates the effects of test articles on TNFα release in percent inhibition.

FIG. 18 shows representative results of this experiment demonstrating the effects of test articles on LPS-induced release of TNFα from PBMCs from healthy donors in absolute numbers (FIG. 18*a*) and percent inhibition (FIG. 18*b*). While Batimastat (BB94) as a small molecule inhibitor of metalloproteinases serves as positive control and results in 98.9% inhibition of LPS-induced release of TNFα, the presence of IgG isotype control has no significant effect on TNFα shedding. In contrast, an equal concentration of the humanized antibodies 16-B-03, 16-B-05, 16-B-07, 23-B-04, 42-B-02 and 42-B-04 of the invention inhibits LPS-induced release of TNFα from PBMCs from healthy donors by 74.2%, 73.5%, 72.8%, 59.4%, 64.3% and 68.5%, respectively.

Example 16: Analysis of Inhibitory Effects of the Antibodies of the Invention on PMA-Induced IL-6R Shedding in Primary Human Material from Healthy Donors In Vitro In the following study, ELISA-based IL-6R release assays were performed to analyze the inhibitory effects of the antibodies of the invention on PMA-induced release of endogenous IL-6R from primary human material obtained from healthy donors using peripheral blood mononuclear cells (PBMCs).

The ELISA-based IL-6R release assay that was used in this example is described below.

In brief, on day 1, Nunc black MaxiSorp® 96-well plates (Thermo Fisher Scientific, USA) were coated overnight with 100 μl per well of mouse anti-human IL-6R capture antibody (provided as part of the DuoSet ELISA kit) at 2 μg/ml TBS at 4° C.

40,000 PBMC from healthy donors (STEMCELL Technologies, Canada) cells in 80 μl of normal growth medium were seeded in each well of Greiner CELLSTAR V-bottom 96-well plates (Greiner Bio-One, Germany) and pre-incubated with 20 μl per well of standard growth medium supplemented with Batimastat (BB94, Abcam, UK) at 50 μM as positive control (for a final concentration of 10 μM in the resulting 100 μl sample volume), human IgG 1 kappa antibody (BioLegend, USA) at 15 μg/ml as isotype control (for a final concentration of 3 μg/ml in the resulting 100 μl sample volume) or antibodies of the invention at 15 μg/ml (for a final concentration of 3 μg/ml in the resulting 100 μl sample volume) at 37° C., 5% $CO_2$ for 30 minutes. In case of stimulation controls, 20 μl of standard growth medium without test articles were added. Subsequently, cells (except those for unstimulated controls) were stimulated with 20 μl per well of PMA (Sigma-Aldrich, USA) at 150 ng/ml in growth medium for a final concentration of 25 ng/ml at 37° C., 5% $CO_2$ for 24 hours.

On day 2, the capture antibody solution was removed and MaxiSorp® plates were blocked with 300 μl per well of TBS, 1% BSA at room temperature for 2 hours.

Meanwhile, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human IL-6R protein (provided as part of the DuoSet ELISA kit) diluted in TBS at defined concentrations were added to the plate as standard references. Plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl biotinylated goat anti-human IL-6R detection antibody (provided as part of the DuoSet ELISA kit) at 100 ng/ml TBS were added per well and, protected from direct light, plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 19A:
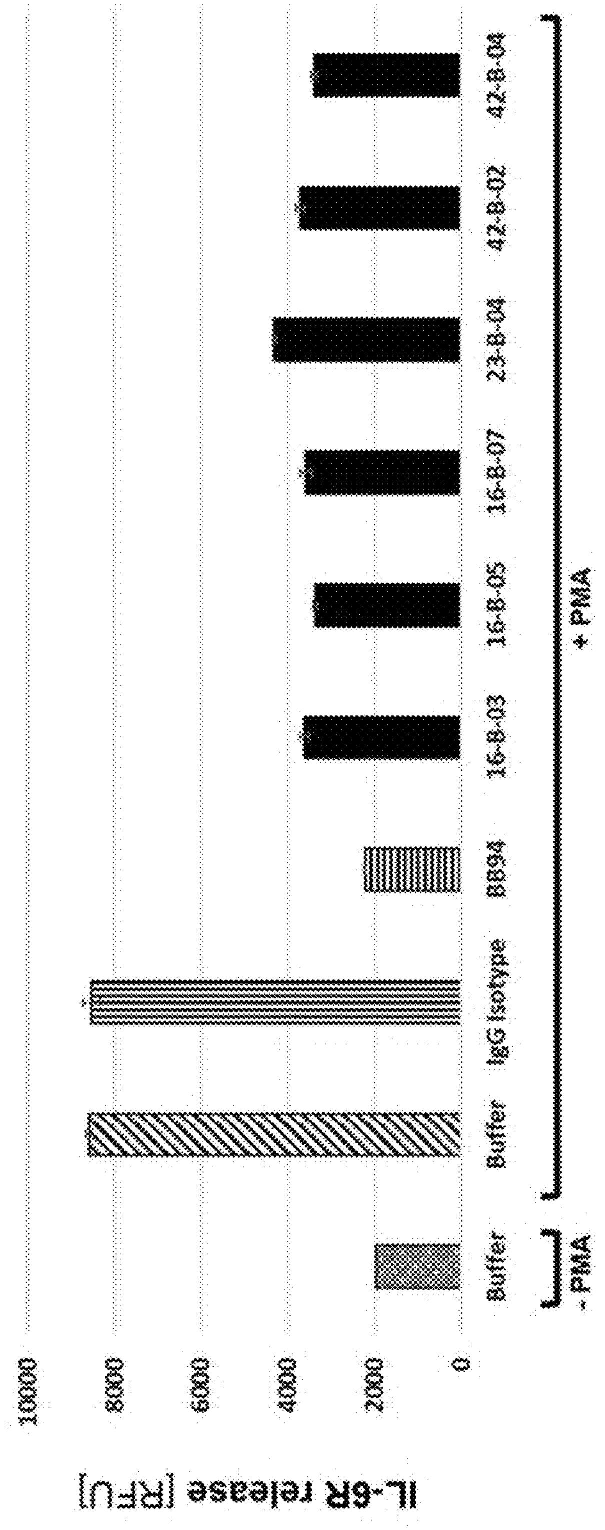
FIG. 19*a* shows results from IL-6R release assays, demonstrating all antibodies of the invention to interfere with PMA-induced shedding of IL-6R in human peripheral blood mononuclear cells (PBMCs) isolated from healthy donors. The data illustrate the effects of test articles in absolute numbers of released IL-6R. The analyzed humanized antibodies result from transient expression of the respective heavy chain/kappa light chain pairs in CHO cells.
Figure 19B:
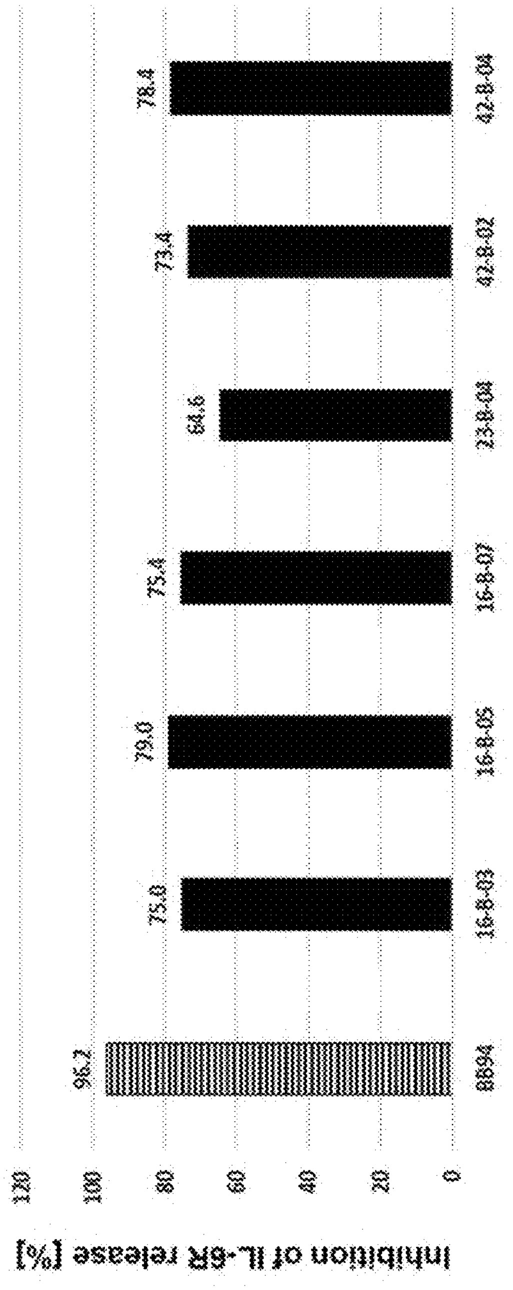
FIG. 19*b* refers to the results depicted in FIG. 19*a* and illustrates the effects of test articles on IL-6R release in percent inhibition.

FIG. 19 shows representative results of this experiment demonstrating the effects of test articles on PMA-induced release of IL-6R from PBMCs from healthy donors in absolute numbers (FIG. 19*a*) and percent inhibition (FIG. 19*b*). While Batimastat (BB94) as a small molecule inhibitor of metalloproteinases serves as positive control and results in 96.2% inhibition of PMA-induced release of IL-6R, the presence of IgG isotype control has no significant effect on IL-6R shedding. In contrast, an equal concentration of the humanized antibodies 16-B-03, 16-B-05, 16-B-07, 23-B-04, 42-B-02 and 42-B-04 of the invention inhibits PMA-induced release of IL-6R from PBMCs from healthy donors by 75.0%, 79.0%, 75.4%, 64.6%, 73.4% and 78.4%, respectively.

Example 17: Analysis of Inhibitory Effects of the Antibodies of the Invention on PMA-Induced HB-EGF Shedding in Primary Human Material from Healthy Donors In Vitro In the following study, ELISA-based HB-EGF release assays were performed to analyze the inhibitory effects of the antibodies of the invention on PMA-induced release of endogenous HB-EGF from primary human material obtained from healthy donors using peripheral blood mononuclear cells (PBMCs).

The ELISA-based HB-EGF release assay that was used in this example is described below.

In brief, on day 1, Nunc black MaxiSorp® 96-well plates (Thermo Fisher Scientific, USA) were coated overnight with 100 μl per well of mouse anti-human HB-EGF capture antibody (provided as part of the DuoSet ELISA kit) at 2 μg/ml TBS at 4° C.

80,000 PBMC from healthy donors (STEMCELL Technologies, Canada) cells in 80 μl of normal growth medium were seeded in each well of Greiner CELLSTAR V-bottom 96-well plates (Greiner Bio-One, Germany) and pre-incubated with 20 μl per well of standard growth medium supplemented with Batimastat (BB94, Abcam, UK) at 50 μM as positive control (for a final concentration of 10 μM in the resulting 100 μl sample volume), human IgG antibody (BioLegend, USA) at 15 μg/ml as isotype control (for a final concentration of 3 μg/ml in the resulting 100 μl sample volume) or antibodies of the invention at 15 μg/ml (for a final concentration of 3 μg/ml in the resulting 100 μl sample volume) at 37° C., 5% $CO_2$ for 30 minutes. In case of stimulation controls, 20 μl of standard growth medium without test articles were added. Subsequently, cells (except those for unstimulated controls) were stimulated with 20 μl per well of PMA (Sigma-Aldrich, USA) at 150 ng/ml in growth medium for a final concentration of 25 ng/ml at 37° C., 5% $CO_2$ for 24 hours. On day 2, the capture antibody solution was removed and MaxiSorp® plates were blocked with 300 μl per well of TBS, 1% BSA at room temperature for 2 hours. Meanwhile, the 96-well plates were centrifuged to pellet cells. In parallel, blocking buffer was removed from the MaxiSorp® plates and plates were washed 4 times with 350 μl TBS-T (Carl Roth, Germany) per well on a 96-head plate washer (Tecan Group, Switzerland). To avoid drying-up, 30 μl TBS were added to each well of the MaxiSorp® plates immediately, followed by the transfer of 70 μl cell-free supernatant per sample. Additionally, 100 μl recombinant human HB-EGF protein (provided as part of the DuoSet ELISA kit) diluted in TBS at defined concentrations were added to the plate as standard references. Plates were incubated at room temperature for 2 hours. After 4 times washing with 350 μl TBS-T (Carl Roth, Germany) per well on a 96-head plate washer (Tecan Group, Switzerland) and careful removal of all buffer traces after the fourth cycle, 100 μl biotinylated goat anti-human HB-EGF detection antibody (provided as part of the DuoSet ELISA kit) at 50 ng/ml TBS were added per well and, protected from direct light, plates were incubated at room temperature for 2 hours.

After 4 times washing with 350 μl TBS-T (Carl Roth, Germany) per well on a 96-head plate washer (Tecan Group, Switzerland) and careful removal of all buffer traces after the fourth cycle, 100 μl streptavidin-AP (R&D Systems, USA) diluted 1:10,000 in TBS were added to each well and, again protected from direct light, plates were incubated at room temperature for 30 minutes. Following another round of 4 times washing with 350 μl TBS-T (Carl Roth, Germany) per well on a 96-head plate washer (Tecan Group, Switzerland) and careful removal of all buffer traces after the fourth cycle, 100 μl AttoPhos substrate solution (Promega, USA) per well was added for incubation in the dark at room temperature for 1 hour. Using an infinite M1000 (Tecan Group, Switzerland) microplate reader, the fluorescence of each well was collected at an excitation wavelength of 435 nm and an emission wavelength of 555 nm.

Figure 20A:
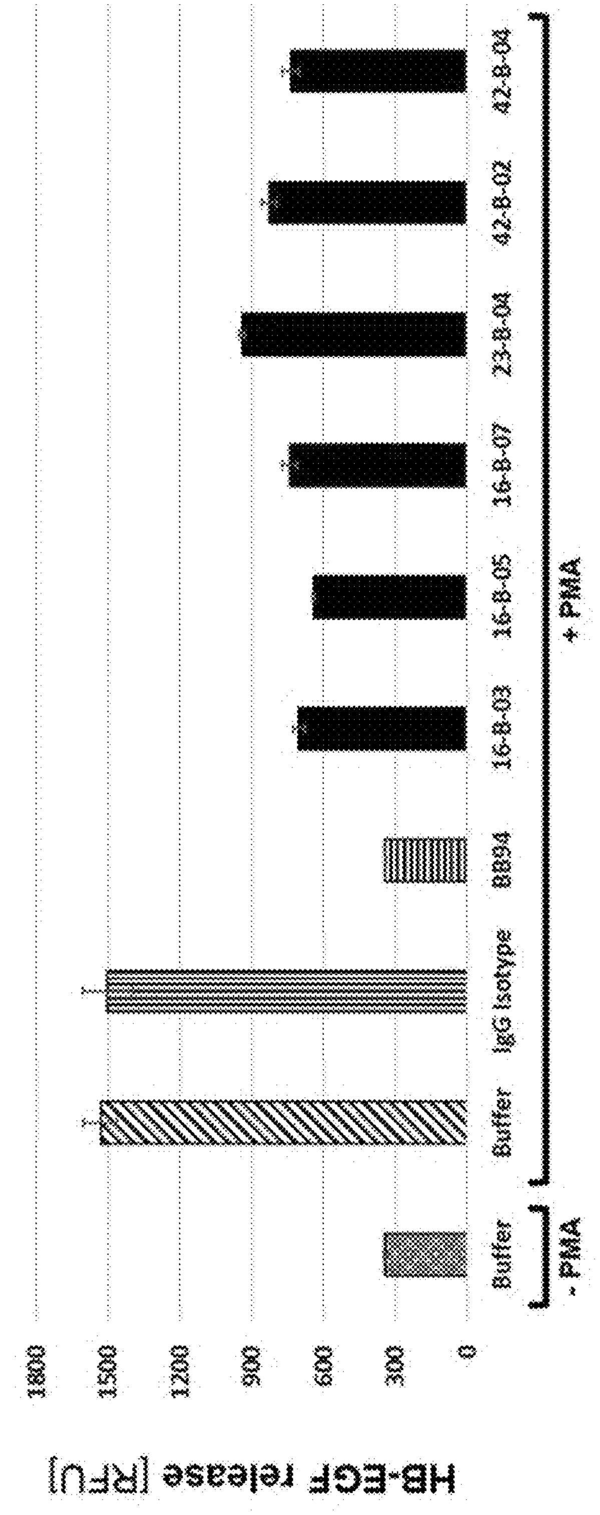
FIG. 20*a* shows results from HB-EGF release assays, demonstrating all antibodies of the invention to interfere with PMA-induced shedding of HB-EGF in human peripheral blood mononuclear cells (PBMCs) isolated from healthy donors. The data illustrate the effects of test articles in absolute numbers of released HB-EGF. The analyzed humanized antibodies result from transient expression of the respective heavy chain/kappa light chain pairs in CHO cells.
Figure 20B:
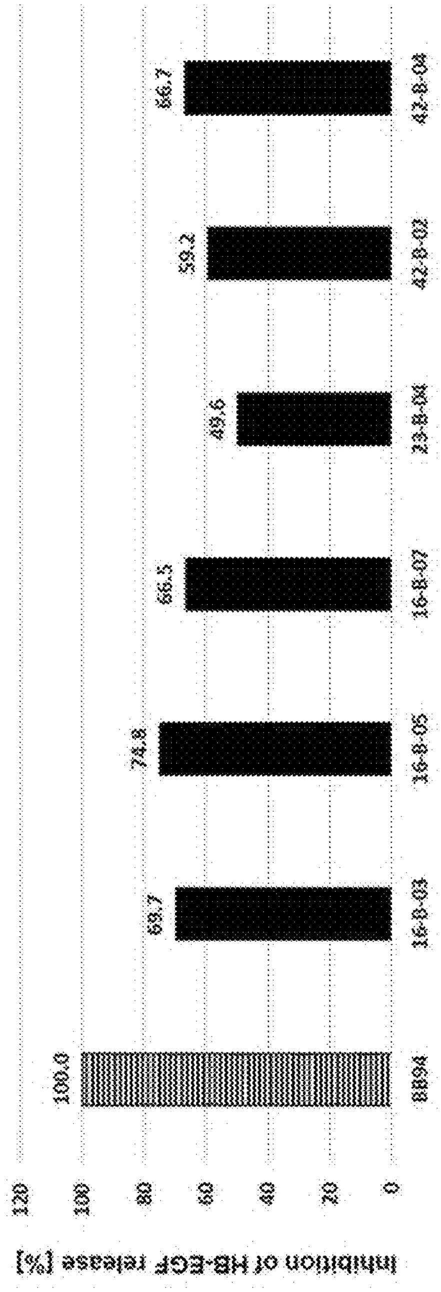
FIG. 20*b* refers to the results depicted in FIG. 20*a* and illustrates the effects of test articles on HB-EGF release in percent inhibition.

FIG. 20 shows representative results of this experiment demonstrating the effects of test articles on PMA-induced release of HB-EGF from PBMCs from healthy donors in absolute numbers (FIG. 20*a*) and percent inhibition (FIG. 20*b*). While Batimastat (BB94) as a small molecule inhibitor of metalloproteinases serves as positive control and results in 100.0% inhibition of PMA-induced release of HB-EGF, the presence of IgG isotype control has no significant effect on HB-EGF shedding. In contrast, an equal concentration of the humanized antibodies 16-B-03, 16-B-05, 16-B-07, 23-B-04, 42-B-02 and 42-B-04 of the invention inhibits PMA-induced release of HB-EGF from PBMCs from healthy donors by 69.7%, 74.8%, 66.5%, 49.6%, 59.2% and 66.7%, respectively.

Example 18: Analysis of Inhibitory Effects of the Antibodies of the Invention on LPS-Induced TNFα Shedding In Vivo In the following study, ELISA-based TNFα release assays were performed to verify the inhibitory effects of the antibodies of the invention on LPS-induced release of endogenous TNFα in a mouse model for septic shock. The experiment was conducted using genetically humanized mice, in which parts of the mouse genomic iRhom2 DNA (exons which encode for the antibody binding site) were replaced by the corresponding human genomic DNA sequences. All animal experiments were approved by the Institutional Animal Care and Use Committee of the Hospital for Special Surgery and Weill Cornell Medicine.

On day 1, one group of mice was injected with the antibodies of the invention at a concentration of 250 μg/kg in 200 μL PBS. A second group was injected with the same volume of PBS only (200 μl PBS per mouse). 1 h later all mice were subjected to an injection of LPS (Sigma, USA) at a concentration of 50 μg/200 μL per mouse (250 ng/μL). All mice were closely monitored and euthanized after 2 h by $CO_2$ inhalation. Blood was removed from the chest cavity and was centrifuged at 4000 g for 10 min at room temperature to remove cells and debris. Clear serum was transferred to a new tube and subsequently diluted 1:10 in PBS for ELISA measurements.

For measuring TNFα release, Mouse TNF-α Uncoated ELISA Kit (Invitrogen, USA) was used. Briefly, on day 1, Costar® 96-well plates (Corning, USA) were coated overnight with 100 μl per well of anti-mouse TNFα capture antibody (provided as part of the ELISA kit) at 1:250 in PBS at 4° C. On day 2, the capture antibody solution was removed, Costar® plates were washed 3 times with 250 μl PBS-Tween 0.05% (Boston Bio, USA) per well with a Nunc Immunowash plate washer (VWR, USA) and plates were blocked for 1 hour with 150 μl of ELISA/ELISPOT Diluent (1X) (provided as part of the kit). Then, blocking buffer was removed from the Costar® plates and plates were washed 3 times with 250 μl PBS-Tween 0.05% (Boston Bio, USA) per well with a Nunc Immunowash plate washer (VWR, USA). Immediately after, 20 μl biotinylated anti-mouse TNFα detection antibody (provided as part of the ELISA kit) at a final dilution of 1:250 in ELISA/ELISPOT Diluent were added to all wells. Then, 80 μl of either clear, 1:10 diluted serum or a standard reference of 80 μl recombinant mouse TNFα protein (provided as part of the ELISA kit) diluted in ELISA/ELISPOT Diluent at defined concentrations were added to the plate. Samples, standards and detection antibody were incubated for 2 h at room temperature. After 3 times washing with 250 μl PBS-Tween 0.05% (Boston Bio, USA) per well with a Nunc Immunowash plate washer (VWR, USA) and careful removal of all buffer traces after the third cycle, 100 μl streptavidin-horseradish peroxidase conjugate (provided as part of ELISA kit) diluted 1:100 in ELISA/ELISPOT Diluent were added to each well and plates were incubated at room temperature for 30 minutes. Following another round of 3 washes with 250 μl PBS-Tween 0.05% (Boston Bio, USA) per well with a Nunc Immunowash plate washer (VWR, USA) and careful removal of all buffer traces after the third cycle, 100 μl TMB substrate solution (BD, USA) per well was added for incubation for 15 minutes. The color reaction was stopped by the addition of 100 μl 2N sulfuric acid (Sigma, USA) and the ELISA plate was read at the wavelength of 450 nm using a Multiskan Titertek Plate reader (VWR, USA).

Figure 21A:
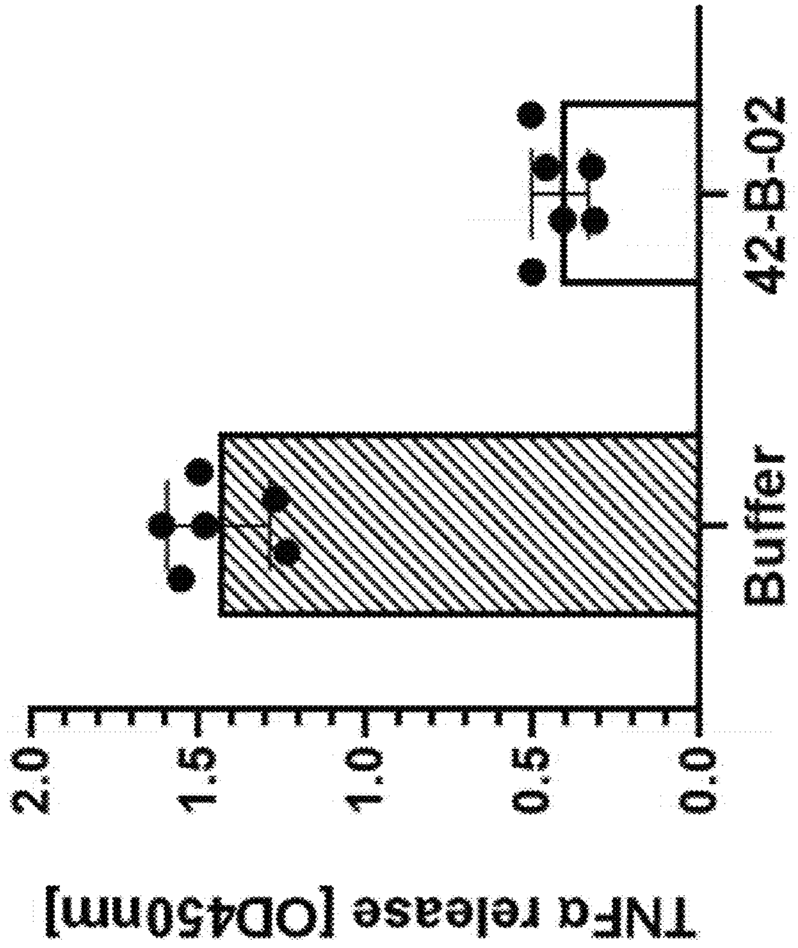
FIG. 21*a* shows results from in vivo septic shock models in genetically humanized mice, demonstrating that the humanized antibody 42-B-02 as a representative example of the antibodies of the invention interferes with LPS-induced shedding of TNFα in genetically humanized mice. The data illustrate the effects of test article in absolute numbers of released TNFα. The analyzed humanized antibodies result from transient expression of the respective heavy chain/kappa light chain pairs in CHO cells.
Figure 21B:
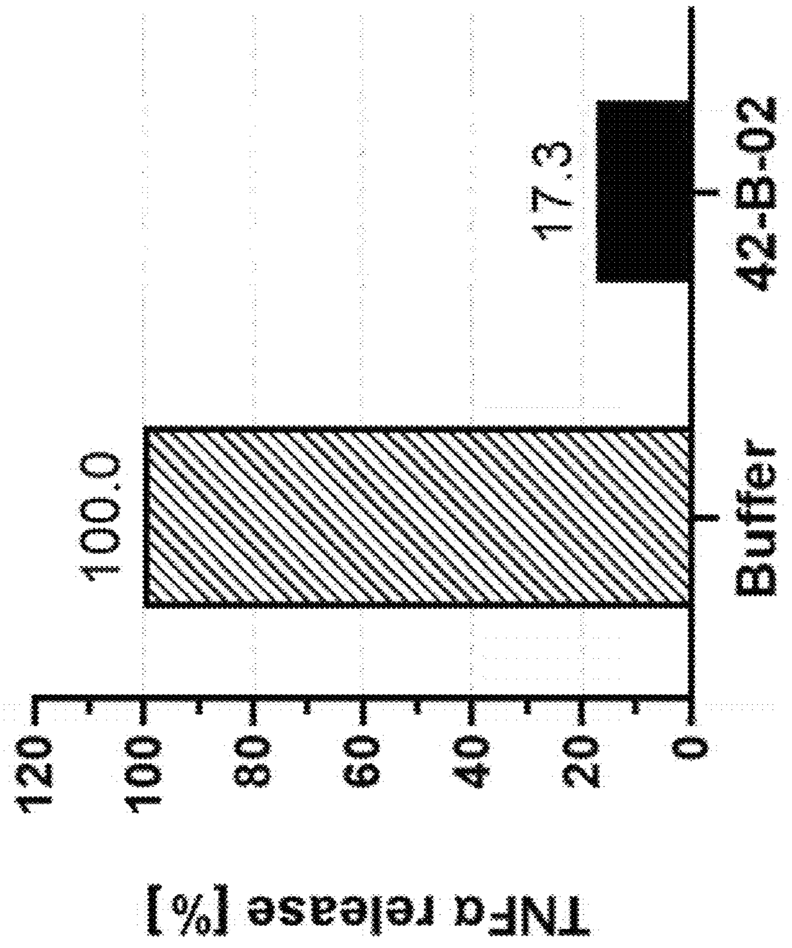
FIG. 21*b* refers to the results depicted in FIG. 21*a* and illustrates the effects of test article on TNFα release in percent compared to the buffer treated control animals, which were set to 100%.

FIG. 21 shows representative results of this experiment demonstrating the effects of test articles on LPS-induced release of TNFα in serum of genetically humanized mice in absolute numbers (FIG. 21*a*) and percent release (FIG. 21*b*). Compared to the LPS-induced release of TNFα in serum of genetically humanized mice, which was set to 100%, the humanized antibody 42-B-02 as a representative example of the antibodies of the invention lead to an LPS-induced release of TNFα in serum of genetically humanized mice of 17.3%.

REFERENCES

Köhler, G. & Milstein, C. (1975): Continuous cultures of fused cells secreting antibody of predefined specificity. In: Nature. Bd. 256, S. 495-497. Jonsson and Malmquist, Advances in Biosensors, 2:291-336 (1992)

Wu et al. Proc. Natl. Acad. Sci. USA, 95:6037-6042 (1998)

Banik, S S R; Doranz, B J (2010). "Mapping complex antibody epitopes". Genetic Engineering & Biotechnology News. 3 (2): 25-8

DeLisser, HM (1999). Epitope mapping. Methods Mol Biol. 96. pp. 11-20

Finco et al, Comparison of competitive ligand-binding assay and bioassay formats for the measurement of neutralizing antibodies to protein therapeutics. J Pharm Biomed Anal. 2011 Jan. 25; 54 (2): 351-8.

Deng et al., Enhancing antibody patent protection using epitope mapping information MAbs. 2018 February-Mar; 10 (2): 204-209

Huston et al., Cell Biophysics, 22:189-224 (1993);

Plückthun and Skerra, Meth. Enzymol., 178:497-515 (1989) and in Day, E. D., Advanced Immunochemistry, Second Ed., Wiley-Liss, Inc., New York, N.Y. (1990)

Harding, The immunogenicity of humanized and fully human antibodies. MAbs. 2010 May-Jun; 2 (3): 256-265.

Eylenstein, et al, Molecular basis of in vitro affinity maturation and functional evolution of a neutralizing anti-human GM-CSF antibody, mAbs, 8:1, 176-186 (2016)

Kabat et al., J. Biol. Chem. 252, 6609-6616 (1977) and Kabat et al., Sequences of protein of immunological interest. (1991)

Chothia et al., J. Mol. Biol. 196:901-917 (1987).

MacCallum et al., J. Mol. Biol. 262:732-745 (1996)

Paul Baran et al, Biol Chem. 2013 May 24; 288 (21): 14756-14768.

Sequences

The following sequences form part of the disclosure of the present application. An ST.26 compliant electronic sequence listing is provided with this application, too. For the avoidance of doubt, if discrepancies exist between the sequences in the following table and the electronic sequence listing, the sequences in this table shall be deemed to be the correct ones.

| SEQ ID No | Clone No | Type | Amino acid sequence |
|---|---|---|---|
| 1 | 16-B-03 | HCVD | QVTLRESGPALVKPTQTLTLTCTFSGFSLSTFALGVGWIRQPPGKALEW LAHIWWDDDKYYNPALKSRLTISKDTSKNQVVLTITNMDPVDTATYYCA RITTYYYGMDYWGQGTLVTVSS |
| 2 | | HCDR1 | TFALGVG |
| 3 | | HCDR2 | HIWWDDDKYYNPALKS |
| 4 | | HCDR3 | ITTYYYGMDY |

-continued

| | | | |
|---|---|---|---|
| 5 | | LCVD | EIVMTQSPDFQSVTPKEKVTITCRASQSIGNHLHWYQQKPDASPKLLIK YASQSISGVPSRFSGSGSGTDFTLTINSLEAEDAATYFCQQSYQWPLTF GQGTKLEIK |
| 6 | | LCDR1 | RASQSIGNHLH |
| 7 | | LCDR2 | YASQSIS |
| 8 | | LCDR3 | QQSYQWPLT |
| 9 | 16-B-05 | HCVD | QVTLRESGPALVKPTQTLTLTCTFSGFSLSTFALGVGWIRQPPGKALEW LAHIWWDEDKYYNPALKSRLTISKDTSKNQVVLTITNMDPVDTATYYCA RITTYYYGMDYWGQGTLVTVSS |
| 10 | | HCDR1 | TFALGVG |
| 11 | | HCDR2 | HIWWDEDKYYNPALKS |
| 12 | | HCDR3 | ITTYYYGMDY |
| 13 | | LCVD | EIVMTQSPDFQSVTPKEKVTITCRASQSIGNHLHWYQQKPDASPKLLIK YASQSISGVPSRESGSGSGTDFTLTINSLEAEDAATYFCQQSYNWPLTF GQGTKLEIK |
| 14 | | LCDR1 | RASQSIGNHLH |
| 15 | | LCDR2 | YASQSIS |
| 16 | | LCDR3 | QQSYNWPLT |
| 17 | 16-B-07 | HCVD | QVTLRESGPALVKPTQTLTLTCTFSGFSLSTFALGVGWIRQPPGKALEW LAHIWWDEDKYYNPALKSRLTISKDTSKNQVVLTITNMDPVDTATYYCA RITTYYYGMDYWGQGTLVTVSS |
| 18 | | HCDR1 | TFALGVG |
| 19 | | HCDR2 | HIWWDEDKYYNPALKS |
| 20 | | HCDR3 | ITTYYYGMDY |
| 21 | | LCVD | EIVMTQSPDFQSVTPKEKVTITCRASQSIGNHLHWYQQKPDASPKLLIK YASQSISGVPSRFSGSGSGTDFTLTINSLEAEDAATYFCQQSYQWPLTF GQGTKLEIK |
| 22 | | LCDR1 | RASQSIGNHLH |
| 23 | | LCDR2 | YASQSIS |
| 24 | | LCDR3 | QQSYQWPLT |
| 25 | 23-B-04 | HCVD | QVTLRESGPALVKPTQTLTLTCTFSGFSLSTFGMGVGWIRQPPGKALEW LAHIWWDDEKYYNSALKSRLTISKDTSKNQVVLTITNMDPVDTATYYCA RISNYGSNYWYFNVWGQGTLVTVSS |
| 26 | | HCDR1 | TFGMGVG |
| 27 | | HCDR2 | HIWWDDEKYYNSALKS |
| 28 | | HCDR3 | ISNYGSNYWYFNV |
| 29 | | LCVD | AIQLTQSPSSLSASVGDRVTITCRASSSVSYMYWYQQKPGKAPKVLIYD TSNLASGVPSRFSGSGSGTDYTLTISSLQPEDFATYYCQQWNAYPLTFG QGTKLEIK |
| 30 | | LCDR1 | RASSSVSYMY |
| 31 | | LCDR2 | DTSNLAS |
| 32 | | LCDR3 | QQWNAYPLT |
| 33 | 42-B-02 | HCVD | QVTLRESGPALVKPTQTLTLTCTFSGFSLSTFGRGVGWIRQPPGKALEW LAHIWWDDEKYYNSALKSRLTISKDTSKNQVVLTITNMDPVDTATYYCA RIQNYGSNYWYFDVWGQGTLVTVSS |
| 34 | | HCDR1 | TFGRGVG |
| 35 | | HCDR2 | HIWWDDEKYYNSALKS |
| 36 | | HCDR3 | IQNYGSNYWYFDV |

-continued

| | | | |
|---|---|---|---|
| 37 | | LCVD | AIQLTQSPSSLSASVGDRVTITCRASSRISYMFWYQQKPGKAPKVLIYD TSNLASGVPSRFSGSGSGTDYTLTISSLQPEDFATYYCQQWNSYPLTFG QGTKLEIK |
| 38 | | LCDR1 | RASSRISYMF |
| 39 | | LCDR2 | DTSNLAS |
| 40 | | LCDR3 | QQWNSYPLT |
| 41 | 42-B-04 | HCVD | QVTLRESGPALVKPTQTLTLTCTFSGFSLSTFGRGVGWIRQPPGKALEW LAHIWWDDEKYYNSALKSRLTISKDTSKNQVVLTITNMDPVDTATYYCA RIQNYGSNYWYFDVWGQGTLVTVSS |
| 42 | | HCDR1 | TFGRGVG |
| 43 | | HCDR2 | HIWWDDEKYYNSALKS |
| 44 | | HCDR3 | IQNYGSNYWYFDV |
| 45 | | LCVD | AIQLTQSPSSLSASVGDRVTITCRASSRISYMFWYQQKPGKAPKVLIYD TSNLASGVPSRFSGSGSGTDYTLTISSLQPEDFATYYCQQWNAYPLTFG QGTKLEIK |
| 46 | | LCDR1 | RASSRISYMF |
| 47 | | LCDR2 | DTSNLAS |
| 48 | | LCDR3 | QQWNAYPLT |
| 49 | | human iRhom2 | MASADKNGGSVSSVSSSRLQSRKPPNLSITIPPPEKETQAPGEQDSMLPEGFQN RRLKKSQPRTWAAHTTACPPSFLPKRKNPAYLKSVSLQEPRSRWQESSEKRPGF RRQASLSQSIRKGAAQWFGVSGDWEGQRQQWQRRSLHHCSMRYGRLKASCQRDL ELPSQEAPSFQGTESPKPCKMPKIVDPLARGRAFRHPEEMDRPHAPHPPLTPGV LSLTSFTSVRSGYSHLPRRKRMSVAHMSLQAAAALLKGRSVLDATGQRCRVVKR SFAFPSFLEEDVVDGADTFDSSFFSKEEMSSMPDDVFESPPLSASYFRGIPHSA SPVSPDGVQIPLKEYGRAPVPGPRRGKRIASKVKHFAFDRKKRHYGLGVVGNWL NRSYRRSISSTVQRQLESFDSHRPYFTYWLTFVHVIITLLVICTYGIAPVGFAQ HVTTQLVLRNKGVYESVKYIQQENFWVGPSSIDLIHLGAKFSPCIRKDGQIEQL VLRERDLERDSGCCVQNDHSGCIQTQRKDCSETLATFVKWQDDTGPPMDKSDLG QKRTSGAVCHQDPRTCEEPASSGAHIWPDDITKWPICTEQARSNHTGFLHMDCE IKGRPCCIGTKGSCEITTREYCEFMHGYFHEEATLCSQVHCLDKVCGLLPFLNP EVPDQFYRLWLSLFLHAGVVHCLVSVVFQMTILRDLEKLAGWHRIAIIFILSGI TGNLASAIFLPYRAEVGPAGSQFGLLACLFVELFQSWPLLERPWKAFLNLSAIV LFLFICGLLPWIDNIAHIFGFLSGLLLAFAFLPYITFGTSDKYRKRALILVSLL AFAGLFAALVLWLYIYPINWPWIEHLTCFPFTSRFCEKYELDQVLH |
| 50 | | human iRhom1 | MSEARRDSTSSLQRKKPPWLKLDIPSAVPLTAEEPSFLQPLRRQAFLRSVSMPA ETAHISSPHHELRRPVLQRQTSITQTIRRGTADWFGVSKDSDSTQKWQRKSIRH CSQRYGKLKPQVLRELDLPSQDNVSLTSTETPPPLYVGPCQLGMQKIIDPLARG RAFRVADDTAEGLSAPHTPVTPGAASLCSESSSRSGFHRLPRRRKRESVAKMSF RAAAALMKGRSVRDGTFRRAQRRSFTPASFLEEDTTDFPDELDTSFFAREGILH EELSTYPDEVFESPSEAALKDWEKAPEQADLTGGALDRSELERSHLMLPLERGW RKQKEGAAAPQPKVRLRQEVVSTAGPRRGQRIAVPVRKLFAREKRPYGLGMVGR LTNRTYRKRIDSFVKRQIEDMDDHRPFFTYWLTFVHSLVTILAVCIYGIAPVGF SQHETVDSVLRNRGVYENVKYVQQENFWIGPSSEALIHLGAKFSPCMRQDPQVH SFIRSAREREKHSACCVRNDRSGCVQTSEEECSSTLAVWVKWPIHPSAPELAGH KRQFGSVCHQDPRVCDEPSSEDPHEWPEDITKWPICTKNSAGNHTNHPHMDCVI TGRPCCIGTKGRCEITSREYCDFMRGYFHEEATLCSQVHCMDDVCGLLPFLNPE VPDQFYRLWLSLFLHAGILHCLVSICFQMTVLRDLEKLAGWHRIAIIYLLSGVT GNLASAIFLPYRAEVGPAGSQFGILACLFVELFQSWQILARPWRAFFKLLAVVL FLFTFGLLPWIDNFAHISGFISGLFLSFAFLPYISFGKFDLYRKRCQIIIFQVV FLGLLAGLVVLFYVYPVRCEWCEFLTCIPFTDKFCEKYELDAQLH |
| 51 | | mouse iRhom2 | MASADKNGSNLPSVSGSRLQSRKPPNLSITIPPPESQAPGEQDSMLPERRKNPA YLKSVSLQEPRGRWQEGAEKRPGFRRQASLSQSIRKSTAQWFGVSGDWEGKRQN WHRRSLHHCSVHYGRLKASCQRELELPSQEVPSFQGTESPKPCKMPKIVDPLAR GRAFRHPDEVDRPHAAHPPLTPGVLSLTSFTSVRSGYSHLPRRKRISVAHMSFQ AAAALLKGRSVLDATGQRCRHVKRSFAYPSFLEEDAVDGADTFDSSFFSKEEMS SMPDDVFESPPLSASYFRGVPHSASPVSPDGVHIPLKEYSGGRALGPGTQRGKR IASKVKHFAFDRKKRHYGLGVVGNWLNRSYRRSISSTVQRQLESFDSHRPYFTY WLTFVHIIITLLVICTYGIAPVGFAQHVTTQLVLKNRGVYESVKYIQQENFWIG PSSIDLIHLGAKFSPCIRKDQQIEQLVRRERDIERTSGCCVQNDRSGCIQTLKK DCSETLATFVKWQNDTGPSDKSDLSQKQPSAVVCHQDPRTCEEPASSGAHIWPD DITKWPICTEQAQSNHTGLLHIDCKIKGRPCCIGTKGSCEITTREYCEFMHGYF HEDATLCSQVHCLDKVCGLLPFLNPEVPDQFYRIWLSLFLHAGIVHCLVSVVFQ MTILRDLEKLAGWHRISIIFILSGITGNLASAIFLPYRAEVGPAGSQFGLLACL FVELFQSWQLLERPWKAFFNLSAIVLFLFICGLLPWIDNIAHIFGFLSGMLLAF |

-continued

| | | | |
|---|---|---|---|
| | | | AFLPYITFGTSDKYRKRALILVSLLVFAGLFASLVLWLYIYPINWPWIEYLTCF PFTSRFCEKYELDQVLH |

| SEQ ID No cDNA/ RNA | Clone No | Type | Amino acid sequence (for RNA replace T by U) |
|---|---|---|---|
| 52/100 | 16-B-03 | HCVD | CAGGTGACCCTGAGGGAGAGCGGCCCCGCCCTGGTGAAGCCCACCCAGACCCTG ACCCTGACCTGCACCTTCAGCGGCTTCAGCCTGAGCACCTTCGCCCTGGGCGTG GGCTGGATCAGGCAGCCCCCCGGCAAGGCCCTGGAGTGGCTGGCCCACATCTGG TGGGACGACGACAAGTACTACAACCCCGCCCTGAAGAGCAGGCTGACCATCAGC AAGGACACCAGCAAGAACCAGGTGGTGCTGACCATCACCAACATGGACCCCGTG GACACCGCCACCTACTACTGCGCCAGGATCACCACCTACTACTACGGCATGGAC TACTGGGGCCAGGGCACCCTGGTGACCGTGAGCAGC |
| 53/101 | | HCDR1 | ACCTTCGCCCTGGGCGTGGGC |
| 54/102 | | HCDR2 | CACATCTGGTGGGACGACGACAAGTACTACAACCCCGCCCTGAAGAGC |
| 55/103 | | HCDR3 | ATCACCACCTACTACTACGGCATGGACTAC |
| 56/104 | | LCVD | GAGATCGTGATGACCCAGAGCCCCGACTTCCAGAGCGTGACCCCCAAGGAGAAG GTGACCATCACCTGCAGGGCCAGCCAGAGCATCGGCAACCACCTGCACTGGTAC CAGCAGAAGCCCGACGCCAGCCCCAAGCTGCTGATCAAGTACGCCAGCCAGAGC ATCAGCGGCGTGCCCAGCAGGTTCAGCGGCAGCGGCAGCGGCACCGACTTCACC CTGACCATCAACAGCCTGGAGGCCGAGGACGCCGCCACCTACTTCTGCCAGCAG AGCTACCAGTGGCCCCTGACCTTCGGCCAGGGCACCAAGCTGGAGATCAAG |
| 57/105 | | LCDR1 | AGGGCCAGCCAGAGCATCGGCAACCACCTGCAC |
| 58/106 | | LCDR2 | TACGCCAGCCAGAGCATCAGC |
| 59/107 | | LCDR3 | CAGCAGAGCTACCAGTGGCCCCTGACC |
| 60/108 | 16-B-05 | HCVD | CAGGTGACCCTGAGGGAGAGCGGCCCCGCCCTGGTGAAGCCCACCCAGACCCTG ACCCTGACCTGCACCTTCAGCGGCTTCAGCCTGAGCACCTTCGCCCTGGGCGTG GGCTGGATCAGGCAGCCCCCCGGCAAGGCCCTGGAGTGGCTGGCCCACATCTGG TGGGACGAGGACAAGTACTACAACCCCGCCCTGAAGAGCAGGCTGACCATCAGC AAGGACACCAGCAAGAACCAGGTGGTGCTGACCATCACCAACATGGACCCCGTG GACACCGCCACCTACTACTGCGCCAGGATCACCACCTACTACTACGGCATGGAC TACTGGGGCCAGGGCACCCTGGTGACCGTGAGCAGC |
| 61/109 | | HCDR1 | ACCTTCGCCCTGGGCGTGGGC |
| 62/110 | | HCDR2 | CACATCTGGTGGGACGAGGACAAGTACTACAACCCCGCCCTGAAGAGC |
| 63/111 | | HCDR3 | ATCACCACCTACTACTACGGCATGGACTAC |
| 64/112 | | LCVD | GAGATCGTGATGACCCAGAGCCCCGACTTCCAGAGCGTGACCCCCAAGGAGAAG GTGACCATCACCTGCAGGGCCAGCCAGAGCATCGGCAACCACCTGCACTGGTAC CAGCAGAAGCCCGACGCCAGCCCCAAGCTGCTGATCAAGTACGCCAGCCAGAGC ATCAGCGGCGTGCCCAGCAGGTTCAGCGGCAGCGGCAGCGGCACCGACTTCACC CTGACCATCAACAGCCTGGAGGCCGAGGACGCCGCCACCTACTTCTGCCAGCAG AGCTACAACTGGCCCCTGACCTTCGGCCAGGGCACCAAGCTGGAGATCAAG |
| 65/113 | | LCDR1 | AGGGCCAGCCAGAGCATCGGCAACCACCTGCAC |
| 66/114 | | LCDR2 | TACGCCAGCCAGAGCATCAGC |
| 67/115 | | LCDR3 | CAGCAGAGCTACAACTGGCCCCTGACC |
| 68/116 | 16-B-07 | HCVD | CAGGTGACCCTGAGGGAGAGCGGCCCCGCCCTGGTGAAGCCCACCCAGACCCTG ACCCTGACCTGCACCTTCAGCGGCTTCAGCCTGAGCACCTTCGCCCTGGGCGTG GGCTGGATCAGGCAGCCCCCCGGCAAGGCCCTGGAGTGGCTGGCCCACATCTGG TGGGACGAGGACAAGTACTACAACCCCGCCCTGAAGAGCAGGCTGACCATCAGC AAGGACACCAGCAAGAACCAGGTGGTGCTGACCATCACCAACATGGACCCCGTG GACACCGCCACCTACTACTGCGCCAGGATCACCACCTACTACTACGGCATGGAC TACTGGGGCCAGGGCACCCTGGTGACCGTGAGCAGC |
| 69/117 | | HCDR1 | ACCTTCGCCCTGGGCGTGGGC |
| 70/118 | | HCDR2 | CACATCTGGTGGGACGAGGACAAGTACTACAACCCCGCCCTGAAGAGC |
| 71/119 | | HCDR3 | ATCACCACCTACTACTACGGCATGGACTAC |
| 72/120 | | LCVD | GAGATCGTGATGACCCAGAGCCCCGACTTCCAGAGCGTGACCCCCAAGGAGAAG GTGACCATCACCTGCAGGGCCAGCCAGAGCATCGGCAACCACCTGCACTGGTAC |

-continued

| | | | |
|---|---|---|---|
| | | | CAGCAGAAGCCCGACGCCAGCCCCAAGCTGCTGATCAAGTACGCCAGCCAGAGC ATCAGCGGCGTGCCCAGCAGGTTCAGCGGCAGCGGCAGCGGCACCGACTTCACC CTGACCATCAACAGCCTGGAGGCCGAGGACGCCGCCACCTACTTCTGCCAGCAG AGCTACCAGTGGCCCCTGACCTTCGGCCAGGGCACCAAGCTGGAGATCAAG |
| 73/121 | | LCDR1 | AGGGCCAGCCAGAGCATCGGCAACCACCTGCAC |
| 74/122 | | LCDR2 | TACGCCAGCCAGAGCATCAGC |
| 75/123 | | LCDR3 | CAGCAGAGCTACCAGTGGCCCCTGACC |
| 76/124 | 23-B-04 | HCVD | CAGGTGACCCTGAGGGAGAGCGGCCCCGCCCTGGTGAAGCCCACCCAGACCCTG ACCCTGACCTGCACCTTCAGCGGCTTCAGCCTGAGCACCTTCGGCATGGGCGTG GGCTGGATCAGGCAGCCCCCCGGCAAGGCCCTGGAGTGGCTGGCCCACATCTGG TGGGACGACGAGAAGTACTACAACAGCGCCCTGAAGAGCAGGCTGACCATCAGC AAGGACACCAGCAAGAACCAGGTGGTGCTGACCATCACCAACATGGACCCCGTG GACACCGCCACCTACTACTGCGCCAGGATCAGCAACTACGGCAGCAACTACTGG TACTTCAACGTGTGGGGCCAGGGCACCCTGGTGACCGTGAGCAGC |
| 77/125 | | HCDR1 | ACCTTCGGCATGGGCGTGGGC |
| 78/126 | | HCDR2 | CACATCTGGTGGGACGACGAGAAGTACTACAACAGCGCCCTGAAGAGC |
| 79/127 | | HCDR3 | ATCAGCAACTACGGCAGCAACTACTGGTACTTCAACGTG |
| 80/128 | | LCVD | GCCATCCAGCTGACCCAGAGCCCCAGCAGCCTGAGCGCCAGCGTGGGCGACAGG GTGACCATCACCTGCAGGGCCAGCAGCAGCGTGAGCTACATGTACTGGTACCAG CAGAAGCCCGGCAAGGCCCCCAAGGTGCTGATCTACGACACCAGCAACCTGGCC AGCGGCGTGCCCAGCAGGTTCAGCGGCAGCGGCAGCGGCACCGACTACACCCTG ACCATCAGCAGCCTGCAGCCCGAGGACTTCGCCACCTACTACTGCCAGCAGTGG AACGCCTACCCCCTGACCTTCGGCCAGGGCACCAAGCTGGAGATCAAG |
| 81/129 | | LCDR1 | AGGGCCAGCAGCAGCGTGAGCTACATGTAC |
| 82/130 | | LCDR2 | GACACCAGCAACCTGGCCAGC |
| 83/131 | | LCDR3 | CAGCAGTGGAACGCCTACCCCCTGACC |
| 84/132 | 42-B-02 | HCVD | CAGGTGACCCTGAGGGAGAGCGGCCCCGCCCTGGTGAAGCCCACCCAGACCCTG ACCCTGACCTGCACCTTCAGCGGCTTCAGCCTGAGCACCTTCGGCAGGGGCGTG GGCTGGATCAGGCAGCCCCCCGGCAAGGCCCTGGAGTGGCTGGCCCACATCTGG TGGGACGACGAGAAGTACTACAACAGCGCCCTGAAGAGCAGGCTGACCATCAGC AAGGACACCAGCAAGAACCAGGTGGTGCTGACCATCACCAACATGGACCCCGTG GACACCGCCACCTACTACTGCGCCAGGATCCAGAACTACGGCAGCAACTACTGG TACTTCGACGTGTGGGGCCAGGGCACCCTGGTGACCGTGAGCAGC |
| 85/133 | | HCDR1 | ACCTTCGGCAGGGGCGTGGGC |
| 86/134 | | HCDR2 | CACATCTGGTGGGACGACGAGAAGTACTACAACAGCGCCCTGAAGAGC |
| 87/135 | | HCDR3 | ATCCAGAACTACGGCAGCAACTACTGGTACTTCGACGTG |
| 88/136 | | LCVD | GCCATCCAGCTGACCCAGAGCCCCAGCAGCCTGAGCGCCAGCGTGGGCGACAGG GTGACCATCACCTGCAGGGCCAGCAGCAGGATCAGCTACATGTTCTGGTACCAG CAGAAGCCCGGCAAGGCCCCCAAGGTGCTGATCTACGACACCAGCAACCTGGCC AGCGGCGTGCCCAGCAGGTTCAGCGGCAGCGGCAGCGGCACCGACTACACCCTG ACCATCAGCAGCCTGCAGCCCGAGGACTTCGCCACCTACTACTGCCAGCAGTGG AACAGCTACCCCCTGACCTTCGGCCAGGGCACCAAGCTGGAGATCAAG |
| 89/137 | | LCDR1 | AGGGCCAGCAGCAGGATCAGCTACATGTTC |
| 90/138 | | LCDR2 | GACACCAGCAACCTGGCCAGC |
| 91/139 | | LCDR3 | CAGCAGTGGAACAGCTACCCCCTGACC |
| 92/140 | 42-B-04 | HCVD | CAGGTGACCCTGAGGGAGAGCGGCCCCGCCCTGGTGAAGCCCACCCAGACCCTG ACCCTGACCTGCACCTTCAGCGGCTTCAGCCTGAGCACCTTCGGCAGGGGCGTG GGCTGGATCAGGCAGCCCCCCGGCAAGGCCCTGGAGTGGCTGGCCCACATCTGG TGGGACGACGAGAAGTACTACAACAGCGCCCTGAAGAGCAGGCTGACCATCAGC AAGGACACCAGCAAGAACCAGGTGGTGCTGACCATCACCAACATGGACCCCGTG GACACCGCCACCTACTACTGCGCCAGGATCCAGAACTACGGCAGCAACTACTGG TACTTCGACGTGTGGGGCCAGGGCACCCTGGTGACCGTGAGCAGC |
| 93/141 | | HCDR1 | ACCTTCGGCAGGGGCGTGGGC |
| 94/142 | | HCDR2 | CACATCTGGTGGGACGACGAGAAGTACTACAACAGCGCCCTGAAGAGC |
| 95/143 | | HCDR3 | ATCCAGAACTACGGCAGCAACTACTGGTACTTCGACGTG |

-continued

| | | |
|---|---|---|
| 96/144 | LCVD | GCCATCCAGCTGACCCAGAGCCCCAGCAGCCTGAGCGCCAGCGTGGGCGACAGG<br>GTGACCATCACCTGCAGGGCCAGCAGCAGGATCAGCTACATGTTCTGGTACCAG<br>CAGAAGCCCGGCAAGGCCCCCAAGGTGCTGATCTACGACACCAGCAACCTGGCC<br>AGCGGCGTGCCCAGCAGGTTCAGCGGCAGCGGCAGCGGCACCGACTACACCCTG<br>ACCATCAGCAGCCTGCAGCCCGAGGACTTCGCCACCTACTACTGCCAGCAGTGG<br>AACGCCTACCCCCTGACCTTCGGCCAGGGCACCAAGCTGGAGATCAAG |
| 97/145 | LCDR1 | AGGGCCAGCAGCAGGATCAGCTACATGTTC |
| 98/146 | LCDR2 | GACACCAGCAACCTGGCCAGC |
| 99/147 | LCDR3 | CAGCAGTGGAACGCCTACCCCCTGACC |

What is claimed is:

1. A humanized antibody binding Inactive Rhomboid family member 2 (iRhom2), or a target-binding fragment, comprising:

a) a set of three heavy chain and three light chain complementarity determining regions (CDR) selected from the group consisting of:

SEQ ID NOs: 2, 3, 4, 6, 7 and 8,

SEQ ID NOs: 18, 19, 20, 22, 23 and 24,

SEQ ID NOs: 26, 27, 28, 30, 31 and 32,

SEQ ID NOs: 34, 35, 36, 38, 39 and 40, and

SEQ ID NOs: 42, 43, 44, 46, 47 and 48, and/or b) a heavy chain/light chain variable domain (HCVD/LCVD) pair selected from the group consisting of:

SEQ ID NOs: 1 and 5,

SEQ ID NOs: 17 and 21,

SEQ ID NOs: 25 and 29,

SEQ ID NOs: 33 and 37, and

SEQ ID NOs: 41 and 45, wherein said antibody or fragment binds to human iRhom2 and/or inhibits or reduces tumor necrosis factor-a-converting enzyme (TACE)/ADAM metallopeptidase domain 17 (ADAM17) activity.

2. The antibody or fragment of claim 1 which, when bound to human iRhom2, binds at least within a region of Loop 1 thereof.

3. The antibody or fragment of claim 1, wherein the inhibition or reduction of TACE/ADAM17 activity is caused by interference with iRhom2-mediated TACE/ADAM17 activation.

4. The antibody or fragment of claim 1, which, when bound to human iRhom2, inhibits or reduces induced TNFα shedding, inhibits or reduces induced IL-6R shedding, and/or inhibits or reduces induced Heparin-binding EGF-like growth factor (HB-EGF) shedding.

5. The antibody or fragment of claim 1, wherein the human iRhom2 to which the antibody or fragment binds comprises:

a) the amino acid sequence set forth in SEQ ID NO 49, or b) an amino acid sequence that has at least 80% sequence identity with SEQ ID NO 49, wherein said sequence maintains iRhom2 activity.

6. The antibody or fragment of claim 1, which is a monoclonal antibody, or a target-binding fragment.

7. The antibody or fragment of claim 1, which is in at least one of the formats selected from the group consisting of: IgG, scFv, Fab, and (Fab)2.

8. The antibody or fragment of claim 1, which is not cross-reactive with human iRhom1.

9. A nucleic acid that encodes for the antibody or fragment of claim 1.

10. A pharmaceutical composition comprising the antibody or fragment of claim 1, or a nucleic acid encoding said antibody or fragment, and one or more pharmaceutically acceptable excipients.

11. A composition comprising (i) the antibody or fragment of claim 1, or a nucleic acid encoding said antibody or fragment, and (ii) one or more therapeutically active compounds.

12. A method for treating an inflammatory condition, wherein the method comprises administering to a human or animal subject, of the antibody or fragment of claim 1, or a nucleic acid encoding said antibody or fragment, in a therapeutically effective dose.

13. A therapeutic kit comprising:

a) the antibody or fragment of claim 1, or a nucleic acid encoding said antibody or fragment;

b) an apparatus for administering the antibody, the fragment, or the nucleic acid of a); and c) instructions for use.

* * * * *